US008178661B2

(12) United States Patent
Bertin

(10) Patent No.: US 8,178,661 B2
(45) Date of Patent: May 15, 2012

(54) MOLECULES OF THE CARD-RELATED PROTEIN FAMILY AND USES THEREOF

(75) Inventor: John Bertin, Watertown, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 90 days.

(21) Appl. No.: 12/287,334

(22) Filed: Oct. 8, 2008

(65) Prior Publication Data
US 2009/0286714 A1 Nov. 19, 2009

Related U.S. Application Data

(60) Division of application No. 10/325,917, filed on Dec. 20, 2002, now Pat. No. 7,452,967, which is a continuation of application No. 09/798,412, filed on Mar. 2, 2001, now abandoned, which is a continuation-in-part of application No. 09/728,260, filed on Dec. 1, 2000, now abandoned, which is a continuation-in-part of application No. 09/685,791, filed on Oct. 10, 2000, now abandoned, which is a continuation-in-part of application No. 09/513,904, filed on Feb. 25, 2000, now abandoned, which is a continuation-in-part of application No. 09/507,533, filed on Feb. 18, 2000, now abandoned.

(60) Provisional application No. 60/168,780, filed on Dec. 3, 1999.

(51) Int. Cl.
C07H 21/02 (2006.01)
(52) U.S. Cl. .......................................... 536/23.1; 435/6.1
(58) Field of Classification Search .......................... None
See application file for complete search history.

(56) References Cited

U.S. PATENT DOCUMENTS 5,804,374 A  9/1998 Baltimore et al.
5,968,781 A  10/1999 Yoon et al. .................... 435/69.7

FOREIGN PATENT DOCUMENTS

WO  WO 99/38972 A2  8/1999
WO  WO 99/40102 A1  8/1999
WO  WO 00/58473 A2  10/2000

OTHER PUBLICATIONS

Bowie (Science, 1990, 257:1306-1310).*
Burgess et al ( J of Cell Bio. 111:2129-2138, 1990).*
Shiozaki E N, 2002, Proceed Natl Acad Sci, USA, 99 (7): 4197-202.*
Rost et al, 2003 (Cell Mol Life Sciences, 60: 2637-2650).*
Barlett et al, 2003 (In: Structural Bioinformatics, Bourne et al, eds, Wiley-Liss, Inc., pp. 387-407).*
Strausberg et al, Oct. 15, 1999, Science, 286(5439): 455-457.*
Bertin, John, et al., "Caspase recruitment domain-containing protein 11 (CARD-containing MAGUK protein 3)," (sequence) GenPept [online] Bethesda, MA, USA: National Center for Biotechnology Information [retrieved Mar. 6, 2008] GenPept Accession No. Q9BXL7.
Srinivasula, SrinivasArinivasa M., et al., "CLAP, a novel caspase recruitment domain-containing protein in the tumor necrosis factor receptor pathway, regulates NF-κB activation and apoptosis," The Journal of Biological Chemistry, vol. 274, No. 25 (Jun. 18, 1999) pp. 17946-17954.
Egawa, Takeshi, et al., "Requirement for CARMA1 in antigen receptor-induced NF-κB activation and lymphocyte proliferation," Current Biology, vol. 13 (Jul. 15, 2003) pp. 1252-1258.
Medoff, Benjamin, D., et al., "CARMA1 is critical for the development of allergic airway inflammation in a murine model of asthma," The Journal of Immunology, vol. 176 (2006) pp. 7272-7277.
Newton, Kim, et al., "Mice lacking the CARD of CARMA1 exhibit defective B lymphocyte development and impaired proliferation of their B and T lymphocytes," Current Biology, vol. 13 (Jul. 15, 2003) pp. 1247-1251.
Thome Margot, et al., "Equine Herpesvirus Protein E10 Induces Membrane Recruitment and Phosphorylation of its Cellular Homologue, Bcl-10,"Journal of Cell Biology, vol. 152(5) (Mar. 5, 2001), pp. 1115-1122.
Bowie, et al., "Deciphering the message inprotein sequences: Tolerance to amino acid substitutions", Science, vol. 247 (Mar. 16, 1990), pp. 1306-1310.
Lazar, et al., "Transforming Growth Factor Alpha: Mutation of Aspartic Acid 47 and Leucine 48 Results in Different Biological Activities", Molecular and Cellular Biology, vol. 8 (Mar. 1988), pp. 1247-1252.
Willis, et al., "Bcl10 Is Involved in t(1;14)(p22,q32) of MALT B Cell Lymphoma and Mutated in Multiple Tumor Types", Cell, vol. 96, pp. 35-45. Petry, et al., "Secondary Structure of the Third Extracellular Loop Responsible for Ligand Selectivity of a Mammalian Gonadotropin-Releasing Hormone Receptor", Journal of Medicinal Chemistry, vol. 45 (2002), pp. 1026-1034.
Wilson, et al., "The structure, organization, activation and plasticity of the erythropoietin receptor", Current Opinion in Structural Biology, vol. 9(6) (1999); pp. 696-704.
Gaide et al., "Carma1, a CARD-containing binding partner of Bcl10, induces Bcl10 phosphorylation and NF-kappaB activation", FEBS Letters, vol. 496(2001) pp. 121-127.
Reiger et al., Glossary of Genetics and Cytogenetics, Classical and Molecular, 4th Ed., Springer-Verlay, Berlin, (1976).
Scientific & Technical Information Center Research Report, Biotech-Chem Library, 2005, US10/325917-21, pp. 21 and WO 2005/8473-A2.

(Continued)

Primary Examiner — Misook Yu
Assistant Examiner — Brad Duffy
(74) Attorney, Agent, or Firm — Millennium Pharmaceuticals, Inc.

(57) ABSTRACT

Novel CARD-9, CARD-10, or CARD-11 polypeptides, proteins, and nucleic acid molecules are disclosed. In addition to isolated CARD-9, CARD-10, or CARD-11 proteins, the invention further provides CARD-9, CARD-10, or CARD-11, fusion proteins, antigenic peptides and anti-CARD-9, CARD-10, or CARD-11 antibodies. The invention also provides CARD-9, CARD-10, or CARD-11 nucleic acid molecules, recombinant expression vectors containing a nucleic acid molecule of the invention, host cells into which the expression vectors have been introduced and non-human transgenic animals in which a CARD-9, CARD-10, or CARD-11 gene has been introduced or disrupted. Diagnostic, screening and therapeutic methods utilizing compositions of the invention are also provided.

15 Claims, 29 Drawing Sheets

OTHER PUBLICATIONS

Bertin, John et al., "CARD9 is a Novel Caspase Recruitment Domain-containing Protein that Interacts with BCL10/CLAP and Activates NF-κB", *The Journal of Biological Chemistry*, vol. 275, No. 52 (Dec. 29, 2000) pp. 41082-41086.

Epstein, Franklin H., "Nuclear Factor-κB—A Pivotal Transcription factor in Chronic Inflammatory Diseases", *The New England Journal of Medicine*, vol. 336, No. 15 (Apr. 3, 1997) pp. 1066-1071.

Fanning, Alan S. et al., "Protein Modules as Organizers of Membrane Structure", *Current Opinion in Cell Biology*, 11:432-439 (1999).

Hofmann, et al., "The CARD Domain: A New Apoptotic Signalling Motif", *TiBS Trends in Biochemical Sciences*, vol. 22 (1997) pp. 155-156.

Imai, Yuzuru, et al., "The CED-4-Homologous Protein FLASH is Involved in fas-mediated Activation of Caspasse-8 during Apoptosis", *Nature*, vol. 398 (Apr. 29, 1999) pp. 777-784.

Koseki, Takeyoshi et al., "CIPER, A Novel NF κb-Activating Protein Containing a Caspase Recruitment Domain with Homology to *Herpesvirus*-2 Protein E10", *The Journal of Biological Chemistry*, vol. 274, No. 15 (Apr. 9, 1999) pp. 9955-9961.

Navab, Mohamad, et a., "Pathogenesis of Atherosclerosis", *The American Journal of Cardiology*, vol. 76 (Sep. 28, 1995) pp. 18C-23C.

Nicholson, D.W., "Caspase Structure, Proteolytic Substrates, and Function During Apoptotic Cell Death", *Cell Death and Differentiation*, vol. 6 (Apr. 29, 1999) pp. 1028-1042.

Srinivasula, Srinivasa M. et al., "CLAP, A Novel Caspase Recruitment Domain-Containing Protein in the Tumor Necrosis Factor Receptor Pathway, Regulates NF-κB Activation and Apoptosis", *The Journal of Biological Chemistry*, vol. 274, No. 25 (Jun. 18, 1999) pp. 17946-17954.

Thome, Margot et al., "Equine Herpesvirus-2 E10 Gene Product, but not its Cellular Homologue, Activates NF-κB Transcription Factor and c-Jun N-terminal Kinase", *The Journal of Biological Chemistry*, vol. 274, No. 15 (Apr. 9, 1999) pp. 9962-9968.

Wang, Cun-Yu et al., "NF-κB Antiapoptosis: Induction of TRAF1 and TRAF2 and c-IAP1 and c-IAP2 to Suppress Caspase-8 Activation", *Science*, vol. 281, No. 5383 (Sep. 11, 1998) pp. 1561-1756.

Yan, Minhong et al., "mE10, A Novel Caspase Recruitment Domain-Containing Proapoptotic Molecule", *The Journal of Biological Chemistry*, vol. 274, No. 15 (Apr. 9, 1999) pp. 10287-10292.

Pomerantz, Joel L., et al., "CARD11 mediates factor-specific activation of NF-κB by the T cell receptor complex," *The European Molecular Biology Organization Journal*, vol. 21, No. 19 (2002) pp. 5184-5194.

Bertin, John, et al., "CARD11 and CARD14 are novel caspase recruitment domain (CARD)/membrane-associated guanylate kinase (MAGUK) family members that interact with BCL10 and activate NF-κB," *The Journal of Biological Chemistry*, vol. 276, No. 15 (Apr. 13, 2001) pp. 11877-11882.

Srinivasula, Srinivasa M., et al., "CLAP, a novel caspase recruitment domain-containing protein in the tumor necrosis factor receptor pathway, regulates NF-κB activation and apoptosis," *The Journal of Biological Chemistry*, vol. 274, No. 25 (Jun. 18, 1999) pp. 17946-17954.

Medoff, Benjamin D., et al., "CARMA1 is critical for the development of allergic airway inflammation in a murine model of asthma," *The Journal of Immunology*, vol. 176 (2006) pp. 7272-7277.

Gaide O et al, FEBS Letters, 2001, V505, N1 (Sep. 7), p. 121-127.

Thome M et al, Journal of cell biology(United States)Mar. 5, 2001, 152 (5) p. 1115-22.

Reiger et al (Glossary of Genetics and Cytogenetics, Classical and Molecular, 4th Ed., Springer-Verlay, Berlin, 1976).

Bowie et al (Science, 1990, 257:1306-1310).

Lazar et al (Molecular and Cellular Biology, 1988, 8:1247-1252).

WO 2005/8473-A2 and MPSRCH search report, 2005, us-10-325-917-11.oligo.rag, p. 21).

Wilson I A et al, 1999, Current opinion in structural biology, 9 (6): p. 696-704.

Petry Renate et al, 2002, Journal of medicinal chemistry, 45 (5): p. 1026-34.

Willis et al, 1999, Cell 96: 35-45.

\* cited by examiner

```
CCACGCGTCCGAGCATCTCCACACTCCCAGAGGCTCGCTCCTGGAGTGCCCATAGCCCAGGCAGCATCCAGCTGGCAGG         79

M   S   D   Y   E   N   D   D   E   C   W    11
TGGCTCCCACAGGACCCTGAGCCTACAGAGGAC ATG TCA GAC TAT GAA AAT GAC GAC GAG TGC TGG            145

S   A   L   E   S   F   R   V   K   L   I   S   V   I   D   P   S   R   I   T           31
AGT GCC CTG GAG AGC TTC CGG GTG AAG CTA ATC TCT GTC ATT GAC CCC TCA CGA ATC ACA          205

P   Y   L   R   Q   C   K   V   L   N   P   D   D   E   E   Q   V   L   S   D           51
CCC TAT CTG CGC CAG TGC AAA GTC CTG AAC CCC GAT GAT GAG GAG CAG GTG CTC AGT GAC          265

P   N   L   V   I   R   K   R   K   V   G   V   L   L   D   I   L   Q   R   T           71
CCC AAC CTG GTC ATC CGC AAG CGG AAA GTG GGT GTG CTC CTG GAC ATC CTG CAG CGG ACA          325

G   H   K   G   Y   V   A   F   L   E   S   L   E   L   Y   Y   P   Q   L   Y           91
GGC CAC AAG GGC TAC GTG GCC TTT CTT GAG AGT CTG GAA CTC TAC TAC CCT CAG TTA TAC          385

R   K   V   T   G   K   E   P   A   R   V   F   S   M   I   I   D   A   S   G          111
AGG AAA GTC ACT GGC AAG GAG CCA GCG CGT GTC TTC TCC ATG ATC ATC GAC GCA TCA GGG          445

E   S   G   L   T   Q   L   L   M   T   E   V   M   K   L   Q   K   K   V   Q          131
GAG TCG GGC CTG ACG CAG CTG CTG ATG ACA GAG GTC ATG AAG CTG CAG AAG AAG GTT CAG          505

D   L   T   A   L   L   S   S   K   D   D   F   I   K   E   L   R   V   K   D          151
GAC CTG ACG GCC CTT CTG AGC TCC AAG GAT GAC TTC ATC AAG GAG CTG AGG GTA AAG GAC          565

S   L   R   K   H   Q   E   R   V   Q   R   L   K   E   E   C   E   L   S          171
AGC CTC CTG CGC AAG CAC CAG GAG CGG GTG CAG CGG CTC AAG GAG GAG TGT GAG CTG AGC          625

S   A   E   L   K   R   C   K   D   E   N   Y   D   L   A   M   R   L   A   H          191
AGT GCC GAG CTG AAG CGC TGC AAG GAT GAG AAC TAC GAC CTG GCC ATG CGC CTG GCT CAC          685

L   S   E   E   K   G   A   A   L   M   R   N   R   D   L   Q   L   E   V   D          211
CTG AGT GAA GAG AAG GGA GCA GCA CTC ATG CGG AAC CGT GAC CTG CAG CTT GAG GTG GAC          745

Q   L   R   H   S   L   M   K   A   E   D   D   C   K   V   E   R   K   H   T          231
CAG CTC ACG CAC AGC CTC ATG AAG GCA GAG GAT GAC TGC AAG GTG GAG CGC AAA CAC ACA          805

L   K   L   R   H   A   M   E   Q   R   P   S   Q   E   L   L   W   D   L   Q          251
CTG AAG CTC CGG CAC GCC ATG GAG CAG CGG CCT AGC CAG GAG CTG CTG TGG GAC CTG CAG          865

Q   E   R   D   L   L   Q   A   R   V   Q   E   L   E   V   S   V   Q   E   G          271
CAG GAG AGG GAC TTG TTG CAG GCC CGG GTG CAG GAG CTG GAG GTC TCC GTG CAG GAG GGT          925

K   L   H   R   N   S   P   Y   I   Q   V   L   E   E   D   W   P   Q   A   L          291
AAG CTA CAC AGG AAT AGC CCA TAC ATC CAG GTG CTG GAG GAG GAC TGG CGT CAG GCA CTG          985

Q   E   H   Q   E   Q   A   S   T   I   F   S   L   R   K   D   L   R   Q   A          311
CAG GAA CAC CAG GAG CAG GCC AGC ACC ATC TTC TCC CTA CGA AAG GAC CTC CGC CAG GCT         1045

E   A   L   R   T   R   C   M   E   E   K   E   M   F   E   L   Q   C   L   A          331
GAG GCC CTC CGG ACC CGG TGC ATG GAG GAA AAG GAG ATG TTC GAG CTG CAG TGC CTG GCC         1105

L   R   K   D   A   K   M   Y   K   D   R   I   E   A   I   L   Q   Q   M   E          351
TTG CGC AAG GAT GCC AAG ATG TAC AAG GAC CGG ATC GAG GCT ATC CTG CAG CAG ATG GAG         1165

E   V   S   I   E   R   D   Q   A   M   T   S   R   E   E   L   H   A   Q   C          371
GAA GTC TCC ATT GAG CGG GAC CAG GCT ATG ACC TCA AGG GAA GAG CTG CAT GCA CAG TGT         1225

A   Q   S   F   Q   D   K   D   K   L   R   K   Q   V   R   E   L   D   E   K          391
GCC CAA AGC TTT CAG GAC AAA GAT AAG CTG CGA AAG CAG GTT CGA GAA CTG GAT GAG AAG         1285

A   D   E   L   Q   L   Q   L   F   Q   T   E   S   R   L   L   A   A   E   G          411
GCC GAC GAG TTG CAG CTG CAG CTG TTC CAG ACC GAG AGC CGA TTA CTG GCC GCT GAG GGC         1345

R   L   K   Q   Q   Q   L   D   M   L   I   L   S   S   D   L   E   D   S   S          431
AGA CTC AAG CAG CAG CAA TTG GAC ATG CTC ATC CTG AGC TCT GAC TTG GAA GAC AGT TCC         1405
```

FIG. 1A

```
      P   R   N   S   Q   E   L   S   L   P   Q   D   L   E   E   D   A   Q   L   S    451
      CCC AGG AAC TCC CAG GAG CTT TCA CTG CCT CAG GAC CTG GAG GAG GAT GCC CAG CTC TCA  1465

D   K   G   V   L   A   D   R   E   S   P   E   Q   P   F   V   V   L   N   K    471
      GAC AAA GGT GTC CTG GCA GAC AGG GAG AGC CCA GAG CAG CCC TTC GTG GTT CTG AAC AAG  1525

K   H   L   S   Q   T   H   D   T   V   P   S   E   P   E   P   E   K   E    491
      AAG CAT CTT TCG CAG ACC CAT GAC ACG GTG CCC AGC GAG CCC CCG GAG AAG GAG         1585

R   R   L   K   E   S   F   E   N   Y   R   R   K   R   A   L   R   K   M    511
      CGG CGC CTC AAG GAG AGC TTC GAG AAC TAC CGC AGG AAG CGG GCG CTC CGC AAG ATG     1645

Q   N   S   W   R   Q   G   E   G   D   H   G   N   T   G   S   D   N   T    531
      CAG AAC AGC TGG CGA CAG GGA GAA GGG GAT CAC GGG AAT ACG ACA GGC AGC GAC AAC ACC 1705

D   T   E   G   S   *                                                          537
      GAC ACC GAG GGC TCC TAG                                                        1723

AGGACCCACGCCGAGGCTGCTGTGTAATTGTGAAGGGATGCTGCGGGTTTTTTACTGTACGCTACACATACGTT     1802

GTACAAGTATTAGAAAAAAAAATGCAGCCTAATAAAATGACCCTCTGAGCTGAAAAAAAAAAAAAAAAAAAAAA     1879
```

FIG. 1B

CARD: domain 1 of 1, from 7 to 98: score 4.3, E = 0.12
        *->aeddrrllrknrlellgeltlsglLdhLleknvLteeeeEkikaknt
            ++    ++l+   r+ l++ + +s +   +L++ +vL++++eE + + ++
   rat   7    DDECWSALESFRVKLISVIDPSRITPYLRQCKVLNPDDEEQVLSDPN   53 trr..dkareLiDsvqkkGnqAfqiFlqaLretdqelladlllde<-*
            +++k+ +L+D++q+ G + + +Fl++L+    ++l+ ++  +e
   rat   54  LVIrkRKVGVLLDILQRTGHKGYVAFLESLELYYPQLYRKVTGKE    98

FIG. 4A

IGPS: domain 1 of 1, from 197 to 213: score 6.0, E = 0.99
        *->GESLMraeDvraaireL<-*
           G +LMr+ D+++ +++L
   rat   197    GAALMRNRDLQLEVDQL    213

FIG. 4B cys_rich_FGFR: domain 1 of 1, from 285 to 338: score -11.7, E = 5.2
        *->peCkqevlrrqqesaerDyrLdpvLykaCksdIekyCaeipnkesse
           ++ +q++++++q+ ++ + ++L    L+ a  + + + C e+
   rat   285   EDWRQALQEHQEQAS-TIFSLRKDLRQA--EALRTRCMEEK------   322 daaevgegqvleCLmenkddee<-*
           e    l+CL   kd +
   rat   323  ------EMFELQCLALRKDAKM    338

FIG. 4C

```
ACTATAGGGAGTCGACCCACGCGTCCGGCTCCTCCCTCCCTGCAGCCCCGGGCAGCATCTCCCAGAGGCTCCGCGGCCC          79

M    S    D      3
AGGCTCCTGGTGTGTCTGCAGTGCAGGTGGCTCCTGGAAGACCCTCAGCCTGCCTGCTGAGGCC ATG  TCG  GAC           152

Y    E    N    D    D    E    C    W    N    V    L    E    G    F    R    V    T    L    T    S    23
TAC  GAG  AAC  GAT  GAC  GAG  TGC  TGG  AAC  GTC  CTG  GAG  GGC  TTC  CGG  GTG  ACG  CTC  ACC  TCG   212

V    I    D    P    S    R    I    T    P    Y    L    R    Q    C    K    V    L    N    P    D    43
GTC  ATC  GAC  CCC  TCA  CGC  ATC  ACA  CCT  TAC  CTG  CGG  CAG  TGC  AAG  GTC  CTG  AAC  CCT  GAT   272

D    E    E    Q    V    L    S    D    P    N    L    V    I    R    K    R    K    V    G    V    63
GAT  GAG  GAG  CAG  GTG  CTC  AGC  GAC  CCC  AAC  CTG  GTC  ATC  CGC  AAA  CGG  AAA  GTG  GGT  GTG   332

L    L    D    I    L    Q    R    T    G    H    K    G    Y    V    A    F    L    E    S    L    83
CTC  CTG  GAC  ATC  CTG  CAG  CGG  ACC  GGC  CAC  AAG  GGC  TAC  GTG  GCC  TTC  CTC  GAG  AGC  CTG   392

E    L    Y    Y    P    Q    L    Y    K    K    V    T    G    K    E    P    A    R    V    F    103
GAG  CTC  TAC  TAC  CCG  CAG  CTG  TAC  AAG  AAG  GTC  ACA  GGC  AAG  GAG  CCA  GCC  CGC  GTC  TTC   452

S    M    I    I    D    A    S    G    E    S    G    L    T    Q    L    L    M    T    E    V    123
TCC  ATG  ATC  ATC  GAC  GCG  TCC  GGG  GAG  TCA  GGC  CTG  ACT  CAG  CTG  CTG  ATG  ACT  GAG  GTC   512

M    K    L    Q    K    K    V    Q    D    L    T    A    L    L    S    S    K    D    D    F    143
ATG  AAG  CTG  CAG  AAG  AAG  GTG  CAG  GAC  CTG  ACC  GCG  CTG  CTG  AGC  TCC  AAA  GAT  GAC  TTC   572

I    K    E    L    R    V    K    D    S    L    L    R    K    H    Q    E    R    V    Q    R    163
ATC  AAG  GAG  CTG  CGG  GTG  AAG  GAC  AGC  CTG  CTG  CGC  AAG  CAC  CAG  GAG  CGT  GTG  CAG  AGG   632

L    K    E    E    C    E    A    G    S    R    E    L    K    R    C    K    E    E    N    Y    183
CTC  AAG  GAG  GAG  TGC  GAG  GCC  GGC  AGC  CGC  GAG  CTC  AAG  CGC  TGC  AAG  GAG  GAG  AAC  TAC   692

D    L    A    M    R    L    A    H    Q    S    E    E    K    G    A    A    L    M    R    N    203
GAC  CTG  GCC  ATG  CGC  CTG  GCG  CAC  CAG  AGT  GAG  GAG  AAG  GGC  GCC  GCG  CTC  ATG  CGG  AAC   752

R    D    L    Q    L    E    I    D    Q    L    K    H    S    L    M    K    A    E    D    D    223
CGT  GAC  CTG  CAG  CTG  GAG  ATT  GAC  CAG  CTC  AAG  CAC  AGC  CTC  ATG  AAG  GCC  GAG  GAC  GAC   812

C    K    V    E    R    K    H    T    L    K    L    R    H    A    M    E    Q    R    P    S    243
TGC  AAG  GTG  GAG  CGC  AAG  CAC  ACG  CTG  AAG  CTC  AGG  CAC  GCC  ATG  GAG  CAG  CGG  CCC  AGC   872

Q    E    L    L    W    E    L    Q    Q    E    K    A    L    L    Q    A    R    V    Q    E    263
CAG  GAG  CTG  CTG  TGG  GAG  CTG  CAG  CAG  GAG  AAG  GCC  CTG  CTC  CAG  GCC  CGG  GTG  CAG  GAG   932

L    E    A    S    V    Q    E    G    K    L    D    R    S    S    P    Y    I    Q    V    L    283
CTG  GAG  GCC  TCC  GTC  CAG  GAG  GGG  AAG  CTG  GAC  AGG  AGC  AGC  CCC  TAC  ATC  CAG  GTA  CTG   992

E    E    D    W    R    Q    A    L    R    D    H    Q    E    Q    A    N    T    I    F    S    303
GAG  GAG  GAC  TGG  CGG  CAG  GCG  CTG  CGG  GAC  CAC  CAG  GAG  CAG  GCC  AAC  ACC  ATC  TTC  TCC   1052

L    R    K    D    L    R    Q    G    E    A    R    R    L    R    C    M    E    E    K    E    323
CTG  CGC  AAG  GAC  CTC  CGC  CAG  GGC  GAG  GCC  CGA  CGC  CTC  CGG  TGC  ATG  GAG  GAG  AAG  GAG   1112

M    F    E    L    Q    C    L    A    L    R    K    D    S    K    M    Y    K    D    R    I    343
ATG  TTC  GAG  CTG  CAG  TGC  CTG  GCA  CTA  CGT  AAG  GAC  TCC  AAG  ATG  TAC  AAG  GAC  CGC  ATC   1172

E    A    I    L    L    Q    M    E    E    V    A    I    E    R    D    Q    A    I    A    T    363
GAG  GCC  ATC  CTG  CTG  CAG  ATG  GAG  GAG  GTC  GCC  ATT  GAG  CGG  GAC  CAG  GCC  ATA  GCC  ACG   1232

R    E    E    L    H    A    Q    H    A    R    G    L    Q    E    K    D    A    L    R    K    383
CGG  GAG  GAG  CTG  CAC  GCA  CAG  CAC  GCC  CGG  GGC  CTG  CAG  GAG  AAG  GAC  GCG  CTG  CGC  AAG   1292

Q    V    R    E    L    G    E    K    A    D    E    L    Q    L    Q    V    F    Q    C    E    403
CAG  GTG  CGG  GAG  CTG  GGC  GAG  AAG  GCG  GAT  GAG  CTG  CAG  CTG  CAG  GTG  TTC  CAG  TGT  GAG   1352

A    Q    L    L    A    V    E    G    R    L    R    R    Q    Q    L    E    T    L    V    L    423
GCG  CAG  CTA  CTG  GCC  GTG  GAG  GGC  AGG  CTC  AGG  CGG  CAG  CAG  CTG  GAG  ACG  CTC  GTC  CTG   1412
```

FIG. 5A

```
  S   S   D   L   E   D   G   S   P   R   R   S   Q   E   L   S   L   P   Q   D    443
AGC TCC GAC CTG GAA GAT GGC TCA CCC AGG AGG TCC CAG GAG CTC TCA CTC CCC CAG GAC   1472

L   E   D   T   Q   L   S   D   K   G   C   L   A   G   G   S   P   K   Q        463
CTG GAG GAC ACC CAG CTC TCA GAC AAA GGC TGC CTT GCC GGG AGC CCG AAA CAG           1532

P   F   A   A   L   H   Q   Q   E   Q   V   L   R   N   P   H   D   A   L   S    483
CCC TTT GCA GCT CTG CAC CAG CAG GAG CAG GTT TTG CGG AAC CCC CAT GAC GCA GGC CTG AGC 1592

S   G   E   P   P   E   K   R   R   L   K   E   S   F   E   N   Y   R           503
AGC GGG GAG CCG CCC GAG AAG CGG CGG CTC AAA GAG AGT TTT GAG AAC TAC CGC           1652

R   K   R   A   L   R   K   M   Q   K   G   W   R   Q   G   E   D   R   E        523
AGG AAG CGC GCC CTC AGG AAG ATG CAG AAA GGA TGG CGG CAG GGG GAG GAC CGG GAG       1712

N   T   T   G   S   D   N   T   T   D   T   E   G   S   *                        537
AAC ACC ACG GGC AGC GAC AAC ACC ACT GAC ACT GAG GGC TCC TAG                       1754

CCGCAGCAGCGCCAGGCCCCGACCAGGGCACACCCCACCCGGGGTGCCGACGCCTGGGGCGCA                   1833

GACTTCCCGAGCCGTCGCTGACTTGGCCTGAACGAGGAATCTGGTGCCCTGAAAGGCCCAGCCGGACTGCCGGGCAT   1912

TGGGGGCCGTTTGTTAAGCGGCACTCATTTTGCGGAGGCCATGCGGTGCTCACCCCCATGCACACGCCATCTGTGT   1991

AACTTCAGGATCTGTTCTGTTTCACCATGTAACACACAATACATGCATGCACTGTATTAGTGTTAAGAAAACACAGCTG 2070

CGTAAATAAACAGCACGGGTGACCCGCA                                                      2098
```

FIG. 5B

```
CARD: domain 1 of 1, from 7 to 98: score -0.1, E = 0.35
            *->aeddrrllrknrlellgeltlsglLdhLleknvLteeeeEkikaknt
               ++    + l+   r+ l + + +s +   +L++ +vL++++eE + + ++
   hCARD9    7     DDECWNVLEGFRVTLTSVIDPSRITPYLRQCKVLNPDDEEQVLSDPN  53 trr..dkareLiDsvqkkGnqAfqiFlqaLretdqelladlllde<-*
               +++k+ +L+D++q+ G + + +Fl++L+   ++l++++  +e
   hCARD9   54   LVIrkRKVGVLLDILQRTGHKGYVAFLESLELYYPQLYKKVTGKE     98
```

FIG. 8A

```
IGPS: domain 1 of 1, from 197 to 213: score 6.4, E = 0.78
           *->GEsLMraeDvraaireL<-*
             G +LMr+ D+++ i++L
   hCARD9  197  GAALMRNRDLQLEIDQL    213
```

FIG. 8B

```
cys_rich_FGFR: domain 1 of 1, from 285 to 338: score -12.1, E = 5.7
            *->peCkqevlrrqqesaerDyrLdpvLykaCksdIeky.Caeipnkess
               ++  +q+++ +q+ ++ + ++L    L+     ++++ +++C e+
   hCARD9  285    EDWRQALRDHQEQAN-TIFSLRKDLR---QGEARRLrCMEEK-----  322 edaaevgegqvleCLmenkddee<-*
              e    l+CL   kd++
   hCARD9  323   -------EMFELQCLALRKDSKM   338
```

FIG. 8C

```
hCARD-9   1 MSDYENDDECWNVLEGFRVTLTSVIDPSRITPYLRQCKVLNPDDEEQVLS  50
            |||||||||||. || |||  | ||||||||||||||||||||||||||||
rCARD-9   1 MSDYENDDECWSALESFRVKLISVIDPSRITPYLRQCKVLNPDDEEQVLS  50

51 DPNLVIRKRKVGVLLDILQRTGHKGYVAFLESLELYYPQLYKKVTGKEPA 100
            |||||||||||||||||||||||||||||||||||||||||:|||||||
         51 DPNLVIRKRKVGVLLDILQRTGHKGYVAFLESLELYYPQLYRKVTGKEPA 100

101 RVFSMIIDASGESGLTQLLMTEVMKLQKKVQDLTALLSSKDDFIKELRVK 150
            |||||||||||||||||||||||||||||||||||||||||||||||||
        101 RVFSMIIDASGESGLTQLLMTEVMKLQKKVQDLTALLSSKDDFIKELRVK 150

151 DSLLRKHQERVQRLKEECEAGSRELKRCKEENYDLAMRLAHQSEEKGAAL 200
            |||||||||||||||||||||  |||||||:|||||||||| ||||||||
        151 DSLLRKHQERVQRLKEECELSSAELKRCKDENYDLAMRLAHLSEEKGAAL 200

201 MRNRDLQLEIDQLKHSLMKAEDDCKVERKHTLKLRHAMEQRPSQELLWEL 250
            ||||||||:|||:||||||||||||||||||||||||||||||||||:|
        201 MRNRDLQLEVDQLRHSLMKAEDDCKVERKHTLKLRHAMEQRPSQELLWDL 250

251 QQEKALLQARVQELEASVQEGKLDRSSPYIQVLEEDWRQALRDHQEQANT 300
            |||: ||||||||| |||||| |-|||||||||||||||..:|||||.|
        251 QQERDLLQARVQELEVSVQEGKLHRNSPYIQVLEEDWRQALQEHQEQAST 300

301 IFSLRKDLRQGEARRLRCMEEKEMFELQCLALRKDSKMYKDRIEAILLQM 350
            ||||||||| ||  | |||||||||||||||||||.|||||||||||.||
        301 IFSLRKDLRQAEAALRTCMEEKEMFELQCLALRKDAKMYKDRIEAILQQM 350

351 EEVAIERDQAIATREELHAQHARGLQEKDALRKQVRELGEKADELQLQVF 400
            |||.||||||. .|||||||| ||.   |:|| |||||||| ||||||||-|
        351 EEVSIERDQAMTSREELHAQCAQSFQDKDKLRKQVRELDEKADELQLQLF 400

401 QCEAQLLAVEGRLRRQQLETLVLSSDLEDGSPRRSQELSLPQDL.EDTQL 449
            | |..||| ||||:.|||: |:|||||||| ||||||||||||||| || ||
        401 QTESRLLAAEGRLKQQQLDMLILSSDLEDSSPRNSQELSLPQDLEEDAQL 450

450 SDKGCLAGGGSPKQPFAALHQEQVLRNPHDAGLSSGEPPEKERRRLKESF 499
            |||| ||  ||-|||  |... | ||  || |||||||||||||
        451 SDKGVLADRESPEQPFVVLNKKH.LSQTHDTVPSSSEPPEKERRRLKESF 499

500 ENYRRKRALRKMQKGWRQGEEDRENTTGSDNTDTEGS 536
            |||||||||||| ||||| | |||||||||||||||
        500 ENYRRKRALRKMQNSWRQGEGDHGNTTGSDNTDTEGS 536
```

FIG. 9

```
                                              M   P   G   R   A   E   A   G   E      9
CCCCGTGCGCCTCTTGCCCGCAGACCCTGAGGACACGGCC     ATG CCG GGC CGG GCG GAG GCG GGG GAG     67

A   E   E   E   A   G   A   G   S   G   S   E   A   E   E   D   A   L   W   E       29
GCC GAG GAG GAG GCC GGG GCC GGC TCG GGG TCT GAG GCG GAG GAG GAC GCG CTG TGG GAG     127

R   I   E   G   V   R   H   R   L   A   R   A   L   N   P   A   K   L   T   P       49
CGA ATC GAG GGC GTC CGG CAT CGG CTG GCT CGC GCC CTG AAC CCG GCC AAG CTC ACG CCG     187

Y   L   R   Q   C   R   V   I   D   E   Q   D   E   E   E   V   L   S   T   Y       69
TAT CTG CGC CAG TGC CGG GTC ATC GAC GAG CAG GAC GAG GAG GAG GTG CTG AGC ACC TAC     247

R   F   P   C   R   V   N   R   T   G   R   L   M   D   I   L   R   C   R   G       89
CGC TTC CCG TGC CGC GTC AAC CGC ACC GGG CGC CTG ATG GAC ATC TTG CGC TGC CGT GGC     307

K   R   G   Y   E   A   F   L   E   A   L   E   F   Y   Y   P   E   H   F   T      109
AAG AGG GGC TAT GAG GCC TTC CTG GAA GCC CTG GAG TTC TAC TAC CCC GAA CAC TTC ACG     367

L   L   T   G   Q   E   P   A   Q   R   C   S   M   I   L   D   E   E   G   P      129
CTG CTC ACG GGC CAG GAA CCC GCC CAG CGC TGC TCC ATG ATC CTC GAT GAG GAG GGG CCT     427

E   G   L   T   Q   F   L   M   T   E   V   R   R   L   R   E   A   R   K   S      149
GAG GGC CTG ACC CAA TTC TTG ATG ACA GAG GTG CGA CGG CTG CGG GAA GCT CGC AAG AGC     487

Q   L   Q   R   E   Q   Q   L   Q   A   R   G   R   V   L   E   E   E   R   A      169
CAG CTG CAG CGG GAG CAG CAA CTG CAG GCC CGG GGC CGG GTG CTC GAG GAG GAG CGG GCA     547

G   L   E   Q   R   L   R   D   Q   Q   Q   A   Q   E   R   C   Q   R   L   R      189
GGG CTG GAG CAG CGG CTG CGG GAC CAG CAG CAG GCT CAG GAG CGC TGT CAA CGG CTG CGG     607

E   D   W   E   A   G   S   L   E   L   L   R   L   K   D   E   N   Y   M   I      209
GAG GAC TGG GAG GCG GGC AGC CTG GAG CTG CTG CGG CTC AAG GAT GAG AAC TAC ATG ATC     667

A   M   R   L   A   Q   L   S   E   E   K   N   S   A   V   L   R   S   R   D      229
GCC ATG CGC CTG GCA CAG CTC AGT GAG GAG AAG AAC TCG GCT GTA CTT CGC AGC CGT GAC     727

L   Q   L   A   V   D   Q   L   K   L   K   V   S   R   L   E   E   E   C   A      249
CTG CAG CTG GCG GTG GAT CAG CTC AAG CTC AAA GTG AGT CGG CTG GAG GAA GAG TGT GCA     787

L   L   R   R   A   R   G   P   P   P   G   A   E   E   K   E   K   E   K   E      269
CTG CTT CGA AGG GCC AGG GGC CCG CCC CCT GGG GCA GAG GAG AAG GAG AAG GAG AAG GAG     847

K   E   K   E   P   D   N   V   D   L   V   S   E   L   R   A   E   N   Q   Q      289
AAG GAG AAG GAG CCA GAC AAT GTG GAC CTT GTC TCT GAG CTG CGT GCT GAG AAC CAG CAG     907

L   T   A   S   L   R   E   L   Q   E   G   L   Q   Q   E   A   S   R   P   G      309
CTG ACG GCG TCA CTG CGG GAG TTG CAG GAG GGC CTG CAG CAG GAG GCG AGC CGG CCG GGG     967

A   P   G   S   E   R   I   L   L   D   I   L   E   H   D   W   R   E   A   Q      329
GCC CCG GGC TCC GAG CGC ATC CTG CTG GAC ATC CTA GAG CAT GAC TGG CGG GAG GCG CAG    1027

D   S   R   Q   E   L   C   Q   K   L   H   A   V   Q   G   E   L   Q   W   A      349
GAC AGC AGG CAG GAG CTG TGC CAG AAG CTG CAT GCC GTG CAG GGG GAG CTG CAG TGG GCC    1087

E   E   L   R   D   Q   Y   L   Q   E   M   E   D   L   R   L   K   H   R   T      369
GAG GAG CTG CGC GAC CAG TAC CTG CAG GAG ATG GAA GAC CTG CGG CTC AAG CAC CGC ACG    1147

L   Q   K   D   C   D   L   Y   K   H   R   M   A   T   V   L   A   Q   L   E      389
CTG CAG AAG GAC TGT GAC CTG TAC AAG CAC CGC ATG GCC ACT GTC CTG GCC CAA CTG GAG    1207

E   I   E   K   E   R   D   Q   A   I   Q   S   R   D   R   I   Q   L   Q   Y      409
GAG ATT GAG AAG GAG CGA GAC CAG GCC ATC CAG AGC CGT GAC CGG ATC CAG TTG CAG TAC    1267

S   Q   S   L   I   E   K   D   Q   Y   R   K   Q   V   R   G   L   E   A   E      429
TCA CAG AGC CTC ATC GAG AAG GAC CAG TAC CGC AAG CAG GTG CGG GGC CTG GAG GCG GAG    1327

R   D   E   L   L   T   T   L   T   S   L   E   G   T   K   A   L   L   E   Y      449
CGG GAT GAG CTG CTG ACA ACG CTC ACC AGC CTG GAG GGC ACC AAG GCT CTG CTG GAG TAT    1387
```

FIG. 10A

```
  Q   L   Q   R   A   Q   G   G   T   C   L   K   A   C   A   S   S   H   S   L   469
CAG CTG CAG CGG GCC CAG GGT GGC ACC TGC CTC AAG GCC TGT GCC TCC TCC CAT TCC CTG  1447

C   S   N   L   S   S   T   W   S   L   S   E   F   P   S   P   L   G   G   P   489
TGC TCC AAC CTC AGC AGC ACT TGG AGC CTG AGC GAG TTC CCC TCC CCT CTG GGA GGC CCA  1507

E   A   T   G   E   A   A   V   M   G   G   P   E   P   H   N   S   E   E   A   509
GAA GCA ACT GGG GAG GCA GCT GTC ATG GGG GGA CCT GAG CCT CAC AAC TCG GAG GAA GCC  1567

T   D   S   E   K   E   I   N   R   L   S   I   L   P   F   P   P   S   A   G   529
ACA GAC AGT GAA AAG GAG ATC AAT CGG CTC TCC ATC CTG CCC TTC CCC CCC AGT GCC GGC  1627

S   I   L   R   R   Q   R   E   E   D   P   A   P   P   K   R   S   F   S   S   549
TCC ATC CTC CGC CGG CAG CGT GAG GAA GAC CCC GCA CCC CCT AAG AGA TCC TTC AGC AGC  1687

M   S   D   I   T   G   S   V   T   L   K   P   W   S   P   G   L   S   S   S   569
ATG TCA GAC ATC ACA GGG AGT GTG ACA CTT AAG CCC TGG TCC CCT GGC CTC TCT TCG TCC  1747

S   S   S   D   S   V   W   P   L   G   K   P   E   G   L   L   A   R   G   C   589
TCA TCC TCT GAC AGC GTG TGG CCT TTG GGA AAG CCG GAA GGC CTC CTG GCT CGG GGC TGT  1807

G   L   D   F   L   N   R   S   L   A   I   R   V   S   G   R   S   P   P   G   609
GGC CTG GAC TTC CTC AAC AGG TCT CTG GCT ATT CGG GTG TCT GGC CGG AGC CCC CCA GGG  1867

G   P   E   P   Q   D   K   G   P   D   G   L   S   F   Y   G   D   R   W   S   629
GGC CCA GAG CCG CAG GAC AAG GGA CCA GAT GGA CTG TCG TTT TAT GGG GAC AGA TGG TCT  1927

G   A   V   V   R   R   V   L   S   G   P   G   S   A   R   M   E   P   R   E   649
GGG GCT GTG GTG CGC AGG GTG CTG TCT GGG CCT GGG TCC GCC AGG ATG GAA CCA AGA GAG  1987

Q   R   V   E   A   A   G   L   E   G   A   C   L   E   A   E   A   Q   Q   R   669
CAA AGG GTG GAA GCT GCT GGT CTG GAG GGG GCG TGC CTG GAA GCC GAG GCC CAG CAG AGA  2047

T   L   L   W   N   Q   G   S   T   L   P   S   L   M   D   S   K   A   C   Q   689
ACC TTG CTC TGG AAT CAG GGG TCC ACA CTC CCC TCC CTG ATG GAC TCG AAG GCC TGC CAG  2107

S   F   H   E   A   L   E   A   W   A   K   G   P   G   A   E   P   F   Y   I   709
TCC TTC CAC GAG GCC CTA GAA GCC TGG GCA AAG GGA CCA GGT GCC GAG CCC TTC TAC ATT  2167

R   A   N   L   T   L   P   E   R   A   D   P   H   A   L   C   V   K   A   Q   729
CGT GCC AAC CTC ACC TTG CCT GAG AGG GCA GAT CCC CAT GCC CTT TGC GTG AAA GCC CAA  2227

E   I   L   R   L   V   D   S   A   Y   K   R   R   Q   E   W   F   C   T   R   749
GAG ATC CTT CGA CTG GTG GAC TCG GCA TAC AAG CGG AGG CAG GAA TGG TTC TGC ACC CGG  2287

V   D   P   L   T   L   R   D   L   D   R   G   T   V   P   N   Y   Q   R   A   769
GTT GAC CCC CTC ACT CTG CGG GAC CTG GAC CGG GGC ACC GTG CCC AAT TAT CAG AGA GCC  2347

Q   Q   L   L   E   V   Q   E   K   C   L   P   S   S   R   H   G   P   R   789
CAG CAG CTC CTA GAA GTT CAG GAG AAA TGC CTG CCC TCC AGC CGG CAC CGA GGC CCC CGC  2407

S   N   L   K   K   R   A   L   D   Q   L   R   L   V   R   P   K   P   V   G   809
AGT AAT CTG AAG AAG AGA GCC CTG GAC CAG CTG CGG CTG GTG AGG CCC AAG CCC GTG GGG  2467

A   P   A   G   D   S   P   D   Q   L   L   L   E   P   C   A   E   P   E   R   829
GCG CCT GCA GGG GAC TCC CCG GAT CAG CTG CTG CTG GAG CCC TGT GCA GAG CCG GAG CGG  2527

S   L   R   P   Y   S   L   V   R   P   L   V   S   A   L   R   P   V   V   849
AGC CTC AGA CCC TAC AGT TTG GTG CGG CCG CTA CTG GTG TCT GCC CTG CGG CCC GTG GTG  2587

L   L   P   E   C   L   A   P   R   L   I   R   N   L   L   D   L   P   S   S   869
CTG TTG CCT GAG TGC CTG GCG CCC CGG CTC ATC CGT AAC CTG CTA GAC CTG CCC AGC TCC  2647

R   L   D   F   Q   V   C   P   A   E   S   L   S   G   E   E   L   C   P   S   889
CGG CTG GAC TTC CAA GTG TGC CCA GCG GAA AGC CTC TCT GGG GAG GAA CTG TGC CCA TCC  2707

S   A   P   G   A   P   K   A   Q   P   A   T   P   G   L   G   S   R   I   R   909
TCA GCG CCT GGA GCC CCC AAG GCT CAG CCT GCC ACC CCT GGG CTA GGC AGC AGG ATC CGG  2767

```
         GCC ATC CAG GAG TCT GTT GGG AAG AAG CAC TGC CTG CTG GAG CTG GGT GCT CGG GGT GTG  2827
 R   E   R   V   Q   N   E   I   Y   P   I   V   I   H   V   E   V   T   E   K    949
CGG GAG CGG GTG CAG AAC GAG ATC TAC CCC ATC GTC ATC CAC GTG GAG GTG ACT GAG AAG  2887
 N   V   R   E   V   R   G   L   L   G   R   P   G   W   R   D   S   E   L   L    969
AAT GTC CGG GAA GTC AGG GGT CTG CTG GGC CGG CCG GGC TGG CGG GAC TCA GAG CTG CTG  2947
 R   Q   C   R   G   S   E   Q   V   L   W   G   L   P   C   S   W   V   Q   V    989
CGG CAG TGC CGT GGC TCA GAG CAG GTG CTC TGG GGG CTG CCC TGC TCC TGG GTG CAG GTG  3007
 P   A   H   E   W   G   H   A   E   E   L   A   K   V   V   R   G   R   I   L   1009
CCC GCC CAT GAG TGG GGA CAC GCA GAG GAG CTG GCC AAG GTG GTG CGC GGC CGC ATC CTG  3067
 Q   E   Q   A   R   L   V   W   V   E   C   G   S   S   R   G   C   P   S   S   1029
CAG GAG CAG GCC CGC CTC GTG TGG GTG GAG TGC GGC AGC AGC AGA GGC TGC CCC AGC AGC  3127
 S   E   A   *                                                                     1033
AGT GAG GCC TGA                                                                    3139
GGCTCATCTGATACCTGCACCTTCTCCCCAAGCCAGCGTGGACCCTGGTGTCTATGGTGAAGCTGGGCCCTCCCACCCT  3218
GAGCCTTCCTAGACCCTTGGACTCTCAGATGCAGGGCCCTTGGCTCTGGCCTCTCACCCCCAAGGCTGTCTCTGGCCCT  3297
GCCGAGCCTATGGGAGTCCGGGACAGAGTGCCCACTCCCCTCTACTTGCTGCTCTGGGCCTCCCCACCTTTCCTGGGG   3376
TCTCCACATTCCCACTAGTGGGTCTTATGTGTGTCTGTGTCTTCTCCTTAAACACTCGCCCTGGAGTCTGTTCTCACAC  3455
CTGTGCGCAGGTTTGCACACTCAAGTTCTCATGGGCAGGCTCAGGTCTGTCCCGCTGCCCTGGGCACGAGGTCTCCTGA  3534
GGACCTGGGCCTGTTCTGCTCCTAGGAGACCTGAGCCCGTTACCGCGTGACTCCCACCATCCAGCTCGCGCTCCTCGTG  3613
GATTCAGCCATGCATGGACTGGGGTGTTCCCTGGCCCATGGTCACCTGTGCCCCTCGTGTCTCCTCACATGGGTGTCTG  3692
TGGTTCTCTCCTGTGTAAATGTCACGCCCCACCCCTGTTTCATGTGGGCACTAACACGTGTGCGTTCCTGGCGGGCACA  3771
CACAGGACCGTGCCTCACAGGGCCCACTCCCTGCCTATGCCTCCCTCTTGGGGGGCCGAGGAGGGCGGCTGCTCTGTCA  3850
TGAGAATGTACGGCCCGTGGATGATTAACGGGCCTTTTTCACTTAGAAGCTGCACATTATGGAGCATTAAACACTTTTG  3929
TCATAAAAAAAAAAAAAAAA                                                               3949
```

FIG. 10C

CARD: domain 1 of 1, from 24 to 115: score -12.0, E = 6.6
    *->aeddrrllrknrleligeltlsglldhlleknvLteeeeEki.kakn
       ++  ++  ++  r +l+  l +  +l  +L++ +v+ e++eE++ +++
hCARD10   24  EDALWERIEGVRHRLARALNPAKLTPYLRQCRVIDEQDEEV1STYR   70 ttrr.dkareLiDsvqkkGnqAfqiFlqaLretdqellad1lide<-*
              r  ++  L D+++  +G    +++Fl+aL+   +e+   l   +e
hCARD10   71  FPCRvNRTGRLMDILRCRGKRGYEAFLEALEFYYPEHFTLLTGQE  115

FIG. 13A

Tropomyosin: domain 1 of 1, from 366 to 398: score 3.1, E = 3.6
    *->KKiqqteeeldkaeErlekaqreLeeeekkreeA<-*
       K ++++ + d ++ r++ +  +Lee ek r +A
hCARD10  366  -KHRTLQKDCDLYKHRMATVLAQLEEIEKERDQA  398

FIG. 13B

```
CCACGCGTCCGCCGCGCCGCCCGCAGCCCCCTCCCGGCCCTGCAGCCCCTGGGCGGGCGGCGCCCCTCGGAGGACGGCT    79

CCGGGCCCGGGGGGACGGAGGGCCTGGTCGCCTGGAGGAAGCCGGAGGCCTGCGTGGAGGAGGCGCCCCGCGCAGCTGG   158

CTGGCGGAGCATGAGCGCCCCAGATCCCAAGCACTGCAAGTCCAGATGCAACGGGAGCCTGGCTCAAGGGACGACAAGA   237

TCCAGCCGGAAAGTGTAGAAGTCACACCCCAATGGCGGGATAGCAGCCCCTGTGTGTGAGCACCCCTCCATGCCAGGAG   316
```

```
                M   D   D   Y   M   E   T   L   K   D   E   E   D   A   L   W   E    17
GAGGGCCAGAG ATG GAT GAC TAC ATG GAG ACG CTG AAG GAT GAA GAG GAC GCC TTG TGG GAG    378

N   V   E   C   N   R   H   M   L   S   R   Y   I   N   P   A   K   L   T   P     37
AAT GTG GAG TGT AAC CGG CAC ATG CTC AGC CGC TAT ATC AAC CCT GCC AAG CTC ACG CCC    438

Y   L   R   Q   C   K   V   I   D   E   Q   D   E   D   E   V   L   N   A   P     57
TAC CTG CGT CAG TGT AAG GTC ATT GAT GAG CAG GAT GAA GAT GAA GTG CTT AAT GCC CCT    498

M   L   P   S   K   I   N   R   A   G   R   L   L   D   I   L   H   T   K   G     77
ATG CTG CCA TCC AAG ATC AAC CGA GCA GGC CGG CTG TTG GAC ATT CTA CAT ACC AAG GGG    558

Q   R   G   Y   V   V   F   L   E   S   L   E   F   Y   Y   P   E   L   Y   K     97
CAA AGG GGC TAT GTG GTC TTC TTG GAG AGC CTA GAA TTT TAT TAC CCA GAA CTG TAC AAA    618

L   V   T   G   K   E   P   T   R   R   F   S   T   I   V   V   E   E   G   H    117
CTG GTG ACT GGG AAA GAG CCC ACT CGG AGA TTC TCC ACC ATT GTG GTG GAG GAA GGC CAC    678

E   G   L   T   H   F   L   M   N   E   V   I   K   L   Q   Q   Q   M   K   A    137
GAG GGC CTC ACG CAC TTC CTG ATG AAC GAG GTC ATC AAG CTG CAG CAG CAG ATG AAG GCC    738

K   D   L   Q   R   C   E   L   L   A   R   L   R   Q   L   E   D   E   K   K    157
AAG GAC CTG CAA CGC TGC GAG CTG CTG GCC AGG TTG CGG CAG CTG GAG GAT GAG AAG AAG    798

Q   M   T   L   T   R   V   E   L   L   T   F   Q   E   R   Y   Y   K   M   K    177
CAG ATG ACG CTG ACG CGC GTG GAG CTG CTA ACC TTC CAG GAG CGG TAC TAC AAG ATG AAG    858

E   E   R   D   S   Y   N   D   E   L   V   K   V   K   D   D   N   Y   N   L    197
GAA GAG CGG GAC AGC TAC AAT GAC GAG CTG GTC AAG GTG AAG GAC GAC AAC TAC AAC TTA    918

A   M   R   Y   A   Q   L   S   E   E   K   N   M   A   V   M   R   S   R   D    217
GCC ATG CGC TAC GCA CAG CTC AGT GAG GAG AAG AAC ATG GCG GTC ATG AGG AGC CGA GAC    978

L   Q   L   E   I   D   Q   L   K   H   R   L   N   K   M   E   E   E   C   K    237
CTC CAA CTC GAG ATC GAT CAG CTA AAG CAC CGG TTG AAT AAG ATG GAG GAG GAA TGT AAG   1038

L   E   R   N   Q   S   L   K   L   K   N   D   I   E   N   R   P   K   K   E    257
CTG GAG AGA AAT CAG TCT CTA AAA CTG AAG AAT GAC ATT GAA AAT CGG CCC AAG AAG GAG   1098

Q   V   L   E   L   E   R   E   N   E   M   L   K   T   K   N   Q   E   L   Q    277
CAG GTT CTG GAA CTG GAG CGG GAG AAT GAA ATG CTG AAG ACC AAA AAC CAG GAG CTG CAG   1158

S   I   I   Q   A   G   K   R   S   L   P   D   S   D   K   A   I   L   D   I    297
TCC ATC ATC CAG GCC GGG AAG CGC AGC CTG CCA GAC TCA GAC AAG GCC ATC CTG GAC ATC   1218

L   E   H   D   R   K   E   A   L   E   D   R   Q   E   L   V   N   R   I   Y    317
TTG GAA CAC GAC CGC AAG GAG GCC CTG GAG GAC AGG CAG GAG CTG GTC AAC AGG ATC TAC   1278

N   L   Q   E   E   A   R   Q   A   E   E   L   R   D   K   Y   L   E   E   K    337
AAC CTG CAG GAG GAG GCC CGC CAG GCA GAG GAG CTG CGA GAC AAG TAC CTG GAG GAG AAG   1338

E   D   L   E   L   K   C   S   T   L   G   K   D   C   E   M   Y   K   H   R    357
GAG GAC CTG GAG CTC AAG TGC TCG ACC CTG GGA AAG GAC TGT GAA ATG TAC AAG CAC CGC   1398

M   N   T   V   M   L   Q   L   E   E   V   E   R   E   R   D   Q   A   F   H    377
ATG AAC ACG GTC ATG CTG CAG CTG GAG GAG GTG GAG CGG GAG CGG GAC CAG GCC TTC CAC   1458

S   R   D   E   A   Q   T   Q   Y   S   Q   C   L   I   E   K   D   K   Y   R    397
TCC CGA GAT GAA GCT CAG ACA CAG TAC TCG CAG TGC TTA ATC GAA AAG GAC AAG TAC AGG   1518
```

FIG. 14A

```
  K   Q   I   R   E   L   E   E   K   N   D   E   M   R   I   E   M   V   R   R   417
AAG CAG ATC CGC GAG CTG GAG GAG AAG AAC GAC GAG ATG AGG ATC GAG ATG GTG CGG CGG 1578

E   A   C   I   V   N   L   E   S   K   L   R   R   L   S   K   D   S   N   N   437
GAG GCC TGC ATC GTC AAC CTG GAG AGC AAG CTG CGG CGC CTC TCC AAG GAC AGC AAC AAC 1638

L   D   Q   S   L   P   R   N   L   P   V   T   I   I   S   Q   D   F   G   D   457
CTG GAC CAG AGT CTG CCC AGG AAC CTG CCA GTA ACC ATC ATC TCT CAG GAC TTT GGG GAT 1698

A   S   P   R   T   N   G   Q   E   A   D   D   S   S   T   S   E   E   S   P   477
GCC AGC CCC AGG ACC AAT GGT CAA GAA GCT GAC GAT TCT TCC ACC TCG GAG GAG TCA CCT 1758

E   D   S   K   Y   F   L   P   Y   H   P   P   Q   R   R   M   N   L   K   G   497
GAA GAC AGC AAG TAC TTC CTG CCC TAC CAT CCG CCC CAG CGC AGG ATG AAC CTG AAG GGC 1818

I   Q   L   Q   R   A   K   S   P   I   S   L   K   R   T   S   D   F   Q   A   517
ATC CAG CTG CAG AGA GCC AAA TCC CCC ATC AGC CTG AAG CGA ACA TCA GAT TTT CAA GCC 1878

K   G   H   E   E   G   T   D   A   S   P   S   S   C   G   S   L   P   I   537
AAG GGG CAC GAG GAA GAA GGC ACG GAC GCC AGC CCT AGC TCC TGC GGA TCT CTG CCC ATC 1938

T   N   S   F   T   K   M   Q   P   P   R   S   R   S   S   I   M   S   I   T   557
ACC AAC TCC TTC ACC AAG ATG CAG CCC CCC CGG AGC CGC AGC AGC ATC ATG TCA ATC ACC 1998

A   E   P   P   G   N   D   S   I   V   R   R   Y   K   E   D   A   P   H   R   577
GCC GAG CCC CCG GGA AAC GAC TCC ATC GTC AGA CGC TAC AAG GAG GAC GCG CCC CAT CGC 2058

S   T   V   E   E   D   N   D   S   G   G   F   D   A   L   D   L   D   D   D   597
AGC ACA GTC GAA GAA GAC AAT GAC AGC GGC GGG TTT GAC GCC TTA GAT CTG GAT GAT GAC 2118

S   H   E   R   Y   S   F   G   P   S   S   I   H   S   S   S   S   S   H   Q   617
AGT CAC GAA CGC TAC TCC TTC GGA CCC TCC TCC ATC CAC TCC TCC TCC TCC TCC CAC CAA 2178

S   E   G   L   D   A   Y   D   L   E   Q   V   N   L   M   F   R   K   F   S   637
TCC GAG GGC CTG GAT GCC TAC GAC CTG GAG CAG GTC AAC CTC ATG TTC AGG AAG TTC TCT 2238

L   E   R   P   F   R   P   S   V   T   S   V   G   H   V   R   G   P   G   P   657
CTG GAA AGA CCC TTC CGG CCT TCG GTC ACC TCT GTG GGG CAC GTG CGG GGC CCA GGG CCC 2298

S   V   Q   H   T   T   L   N   G   D   S   L   T   S   Q   L   T   L   L   G   677
TCG GTG CAG CAC ACG ACG CTG AAT GGC GAC AGC CTC ACC TCC CAG CTC ACC CTG CTG GGG 2358

G   N   A   R   G   S   F   V   H   S   V   K   P   G   S   L   A   E   K   A   697
GGC AAC GCG CGA GGG AGC TTC GTG CAC TCG GTC AAG CCT GGC TCT CTG GCC GAG AAA GCC 2418

G   L   R   E   G   H   Q   L   L   L   L   E   G   C   I   R   G   E   R   Q   717
GGC CTC CGT GAG GGC CAC CAG CTG CTG CTG CTA GAA GGC TGC ATC CGA GGC GAG AGG CAG 2478

S   V   P   L   D   T   C   T   K   E   E   A   H   W   T   I   Q   R   C   S   737
AGT GTC CCG TTG GAC ACA TGC ACC AAA GAG GAA GCC CAC TGG ACC ATC CAG AGG TGC AGC 2538

G   P   V   T   L   H   Y   K   V   N   H   E   G   Y   R   K   L   V   K   D   757
GGC CCC GTC ACG CTG CAC TAC AAG GTC AAC CAC GAA GGG TAC CGG AAG CTG GTG AAG GAC 2598

M   E   D   G   L   I   T   S   G   D   S   F   Y   I   R   L   N   L   N   I   777
ATG GAG GAC GGC CTG ATC ACA TCG GGG GAC TCG TTC TAC ATC CGG CTG AAC CTG AAC ATC 2658

S   S   Q   L   D   A   C   T   M   S   L   K   C   D   D   V   V   H   V   R   797
TCC AGC CAG CTG GAC GCC TGC ACC ATG TCC CTG AAG TGT GAC GAT GTT GTG CAC GTC CGT 2718

D   T   M   Y   Q   D   R   H   E   W   P   I   A   R   V   D   P   F   T   D   817
GAC ACC ATG TAC CAG GAC AGG CAC GAG TGG CCG ATC GCG CGG GTC GAC CCT TTC ACA GAC 2778

H   D   L   D   M   G   T   I   P   S   Y   S   R   A   Q   Q   L   L   L   V   837
CAT GAC CTG GAT ATG GGC ACC ATA CCC AGC TAC AGC CGA GCC CAG CAG CTC CTC CTG GTG 2838

K   L   Q   R   L   M   H   R   G   S   R   E   E   V   D   G   T   H   H   T   857
AAA CTG CAG CGC CTG ATG CAC CGA GGC AGC CGG GAG GAG GTA GAC GGC ACC CAC CAC ACC 2898

L   R   A   L   R   N   T   L   Q   P   E   E   A   L   S   T   S   D   P   R   877
CTG CGG GCA CTC CGG AAC ACC CTG CAG CCG GAA GAA GCG CTT TCA ACA AGC GAC CCC CGG 2958
```

FIG. 14B

```
      V   S   P   R   L   S   R   A   S   F   L   F   G   Q   L   L   Q   F   V   S    897
     GTC AGC CCC CGT CTC TCG CGA GCA AGC TTC CTT TTT GGC CAG CTC CTT CAG TTC GTC AGC   3018

R   S   E   N   K   Y   K   R   M   N   S   M   E   R   V   R   I   I   S   G    917
     AGG TCC GAG AAC AAG TAT AAG CGG ATG AAC AGC AAT GAG CGG GTC CGC ATC ATC TCG GGG   3078

S   P   L   G   S   L   A   R   S   S   L   D   A   T   K   L   L   T   E   K    937
     AGT CCG CTA GGG AGC CTG GCC CGG TCC TCG CTG GAC GCC ACC AAG CTC TTG ACT GAG AAG   3138

Q   E   E   L   D   P   E   S   E   L   G   K   N   L   S   L   I   P   Y   S    957
     CAG GAA GAG CTG GAC CCT GAG AGC GAG CTG GGC AAG AAC CTC AGC CTC ATC CCC TAC AGC   3198

L   V   R   A   F   Y   C   E   R   R   R   P   V   L   F   T   P   T   V   L    977
     CTG GTA CGC GCC TTC TAC TGC GAG CGC CGC CGG CCC GTG CTC TTC ACA CCC ACC GTG CTG   3258

A   K   T   L   V   Q   R   L   L   N   S   G   G   A   M   E   F   T   I   C    997
     GCC AAG ACG CTG GTG CAG AGG CTG CTC AAC TCG GGA GGT GCC ATG GAG TTC ACC ATC TGC   3318

K   S   D   I   V   T   R   D   E   F   L   R   R   Q   K   T   E   T   I   I   1017
     AAG TCA GAT ATC GTC ACA AGA GAT GAG TTC CTC AGA AGG CAG AAG ACG GAG ACC ATC ATC   3378

Y   S   R   E   K   N   P   N   A   F   E   C   I   A   P   A   N   I   E   A   1037
     TAC TCC CGA GAG AAG AAC CCC AAC GCG TTC GAA TGC ATC GCC CCT GCC AAC ATT GAA GCT   3438

V   A   A   K   N   K   H   C   L   L   E   A   G   I   G   C   T   R   D   L   1057
     GTG GCC GCC AAG AAC AAG CAC TGC CTG CTG GAG GCT GGG ATC GGC TGC ACA AGA GAC TTG   3498

I   K   S   N   I   Y   P   I   V   L   F   I   R   V   C   E   K   N   I   K   1077
     ATC AAG TCC AAC ATC TAC CCC ATC GTG CTC TTC ATC CGG GTG TGT GAG AAG AAC ATC AAG   3558

R   F   R   K   L   L   P   R   P   E   T   E   E   E   F   L   R   V   C   R   1097
     AGG TTC AGA AAG CTG CTG CCC CGG CCT GAG ACG GAG GAG GAG TTC CTG CGC GTG TGC CGG   3618

L   K   E   K   E   L   E   A   L   P   C   L   Y   A   T   V   E   P   D   M   1117
     CTG AAG GAG AAG GAG CTG GAG GCC CTG CCG TGC CTG TAC GCC ACG GTG GAA CCT GAC ATG   3678

W   G   S   V   E   E   L   L   R   V   V   K   D   K   I   G   E   E   Q   R   1137
     TGG GGC AGC GTA GAG GAG CTG CTC CGC GTT GTC AAG GAC AAG ATC GGC GAG GAG CAG CGC   3738

K   T   I   W   V   D   E   D   Q   L   *                                       1148
     AAG ACC ATC TGG GTG GAC GAG GAC CAG CTG TGA                                       3771

GGCGGGCGCCCTGGGCAGAGAGACTCTGTGGCGCGGGGCATCCTATGAGGCAGGCACCCTGGGCAGAGAGATGCAGTGG   3850

GTGCGGGGGGATCCTGTGGCCCACAGAGCTGCCCCAGCAGACGCTCCGCCCCACCCGGTGATGGAGCCCCGGGGGGACA   3929

GTCGTGCCTGGGGAGGAGCAGGGTACAGCCCATTCCCCCAGCCCTGGCTGACCTGGCCTAGCAGTTTGGCCCTGCTGGC   4008

CTTAGCAGGGAGACAGGGGAGCAAAGAACGCCAAGCCGGAGGCCCGAGGCCAGCCGGCCTCTCGAGAGCCAGAGCAGCA   4087

GTTGAATGTAATGCTGGGGACAGGCATGCTGCCGCCAGTAGGGCGGGGACCCGGACAGCCAGGTGACTACCAGTCCTGG   4166

GGACACACTCACCATAAACACATCCCCAGGCAGGACAGATCGGGGAAGGGGTGTGTACCAGGCTATGATTTCTCTTGCA   4245

TTAAAATGTATTATTAAAAAAAAAAAAAAAA                                                   4276
```

FIG. 14C

```
CARD: domain 1 of 1, from 12 to 103: score 1.0, E = 0.26
              *->aeddrrllrknrlellgeltlsglLdhLleknvLteeeeEkikaknt
                ++   +  ++ nr +l+  + + +l  +L++ +v+ e++e+++ +++
    hCARD11  12    EDALWENVECNRHMLSRYINPAKLTPYLRQCKVIDEQDEDEVLNAPM  58 trr..dkareLiDsvqkkGnqAfqiFlqaLretdqelladlllde<-*
              +++  +a  L+D++ +kG+  +  +Fl++L+    +el++ +   +e
    hCARD11  59  LPSkiNRAGRLLDILHTKGQRGYVVFLESLEFYYPELYKLVTGKE        103
```

FIG. 17A

```
PDZ: domain 1 of 1, from 635 to 747: score 5.2, E = 0.39
              *->eitlekevkrgglGfsikggsdk.........................
                 +  +le++        f++++  s ++ ++++++ ++++ ++++ +++ +
    hCARD11  635    KFSLERP-------FRPSVTSVGhvrgpgpsvqhttlngdsltsqlt 674

.......givvsevlpGsgaAeagGrLkeGDvIlsvNG........qdve
              +++  +g  +v  +v  pG +  Ae++G  L+eG+++l    G  +++++++++
    hCARD11  675 llggnarGSFVHSVKPG-SLAEKAG-LREGHQLLLLEGcirgerqsVPLD 722 nmsheravlaikgsggevtLtvlRd<-*
              + e+a    i+  ++g+vtL   +  +
    hCARD11  723  TCTKEEAHWTIQRCSGPVTLHYKVN         747
```

FIG. 17B

```
Guanylate_kin: domain 1 of 1, from 1003 to 1091: score -34.1, E = 0.58
              *->TRpVpRpgEvdGkdYhFVssrEemekdIaaneFlEygefqg.nyYGT
                 TR+             +F+   r + e   I     e       ++n +
    hCARD11  1003   TRD-----------EFLR-RQKTETIIYSRE-------KNpNAFEC 1029 slet.vrqvakqgKiciLDvepQgvkrlrtaelsNPivvFIaPpSlqele
              +  +++++++va+++K+c+L+   +    + l +   + Piv+FI+    +    +
    hCARD11  1030  IAPAnIEAVAAKNKHCLLEAGIGCTRDLIKSNIY-PIVLFIRVCE-KNIK 1077 krLegr.nkesEes<-*
              +  ++ ++++e+Ee+
    hCARD11  1078 RFRKLLpRPETEEE        1091
```

FIG. 17C

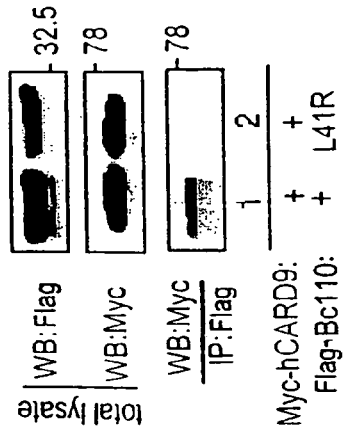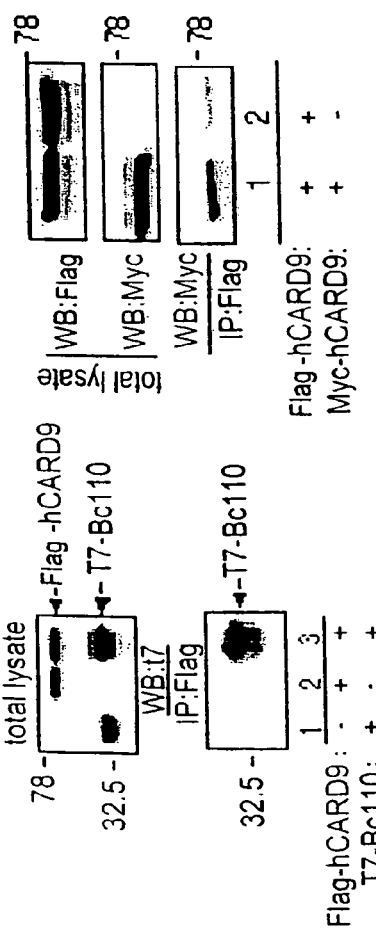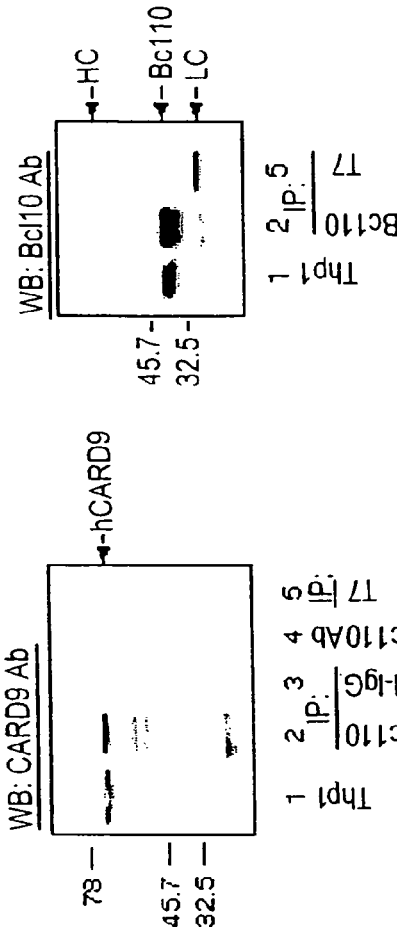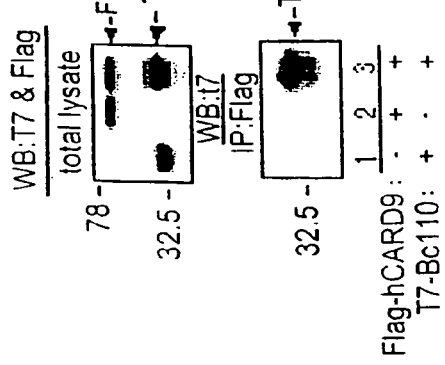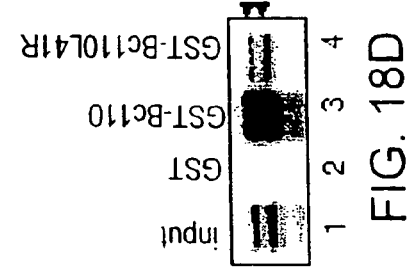

US 8,178,661 B2

MOLECULES OF THE CARD-RELATED PROTEIN FAMILY AND USES THEREOF

CROSS REFERENCE TO RELATED APPLICATIONS

This application is a divisional of U.S. application Ser. No. 10/325,917, filed Dec. 20, 2002 (now U.S. Pat. No. 7,452, 967), which is a continuation of U.S. application Ser. No. 09/798,412, filed Mar. 2, 2001 (now abandoned), which is a continuation-in-part of U.S. application Ser. No. 09/728,260, filed Dec. 1, 2000 (now abandoned), which is a continuation-in-part of U.S. application Ser. No. 09/685,791, filed Oct. 10, 2000 (now abandoned), which is a continuation-in-part of U.S. application Ser. No. 09/513,904, filed Feb. 25, 2000 (now abandoned), which is a continuation-in-part of application Ser. No. 09/507,533, filed Feb. 18, 2000 (now abandoned), which claimed priority from provisional application Ser. No. 60/168,780, filed Dec. 3, 1999. The entire contents of each of these applications are herein incorporated by reference.

The contents of the Sequence Listing are submitted herewith on compact disc in duplicate. Each duplicate compact disc has a copy of the Sequence Listing file, created on Oct. 29, 2001 and named "sequence listing.txt," the contents of which are incorporated herein by this reference. This file is 86 kB (88,064 bytes) and was copied onto compact disc on Oct. 7, 2008.

BACKGROUND OF THE INVENTION

In multicellular organisms, homeostasis is maintained by balancing the rate of cell proliferation against the rate of cell death. Cell proliferation is influenced by numerous growth factors and the expression of proto-oncogenes, which typically encourage progression through the cell cycle. In contrast, numerous events, including the expression of tumor suppresser genes, can lead to an arrest of cellular proliferation.

A particular type of cell death called apoptosis occurs in differentiated cells when an internal suicide program is activated. This program can be initiated by a variety of external signals as well as signals that are generated within the cell in response to, for example, genetic damage. For many years, the magnitude of apoptotic cell death was not appreciated because the dying cells are quickly eliminated by phagocytes, without an inflammatory response.

The mechanisms that mediate apoptosis have been intensively studied. These mechanisms involve the activation of endogenous proteases, loss of mitochondrial function, and structural changes such as disruption of the cytoskeleton, cell shrinkage, membrane blebbing, and nuclear condensation due to degradation of DNA.

The various signals that trigger apoptosis are thought to bring about these events by converging on a common cell death pathway, the core components of which are highly conserved from worms, such as *C. elegans*, to humans. In fact, invertebrate model systems have been invaluable tools in identifying and characterizing the genes that control apoptosis. Despite this conservation of certain core components, apoptotic signaling in mammals is much more complex than in invertebrates. For example, in mammals there are multiple homologues of the core components in the cell death signaling pathway.

Caspases, a class of proteins central to the apoptotic program, are responsible for the degradation of cellular proteins that leads to the morphological changes seen in cells undergoing apoptosis. Caspases are cysteine proteases having specificity for aspartate at the substrate cleavage site. Generally, caspases are classified as either initiator caspases or effector caspases, both of which are zymogens that are activated by proteolysis that generates an active species. An effector caspase is activated by an initiator caspase which cleaves the effector caspase. Initiator caspases are activated by an autoproteolytic mechanism that is often dependent upon oligomerization directed by association of the caspase with an adapter molecule.

Apoptotic signaling is dependent on protein-protein interactions. At least three different protein-protein interaction domains, the death domain, the death effector domain and the caspase recruitment domain (CARD), have been identified within proteins involved in apoptosis. A fourth protein-protein interaction domain, the death recruiting domain (DRD) was recently identified in murine FLASH (Imai et al. (1999) *Nature* 398:777-85).

Many caspases and proteins that interact with caspases possess a CARD domain. Hofmann et al. ((1997) *TIBS* 22:155) and others have postulated that certain apoptotic proteins bind to each other via their CARD domains and that different subtypes of CARD domains may confer binding specificity, regulating the activity of various caspases, for example.

Nuclear factor-κB (NF-κB) is a transcription factor that is expressed in many cell types and activates genes that have NF-κB sites in their promoters. Molecules that regulate NF-κB activation play a critical role in both apoptosis and in the stress-response of cells. With respect to stress-response, NF-κB activates genes that control immune defense mechanisms and inflammation. The CARD-containing proteins RICK, CARD-4 and Bcl-10 also induce activation of the NF-κB transcription factor suggesting that CARD/CARD signaling complexes regulate activation of the IKK complex (Inohara et al. 1998 *Proc. Natl. Acad. Sci. USA* 273:12296; Bertin et al. 1999 *J. Biol. Chem.* 224:12955; Willis et al. 1999 *Cell* 96: 33). In unstimulated cells, NF-κB is found sequestered in the cytoplasm through interactions with inhibitory IκB proteins. Inhibition is relieved by the phosphorylation and proteosomal degradation of IκB proteins by proinflammatory cytokines. Phosphorylation is mediated by the IKK complex which is comprised of at least three major proteins: two kinases designated IKKα and IKKβ that directly phosphorylate the IκB inhibitory proteins, and a noncatalytic subunit called IKKγ that functions to link the IKKs to upstream regulatory molecules (Zhang et al., 2000). Recently, RICK has been found to function as upstream regulatory molecules of the IKK complex (Inohara et al. 2000 *J. Biol. Chem.* 275:27823). RICK interacts directly with IKKγ suggesting that it functions as signaling adaptor between the IKK complex and an upstream CARD-containing NF-κB activator. Indeed, CARD-4 forms a CARD/CARD signaling complex with RICK that induces activation of the IKK complex and the subsequent release of NF-κB (Bertin et al. 1999 *J. Biol. Chem.* 224:12955; Inohara et al. 1999 *J. Biol. Chem.* 274:14566; Inohara et al. 2000 *J. Biol. Chem.* 275:27823).

At least two dozen stimuli that activate NF-κB are known, including cytokines, protein kinase C activators, oxidants, viruses, and immune system stimuli. NK-κB is stimulated via signaling through the tumor necrosis factor family receptors (TNFRs) and the interleukin-1/Toll receptor. Tumor necrosis factor family members bind to their cognate receptors, including Fas (CD95/APO-1), TRAMP (DR3/WSL-1/AIR/LARD), CD37, CD30, CD40, TNFR1 and TNFR2, and regulate apoptosis, cell proliferation, and proinflammatory responses. For example, the proinflammatory cytokines TNF-α and IL-1 induce NF-κB activation by binding their cell-surface receptors and activating the NF-κB-inducing kinase, NIK. In the case of TNF-α, binding to TNF-R1 induces aggregation of its death domain and assembly of a signaling complex containing TRADD, TRAF2, and RIP. Binding of IL-1 to its receptor, IL-1R, induces aggregation of the receptor and assembly of a signaling complex which includes AcP, MyD88, IRAK1, IRAK2, and TRAF6. Both the TNF-R1 complex and the IL-1R complex trigger activation of NIK. Activated NIK phosphorylates the IkB kinases IkB-a and IkB-b which phosphorylate IkB, leading to its degradation and, as a consequence, the activation of NF-κB.

Fas, a cell surface receptor that is a member of the TNFR family, can induce apoptosis upon binding with its ligand, FasL (CD95L). Fas interacts with FADD (MORT) via death domains present in both proteins. When bound to Fas, FADD interacts with caspase-8 (FLICE/MACH/Mch5) through death effector domains present in both proteins. The complex of Fas, FADD and caspase-8 is referred to as the death-inducing signaling complex (DISC). Recently, FLASH, a protein having a DRD as well as a CED-4-like domain, has been identified as a component of DISC that is required for caspase-8 activation during Fas-mediated apoptosis (Imai et al. (1999) *Nature* 398:777-85). In the DISC, caspase-8 undergoes oligomerization-dependent autoproteolysis, leading to activation. Activated caspase-8 cleaves several effector caspases, including caspase-3, caspase-6, and caspase-7, by proteolytic cleavage. These effector caspases cleave various death substrates involved in the morphological changes and DNA fragmentation that is central to apoptosis.

Transient expression of FLASH activates caspase-8. However, a truncated form of FLASH lacking either its DRD or CED-4-like domain does not allow activation of caspase-8 or Fas-mediated apoptosis. Thus, it appears that FLASH is involved in both Fas- and TNF-induced apoptosis mediated by activated caspase-8 (Imai et al. (1999) *Nature* 398:777-85).

Bcl-10 (mE10/CIPER/CLAP/c-CARMEN) is a CARD domain containing pro-apoptotic protein that induces NF-κB activation (Koseki et al. (1999) *J. Biol. Chem.* 274:9955-61; Yan et al. (1999) *J. Biol. Chem.* 274:10287-92; Thome et al. (1999) *J. Biol. Chem.* 274:9962-68; Srinivasula et al. (1999) *J. Biol. Chem.* 274:17946-54)). Bcl-10 activates NF-κB by acting upstream of NIK and IkB kinase (Srinivasula et al., supra). Significantly, Bcl-10 is involved in t(1;14)(p22;q23) of MALT B cell lymphoma (Willis et al. (1999) *Cell* 96:35-45; Zhang et al. (1999) *Nat. Genet.* 22:63-8). Bcl-10 expressed in MALT lymphoma exhibits a frameshift mutation that causes truncation of Bcl-10 distal to its CARD domain. The truncated form of Bcl-10 activates NF-κB, but does not induce apoptosis (Willis et al. (1999) *Cell* 96:35-45). Expression of NF-κB is associated with suppression of apoptosis and increased cell survival in certain systems. Thus, mutant Bcl-10 may promote continued cell proliferation by two different mechanisms. Bcl-10 mutations similar to that observed in MALT lymphoma occur in many other tumor types, suggesting that Bcl-10 may be commonly involved in malignancy. Bcl-10 has a bipartite structure consisting of an N-terminal CARD domain and a C-terminal effector domain that mediates activation of NF-κB.

Bcl-10 has been implicated as a positive regulator of lymphocyte activation and proliferation triggered by antigen receptor engagement (Ruland et al. (2001) *Cell* 104:33-42). Mice lacking Bcl-10 are severely immunodeficient, e.g., impaired humoral and cellular immune responses, and have lymphocytes defective in antigen induced NF-kB activation.

Thus, Bcl-10 appears to act as a mediator of NF-κB activation in response to antigen receptor signaling in B and T cells. In addition, approximately one third of Bcl-10 deficient embryos developed exencephaly, implicating a role for Bcl-10 in normal CNS development, possibly via positive regulation of neuronal survival (Ruland et al. supra).

Murine FLASH is a protein involved in Fas-mediated activation of caspase-8 during apoptosis (Imani et al. (1999) *Nature* 398:777-85). Transient expression of murine FLASH activates caspase-8. It appears that the DRD domain (amino acids 1584-1751) and the CED-4-like domain (amino acids 939-1191) of murine FLASH are required for activation of caspase-8. In addition, the exencephaly seen in about one third of bcl-10-/- embryos suggests that Bcl-10 may be involved in the positive regulation of neuronal survival.

NF-kB and the NF-kB pathway have been implicated in mediating chronic inflammation in inflammatory diseases such as asthma, ulcerative colitis, rheumatoid arthritis (Barnes & Epstein (1997) *New England Journal of Medicine* 336:1066) and inhibiting NF-kB or NF-kB pathways may be an effective way of treating these diseases. Binding sites for the transcription factor NF-kB are present in the promoter regions of the genes of many of the proinflammatory cytokines, chemokines, enzymes, immune receptors, and adhesion molecules important in inducing acute inflammatory responses associated with critical illnesses. Because increased activation of NF-kB can lead to enhanced expression of proinflammatory mediators, NF-kB activation may be an important event in the development of, for example, multiple organ dysfunction associated with infection, blood loss, and ischemia-reperfusion injury (Abraham (2000) *Crit. Care Med* 28(4 Suppl):N100-4).

NF-kB and the NF-kB pathway have also been implicated in atherosclerosis (Navab et al. (1995) *American Journal of Cardiology* 76:18C), especially in mediating fatty streak formation, and inhibiting NF-κB or NF-κB pathways may be an effective therapy for atherosclerosis. Among the genes activated by NF-kB are cIAP-1, cIAP-2, TRAF1, and TRAF2, all of which have been shown to protect cells from TNF-I induced cell death (Wang et al. (1998) *Science* 281:1680-83).

SUMMARY OF THE INVENTION

The invention features nucleic acid molecules encoding rat CARD-9, human CARD-9, human CARD-10, and human CARD-11. These proteins, like many others having a CARD domain, play roles in apoptotic and inflammatory signaling pathways. CARD-9, CARD-10, and CARD-11 participate in the network of interactions that modulate caspase activity. Upon activation, CARD-9, CARD-10, and CARD-11 likely bind and activate a CARD containing protein via a CARD-CARD interaction leading to a modulation of apoptosis and or stress related pathways (e.g., NF-κB activation).

CARD-9, CARD-10, and CARD-11 molecules are useful as modulating agents in regulating a variety of cellular processes including cell growth and cell death. In one aspect, this invention provides isolated nucleic acid molecules encoding CARD-9, CARD-10, or CARD-11 proteins or biologically active portions thereof, as well as nucleic acid fragments suitable as primers or hybridization probes for the detection of CARD-9, CARD-10, or CARD-11 encoding nucleic acids.

The invention encompasses methods of diagnosing and treating patients who are suffering from a disorder associated with an abnormal level or rate (undesirably high or undesirably low) of apoptotic cell death, abnormal activity of the Fas/APO-1 receptor complex, abnormal activity of the TNF receptor complex, or abnormal activity of a caspase by administering a compound that modulates the expression of CARD-9, CARD-10, or CARD-11 (at the DNA, mRNA or protein level, e.g., by altering mRNA splicing) or by altering the activity of CARD-9, CARD-10, or CARD-11. Examples of such compounds include small molecules, antisense nucleic acid molecules, ribozymes, and polypeptides.

Certain disorders are associated with an increased number of surviving cells, which are produced and continue to survive or proliferate when apoptosis is inhibited or occurs at an undesirably low rate. CARD-9, CARD-10, or CARD-11 and compounds that modulate the expression or activity of CARD-9, CARD-10, or CARD-11 can be used to treat or diagnose such disorders. These disorders include cancer (particularly follicular lymphomas, chronic myelogenous leukemia, melanoma, colon cancer, lung carcinoma, carcinomas associated with mutations in p53, and hormone-dependent tumors such as breast cancer, prostate cancer, and ovarian cancer). Such compounds can also be used to treat viral infections (such as those caused by herpesviruses, poxviruses, and adenoviruses). Failure to remove autoimmune cells that arise during development or that develop as a result of somatic mutation during an immune response can result in autoimmune disease. Thus, autoimmune disorders can be caused by an undesirably low levels of apoptosis. Accordingly, CARD-9, CARD-10, or CARD-11 and modulators of CARD-9, CARD-10, or CARD-11 activity or expression can be used to treat autoimmune disorders (e.g., systemic lupus erythematosis, immune-mediated glomerulonephritis, and arthritis).

Many diseases are associated with an undesirably high rate of apoptosis. CARD-9, CARD-10, or CARD-11 and modulators of CARD-9, CARD-10, or CARD-11 expression or activity can be used to treat or diagnose such disorders. For example, populations of cells are often depleted in the event of viral infection, with perhaps the most dramatic example being the cell depletion caused by the human immunodeficiency virus (HIV). Surprisingly, most T cells that die during HIV infections do not appear to be infected with HIV. Although a number of explanations have been proposed, recent evidence suggests that stimulation of the CD4 receptor results in the enhanced susceptibility of uninfected T cells to undergo apoptosis. A wide variety of neurological diseases are characterized by the gradual loss of specific sets of neurons. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

Proteins containing a CARD domain are thought to be involved in various inflammatory disorders. Accordingly, CARD-9, CARD-10, or CARD-11 polypeptides, nucleic acids and modulators of CARD-9, CARD-10, or CARD-11 expression or activity can be used to treat immune disorders. Such immune disorders include, but are not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis), certain viral infections, including HIV, and bacterial infections, including tuberculosis and lepromatous leprosy.

In addition to the aforementioned disorders, CARD-9, CARD-10, or CARD-11 polypeptides, nucleic acids, and modulators of CARD-9, CARD-10, or CARD-11 expression or activity can be used to treat disorders of cell signaling and disorders of tissues in which CARD-9, CARD-10, or CARD-11 is expressed.

The invention features a nucleic acid molecule which is at least 45% (or 55%, 65%, 75%, 85%, 95%, or 98%) identical to the nucleotide sequence shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, or a complement thereof.

The invention features a nucleic acid molecule which includes a fragment of at least 150 (300, 325, 350, 375, 400, 425, 450, 500, 550, 600, 650, 700, 800, 900, 1000, 1200, 1400, 1600, 1800, 2000, 2200, 2400, 2600, 2800, 3000, 3200, 3400, 3600, 3800, 4000, 4200, or 4250) nucleotides of the nucleotide sequence shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, or a complement thereof.

In an embodiment, a CARD-9 nucleic acid molecule has the nucleotide sequence shown in SEQ ID NO:1, or SEQ ID NO:3.

Also within the invention is a nucleic acid molecule which encodes a fragment of a polypeptide having the amino acid sequence of SEQ ID NO:2.

The invention includes a nucleic acid molecule which encodes a naturally occurring allelic variant of a polypeptide comprising the amino acid sequence of SEQ ID NO:2, wherein the nucleic acid molecule hybridizes to a nucleic acid molecule consisting of SEQ ID NO:1, or SEQ ID NO:3.

In general, an allelic variant of a gene will be readily identifiable as mapping to the same chromosomal location as said gene.

The invention also includes a nucleic acid molecule encoding a naturally occurring polypeptide, wherein the nucleic acid hybridizes to a nucleic acid molecule consisting of SEQ ID NO:3 under stringent conditions (e.g., hybridization in 6× sodium chloride/sodium citrate (SSC) at about 60° C., followed by one or more washes in 0.2×SSC, 0.1% SDS at 65° C.), and wherein the nucleic acid encodes a polypeptide of 533-539 amino acids in length, preferably 536 amino acids, having a molecular weight of approximately 62.2 kD prior to post-translational modifications. Thus, the invention encompasses a nucleic acid molecule which includes the sequence of the protein coding region of a naturally occurring mRNA (or the corresponding cDNA sequence) that is expressed in a human cell.

Also within the invention are: an isolated CARD-9 protein having an amino acid sequence that is at least about 65%, preferably 75%, 85%, 95%, or 98% identical to the amino acid sequence of SEQ ID NO:2; an isolated CARD-9 protein having an amino acid sequence that is at least about 65%, preferably 75%, 85%, 95%, or 98% identical to the CARD domain of SEQ ID NO:2 (e.g., about amino acid residues 7-98 of SEQ ID NO:2); an isolated CARD-9 protein having an amino acid sequence that is at least about 65%, preferably 75%, 85%, 95%, or 98% identical to the coiled-coil domain of SEQ ID NO:2 (e.g., about amino acid residues 140-416 of SEQ ID NO:2); an isolated CARD-9 protein having an amino acid sequence that is at least about 65%, preferably 75%, 85%, 95%, or 98% identical to the indole-3-glycerol phosphate synthase homology domain of SEQ ID NO:2 (e.g., about amino acid residues 197-213 of SEQ ID NO:2); and an isolated CARD-9 protein having an amino acid sequence that is at least about 65%, preferably 75%, 85%, 95%, or 98% identical to the cysteine rich repeat homology domain of SEQ ID NO:2 (e.g., about amino acid residues 285-338 of SEQ ID NO:2).

In an embodiment, a CARD-9 nucleic acid molecule has the nucleotide sequence shown in SEQ ID NO:4, or SEQ ID NO:6.

Also within the invention is a nucleic acid molecule which encodes a fragment of a polypeptide having the amino acid sequence of SEQ ID NO:5.

The invention includes a nucleic acid molecule which encodes a naturally occurring allelic variant of a polypeptide comprising the amino acid sequence of SEQ ID NO:5, wherein the nucleic acid molecule hybridizes to a nucleic acid molecule consisting of SEQ ID NO:4, or SEQ ID NO:6.

In general, an allelic variant of a gene will be readily identifiable as mapping to the same chromosomal location as said gene.

The invention also includes a nucleic acid molecule encoding a naturally occurring polypeptide, wherein the nucleic acid hybridizes to a nucleic acid molecule consisting of SEQ ID NO:6 under stringent conditions (e.g., hybridization in 6× sodium chloride/sodium citrate (SSC) at about 60° C., followed by one or more washes in 0.2×SSC, 0.1% SDS at 65° C.), and wherein the nucleic acid encodes a polypeptide of 533-539 amino acids in length, preferably 536 amino acids, having a molecular weight of approximately 62.2 kD prior to post-translational modifications. Thus, the invention encompasses a nucleic acid molecule which includes the sequence of the protein coding region of a naturally occurring mRNA (or the corresponding cDNA sequence) that is expressed in a human cell.

Also within the invention are: an isolated CARD-9 protein having an amino acid sequence that is at least about 65%, preferably 75%, 85%, 95%, or 98% identical to the amino acid sequence of SEQ ID NO:5; an isolated CARD-9 protein having an amino acid sequence that is at least about 65%, preferably 75%, 85%, 95%, or 98% identical to the CARD domain of SEQ ID NO:5 (e.g., about amino acid residues 7-98 of SEQ ID NO:5); an isolated CARD-9 protein having an amino acid sequence that is at least about 65%, preferably 75%, 85%, 95%, or 98% identical to the coiled-coil domain of SEQ ID NO:5 (e.g., about amino acid residues 140-416 of SEQ ID NO:5); an isolated CARD-9 protein having an amino acid sequence that is at least about 65%, preferably 75%, 85%, 95%, or 98% identical to the indole-3-glycerol phosphate synthase homology domain of SEQ ID NO:5 (e.g., about amino acid residues 197-213 of SEQ ID NO:5); and an isolated CARD-9 protein having an amino acid sequence that is at least about 65%, preferably 75%, 85%, 95%, or 98% identical to the cysteine rich repeat homology domain of SEQ ID NO:5 (e.g., about amino acid residues 285-338 of SEQ ID NO:5).

In an embodiment, a CARD-10 nucleic acid molecule has the nucleotide sequence shown in SEQ ID NO:7, or SEQ ID NO:9.

Also within the invention is a nucleic acid molecule which encodes a fragment of a polypeptide having the amino acid sequence of SEQ ID NO:8.

The invention includes a nucleic acid molecule which encodes a naturally occurring allelic variant of a polypeptide comprising the amino acid sequence of SEQ ID NO:8, wherein the nucleic acid molecule hybridizes to a nucleic acid molecule consisting of SEQ ID NO:7, or SEQ ID NO:9.

In general, an allelic variant of a gene will be readily identifiable as mapping to the same chromosomal location as said gene.

The invention also includes a nucleic acid molecule encoding a naturally occurring polypeptide, wherein the nucleic acid hybridizes to a nucleic acid molecule consisting of SEQ ID NO:9 under stringent conditions (e.g., hybridization in 6× sodium chloride/sodium citrate (SSC) at about 60° C., followed by one or more washes in 0.2×SSC, 0.1% SDS at 65° C.), and wherein the nucleic acid encodes a polypeptide of 1029-1035 amino acids in length, preferably 1032 amino acids, having a molecular weight of approximately 115.9 kD prior to post-translational modifications. Thus, the invention encompasses a nucleic acid molecule which includes the sequence of the protein coding region of a naturally occurring mRNA (or the corresponding cDNA sequence) that is expressed in a human cell.

Also within the invention are: an isolated CARD-10 protein having an amino acid sequence that is at least about 65%, preferably 75%, 85%, 95%, or 98% identical to the amino acid sequence of SEQ ID NO:8; an isolated CARD-10 protein having an amino acid sequence that is at least about 85%, 95%, or 98% identical to the CARD domain of SEQ ID NO:8 (e.g., about amino acid residues 23-123 of SEQ ID NO:8); an isolated CARD-10 protein having an amino acid sequence that is at least about 85%, 95%, or 98% identical to the coiled-coil domain of SEQ ID NO:8 (e.g., about amino acid residues 147-457 of SEQ ID NO:8); an isolated CARD-10 protein having an amino acid sequence that is at least about 85%, 95%, or 98% identical to the SH3 domain of SEQ ID NO:8 (e.g., about amino acid residues 704-772 of SEQ ID NO:8); an isolated CARD-10 protein having an amino acid sequence that is at least about 85%, 95%, or 98% identical to the guanylate kinase (GUK) domain of SEQ ID NO:8 (e.g., about amino acid residues 830-1032 of SEQ ID NO:8); and an isolated CARD-10 protein having an amino acid sequence that is at least about 85%, 95%, or 98% identical to the tropomyosin domain of SEQ ID NO:8 (e.g., about amino acid residues 366-398 of SEQ ID NO:8);

In an embodiment, a CARD-11 nucleic acid molecule has the nucleotide sequence shown in SEQ ID NO: 10, or SEQ ID NO: 12.

Also within the invention is a nucleic acid molecule which encodes a fragment of a polypeptide having the amino acid sequence of SEQ ID NO: 11.

The invention includes a nucleic acid molecule which encodes a naturally occurring allelic variant of a polypeptide comprising the amino acid sequence of SEQ ID NO: 11, wherein the nucleic acid molecule hybridizes to a nucleic acid molecule consisting of SEQ ID NO: 10 or SEQ ID NO:12.

In general, an allelic variant of a gene will be readily identifiable as mapping to the same chromosomal location as said gene.

The invention also includes a nucleic acid molecule encoding a naturally occurring polypeptide, wherein the nucleic acid hybridizes to a nucleic acid molecule consisting of SEQ ID NO:12 under stringent conditions (e.g., hybridization in 6× sodium chloride/sodium citrate (SSC) at about 60° C., followed by one or more washes in 0.2×SSC, 0.1% SDS at 65° C.), and wherein the nucleic acid encodes a polypeptide of 1144-1150 amino acids in length, preferably 1147 amino acids, having a molecular weight of approximately 132.6 kD prior to post-translational modifications. Thus, the invention encompasses a nucleic acid molecule which includes the sequence of the protein coding region of a naturally occurring mRNA (or the corresponding cDNA sequence) that is expressed in a human cell.

Also within the invention are: an isolated CARD-11 protein having an amino acid sequence that is at least about 65%, preferably 75%, 85%, 95%, or 98% identical to the amino acid sequence of SEQ ID NO:11; an isolated CARD-11 protein having an amino acid sequence that is at least about 65%, preferably 75%, 85%, 95%, or 98% identical to the CARD domain of SEQ ID NO:11 (e.g., about amino acid residues 6-112 of SEQ ID NO:11); an isolated CARD-11 protein having an amino acid sequence that is at least about 65%, preferably 75%, 85%, 95%, or 98% identical to the coiled-coil domain of SEQ ID NO:11 (e.g., about amino acid residues 130-431 of SEQ ID NO:11); an isolated CARD-11 protein having an amino acid sequence that is at least about 65%, preferably 75%, 85%, 95%, or 98% identical to the PDZ domain of SEQ ID NO:11 (e.g., about amino acid residues 635-748 of SEQ ID NO:11); an isolated CARD-11 protein having an amino acid sequence that is at least about 65%, preferably 75%, 85%, 95%, or 98% identical to the SH3 domain of SEQ ID NO:11 (e.g., about amino acid residues 766-834 of SEQ ID NO:11); and an isolated CARD-11 protein having an amino acid sequence that is at least about 65%, preferably 75%, 85%, 95%, or 98% identical to the guanylate kinase (GUK) domain of SEQ ID NO:11 (e.g., about amino acid residues 882-1147 of SEQ ID NO:11);

Also within the invention are: an isolated CARD-9 protein which is encoded by a nucleic acid molecule having a nucleotide sequence that is at least about 65%, preferably 75%, 85%, or 95% identical to SEQ ID NO:3; an isolated CARD-9 protein which is encoded by a nucleic acid molecule having a nucleotide sequence at least about 65% preferably 75%, 85%, or 95% identical to the CARD domain encoding portion of SEQ ID NO:3; an isolated CARD-9 protein which is encoded by a nucleic acid molecule having a nucleotide sequence at least about 65% preferably 75%, 85%, or 95% identical to the coiled-coil domain encoding portion of SEQ ID NO:3; an isolated CARD-9 protein which is encoded by a nucleic acid molecule having a nucleotide sequence at least about 65% preferably 75%, 85%, or 95% identical to the indole-3-glycerol phosphate synthase homology domain encoding portion of SEQ ID NO:3; an isolated CARD-9 protein which is encoded by a nucleic acid molecule having a nucleotide sequence at least about 65% preferably 75%, 85%, or 95% identical to the cysteine rich repeat homology domain encoding portion of SEQ ID NO:3; and an isolated CARD-9 protein which is encoded by a nucleic acid molecule having a nucleotide sequence which hybridizes under stringent hybridization conditions to a nucleic acid molecule having the nucleotide sequence of SEQ ID NO:3.

Also within the invention are: an isolated CARD-9 protein which is encoded by a nucleic acid molecule having a nucleotide sequence that is at least about 65%, preferably 75%, 85%, or 95% identical to SEQ ID NO:6; an isolated CARD-9 protein which is encoded by a nucleic acid molecule having a nucleotide sequence at least about 65% preferably 75%, 85%, or 95% identical to the CARD domain encoding portion of SEQ ID NO:6; an isolated CARD-9 protein which is encoded by a nucleic acid molecule having a nucleotide sequence at least about 65% preferably 75%, 85%, or 95% identical to the coiled-coil domain encoding portion of SEQ ID NO:6; an isolated CARD-9 protein which is encoded by a nucleic acid molecule having a nucleotide sequence at least about 65% preferably 75%, 85%, or 95% identical to the indole-3-glycerol phosphate synthase homology domain encoding portion of SEQ ID NO:6; an isolated CARD-9 protein which is encoded by a nucleic acid molecule having a nucleotide sequence at least about 65% preferably 75%, 85%, or 95% identical to the cysteine rich repeat homology domain encoding portion of SEQ ID NO:6; and an isolated CARD-9 protein which is encoded by a nucleic acid molecule having a nucleotide sequence which hybridizes under stringent hybridization conditions to a nucleic acid molecule having the nucleotide sequence of SEQ ID NO:6.

Also within the invention are: an isolated CARD-10 protein which is encoded by a nucleic acid molecule having a nucleotide sequence that is at least about 65%, preferably 75%, 85%, or 95% identical to SEQ ID NO:9; an isolated CARD-10 protein which is encoded by a nucleic acid molecule having a nucleotide sequence at least about 65% preferably 75%, 85%, or 95% identical to the CARD domain encoding portion of SEQ ID NO:9; an isolated CARD-10 protein which is encoded by a nucleic acid molecule having a nucleotide sequence at least about 65% preferably 75%, 85%, or 95% identical to the coiled-coil domain encoding portion of SEQ ID NO:9; an isolated CARD-10 protein which is encoded by a nucleic acid molecule having a nucleotide sequence at least about 65% preferably 75%, 85%, or 95% identical to the SH3 domain encoding portion of SEQ ID NO:9; an isolated CARD-10 protein which is encoded by a nucleic acid molecule having a nucleotide sequence at least about 65% preferably 75%, 85%, or 95% identical to the guanylate kinase (GUK) domain encoding portion of SEQ ID NO:9; an isolated CARD-10 protein which is encoded by a nucleic acid molecule having a nucleotide sequence at least about 65% preferably 75%, 85%, or 95% identical to the tropomyosin domain encoding portion of SEQ ID NO:9; and an isolated CARD-10 protein which is encoded by a nucleic acid molecule having a nucleotide sequence which hybridizes under stringent hybridization conditions to a nucleic acid molecule having the nucleotide sequence of SEQ ID NO:9.

Also within the invention are: an isolated CARD-11 protein which is encoded by a nucleic acid molecule having a nucleotide sequence that is at least about 65%, preferably 75%, 85%, or 95% identical to SEQ ID NO:12; an isolated CARD-11 protein which is encoded by a nucleic acid molecule having a nucleotide sequence at least about 65% preferably 75%, 85%, or 95% identical to the CARD domain encoding portion of SEQ ID NO:12; an isolated CARD-11 protein which is encoded by a nucleic acid molecule having a nucleotide sequence at least about 65% preferably 75%, 85%, or 95% identical to the coiled-coil domain encoding portion of SEQ ID NO:12; an isolated CARD-11 protein which is encoded by a nucleic acid molecule having a nucleotide sequence at least about 65% preferably 75%, 85%, or 95% identical to the PDZ domain encoding portion of SEQ ID NO:12; an isolated CARD-11 protein which is encoded by a nucleic acid molecule having a nucleotide sequence at least about 65% preferably 75%, 85%, or 95% identical to the SH3 domain encoding portion of SEQ ID NO:12; an isolated CARD-11 protein which is encoded by a nucleic acid molecule having a nucleotide sequence at least about 65% preferably 75%, 85%, or 95% identical to the guanylate kinase (GUK) domain encoding portion of SEQ ID NO:12; and an isolated CARD-11 protein which is encoded by a nucleic acid molecule having a nucleotide sequence which hybridizes under stringent hybridization conditions to a nucleic acid molecule having the nucleotide sequence of SEQ ID NO:12.

The CARD-9, CARD-10, or CARD-11 polypeptides, nucleic acids, and antibodies of the invention may be useful for mapping the location of the CARD-9, CARD-10, or CARD-11 genes as well as the location of genes associated with diseases that map to the same region as the CARD-9, CARD-10, or CARD-11 genes. The CARD-10 gene is located in chromosome 22q13.1. The CARD-10 polypeptides, nucleic acids, and antibodies of the invention may be useful for mapping the location of the CARD-10 gene as well as the location of genes associated with the following diseases: spinocerebellar ataxia 10 and meningioma 1, both of which map to chromosome 22 in the region of the CARD-10 gene.

Another embodiment of the invention features CARD-9, CARD-10, or CARD-11 nucleic acid molecules which specifically detect CARD-9, CARD-10, or CARD-11 nucleic acid molecules, relative to nucleic acid molecules encoding other members of the CARD superfamily. For example, in one embodiment, a CARD-9, CARD-10, or CARD-11 nucleic acid molecule hybridizes under stringent conditions to a nucleic acid molecule comprising the nucleotide sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or a complement thereof. In another embodiment, the CARD-9, CARD-10, or CARD-11 nucleic acid molecule is at least 300 (350, 400, 450, 500, 550, 600, 650, 700, 800, 900, 1000, 1200, 1400, 1600, 1800, 2000, 2200, 2400, 2600, 2800, 3000, 3200, 3400, 3600, 3800, 4000, 4200, or 4250) nucleotides in length and hybridizes under stringent conditions to a nucleic acid molecule comprising the nucleotide sequence shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, or a complement thereof. In another embodiment, an isolated CARD-9, CARD-10, or CARD-11 nucleic acid molecule comprises the CARD domain encoding portion of SEQ ID NO:3, SEQ ID NO:6, SEQ ID NO:9, SEQ ID NO:12 or a complement thereof. In yet another embodiment, the invention provides an isolated nucleic acid molecule which is antisense to the coding strand of a CARD-9, CARD-10, or CARD-11 nucleic acid.

Another aspect of the invention provides a vector, e.g., a recombinant expression vector, comprising a CARD-9, CARD-10, or CARD-11 nucleic acid molecule of the invention. In another embodiment the invention provides a host cell containing such a vector. The invention also provides a method for producing CARD-9, CARD-10, or CARD-11 protein by culturing, in a suitable medium, a host cell of the invention containing a recombinant expression vector such that a CARD-9, CARD-10, or CARD-11 protein is produced.

Another aspect of this invention features isolated or recombinant CARD-9, CARD-10, or CARD-11 proteins and polypeptides. Preferred CARD-9, CARD-10, or CARD-11 proteins and polypeptides possess at least one biological activity possessed by naturally occurring human CARD-9, CARD-10, or CARD-11, e.g., (1) the ability to form protein:protein interactions with proteins in the apoptotic signaling pathway; (2) the ability to form CARD-CARD interactions with proteins in the apoptotic signaling pathway, e.g., Bcl-10; (3) the ability to bind a CARD-9, CARD-10, or CARD-11 ligand; (4) the ability to bind to an intracellular target; and (5) the ability to activate the NF-κB pathway. Other activities include: (1) modulation of cellular proliferation; (2) modulation of cellular differentiation; (3) modulation of cellular death; (4) modulation of the NF-κB pathway; and (5) modulation of stress-responsive signaling pathways.

The CARD-9, CARD-10, or CARD-11 proteins of the present invention, or biologically active portions thereof, can be operatively linked to a non-CARD-9, CARD-10, or CARD-11 polypeptide (e.g., heterologous amino acid sequences) to form CARD-9, CARD-10, or CARD-11 fusion proteins, respectively. The invention further features antibodies that specifically bind CARD-9, CARD-10, or CARD-11 proteins, such as monoclonal or polyclonal antibodies. In addition, the CARD-9, CARD-10, or CARD-11 proteins or biologically active portions thereof can be incorporated into pharmaceutical compositions, which optionally include pharmaceutically acceptable carriers.

In another aspect, the present invention provides a method for detecting the presence of CARD-9, CARD-10, or CARD-11 activity or expression in a biological sample by contacting the biological sample with an agent capable of detecting an indicator of CARD-9, CARD-10, or CARD-11 activity such that the presence of CARD-9, CARD-10, or CARD-11 activity is detected in the biological sample.

In another aspect, the invention provides a method for modulating CARD-9, CARD-10, or CARD-11 activity comprising contacting a cell with an agent that modulates (inhibits or stimulates) CARD-9, CARD-10, or CARD-11 activity or expression such that CARD-9, CARD-10, or CARD-11 activity or expression in the cell is modulated. Examples of CARD-9, CARD-10, or CARD-11 activities include the ability to bind to Bcl-10, stimulate the phosphorylation of Bcl-10, and stimulate the activation of NF-kB. In one embodiment, the agent is an antibody that specifically binds to CARD-9, CARD-10, or CARD-11 protein. In another embodiment, the agent modulates (increases or decreases) expression of CARD-9, CARD-10, or CARD-11 by modulating transcription of a CARD-9, CARD-10, or CARD-11 gene, splicing of a CARD-9, CARD-10, or CARD-11 mRNA, or translation of a CARD-9, CARD-10, or CARD-11 mRNA. In yet another embodiment, the agent is a nucleic acid molecule having a nucleotide sequence that is antisense to the coding strand of the CARD-9, CARD-10, or CARD-11 mRNA or the CARD-9, CARD-10, or CARD-11 gene.

In one embodiment, the methods of the present invention are used to treat a subject having a disorder characterized by aberrant CARD-9, CARD-10, or CARD-11 protein or nucleic acid expression or activity or related to CARD-9, CARD-10, or CARD-11 expression or activity by administering an agent which is a CARD-9, CARD-10, or CARD-11 modulator to the subject. In one embodiment, the CARD-9, CARD-10, or CARD-11 modulator is a CARD-9, CARD-10, or CARD-11 protein. In another embodiment the CARD-9, CARD-10, or CARD-11 modulator is a CARD-9, CARD-10, or CARD-11 nucleic acid molecule. In other embodiments, the CARD-9, CARD-10, or CARD-11 modulator is a peptide, peptidomimetic, or other small molecule.

The present invention also provides a diagnostic assay for identifying the presence or absence of a genetic lesion or mutation characterized by at least one of: (i) aberrant modification or mutation of a gene encoding a CARD-9, CARD-10, or CARD-11 protein; (ii) mis-regulation of a gene encoding a CARD-9, CARD-10, or CARD-11 protein; (iii) aberrant RNA splicing; and (iv) aberrant post-translational modification of a CARD-9, CARD-10, or CARD-11 protein, wherein a wild-type form of the gene encodes a protein with a CARD-9, CARD-10, or CARD-11 activity.

In another aspect, the invention provides a method for identifying a compound that modulates (increases or decreases) the ability of CARD-11 to stimulate the phosphorylation of Bcl-10. In general, the method entails measuring the ability of CARD-11 to stimulate the phosphorylation of Bcl-10 in the presence and absence of a test compound or test compounds, and identifying the compound or compounds that modulate the ability of CARD-11 to stimulate the phosphorylation of Bcl-10.

In another aspect, the invention provides a method for identifying a compound that binds to or modulates the activity of a CARD-9, CARD-10, or CARD-11 protein. In general, such methods entail measuring a biological activity of a CARD-9, CARD-10, or CARD-11 protein in the presence and absence of a test compound and identifying those compounds which alter the activity of the CARD-9, CARD-10, or CARD-11 protein.

The invention also features methods for identifying a compound which modulates the expression of CARD-9, CARD-10, or CARD-11 by measuring the expression of CARD-9, CARD-10, or CARD-11 in the presence and absence of a compound.

In another aspect, the invention features an isolated nucleic acid molecule comprising a nucleic acid sequence encoding a polypeptide comprising the amino acid sequence of SEQ ID NO:8. In one embodiment, the isolated nucleic acid molecule comprises a nucleic acid sequence encoding a polypeptide consisting of the amino acid sequence of SEQ ID NO:8.

In another aspect, the invention features an isolated nucleic acid molecule comprising a nucleic acid sequence encoding a polypeptide comprising at least 25, e.g., at least 50, 100, 200, 400, 800, 1000, or 1100, contiguous amino acids of the amino acid sequence of SEQ ID NO:8.

In another aspect, the invention features an isolated nucleic acid molecule comprising the nucleotide sequence of SEQ ID NO:9. In one embodiment, the isolated nucleic acid molecule comprises the nucleotide sequence of SEQ ID NO:7.

In another aspect, the invention features an isolated nucleic acid molecule comprising at least 50, e.g., at least 100, 200, 400, 800, 1200, 1600, 2000, 2500, or 3000, contiguous nucleotides of the nucleotide sequence of SEQ ID NO:7.

In another aspect, the invention features an isolated nucleic acid molecule comprising a nucleic acid sequence encoding a fusion protein comprising amino acids 23-123 of SEQ ID NO:8. In one embodiment, the nucleic acid molecule comprises a nucleic acid sequence encoding a fusion protein comprising the entire sequence of SEQ ID NO:8.

In another aspect, the invention features an isolated nucleic acid molecule comprising a nucleotide sequence encoding a polypeptide comprising an amino acid sequence that is at least 85% identical to the amino acid sequence of SEQ ID NO:8, wherein percent identity is calculated using ALIGN program in the GCG software package using a PAM120 weight residue table, a gap length penalty of 12, and a gap penalty of 4.

In another aspect, the invention features an isolated nucleic acid molecule that hybridizes to a nucleic acid molecule consisting of the nucleotide sequence of SEQ ID NO:7 under conditions of incubation at 45° C. in 6.0×SSC followed by washing in 0.2×SSC/0.1% SDS at 50° C.

In another aspect, the invention features an isolated nucleic acid molecule that hybridizes to a nucleic acid molecule consisting of the nucleotide sequence of SEQ ID NO:7 under conditions of incubation at 45° C. in 6.0×SSC followed by washing in 0.2×SSC/0.1% SDS at 65° C.

In another aspect, the invention features a nucleic acid described herein, further comprising vector nucleic acid sequences.

In another aspect, the invention features a host cell, e.g., a mammalian host cell, containing a nucleic acid described herein.

In another aspect, the invention features an isolated polypeptide comprising the amino acid sequence of SEQ ID NO:8. In one embodiment, the polypeptide consists of the amino acid sequence of SEQ ID NO:8.

In another aspect, the invention features an isolated polypeptide comprising at least 25, e.g., at least 50, 100, 200, 400, 800, 1000, or 1100, contiguous amino acids of the amino acid sequence of SEQ ID NO:8.

In another aspect, the invention features a fusion protein comprising amino acids 23-123 of SEQ ID NO:8. In one embodiment, the fusion protein comprises the entire sequence of SEQ ID NO:8.

In another aspect, the invention features an antibody which selectively binds to a polypeptide comprising the amino acid sequence of SEQ ID NO:8.

In another aspect, the invention features a method for producing a polypeptide comprising the amino acid sequence of SEQ ID NO:8, the method comprising culturing a host cell described herein under conditions in which a polypeptide comprising the amino acid sequence of SEQ ID NO:8 is expressed.

In another aspect, the invention features a method for detecting the presence of a polypeptide in a sample, the method comprising: contacting the sample with a compound that selectively binds to a polypeptide comprising the amino acid sequence of SEQ ID NO:8; and determining whether the compound binds to a polypeptide in the sample. In one embodiment of the method, the compound that selectively binds to the polypeptide is an antibody.

In another aspect, the invention features a kit comprising a compound that selectively binds to a polypeptide comprising the amino acid sequence of SEQ ID NO:8 and instructions for use. In one embodiment of the kit, the compound that selectively binds to the polypeptide is an antibody.

In another aspect, the invention features a method for identifying a compound that binds to a polypeptide, the method comprising the steps of: contacting a cell or a sample comprising a polypeptide comprising amino acids 23-123 of SEQ ID NO:8 with a test compound; and determining whether the polypeptide binds to the test compound. In one embodiment, the polypeptide comprises the amino acid sequence of SEQ ID NO:8.

In another aspect, the invention features a method for identifying a compound that modulates (increases or decreases) the ability of a polypeptide to bind to Bcl-10, the method comprising: contacting a polypeptide comprising amino acids 23-123 of SEQ ID NO:8 with a test compound; and determining the effect of the test compound on the ability of the polypeptide to bind to Bcl-10. In one embodiment, the polypeptide comprises the amino acid sequence of SEQ ID NO:8. In general, the method entails measuring the ability of the polypeptide to bind to Bcl-10 in the presence and absence of a test compound or test compounds, and identifying the compound or compounds that modulate the ability of the polypeptide to bind to Bcl-10.

In another aspect, the invention features a method for identifying a compound that modulates (increases or decreases) the ability of a polypeptide to increase the activity of NF-κB, the method comprising: contacting a polypeptide comprising amino acids 23-123 of SEQ ID NO:8 with a test compound; and determining the effect of the test compound on the ability of the polypeptide to increase the activity of NF-κB. In one embodiment, the polypeptide comprises the amino acid sequence of SEQ ID NO:8. In general, the method entails measuring the ability of the polypeptide to increase the activity of NF-kB in the presence and absence of a test compound or test compounds, and identifying the compound or compounds that modulate the ability of the polypeptide to increase the activity of NF-kB.

In another aspect, the invention features a method for detecting the presence of a nucleic acid molecule in a sample, the method comprising: contacting the sample with a nucleic acid probe or primer which selectively hybridizes to a nucleic acid molecule comprising SEQ ID NO:7 or SEQ ID NO:9; and determining whether the nucleic acid probe or primer binds to a nucleic acid molecule in the sample. In one embodiment, the sample comprises mRNA molecules and is contacted with a nucleic acid probe.

In another aspect, the invention features a method for modulating the activity of a polypeptide, the method comprising contacting a polypeptide comprising the amino acid sequence of SEQ ID NO:8 or a cell expressing the polypeptide with a compound that binds to the polypeptide in a sufficient concentration to modulate the activity of the polypeptide. In one embodiment, the compound modulates the ability of the polypeptide to bind to Bcl-10. In another embodiment, the compound modulates the ability of the polypeptide to increase the activity of NF-κB.

In another aspect, the invention features a method of treating a disorder associated with inappropriate apoptosis, the method comprising: selecting an individual that has a disorder associated with inappropriate apoptosis; and modulating the expression or activity of a polypeptide comprising the amino acid sequence of SEQ ID NO:8.

In another aspect, the invention features a method of treating a disorder associated with inappropriate lymphocyte activation, the method comprising: selecting an individual that has a disorder associated with inappropriate lymphocyte activation; and modulating the expression or activity of a polypeptide comprising the amino acid sequence of SEQ ID NO:8.

Other features and advantages of the invention will be apparent from the following detailed description and claims.

BRIEF DESCRIPTION OF THE DRAWINGS

FIGS. 1A-B depict the cDNA sequence (SEQ ID NO:1) and the predicted amino acid sequence (SEQ ID NO:2) of rat CARD-9. The open reading frame of rat CARD-9 (SEQ ID NO:1) extends from nucleotide 113 to nucleotide 1720 of SEQ ID NO:1 (SEQ ID NO:3).

FIG. 4A depicts an alignment of amino acids 7-98 of rat CARD-9 (amino acid residues 7-98 of SEQ ID NO:2) with a consensus caspase recruitment domain (CARD) derived from a hidden Markov model (SEQ ID NO:13).

FIG. 4B depicts an alignment of amino acids 197-213 of rat CARD-9 (amino acid residues 197-213 of SEQ ID NO:2) with a consensus indole-3-glycerol phosphate synthase domain derived from a hidden Markov model (SEQ ID NO:14).

FIG. 4C depicts an alignment of amino acids 285-338 of rat CARD-9 (amino acid residues 285-338 of SEQ ID NO:2) with a consensus cysteine rich repeat domain derived from a hidden Markov model (SEQ ID NO:15).

FIGS. 5A-B depict the cDNA sequence (SEQ ID NO:4) and the predicted amino acid sequence (SEQ ID NO:5) of human CARD-9. The open reading frame of human CARD-9 (SEQ ID NO:4) extends from nucleotide 144 to nucleotide 1751 of SEQ ID NO:4 (SEQ ID NO:6).

FIG. 8A depicts an alignment of amino acids 7-98 of human CARD-9 (amino acid residues 7-98 of SEQ ID NO:5) with a consensus caspase recruitment domain (CARD) derived from a hidden Markov model (SEQ ID NO:13).

FIG. 8B depicts an alignment of amino acids 197-213 of human CARD-9 (amino acid residues 197-213 of SEQ ID NO:5) with a consensus indole-3-glycerol phosphate synthase domain derived from a hidden Markov model (SEQ ID NO:14).

FIG. 8C depicts an alignment of amino acids 285-338 of human CARD-9 (amino acid residues 285-338 of SEQ ID NO:5) with a consensus cysteine rich repeat domain derived from a hidden Markov model (SEQ ID NO:15).

FIG. 9 depicts an alignment of amino acids 1-536 of rat CARD-9 (amino acid residues 1-536 of SEQ ID NO:2) and amino acids 1-536 of human CARD-9 (amino acid residues 1-536 of SEQ ID NO:5). This alignment was created using GAP (gap weight 12; length weight 4). In this alignment the sequences are 86.1% identical.

FIGS. 10A-C depict the cDNA sequence (SEQ ID NO:7) and the predicted amino acid sequence (SEQ ID NO:8) of human CARD-10. The open reading frame of human CARD-10 (SEQ ID NO:7) extends from nucleotide 41 to nucleotide 3136 of SEQ ID NO:7 (SEQ ID NO:9).

FIG. 13A depicts an alignment of amino acids 24-115 of human CARD-10 (amino acid residues 24-115 of SEQ ID NO:8) with a consensus caspase recruitment domain (CARD) derived from a hidden Markov model (SEQ ID NO:13).

FIG. 13B depicts an alignment of amino acids 366-398 of human CARD-10 (amino acid residues 366-398 of SEQ ID NO:8) with a consensus tropomyosin domain derived from a hidden Markov model (SEQ ID NO:16).

FIGS. 14A-C depict the cDNA sequence (SEQ ID NO:10) and the predicted amino acid sequence (SEQ ID NO:11) of human CARD-11. The open reading frame of human CARD-11 (SEQ ID NO:10) extends from nucleotide 328 to nucleotide 3768 of SEQ ID NO:10 (SEQ ID NO:12).

FIG. 17A depicts an alignment of amino acids 12-103 of human CARD-11 (amino acid residues 12-103 of SEQ ID NO:11) with a consensus caspase recruitment domain (CARD) derived from a hidden Markov model (SEQ ID NO:13).

FIG. 17B depicts an alignment of amino acids 635-747 of human CARD-11 (amino acid residues 635-747 of SEQ ID NO:11) with a consensus PDZ domain derived from a hidden Markov model (SEQ ID NO:17).

FIG. 17C depicts an alignment of amino acids 1003-1091 of human CARD-1 (amino acid residues 1003-1091 of SEQ ID NO:11) with a consensus GUK domain derived from a hidden Markov model (SEQ ID NO:18).

FIGS. 18A, 18B, 18C, 18D, 18E, and 18F depict the results of a series of experiments demonstration that CARD-9 interacts directly with Bcl-10. In these studies, 293T cells were transfected with expression plasmids encoding T7 epitope-tagged, Flag epitope-tagged, or Myc-epitope-tagged Bcl-10 or CARD-9 as indicated. After 36 h, extracts were prepared and immunoprecipitated (IP) with a monoclonal antibody to the Flag epitope. The immunoprecipitates were analyzed by SDS-PAGE and immunoblotted with a horseradish peroxidase-conjugated T7-antibody (FIG. 18A) or MYC-antibody (FIGS. 18B and 18C). The cellular extracts were also immunoblotted (WB) with anti-Flag and anti-T7 antibody (upper panel of FIG. 18A), anti-Flag or anti-Myc antibody (upper and middle panel of FIG. 18D and FIG. 18C). FIG. 18A demonstrates the in vivo interaction of CARD-9 with Bcl-10. FIG. 18B and FIG. 18C demonstrate that CARD-9 can self-associate and interact with Bcl-10 through the CARD domain. FIG. 18D demonstrates in vitro interaction of CARD-9 with GST-Bcl-10. In this study, $^{35}$S-labeled CARD-9 (lane 1, 5% input) was precipitated with an equal amount of glutathione sepharose beads bound to an equal amount of proteins, GST (lane2), GST-Bcl-10 (lane3), GST-Bcl-10-L41R (lane 4) and then analyzed by SDS-PAGE and autoradiography. The point mutation L41R within the CARD domain abrogates its ability to interact with CARD-9. FIG. 18E and FIG. 18F demonstrate the endogenous interaction of CARD-9 with Bcl-10. Thp1 cell ($5\times10^6$) extracts were collected and immunoprecipitated with a monoclonal antibody to the Bcl-10 epitope (FIG. 18E and FIG. 18F, lane 2), T7 antibody (FIG. 18E and FIG. 18F, lane 5; HC, heavy chain; LC, light chain), or anti-mouse IgG agarose (FIG. 18E, lane 3). The immunoprecipitates were analyzed by SDS-PAGE and immunoblotted with CARD-9 polyclonal antibody (FIG. 18D) or Bcl-10 monoclonal antibody (FIG. 18E). The cellular extracts were also immunoblotted (WB) with polyclonal CARD-9 antibody (FIG. 18E, lane 1) or monoclonal Bcl-10 antibody (FIG. 18F, lane 1) to detect the endogenous protein expression. Also, Bcl-10 antibody was incubated with the anti-mouse IgG agarose and analyzed by immunoblotting with CARD-9 antibody to rule out the possibility of cross-reaction (FIG. 18E, lane 4).

DETAILED DESCRIPTION OF THE INVENTION

Figure 2:
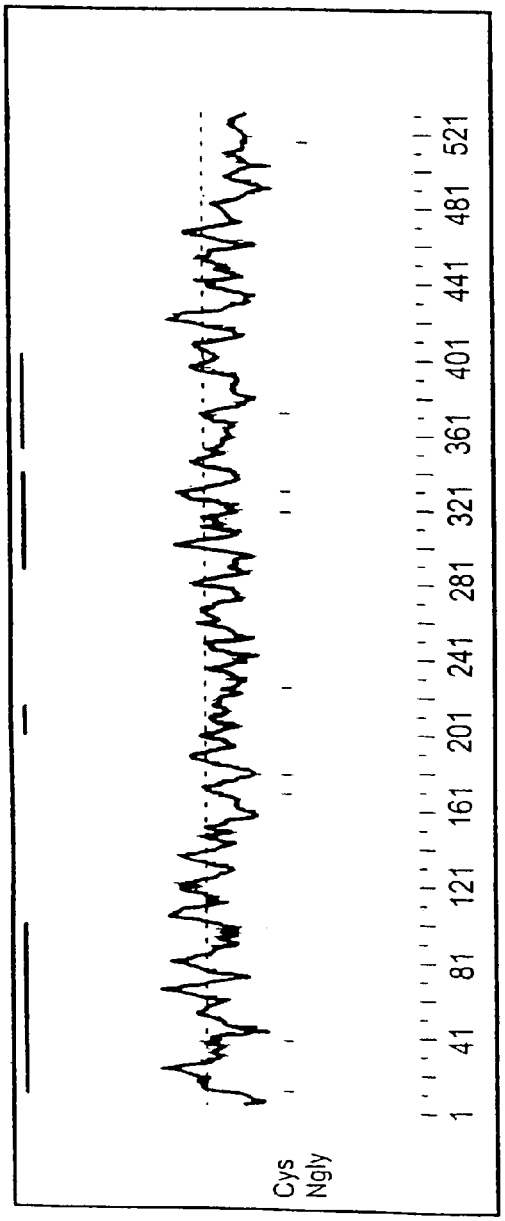
FIG. 2 depicts a hydropathy plot of rat CARD-9. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

The present invention is based, in part, on the identification of a predicted mRNA sequence encoding rat CARD-9 protein. A nucleotide sequence encoding a rat CARD-9 protein is shown in FIGS. 1A-B (SEQ ID NO:1; SEQ ID NO:3 includes the open reading frame only). A predicted amino acid sequence of rat CARD-9 protein is also shown in FIGS. 1A-B (SEQ ID NO:2).

The present invention is also based, in part, on the identification of a predicted mRNA sequence encoding human CARD-9 protein. A nucleotide sequence encoding a human CARD-9 protein is shown in FIGS. 5A-B (SEQ ID NO:4; SEQ ID NO:6 includes the open reading frame only). A predicted amino acid sequence of human CARD-9 protein is also shown in FIGS. 5A-B (SEQ ID NO:5).

The present invention is also based, in part, on the identification of a predicted mRNA sequence encoding human CARD-10 protein. A nucleotide sequence encoding a human CARD-10 protein is shown in FIGS. 10A-C (SEQ ID NO:7; SEQ ID NO:9 includes the open reading frame only). A predicted amino acid sequence of human CARD-10 protein is also shown in FIGS. 10A-C (SEQ ID NO:8).

The present invention is also based, in part, on the identification of a predicted mRNA sequence encoding human CARD-11 protein. A nucleotide sequence encoding a human CARD-11 protein is shown in FIGS. 14A-C (SEQ ID NO:10; SEQ ID NO:12 includes the open reading frame only). A predicted amino acid sequence of human CARD-11 protein is also shown in FIGS. 14A-C (SEQ ID NO:11).

Identification of Rat CARD-9

A cDNA encoding rat CARD-9 was identified by a hidden Markov model (HMM) search for CARD-encoding cDNA sequences present in a proprietary rat neuronal cDNA library. The search of the translated cDNA sequence database was performed in three reading frames, forward and reverse. This search led to the identification of a sequence predicted to encode a CARD domain-containing protein later identified as rat CARD-9.

FIGS. 1A-B depict the sequence of a 1879 nucleotide cDNA (SEQ ID NO:1) which includes a predicted open reading frame (SEQ ID NO:3; nucleotides 113-1720 of SEQ ID NO:1) encoding a 536 amino acid rat CARD-9 protein (SEQ ID NO:3). Rat CARD-9 is predicted to be an intracellular protein. This CARD-9 protein is predicted to have a molecular weight of 62.2 kD prior to post-translational modifications.

The predicted amino acid sequence of rat CARD-9 was compared to amino acid sequences of known proteins and various motifs were identified. The 536 amino acid rat CARD-9 protein includes an N-glycosylation site (e.g., about amino acid residues 524-527 of SEQ ID NO:2); two cAMP- and cGMP-dependent protein kinase phosphorylation sites (e.g., about amino acid residues 92-95 and 228-231 of SEQ ID NO:2); nine protein kinase C phosphorylation sites (e.g., about amino acid residues 16-18, 95-97, 138-140, 231-233, 303-305, 362-364, 431-433, 451-453, and 514-516 of SEQ ID NO:2); 13 casein kinase II phosphorylation sites (e.g., about amino acid residues 2-5, 12-15, 23-26, 95-98, 138-141, 171-174, 267-270, 362-365, 374-377, 425-428, 483-486, 526-529, and 531-534 of SEQ ID NO:2); a tyrosine kinase phosphorylation site (e.g., about amino acid residues 176-183 of SEQ ID NO:2); and an N-myristoylation site (e.g., about amino acid residues 523-528 of SEQ ID NO:2).

FIG. 2 depicts a hydropathy plot of rat CARD-9. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

Figure 3:
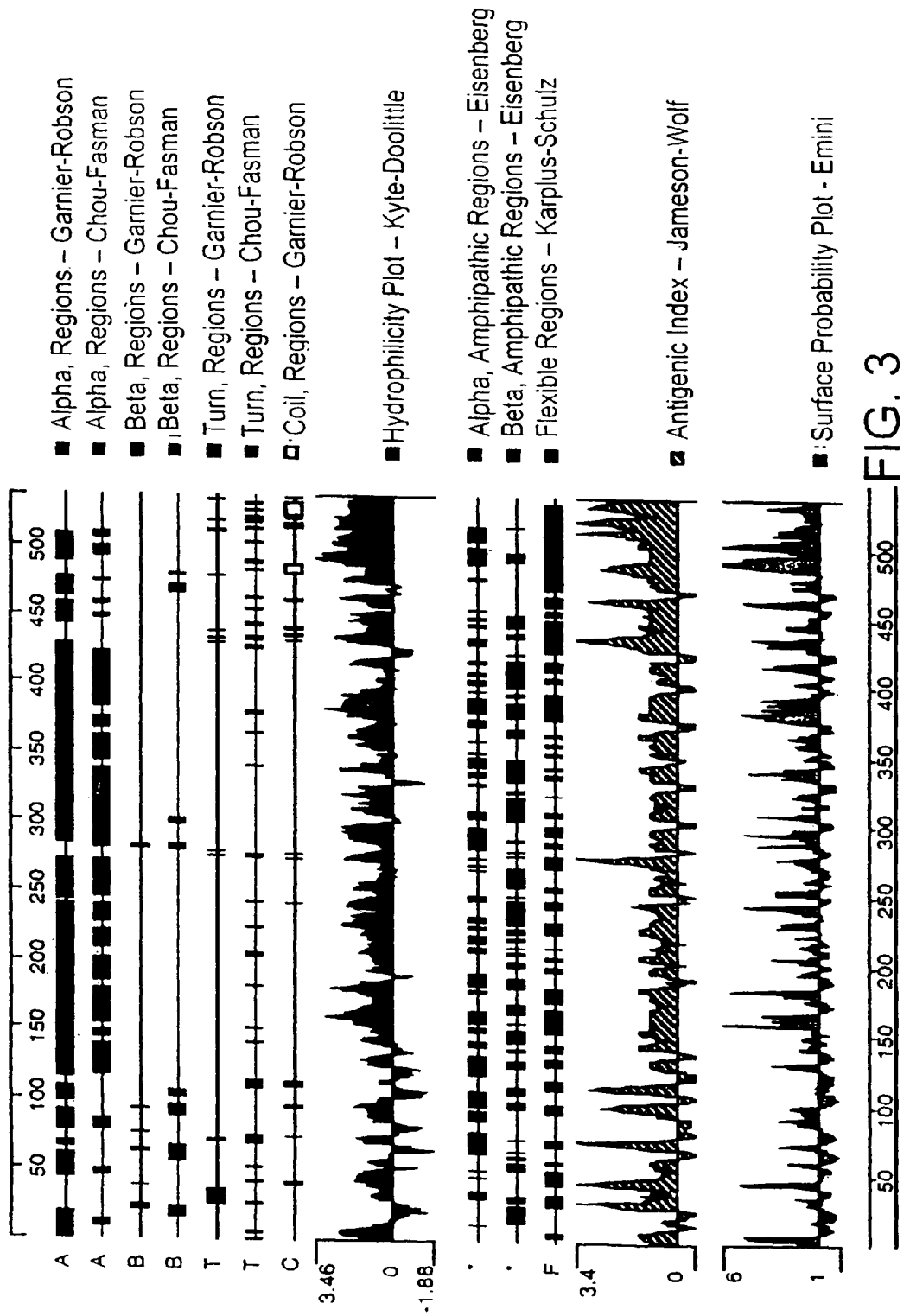
FIG. 3 depicts a plot showing the predicted structural features of rat CARD-9. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

A plot showing the predicted structural features of rat CARD-9 is presented in FIG. 3. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

An analysis of the predicted rat CARD-9 amino acid sequence showed it to contain several potential functional domains: a CARD domain (e.g., about amino acid residues 7-98 of SEQ ID NO:2); a coiled-coil domain (e.g., about amino acid residues 140-416 of SEQ ID NO:2); an indole-3-glycerol phosphate synthase homology region (e.g., about amino acid residues 197-213 of SEQ ID NO:2); and a cysteine rich repeat homology region (e.g., about amino acid residues 285-338 of SEQ ID NO:2).

FIG. 4A depicts an alignment of amino acids 7-98 of rat CARD-9 (amino acid residues 7-98 of SEQ ID NO:2) with a consensus caspase recruitment domain (CARD) derived from a HMM.

FIG. 4B depicts an alignment of amino acids 197-213 of rat CARD-9 (amino acid residues 197-213 of SEQ ID NO:2) with a consensus indole-3-glycerol phosphate synthase domain derived from a HMM.

FIG. 4C depicts an alignment of amino acids 285-338 of rat CARD-9 (amino acid residues 285-338 of SEQ ID NO:2) with a consensus cysteine rich repeat domain derived from a HMM.

The domain alignments depicted in FIGS. 4A-C were identified by homology searching using consensus domains derived from hidden Markov models (HMMs). HMMs can be used to perform multiple sequence alignment and very sensitive database searching, using statistical descriptions of a domain's consensus sequence. For more information on HMM searches, see, e.g., the HMM website maintained by Washington University. In the alignments of FIGS. 4A-C a single letter amino acid designation at a position on the line between the CARD-9 sequence and the HMM-generated consensus domain sequence indicates an exact match between the two. A "+" in this middle line indicates a conservative substitution at the particular residue of CARD-9. Amino acid residues located in the domains identified by the VIM search may be important for the appropriate functioning of the CARD-9 protein. For this reason, amino acid substitutions with respect to the sequence of SEQ ID NO:2 that are outside of the domains homologous to HMM consensus domains may be less detrimental to the activity of the CARD-9 protein.

Identification of Human CARD-9

A cDNA encoding human CARD-9 was identified by using the rat CARD-9 cDNA described above to conduct a BLAST search of cDNA sequences from a proprietary human megakaryocyte library. This search led to the identification of a sequence predicted to encode a CARD domain-containing protein later identified as human CARD-9.

FIGS. 5A-B depict the sequence of a 2098 nucleotide cDNA (SEQ ID NO:4) which includes a predicted open reading frame (SEQ ID NO:6; nucleotides 144-1751 of SEQ ID NO:4) encoding a 536 amino acid human CARD-9 protein (SEQ ID NO:5). Human CARD-9 is predicted to be an intracellular protein. This CARD-9 protein is predicted to have a molecular weight of 62.2 kD prior to post-translational modifications.

The predicted amino acid sequence of human CARD-9 was compared to amino acid sequences of known proteins and various motifs were identified. The 536 amino acid human CARD-9 protein includes an N-glycosylation site (e.g., about amino acid residues 524-527 of SEQ ID NO:5); three cAMP- and cGMP-dependent protein kinase phosphorylation sites (e.g., about amino acid residues 92-95, 228-231, and 333-336 of SEQ ID NO:5); seven protein kinase C phosphorylation sites (e.g., about amino acid residues 95-97, 138-140, 231-233, 303-305, 431-433, 450-452, and 460-462 of SEQ ID NO:5); ten casein kinase II phosphorylation sites (e.g., about amino acid residues 2-5, 23-26, 95-98, 138-141, 267-270, 363-366, 425-428, 483-486, 526-529, and 531-534 of SEQ ID NO:5); a tyrosine kinase phosphorylation site (e.g., about amino acid residues 176-183 of SEQ ID NO:5); and three N-myristoylation sites (e.g., about amino acid residues 453-458, 481-486, and 527-532 of SEQ ID NO:5).

Figure 6:
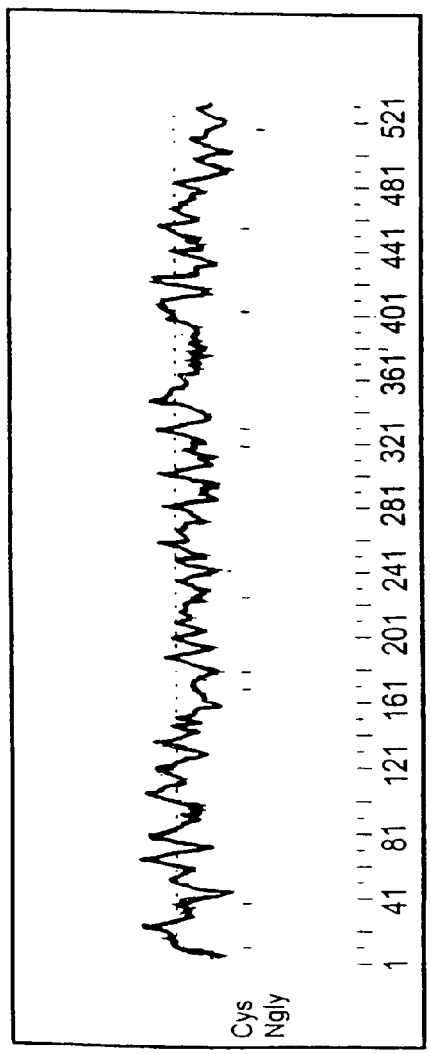
FIG. 6 depicts a hydropathy plot of human CARD-9. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

FIG. 6 depicts a hydropathy plot of human CARD-9. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

Figure 7:
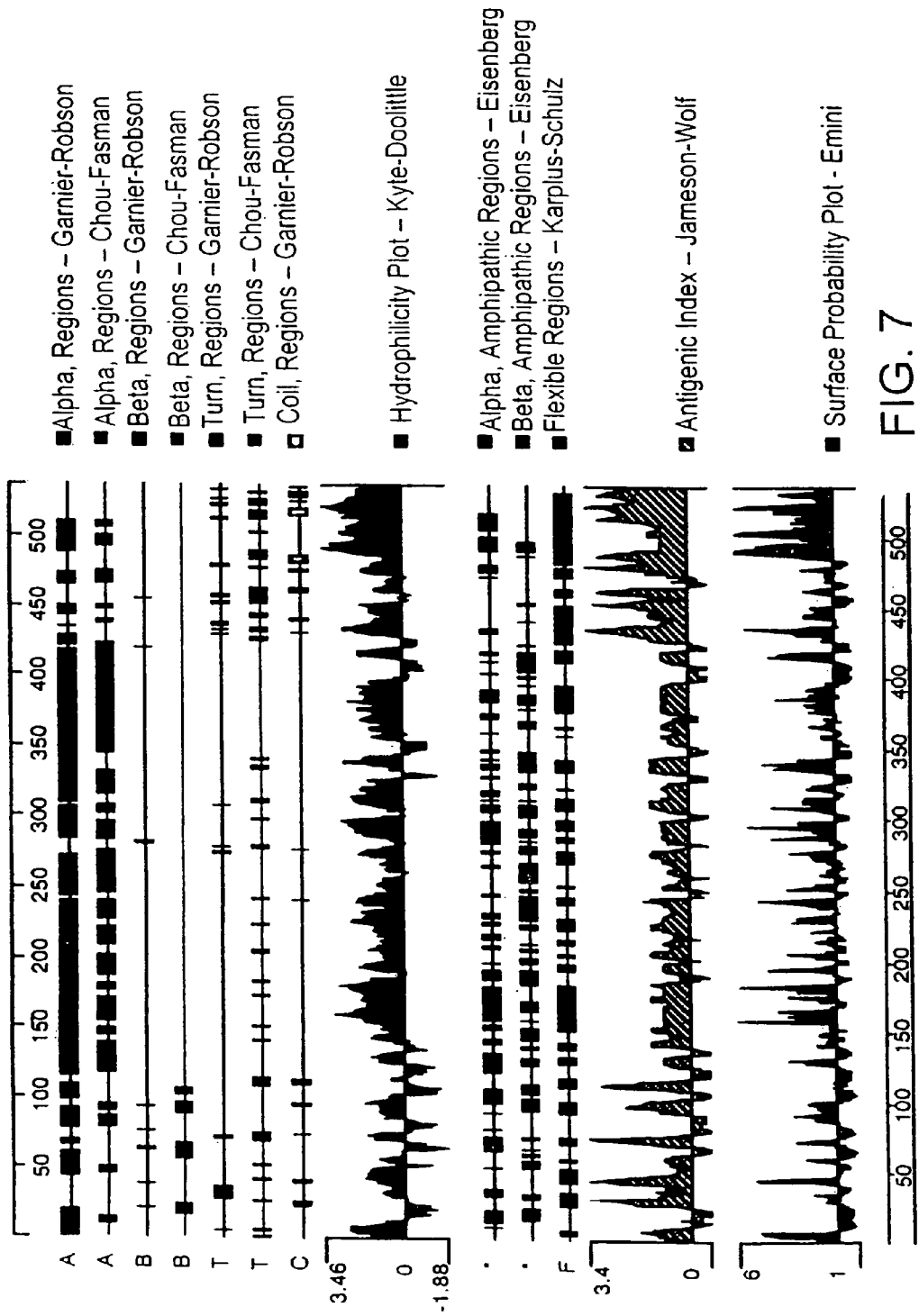
FIG. 7 depicts a plot showing the predicted structural features of human CARD-9. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

A plot showing the predicted structural features of human CARD-9 is presented in FIG. 7. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

An analysis of the predicted human CARD-9 amino acid sequence showed it to contain several potential functional domains: a CARD domain (e.g., about amino acid residues 7-98 of SEQ ID NO:5); a coiled-coil domain (e.g., about amino acid residues 140-416 of SEQ ID NO:5); an indole-3-glycerol phosphate synthase homology region (e.g., about amino acid residues 197-213 of SEQ ID NO:5); and a cysteine rich repeat homology region (e.g., about amino acid residues 285-338 of SEQ ID NO:5).

FIG. 8A depicts an alignment of amino acids 7-98 of human CARD-9 (amino acid residues 7-98 of SEQ ID NO:5) with a consensus caspase recruitment domain (CARD) derived from a HMM.

FIG. 8B depicts an alignment of amino acids 197-213 of human CARD-9 (amino acid residues 197-213 of SEQ ID NO:5) with a consensus indole-3-glycerol phosphate synthase domain derived from a HMM.

FIG. 8C depicts an alignment of amino acids 285-338 of human CARD-9 (amino acid residues 285-338 of SEQ ID NO:5) with a consensus cysteine rich repeat domain derived from a HMM.

The domain alignments of FIGS. 8A-C were identified by homology searching using consensus domains derived from hidden Markov models (HMMs). HMMs can be used to do multiple sequence alignment and very sensitive database searching, using statistical descriptions of a domain's consensus sequence. For more information on HMM searches, see, e.g., the HMM website maintained by Washington University. In the alignments of FIGS. 8A-C a single letter amino acid designation at a position on the line between the CARD-9 sequence and the HMM-generated consensus domain sequence indicates an exact match between the two. A "+" in this middle line indicates a conservative substitution at the particular residue of CARD-9. Amino acid residues located in the domains identified by the HMM search may be important for the appropriate functioning of the CARD-9 protein. For this reason, amino acid substitutions with respect to the sequence of SEQ ID NO:5 that are outside of the domains homologous to HMM consensus domains may be less detrimental to the activity of the CARD-9 protein.

The N-terminal region of CARD-9 (residues 7-98) shares significant similarity with CARD motifs found in many apoptosis proteins, including those found in Bcl-10/CLAP (29% identity, 44% similarity) and RAIDD (28% identity, 40% similarity).

The central region of CARD-9 (residues 140-420 or residues 140-416) contains heptad repeats characteristic of coiled-coil structures that function in protein oligomerization. The COILS2 (Lupas, 1996, *Trends Biochem. Sci.* 21:375) program predicts the existence of at least three coiled-coil regions with a probability of greater than 80% (residues 140-230, 243-277 and 332-419) that are interrupted by regions predicted to have low coiled-coil potential. Correspondingly, BLAST analysis of this region showed strong similarity to coiled-coil regions of other proteins, including myosins and plectins.

Northern blot analysis was performed and a 2.1-kilobase transcript corresponding to CARD-9 was identified in a variety of human adult tissues, including spleen, liver, placenta, lung, PBL and brain. CARD-9 was also expressed abundantly in the HL60 cancer cell line and showed some expression in fetal liver tissue.

FIG. 9 depicts an alignment of amino acids 1-536 of rat CARD-9 (amino acid residues 1-536 of SEQ ID NO:2) and amino acids 1-536 of human CARD-9 (amino acid residues 1-536 of SEQ ID NO:5). This alignment was created using GAP (gap weight 12; length weight 4). In this alignment the sequences are 86.1% identical.

Identification of Human CARD-10

A cDNA encoding human CARD-10 was identified by using the rat CARD-9 cDNA described above to conduct a BLAST search of cDNA sequences from a proprietary skin library. 3' RACE was performed on a partial cDNA isolated from the skin library to determine the 3' sequences of the cDNA. The cDNA sequence was predicted to encode a CARD domain-containing protein and was later identified as human CARD-10.

FIGS. 10A-C depict the sequence of a 3949 nucleotide cDNA (SEQ ID NO:7) which includes a predicted open reading frame (SEQ ID NO:9; nucleotides 41-3136 of SEQ ID NO:7) encoding a 1032 amino acid human CARD-10 protein (SEQ ID NO:8). Human CARD-10 is predicted to be an intracellular protein. This CARD-10 protein is predicted to have a molecular weight of 115.9 kD prior to post-translational modifications.

The predicted amino acid sequence of human CARD-10 was compared to amino acid sequences of known proteins and various motifs were identified. The 1032 amino acid human CARD-10 protein includes four N-glycosylation sites (e.g., about amino acid residues 76-79, 472-475, 595-598, and 712-715 of SEQ ID NO:8); a glycosaminoglycan attachment site (e.g., about amino acid residues 638-641 of SEQ ID NO:8); 14 protein kinase C phosphorylation sites (e.g., about amino acid residues 68-70, 78-80, 293-295, 313-315, 512-514, 558-560, 603-605, 642-644, 754-756, 782-784, 830-832, 868-870, 947-949, and 1022-1024 of SEQ ID NO:8); 19 casein kinase II phosphorylation sites (e.g., about amino acid residues 18-21, 112-115, 242-245, 293-296, 331-334, 412-415, 438-441, 478-481, 510-513, 549-552, 570-573, 681-684, 690-693, 714-717, 748-751, 754-757, 869-872, 882-885, and 1028-1031 of SEQ ID NO:8); two tyrosine kinase phosphorylation sites (e.g., about amino acid residues 201-207 and 733-739 of SEQ ID NO:8); 11 N-myristoylation sites (e.g., about amino acid residues 15-20, 113-118, 309-314, 487-492, 565-570, 656-661, 761-766, 809-814, 893-898, 981-986, and 1021-1026 of SEQ ID NO:8); two amidation sites (e.g., about amino acid residues 88-91 and 915-918 of SEQ ID NO:8); and two leucine zipper patterns (e.g., about amino acid residues 230-251 and 426-447 of SEQ ID NO:8).

Figure 11:
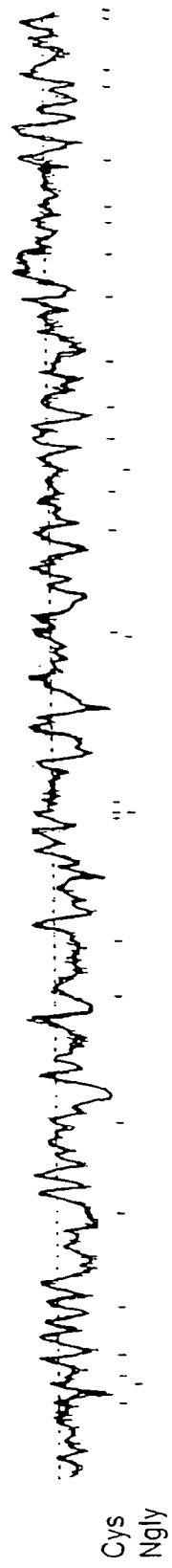
FIG. 11 depicts a hydropathy plot of human CARD-10. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

FIG. 11 depicts a hydropathy plot of human CARD-10. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

Figure 12:
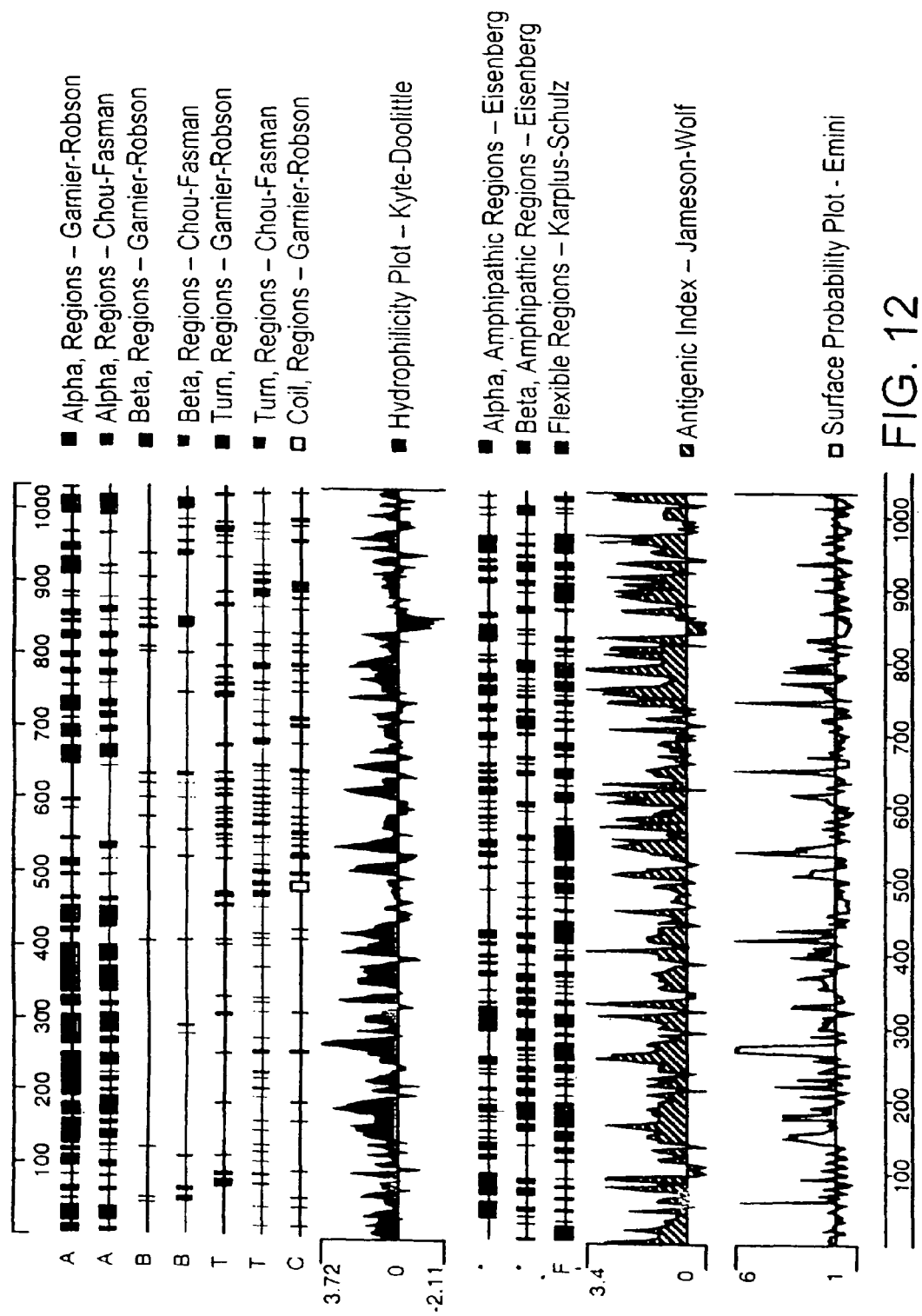
FIG. 12 depicts a plot showing the predicted structural features of human CARD-10. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

A plot showing the predicted structural features of human CARD-10 is presented in FIG. 12. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

An analysis of the predicted human CARD-10 amino acid sequence showed it to contain several potential functional domains: a CARD domain (e.g., about amino acid residues 23-123 of SEQ ID NO:8); a coiled-coil domain (e.g., about amino acid residues 147-457 of SEQ ID NO:8); an SH3 domain (e.g., about amino acid residues 704-772 of SEQ ID NO:8); a guanylate kinase (GUK) domain (e.g., about amino acid residues 830-1032 of SEQ ID NO:8); and a tropomyosin domain (e.g., about amino acid residues 366-398 of SEQ ID NO:8).

Although the CARD of CARD-10 shows significant similarity to those found in other CARD family members, it is highly similar to the CARD domains of CARD-11 (58% identity), CARD-14 (46% identity) and CARD-9 (46%). Adjacent to the N-terminal CARD domain are coiled-coil structures with extensive regions of heptad repeats that function in protein oligomerization and activation (Lupas, 1996, *Trends Biochem. Sci.* 21:375). The COILS2 program predicts with a probability of greater than 70% at least four coiled-coil structures in CARD-10 (e.g., located at about residues 138-206, 210-256, 263-307, and 326-456 of SEQ ID NO:8) that are interrupted by regions with a lower coiled-coil potential. The PDZ/SH3/GUK tripartite structure found at the C-terminus classifies CARD-10 as a member of the MAGUK family of proteins that function to organize signaling complexes at plasma membranes.

Northern blot analysis was performed and a 4.4-kilobase transcript corresponding to CARD-10 was identified in a variety of human adult tissues, including heart, muscle, kidney, liver, intestine, placenta, and lung. CARD-10 also showed abundant expression in lung, liver, and kidney fetal tissues, as well as in multiple cancer cell lines, including HeLa S3, Chronic Myelogenous Leukemia K562 cells, Colorectal Adenocarcinoma SW480 cells and Lung Carcinoma A549 cells.

FIG. 13A depicts an alignment of amino acids 24-115 of human CARD-10 (amino acid residues 24-115 of SEQ ID NO:8) with a consensus caspase recruitment domain (CARD) derived from a HMM.

FIG. 13B depicts an alignment of amino acids 366-398 of human CARD-10 (amino acid residues 366-398 of SEQ ID NO:8) with a consensus tropomyosin domain derived from a HMM.

The domain alignments of FIGS. 13A-B were identified by homology searching using consensus domains derived from hidden Markov models (HMMs). HAMs can be used to do multiple sequence alignment and very sensitive database searching, using statistical descriptions of a domain's consensus sequence. For more information on HMM searches, see, e.g., the HMM website maintained by Washington University. In the alignments of FIGS. 13A-B a single letter amino acid designation at a position on the line between the CARD-10 sequence and the HMM-generated consensus domain sequence indicates an exact match between the two. A "+" in this middle line indicates a conservative substitution at the particular residue of CARD-10. Amino acid residues located in the domains identified by the H search may be important for the appropriate functioning of the CARD-10 protein. For this reason, amino acid substitutions with respect to the sequence of SEQ ID NO:8 that are outside of the domains homologous to HMM consensus domains may be less detrimental to the activity of the CARD-10 protein.

The CARD-10 amino acid sequence was used to perform a BLASTP search against the publicly available PROT database (see the BLAST website maintained by Washington University). This search identified two clones (GenBank™ Accession Numbers CAB63075 and CAB63076) that are each 99% identical to CARD-10 in a region spanning amino acids 705-1032 of CARD-10. These clones were generated from bacterial clone contigs of human chromosome 22. This analysis indicates that the gene for CARD-10 is located on chromosome 22.

The map position of the CARD-10 gene was determined by performing a BLASTN search using the 3,949 nucleotide CARD-10 sequence of SEQ ID NO:7 against the publicly available High Throughput Genome Sequencing (HTGS) nucleotide database (for information on the HTG database, see the HTGS website at the National Center for Biotechnology Information, Bethesda, Md.). This search identified clone 889J22, GenBank™ Accession Number AL031406, located on human chromosome 22q13.1, with which a portion of the CARD-10 cDNA shares 99% identity over a stretch of 1037 nucleotides.

Several diseases or inherited traits map to the same region of chromosome 22q as the CARD-10 gene, suggesting a potential role for CARD-10 in a disease pathology. These diseases include: spinocerebellar ataxia 10 ("SCA10" maps to 22q13 and is characterized by cerebellar dysfunction and seizures; OMIM No. 603516); and meningioma 1 ("MN1" maps to 22q12.3-qter and is characterized by familial and sporadic meningiomas; OMIM No. 156100). The OMIM (Online Mendelian Inheritance in Man) database is a catalog of human genes and genetic disorders developed for the World Wide Web by the National Center for Biotechnology Information. The database can be found at the OMIM website at the National Center for Biotechnology Information, Bethesda, Md. and contains textual information, pictures, and reference information. The entire content of the OMIM reference numbers cited above are incorporated by reference.

Identification of Human CARD-11

A cDNA encoding human CARD-11 was identified by using the rat CARD-9 cDNA described above to conduct a BLAST search of cDNA sequences from a proprietary T cell library. A cDNA sequence was predicted to encode a CARD domain-containing protein, later identified as human CARD-1.

FIGS. 14A-C depict the sequence of a 4276 nucleotide cDNA (SEQ ID NO:10) which includes a predicted open reading frame (SEQ ID NO:12; nucleotides 328-3768 of SEQ ID NO:10) encoding a 1147 amino acid human CARD-11 protein (SEQ ID NO:11). Human CARD-11 is predicted to be an intracellular protein. This CARD-11 protein is predicted to have a molecular weight of 132.6 kD prior to post-translational modifications.

The predicted amino acid sequence of human CARD-11 was compared to amino acid sequences of known proteins and various motifs were identified. The 1147 amino acid human CARD-11 protein includes five N-glycosylation sites (e.g., about amino acid residues 241-244, 563-566, 584-587, 776-779, and 950-953 of SEQ ID NO:11); four cAMP- and cGMP-dependent protein kinase phosphorylation sites (e.g., about amino acid residues 106-109, 429-432, 510-513, and 634-637 of SEQ ID NO:11); 12 protein kinase C phosphorylation sites (e.g., about amino acid residues 7-9, 100-102, 105-107, 243-245, 290-292, 459-461, 508-510, 687-689, 787-789, 857-859, 879-881, and 935-937 of SEQ ID NO:11); 22 casein kinase II phosphorylation sites (e.g., about amino acid residues 7-10, 100-103, 162-165, 168-171, 182-185, 286-289, 378-381, 471-474, 476-479, 578-581, 692-695, 725-728, 764-767, 779-782, 816-819, 847-850, 872-875, 897-900, 926-929, 1003-1006, 1088-1091, and 1120-1123 of SEQ ID NO:11); three tyrosine kinase phosphorylation sites (e.g., about amino acid residues 175-183, 189-195, and 1010-1018 of SEQ ID NO:11); nine N-myristoylation sites (e.g., about amino acid residues 587-592, 678-683, 698-703, 710-715, 761-766, 823-828, 853-858, 917-922, and 1050-1055 of SEQ ID NO:11); and an amidation site (e.g., about amino acid residues 282-285 of SEQ ID NO:11).

Figure 15:
FIG. 15 depicts a hydropathy plot of human CARD-11. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

FIG. 15 depicts a hydropathy plot of human CARD-11. Relatively hydrophobic residues are above the dashed horizontal line, and relatively hydrophilic residues are below the dashed horizontal line. The cysteine residues (cys) are indicated by short vertical lines just below the hydropathy trace.

Figure 16:
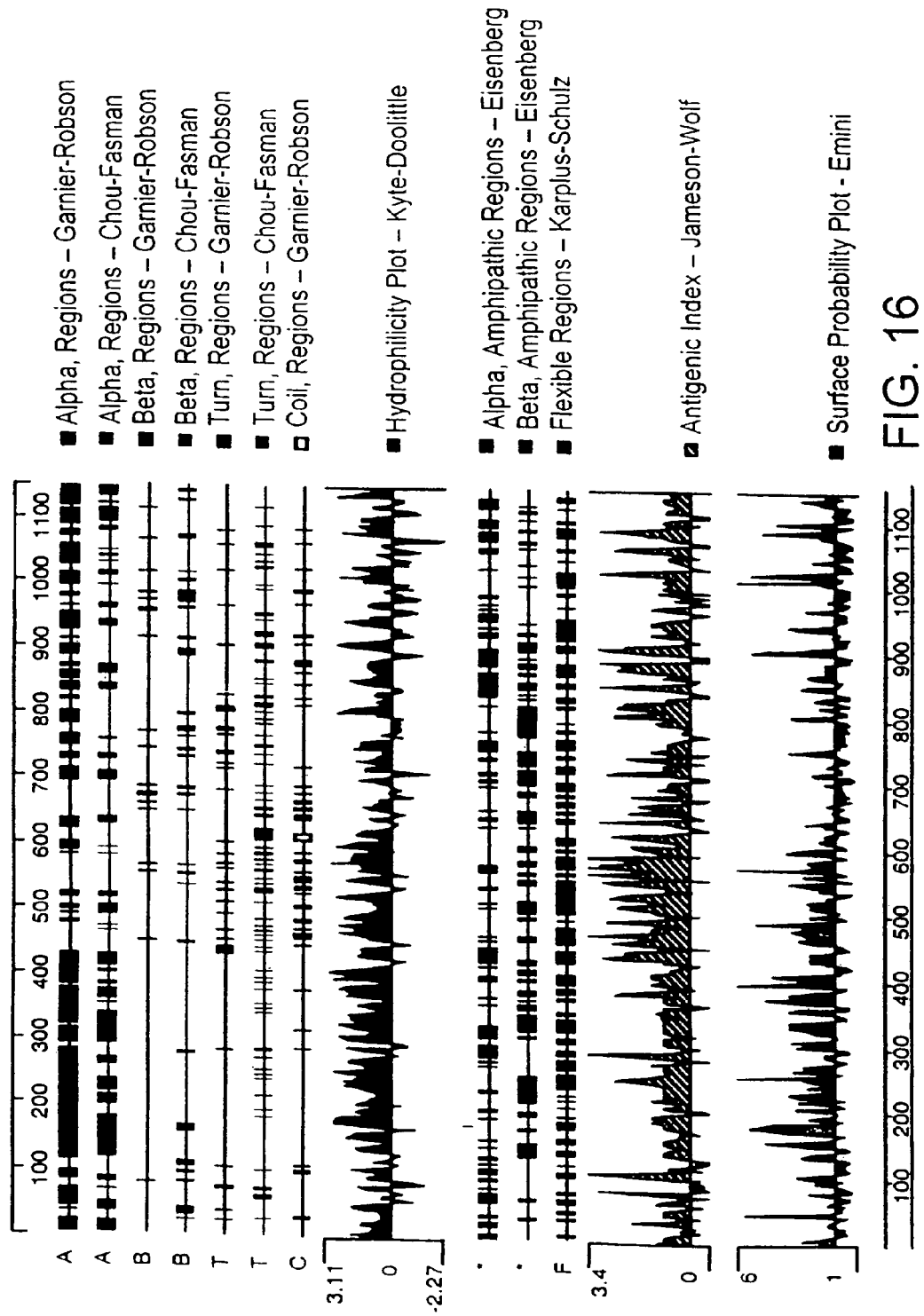
FIG. 16 depicts a plot showing the predicted structural features of human CARD-11. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

A plot showing the predicted structural features of human CARD-11 is presented in FIG. 16. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

An analysis of the predicted human CARD-11 amino acid sequence showed it to contain several potential functional domains: a CARD domain (e.g., about amino acid residues 6-112 of SEQ ID NO:11); a coiled-coil domain (e.g., about amino acid residues 130-431 of SEQ ID NO:1; containing domains at amino acid residues 130-158 and 165-433 of SEQ ID NO:11); a PDZ domain (e.g., about amino acid residues 635-748 of SEQ ID NO:11); an SH3 domain (e.g., about amino acid residues 766-834 of SEQ ID NO:11); and a guanylate kinase (GUK) domain (e.g., about amino acid residues 882-1147 of SEQ ID NO:11).

Northern blot analysis revealed that CARD-11 is expressed as a 4.4-kilobase transcript in a variety of adult tissues, including thymus, spleen, liver and PBLs, but is not significantly expressed in brain, heart, muscle, colon, kidney, intestine, and placenta. Low expression is present in lung. CARD11 also showed abundant expression in specific cancer cell lines, including Promyelocytic Leukemia HL-60 cells, Chronic Myelogenous Leukemia K562 cells, Burkitt's Lymphoma Raji cells and Colorectal Adenocarcinoma SW480 cells.

FIG. 17A depicts an alignment of amino acids 12-103 of human CARD-11 (amino acid residues 12-103 of SEQ ID NO:11) with a consensus caspase recruitment domain (CARD) derived from a HMM.

FIG. 17B depicts an alignment of amino acids 635-747 of human CARD-11 (amino acid residues 635-747 of SEQ ID NO:11) with a consensus PDZ domain derived from a HMM.

FIG. 17C depicts an alignment of amino acids 1003-1091 of human CARD-11 (amino acid residues 1003-1091 of SEQ ID NO:11) with a consensus GUK domain derived from a HMM.

The domain alignments of FIGS. 17A-C were identified by homology searching using consensus domains derived from hidden Markov models (HMMs). HMMs can be used to do multiple sequence alignment and very sensitive database searching, using statistical descriptions of a domain's consensus sequence. For more information on HMM searches, see, e.g., the HMM website maintained by Washington University. In the alignments of FIGS. 17A-C a single letter amino acid designation at a position on the line between the CARD-11 sequence and the HMM-generated consensus domain sequence indicates an exact match between the two. A "+" in this middle line indicates a conservative substitution at the particular residue of CARD-11. Amino acid residues located in the domains identified by the HMM search may be important for the appropriate functioning of the CARD-11 protein. For this reason, amino acid substitutions with respect to the sequence of SEQ ID NO:11 that are outside of the domains homologous to HMM consensus domains may be less detrimental to the activity of the CARD-11 protein.

Identification of an Interaction Between CARD-9, CARD-10 and CARD-11 and Bcl-10

A mammalian two-hybrid screening assay revealed that CARD-9, CARD-10, and CARD-11 interact with the CARD domain of Bcl-10 (CARD-1).

The Stratagene® Mammalian Two-Hybrid Assay Kit (Stratagene, Inc; La Jolla, Calif.) was used to prepare a vector expressing a protein (Gal4-BD/CARD-9, Gal4-BD/CARD-10, or Gal4-BD/CARD-11) consisting of the DNA binding domain of yeast Gal4 (amino acids 1-147) fused to human CARD-9, CARD-10, or CARD-11. For a description of the Stratagene® Mammalian Two-Hybrid Assay Kit, see e.g., Hosfield and Chang (1999) *Strategies Newsletter* 2(2):62-65. In addition, a library of DNA sequences encoding CARD domains was used to create a library of expression vectors encoding the murine NF-κB transcriptional activation domain (amino acids 364-550) fused to a CARD domain (NF-κB-AD/CARD). The Gal4-BD/CARD-9, Gal4-BD/CARD-10, or Gal4-BD/CARD-11 vector, the NF-κB-AD/CARD domain vector library, and a luciferase reporter construct were introduced into human 293T embryonic kidney cells. If a given CARD domain expressed fused to the NF-κB transcriptional activation domain interacts with CARD-9, CARD-10, or CARD-11, the NF-κB transcriptional activation domain will be brought into proximity with the promoter controlling luciferase expression, activating luciferase expression and permitting detection of the interaction. This analysis revealed that CARD-9, CARD-10, and CARD-11 interact with the CARD domain of Bcl-10. Interactions between Bcl-10 and CARD-9, CARD-10, and CARD-11 are described in further detail in later sections of this application.

Bcl-10 activates NF-κB and apoptosis. It is thought that these functions are mediated by its C-terminal domain. The N-terminal CARD domain of Bcl-10 is thought mediate these activation functions upon CARD-CARD binding with an upstream CARD signaling protein. The finding that CARD-9, CARD-10, and CARD-11 bind to the CARD domain of Bcl-10 suggests that these proteins are upstream signaling proteins that regulate Bcl-10 functions (i.e. NF-κB and apoptosis). CARD-9, CARD-10, and CARD-11 likely interact with Bcl-10 via their respective CARD domains. Oligomerization of CARD-9, CARD-10, or CARD-11 likely brings about an oligomerization of Bcl-10 following CARD-CARD interactions between Bcl-10 and CARD-9, CARD-10, or CARD-11. This subsequent oligomerization of Bcl-10 is expected to result in its activation.

CARD-9, CARD-10, CARD-11, and/or splice variants thereof may be either positive or negative regulators of Bcl-10 function. Thus, these proteins are potential targets for regulating inflammation, cancer, NF-κB signaling, and apoptosis in human disease.

Modulation of NF-κB Activity by CARD-10 and CARD-11

The binding of CARD-10 and CARD-11 to Bcl-10 described above suggests that CARD-10-Bcl-10 and CARD-11-Bcl-10 interactions are part of a signaling pathway involved in apoptosis and NF-κB activation. Consistent with this signal transduction model, CARD-10 and CARD-11 were both shown to be inducers of NF-κB activation. Expression of CARD-10 resulted in a 134-fold increase in NF-κB activity, whereas CARD-11 expression resulted in a 24-fold increase in NF-κB activity. To evaluate whether the CARD-10- and CARD-11-mediated NF-κB activation occurs via a Bcl-10 interaction, a Bcl-10 dominant negative deletion mutant (amino acids 1-104) was co-expressed with either CARD-10 or CARD-11. The dominant negative Bcl-10 reduced CARD-10 activation of NF-κB by 35-fold (to 10 times above background). CARD-11 activation was reduced by 4-fold (to 1.7 times above background). This suggests that CARD-10 and CARD-11 are upstream regulators of Bcl-10-mediated NF-κB activation. Modulation of NF-κB activity by and CARD-10 and CARD-11, as well as CARD-9, is described in further detail in later sections of this application.

The NF-κB activity assay was performed by co-transfecting an NF-κB reporter plasmid with a construct encoding CARD-10 or CARD-11. In the reporter plasmid, the luciferase gene was placed under the control of the NF-κB promoter. Relative luciferase activity was determined at the end of the experiment to assess NF-κB pathway activation by CARD-10 or CARD-11.

CARD-9 Interactions with Bcl-10

Mammalian two-hybrid analysis, in vitro binding assays, and in situ binding assays were used to further study the interaction of CARD-9 and Bcl-10. To carry out these studies and additional studies on CARD-9, a variety of plasmid were constructed. Plasmids expressing CARD-9 with either FLAG or Myc epitopes were constructed by inserting the open reading frame of CARD-9 into expression vectors pFLAG CMV-2, pMYC CMV-2, and pCI (Promega), respectively. Constructs encoding epitope-tagged Bcl-10 were described previously (Srinivasula et al. 1999 *J. Biol. Chem.* 274:17946). Plasmids expressing GFP fusions were constructed using pEGFP (Clontech). For mammalian two-hybrid assays, pCMV-CARD-9-CARD/AD and pCMV-CARD-9-CARD/BD plasmids were constructed by inserting the CARD domain (residues 1-110) of CARD-9 into pCMV-AD and pCMV-BD, respectively (Stratagene). pCMV-CARD/AD and pCMV-CARD/BD plasmids were constructed by inserting individual CARD domains into pCMV-CARD/AD and pCMV-BD, respectively (Stratagene): Bcl-10 (residues 1-104), ARC (residues 1-110), RICK (residues 417-540), CARD4 (residues 1-119), ASC (residues 92-195), caspase-1 (residues 1-110), caspase-2 (residues 1-122), caspase-4 (residues 1-108), caspase-9 (residues 1-111), caspase-11 (residues 1-122), caspase-12 (residues 1-121), IAP-1 (residues 423-543), IAP-2 (residues 450-557), Apaf-1 (residues 1-108) and RAIDD (residues 1-108). The Bcl-10 monoclonal antibody (Du et al., 2000) was a gift from M. Dyer. Affinity purified CARD-9 antibody was raised in rabbits injected with a 15-mer peptide (QKGWRQGEEDRENTT; SEQ ID NO:19) corresponding to residues 512-526 of CARD-9 (Research Genetics).

For the additional mammalian two-hybrid assays, 293T cells in 6-well plates (35-mm wells) were transfected with the following plasmids: 750 ng of pCMV-CARD-9/AD, 750 ng of pCMV-CARD/BD, 250 ng of pFR-Luc firefly reporter (Stratagene), and 250 ng of pRL-TK renilla reporter (Promega). For NF-κB assays, 293T cells were transfected with the following plasmids: 900 ng of pNF-kB luciferase reporter (Stratagene), 100 ng of pRL-TK renilla reporter (Promega) and 1000 ng of indicated expression plasmids. Cells were harvested 24 h after transfection, and firefly luciferase activity was determined using the Dual-Luciferase Reporter Assay System (Promega). In addition, renilla luciferase activity was determined and used to normalize transfection efficiencies.

Transfection of 293T cells with plasmids expressing the CARD of CARD-9 fused to the transcriptional activation domain of mouse NF-κB (CARD-9-CARD/AD) and the CARD of Bcl-10 fused to the DNA-binding domain of the yeast protein GAL4 (Bcl-10-CARD/BD) activated the mammalian two-hybrid reporter plasmid resulting in a 250-fold increase in relative luciferase activity. Likewise, expression of CARD-9-CARD/BD and Bcl-10-CARD/AD increased luciferase activity 75-fold. Co-expression of CARD-9-CARD with other CARD domains failed to activate luciferase expression indicating that the CARD of CARD-9 interacts selectively with the CARD of Bcl-10.

The in vivo relationship between CARD-9 and Bcl-10 was investigated by coexpressing Flag-tagged CARD-9 and T7-tagged Bcl-10. Briefly, 293T cells transfected with plasmids expressing Flag-tagged CARD-9 and T7-tagged Bcl-10 were lysed in 50 mM Tris, pH 7.6, 150 mM NaCl, 0.1% Nonidet P-40 buffer and incubated with anti-FLAG-M2 monoclonal antibody (Eastman Kodak Co) or Bcl-10 monoclonal antibody. The immune complexes were precipitated with protein G-Sepharose (Amersham Pharmacia Bio) or mouse IgG agarose (Sigma Co.), washed extensively, and then subjected to SDS-polyacrylamide gel electrophoresis and immunoblotted with polyclonal antibodies. Immunoprecipitation of Flag-tagged CARD-9 quantitatively coprecipitated T7-tagged Bcl-10 (FIG. 18A). This association was dependant on the N-terminal CARD domain of Bcl-10 since CARD-9 failed to coprecipitate a variant Bcl-10 with a point mutation (L41R; Srinivasula et al. 1999 *J. Biol. Chem.* 274: 17946) that disrupts CARD-mediated homodimerization (FIG. 18B). In addition, CARD-9 self-associated when expressed in cells suggesting that oligomerization may play a role in protein function (FIG. 18C).

To rule out the possibility that other proteins were necessary for the CARD-9/Bcl-10 interaction, the interaction of radiolabeled CARD-9 with GST-Bcl-10 was studied in vitro using a technique described previously (Ahmad et al. 1997 *Cancer Research* 57:615-619). Briefly Bcl-10 WT and L41R mutant were expressed in DH5 alpha bacteria as GST fusion proteins and equal amount of proteins were immobilized on glutathione-sepharose (Amersham-Pharmacia). Equal amount of S35 methionine-labeled CARD-9 protein was incubated with the protein bound sepharose beads in 100l of binding buffer (50 mM Tris-Cl pH 7.6, 120 mM NaCl, 0.5% Brij and protease inhibitors) for 3 hours. The beads were washed 4 times with the same buffer and boiled in SDS sample buffer. The proteins were then resolved on a 10% SDS gel and visualized by autoradiography. This analysis revealed that CARD-9 associates directly with Bcl-10 (FIG. 18D). The amount of CARD-9 that associated with GST-Bcl-10 (L41R) was greatly reduced confirming the importance of the Bcl-10 CARD domain in mediating interactions between these two proteins.

Components of signaling pathways are frequently found pre-assembled together within the cell to ensure a rapid response to upstream stimuli. To examine the interactions between endogenous CARD-9 and Bcl-10, a polyclonal antibody that specifically recognizes CARD-9 was used. Immunoblot analysis of extracts derived from human monocyte Thp1 cells revealed a predominant band of approximately 70 kDa corresponding to endogenous CARD-9 (FIG. 18E, lane 1), and a 40 kDa band corresponding to endogenous Bcl-10 (FIG. 18F, lane 1). Immunoprecipitation of Bcl-10 coprecipitated CARD-9 indicating that both endogenous proteins are associated with each other within Thp1 cells (FIG. 18E, lane 2).

To determine the cellular localization of CARD-9, and to confirm that CARD-9 associated intracellularly with Bcl-10 when the two proteins were co-expressed, Rat-1 cells were transfected with a Myc-tagged vector encoding full-length CARD-9, and with an HA-tagged vector encoding full-length Bcl-10. The expressed proteins were detected using a mixture of a monoclonal anti-Myc antibody and a polyclonal rabbit anti-HA antibody. Briefly, Rat-1 cells were transfected in glass chamber slides (BioCoat, Becton-Dickinson Labware) with pCI-Bcl-10-HA or pCI-Card-9-myc, alone or together, using FuGENE-6 (Roche Molecular Biochemicals) for 20 hours. Cells were fixed in 4% paraformaldehyde, permeabilized and blocked in buffer containing 0.4% Triton X-100, and sequentially incubated with primary and secondary antibodies. Antibodies were rabbit anti-HA polyclonal Y-11 (Santa Cruz Biotechnology), mouse anti-myc monoclonal 9E10 (Oncogene Research Products), Alexa-488 Goat anti-mouse IgG (Molecular Probes) and Texas-Red Goat anti-rabbit IgG (Jackson Immunoresearch Laboratories). No cross-reactivity was observed between any of the antibodies. Nuclei were stained with Hoechst 33258. Images were acquired using a Nikon E800 microscope with a 60× (oil) objective and Spot digital camera (Diagnostic Instruments, Inc.) driven by MetaMorph software (Universal Imaging Corp.) with final images prepared using Adobe PhotoShop.

The two proteins exhibited distinctly different patterns of cellular localization when either vector was transfected alone. Whereas Bcl-10 exhibited either a clear pattern of discrete cytoplasmic filaments, or a diffuse whole-cell distribution, CARD-9 displayed a somewhat punctate cytoplasmic or whole-cell distribution, but was not observed to form filament-like structures. When the two proteins were co-expressed in the same cell, however, some of the CARD-9 was found to co-localize with the Bcl-10 filaments. This finding is consistent with the interaction of CARD-9 with Bcl-10 observed in co-immunoprecipitation experiments, and suggests that CARD-9 is recruited to a cytoplasmic signaling complex with Bcl-10.

Modulation of NF-κB Activity by CARD-9

Figure 19A:
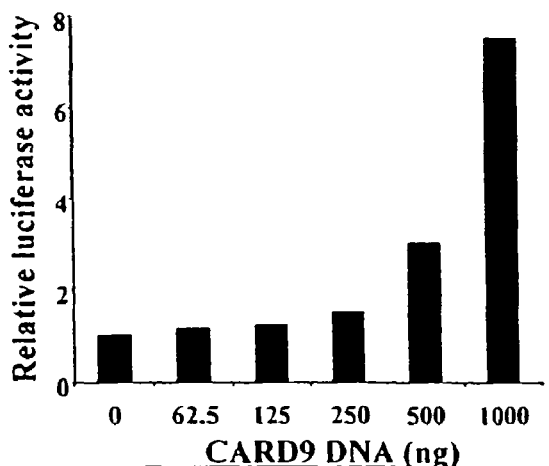
FIG. 19A depicts the results of an experiment demonstrating the concentration-dependent activation of NF-PB activity by CARD-9. In this study, plasmids expressing CARD-9 were transfected into 293T cells and relative luciferase activities were determined to measure induction of NF-PB activity.
Figure 19B:
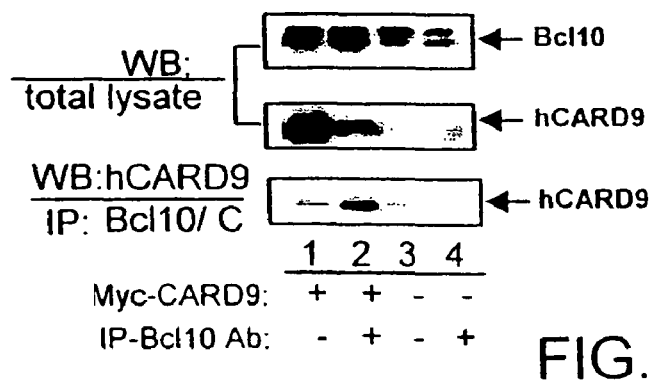
FIG. 19B depicts the results of an experiment demonstrating that CARD-9 interacts with endogenous Bcl10. In this study, cell extracts were immunoprecipitated (IP) with BCl10 antibodies and immunoblotted (WB) with anti-Myc antibodies to detect epitope-tagged CARD-9.
Figure 19C:
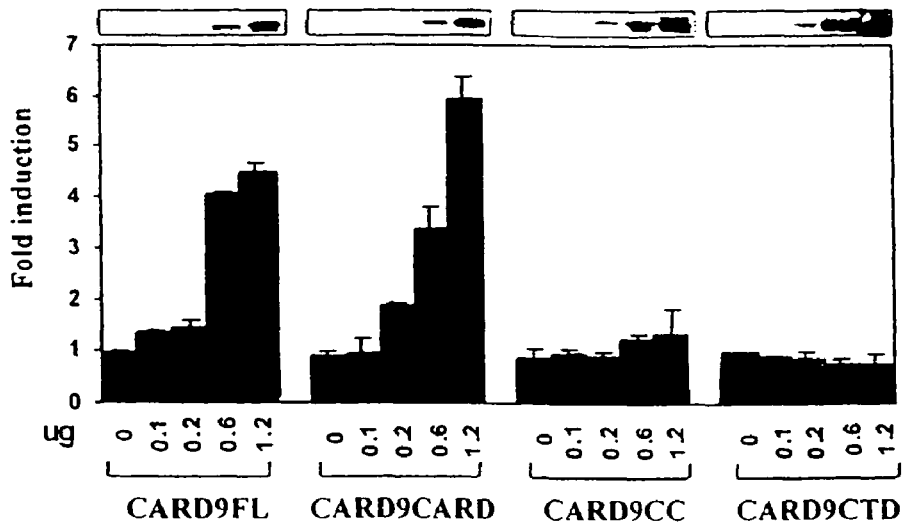
FIG. 19C depicts the results of a functional mapping study of the CARD-9 NF-PB-activating domain. In this study, plasmids expressing individual domains fused to GFP were transfected into 293T cells and induction of NF-PB activity was measured.

The ability of CARD-9 to activate NF-κB was investigated using a luciferase reporter gene directed by an NF-κB-responsive promoter. Expression of CARD-9 in 293T cells induced NF-κB activity 8-fold compared to empty vector (FIG. 19A). Activation was specific for NF-κB signaling since CARD-9 failed to activate a luciferase reporter gene with AP-1 promoter elements. Activation of NF-κB by CARD-9 correlated with binding to endogenous Bcl-10 suggesting that CARD-9 forms a CARD-9/Bcl-10 signaling complex within the transfected cells (FIG. 19B). The domains of CARD-9 that mediate the activation of NF-κB were investigated (FIG. 19C). Since individual domains of CARD-9 were either unstable or insoluble, the CARD (residues 1-98), coiled-coil (residues 140-418) and C-terminal (residues 99-536) domains of CARD-9 were fused to GFP and expressed the fusion proteins in 293T cells. The CARD-GFP fusion activated NF-κB signaling to levels similar to that obtained with CARD-9-GFP. The coiled-coil and C-terminal domains when fused to GFP failed to activate reporter gene expression establishing the CARD domain as the NF-κB activating domain of CARD-9.

These results, taken with the finding of a direct interaction between CARD-9 and Bcl-10 suggest that CARD-9 is a specific regulator of Bcl-10 function. CARD-9 could play a role as an upstream signaling molecule that recruits Bcl-10 through CARD/CARD interactions. The resulting signaling complex may interact directly or indirectly with components of the IKK complex resulting in its activation, e.g., through oligomerization of IKKγ. Indeed the data described above data shows that both CARD-9 and Bcl-10 form large oligomeric complexes (filaments) when overexpressed in mammalian cells. Furthermore, enforced oligomerization of the C-terminus of Bcl-10/CLAP is thought to induce NF-κB activation, suggesting that the CARD domain of Bcl-10 functions as an oligomerization domain that transduces the activation signal to the IKK complex through its C-terminal domain. The ability of CARD-9 to form a complex with Bcl-10 via CARD/CARD interactions supports the idea that Bcl-10 functions as an adaptor between the effector IKK complex and the proximal signaling complexes that interact with CARD-9. Signaling molecules upstream of CARD-9 are predicted to transduce their signals to Bcl-10 through direct interactions with the C-terminal coiled-coil domain of CARD-9. Taken together, these results identify CARD-9 as an important mediator of NF-κB signaling through Bcl-10.

Modulation of NF-κB Activity by CARD-11

Studies on the activation of NF-kB activity by CARD-11 were performed as follows. For NF-kB assays, 293T cells were transfected with the following plasmids: 900 ng of pNF-kB luciferase reporter (Stratagene), 100 ng of pRL-TK renilla reporter (Promega) and 1000 ng of indicated expression plasmids. Cells were harvested 24 h after transfection, and firefly luciferase activity was determined using the Dual-Luciferase Reporter Assay System (Promega). In addition, renilla luciferase activity was determined and used to normalize transfection efficiencies.

Figure 20A:
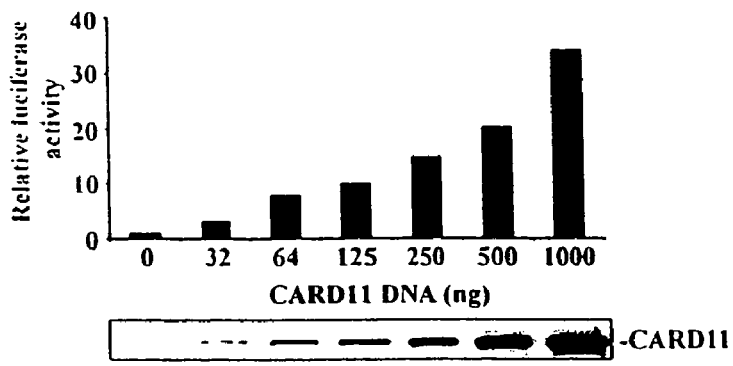
FIG. 20A depicts the concentration-dependent activation of NF-PB activity by CARD-11.
Figure 20B:
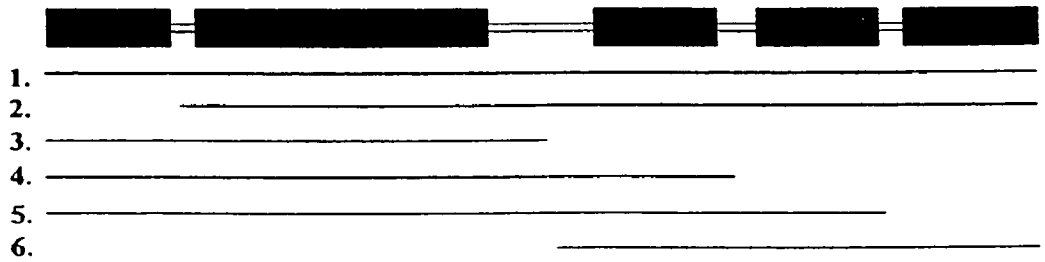
FIG. 20B is a schematic depiction of deletion mutants of CARD-11 used to map domains involved in the induction of NF-PB activity. Bars indicate domains expressed: construct 1 (CARD-11, residues 1-1147), construct 2 (CARD-11, residues 127-1147), construct 3 (CARD-11, residues 1-468), construct 4 (CARD-11, residues 1-759), construct 5 (CARD-11, residues 1-869), construct 6 (CARD-11, residues 469-1147
Figure 20C:
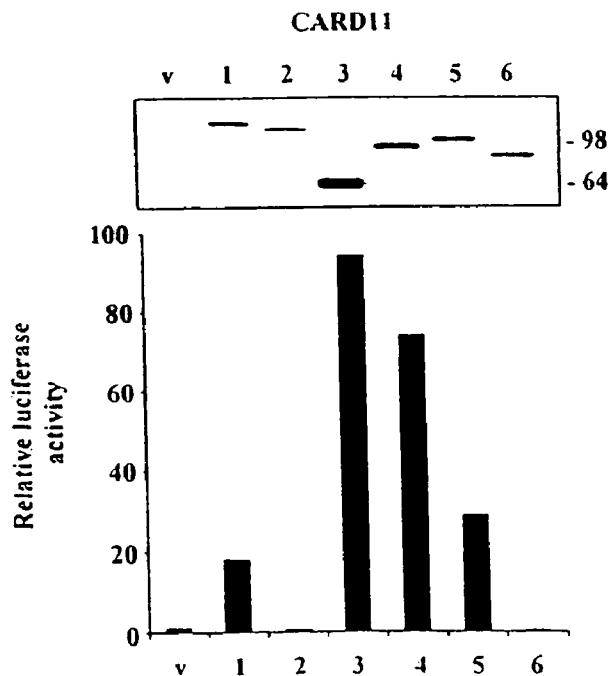
FIG. 20C depicts the induction of NF-PB activity by CARD-11 deletion mutants.

These studies showed that when CARD-11 is expressed in 293T cells, NF-kB activity is induced 20- to 40-fold compared to empty vector (FIG. 20A). NF-kB signaling occurred through the IKK complex since dominant-negative versions of IKK-g and IKK-b blocked the ability of CARD-11 to induce NF-kB activity (data not shown). To determine the role of individual domains in NF-kB signaling, a series of N- and C-terminal truncation mutants of CARD-11 were constructed (FIG. 20B). The N-terminal CARD of CARD-11 was essential for NF-kB signaling since deletion of this domain eliminated the induction of NF-kB activity (FIG. 20C). Immunoblot analysis revealed that the mutant proteins were expressed at levels similar to wt protein indicating that loss of function was not due to reduced levels of expression. In contrast, the C-terminal PDZ, SH3 and GUK domains were not required for NF-κB signaling since deletion of these domains had no effect on the ability of CARD-11 to induce NF-κB activity. However, a CARD-11 mutant lacking its C-terminal PDZ, SH3 and GUK domains induced NF-kB activity to levels 4- to 5-fold greater than that obtained with wt protein (FIG. 20C). Thus, the C-terminal domains may function to negatively regulate induction of NF-kB signaling by CARD-11.

CARD-11 Interactions with Bcl-10

To identify the binding partners of CARD-11, a mammalian two-hybrid analysis was performed using the CARD domains of 15 known proteins. For mammalian two-hybrid assays, 293T cells in 6-well plates (35-mm wells) were transfected with the following plasmids: 750 ng of pCMV-CARD-11/AD, 750 ng of pCMV-BD fused to individual CARD domains, 250 ng of pFR-Luc firefly reporter (Stratagene), and 250 ng of pRL-TK renilla reporter (Promega). pCMV-CARD-11/AD and pCMV-CARD/BD plasmids were constructed by inserting individual CARD domains into pCMV-CARD/AD and pCMV-BD, respectively (Stratagene): Bcl-10 (residues 1-104), ARC (residues 1-110), RICK (residues 417-540), CARD-4 (residues 1-119), ASC (residues 92-195), caspase-1 (residues 1-110), caspase-2 (residues 1-122), caspase-4 (residues 1-108), caspase-9 (residues 1-111), caspase-11 (residues 1-122), caspase-12 (residues 1-121), IAP-1 (residues 423-543), IAP-2 (residues 450-557), Apaf-1 (residues 1-108) and RAIDD (residues 1-108). Cells were harvested 24 hours after transfection, and firefly luciferase activity was determined using the Dual-Luciferase Reporter Assay System (Promega). In addition, renilla luciferase activity was determined and used to normalize transfection efficiencies.

The CARD of CARD-11 interacted with the CARD of Bcl10 resulting in a 17-fold increase in relative luciferase activity. Co-expression of CARD-11-CARD with other CARD domains failed to activate luciferase expression indicating that the CARD of CARD-11 interacts selectively with the CARD of Bcl-10. These data suggest that CARD-11 is a signaling partner of Bcl-10.

Figure 21:
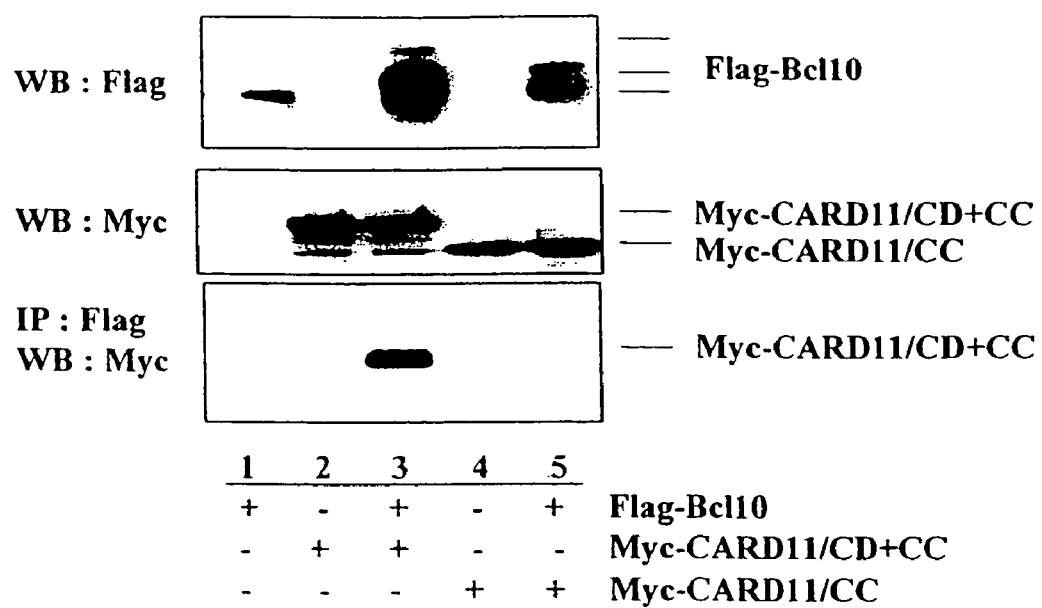
FIG. 21 depicts the results of experiments demonstrating that CARD-11 interacts with Bcl-10 in mammalian cells. 293T cells were transfected with the indicated combinations of expression constructs encoding Flag-Bcl-10, Myc-CARD-11/CARD+CC and Myc-CARD-11/CC. Cell lysates were collected and immunoprecipitated (IP) and immunoblotted (WB) with either Flag or Myc antibodies.

The interaction between CARD-11 and Bcl-10 was next examined in cells by overexpressing CARD-11 is cells and performing co-immunoprecipitation assays. These assays were performed as follows. Plasmids expressing CARD-11 with C-terminal Myc epitopes were constructed using pCMV-Tag 5A (Stratagene Corp., La Jolla, Calif.). Constructs encoding epitope-tagged Bcl-10 were described previously (Srinivasula et al., 1991 *J. Biol. Chem.* 274:17946). 293T cells transfected with the plasmids were lysed in 50 mM Tris, pH 8.0, 120 mM NaCl, 1 mM EDTA, 0.5% Nonidet P-40 buffer and incubated with anti-Flag-M2 monoclonal antibody (Sigma Co.). The immune complexes were precipitated with protein G-Sepharose (Amersham Pharmacia Bio), washed extensively, and then subjected to SDS-polyacrylamide gel electrophoresis and immunoblotted with polyclonal anti-Myc antibodies (Santa Cruz Biotechnology, Inc.). This study showed that Flag-tagged Bcl-10 quantitatively co-precipitated Myc-tagged CARD-11 (FIG. 21, lane 3). The association is mediated by the N-terminal CARD domain of CARD-11 as demonstrated by the fact that Bcl-10 did not co-precipitate with a truncated form of CARD11 lacking its CARD (FIG. 21, lane 5).

To confirm the interaction between CARD-11 and Bcl-10, co-localization experiments were performed with full-length CARD-11. In these studies, cells were transfected in glass chamber slides (BioCoat, Becton-Dickinson Labware) with plasmids expressing HA-tagged Bcl10 and Myc-tagged CARD-11 using FuGENE-6 (Roche Molecular Biochemicals) for 20 h. Cells were fixed in 4% paraformaldehyde, permeabilized and blocked in buffer containing 0.4% Trition X-100, and sequentially incubated with primary and secondary antibodies: rabbit anti-HA polyclonal Y-11 (Santa Cruz Biotechnology), mouse anti-Myc monoclonal 9E10 (Oncogene Research Products), Alexa-488 Goat anti-mouse IgG (Molecular Probes) and Alexa-594 Goat anti-rabbit IgG (molecular probes). No cross-reactivity was observed between any of the antibodies. Images were acquired using a Nikon T200 microscope with a 60× oil objective and an Orca100 digital camera (Hammamatsu, Inc.) driven by MetaMorph software (Universal Imaging Corp.). Final images were prepared using Adobe PhotoShop.

When these two proteins were co-expressed in the same cell, some of the CARD-11 was found to co-localize with the Bcl-10. This finding is consistent with an intracellular interaction between CARD-11 and Bcl-10, and suggests that CARD-11 may be recruited to a cytoplasmic signaling complex with Bcl10. To test whether the CARD domain of CARD-11 was required for this interaction, the localization of a CARD-11 truncation mutant lacking the N-terminal CARD (CARD-11/DCARD) was examined. When expressed alone, CARD-11/DCARD displayed a similar cellular localization pattern to that of full-length CARD-11. When co-expressed with Bcl-10, however, CARD-11/DCARD was not found to co-localize with Bcl-10.

Given that the C-terminal PDZ/SH3/GUK domain of CARD-11 is inhibitory in NF-kB assays, this domain might interfere with the interaction between CARD-11 and Bcl10.

To test this idea, a CARD-11 protein lacking its C-terminal domain (CARD11/CARD+CC) was expressed. CARD11/CARD+CC was mainly localized to the cytoplasm when expressed alone. When co-expressed with Bcl-10, however, some of the CARD-11/CARD+CC was found in cytoplasmic aggregates that co-localized with Bcl-10. Deletion of the CARD domain of this vector abolished co-localization the Bcl10 cytoplasmic aggregates.

Figure 22:
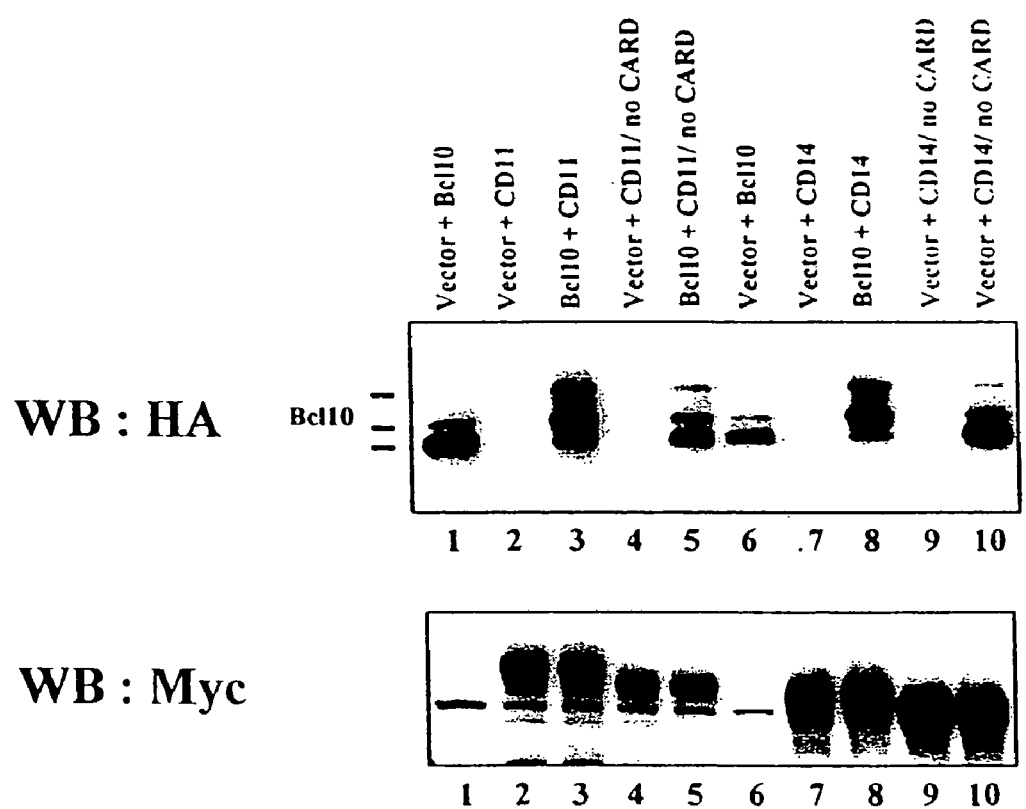
FIG. 22 depicts the results of an experiment demonstrating that CARD-11 induces phosphorylation of Bcl-10. 293T cells were transfected with expression constructs encoding HA-Bcl-10 and either Myc-tagged CARD-11. Cell lysates were collected and immunoblotted (WB) with HA and Myc antibodies to detect Bcl-10 and CARD-11 proteins.

Bcl-10 migrates in SDS gels as a triplet ranging in size from 29 to 32 kDa due to phosphorylation of its C-terminal domain (Srinivasula et al. 1999 *J. Biol. Chem.* 274:17946; Koseki et al., 1999 *J. Biol. Chem.* 274:9955-61). Treatment of cell lysates with calf intestinal alkaline phosphatase eliminates the slower migrating forms demonstrating that the fastest migrating band represents unphosphorylated Bcl-10. Since phosphorylation can play a critical role in signal transduction, studies were performed to determine whether co-expression of CARD-11 induces the phosphorylation of Bcl-10 (FIG. 22). When expressed alone, HA-tagged Bcl-10 is primarily unphosphorylated (lane 1, lower band). However, co-expression of CARD-11 markedly increased the amount of phosphorylated Bcl-10 represented by the slower migrating bands (lane 3 and 8, middle and upper bands). Co-expression of the NF-κB activator CARD-4 did not induce phosphorylation of Bcl-10 indicating that the observed increase in phosphorylated Bcl-10 is specific to co-expression with CARD11 (data not shown). The induction of Bcl-10 phosphorylation is dependent on the N-terminal CARD of CARD-11 since co-expression of truncated mutants lacking these domains has no effect on Bcl-10 phosphorylation levels (lane 5 and 10). Immunoblot analysis revealed that the Myc-tagged truncation mutants were expressed at levels similar to wt protein suggesting that loss of function is not due to reduced levels of expression. Taken together, these data suggest that CARD-11 induces phosphorylation of Bcl-10 via its N-terminal CARD domain.

CARD-11 is a specific regulator of Bcl-10 function. The finding that CARD-11 binds to Bcl-10 through a CARD/CARD interaction suggests that this molecule functions as upstream activator of Bcl-10. As discussed above, CARD-9 also binds to the CARD activation domain of Bcl-10 and signals NF-κB activation. Thus, CARD-11 and CARD-9 constitute a subclass of CARD proteins that may function to transduce upstream stimuli to the activation of Bcl-10 and NF-kB. In response to upstream signals, the coiled-coil domains could mediate self-association of CARD-11 resulting in the aggregation and activation of Bcl-10. Bcl-10 might then engage and oligomerize IKKg resulting in the activation of the IKK complex and NF-kB (Inohara et al. 1999 *J. Biol. Chem.* 274:14566; Poyet et al., 1999). Thus, CARD-11 could function in a manner analogous to Apaf-1 and CARD-4 that function as upstream regulators to induce oligomerization and activation of their respective downstream CARD binding partners. The data showing that CARD-11 induces the phosphorylation of Bcl-10 suggests that signal transduction may involve the participation of a serine/threonine kinase. The C-terminal PDZ/SH3/GUK domains of CARD-11 may function in an analogous manner to the C-terminal LRR domain of CARD-4 and the WD-40 domain of Apaf-1 to regulate protein activation by upstream signals. PDZ/SH3/GUK domains identify MAGUK family members, a class of proteins that associate with the plasma membrane (Fanning and Anderson, 1999 *Curr Opin Cell Biol* 11:432-9). Interestingly, the PDZ domain found in many MAGUK proteins has been shown to interact with the intracellular domains of specific receptors. Thus, CARD-11 may function as a scaffolding protein to assemble a multi-protein complex at the intracellular domain of a receptor that signals the activation of NF-κB.

CARD-10 Interactions with Bcl-10

Figure 23:
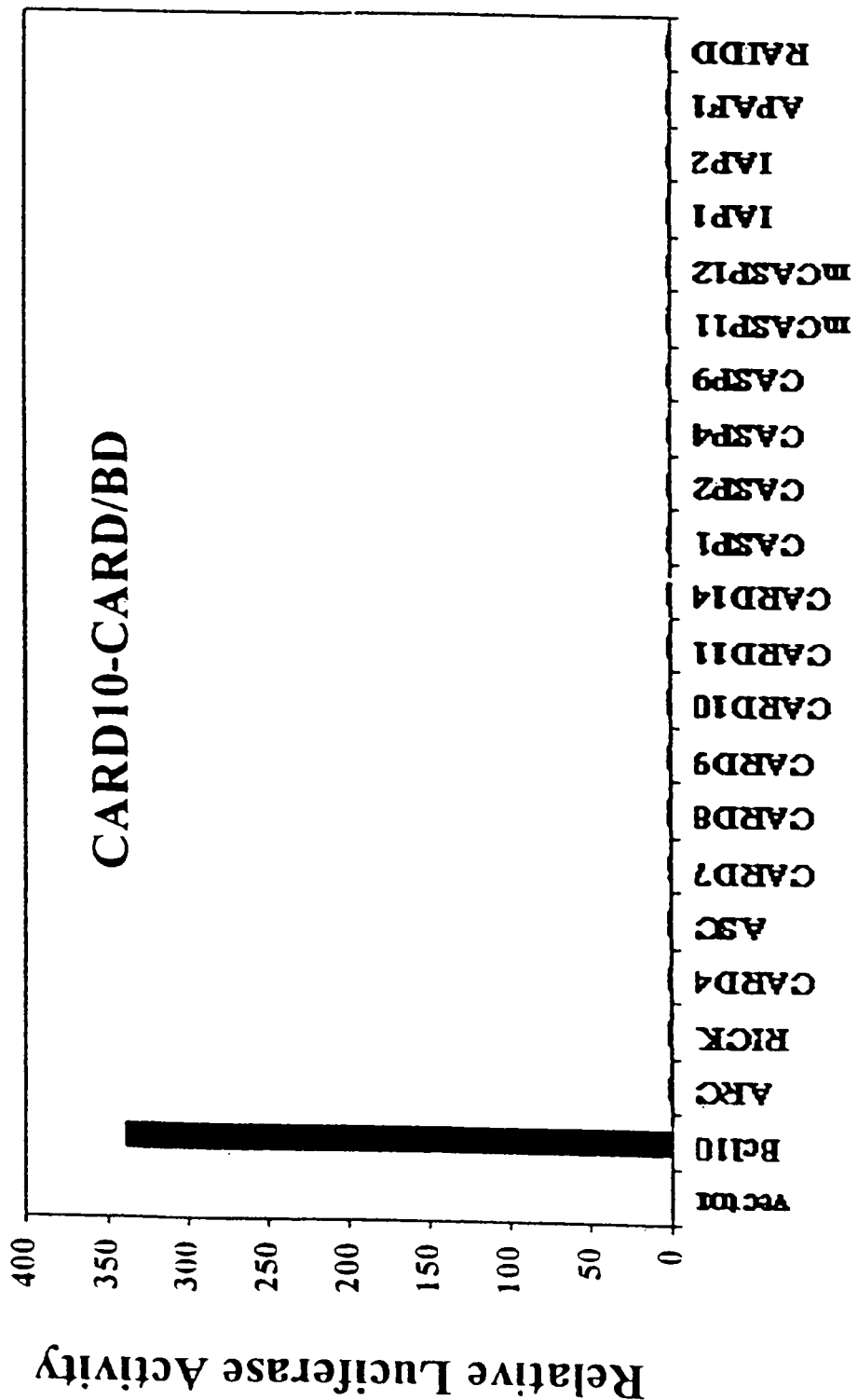
FIG. 23 depicts the results of experiments demonstrating that the CARD domain of CARD-10 interacts with the CARD domain of Bcl-10 in a mammalian two-hybrid assay.

Mammalian two-hybrid analysis was performed to screen a collection of CARD domains for selective interaction with the CARD of CARD-10. The CARD of CARD-10 interacted with the CARD of Bcl-10, resulting in a 340-fold increase in relative luciferase activity (FIG. 23). Co-expression of the CARD-10 CARD with 20 other CARDs failed to activate luciferase expression, indicating that the CARD of CARD-10 interacts selectively with the CARD of Bcl-10 (FIG. 23).

The mammalian two-hybrid analysis was performed as follows. 293T cells were transfected with the mammalian two-hybrid reporter construct pFR-Luc (Stratagene) and the CARD of CARD-10 fused to the binding domain was screened against a panel of individual CARDs fused to the DNA-binding domain. After 24 hours, cells were collected and assayed for relative luciferase activity as a measure or protein-protein interaction. The pCMV-CARD10-CARD/BD plasmids were constructed by inserting the CARD domain of CARD-10 (residues 1-138 of SEQ ID NO:8) into pCMV-BD (Stratagene). The panel of CARD domains used for the mammalian two-hybrid screen was described previously (Bertin et al. 2000 *J. Biol. Chem.* 275:41082). 293T cells in 6-well plates (35-mm wells) were transfected with the following plasmids: 750 ng of pCMV-CARD-10/BD; 750 ng of pCMV-AD fused to individual CARD domains; 250 ng of pFR-Luc firefly reporter (Stratagene); and 250 ng of pRL-TK renilla reporter (Promega). Cells were harvested 24 hours after transfection, and firefly luciferase activity was determined using the Dual-Luciferase Reporter Assay System (Promega). In addition, renilla luciferase activity was determined and used to normalize transfection efficiencies.

The finding that the CARD of CARD-10 selectively interacts with the CARD of Bcl-10 by mammalian two-hybrid analysis suggested that CARD-10 may be a signaling partner of Bcl-10. Interactions between these two proteins, when overexpressed in cells, were therefore examined. Plasmids expressing CARD-10 with C-terminal FLAG epitopes were constructed using pCMV-Tag 4A (Stratagene). Constructs encoding epitope-tagged Bcl-10 were described previously (Srinivasula et al. 1999 *J. Biol. Chem.* 274:17946).

Figure 24A:
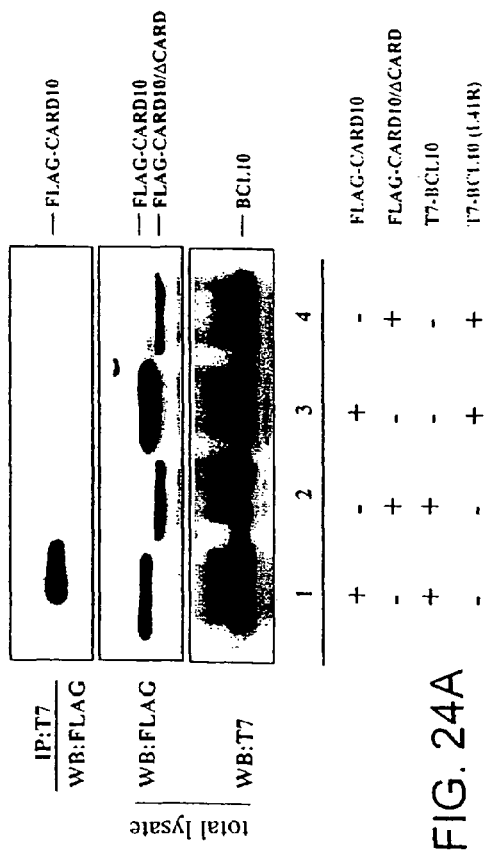
FIG. 24A depicts the results of experiments demonstrating that CARD-10 interacts with Bcl-10 in mammalian cells. 293T cells were transfected with the indicated CARD-10 and Bcl-10 expression constructs. Cell extracts were immunoprecipitated (IP) with an anti-Bcl-10 antibody and immunoblotted (WB) with an anti-FLAG antibody to detect epitope tagged CARD-10.

Immunoprecipitation of T7-tagged Bcl-10 quantitatively co-precipitated FLAG-tagged CARD-10 (FIG. 24A, lane 1). This interaction was dependent on the CARDs of both proteins. CARD-10 failed to associate with a variant Bcl-10 with a point mutation (L41R; Srinivasula et al. 1999 J. Biol. Chem. 274:17946) that disrupts CARD-mediated homodimerization (FIG. 24A, lane 3). In addition, a CARD-10 truncation mutant lacking its CARD domain failed to co-precipitate with Bcl-10 (FIG. 24A, lane 2) or the Bcl-10 L41R mutant (FIG. 24A, lane 4).

Figure 24B:
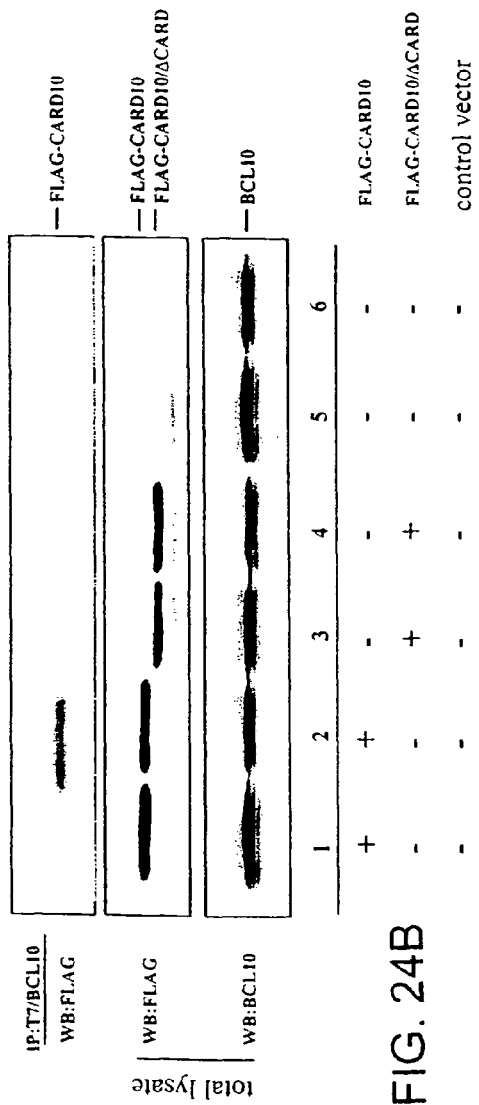
FIG. 24B depicts the results of experiments demonstrating that CARD-10 interacts with endogenous Bcl-10 in mammalian cells. 293T cells were transfected with the indicated CARD-10 expression constructs. Cell extracts were immunoprecipitated (IP) with either anti-Bcl-10 antibodies (lanes 2, 4, and 6) or control T7 monoclonal antibodies (lanes 1, 3, and 5) and immunoblotted (WB) with anti-FLAG antibodies to detect epitope tagged CARD-10.

CARD-10, when overexpressed in cells, was shown to interact with endogenous Bcl-10 (FIG. 24B). Endogenous Bcl-10 immunoprecipitated FLAG-CARD-1 (FIG. 24B, lane 2), but not FLAG-CARD10/ACARD (FIG. 24B, lane 4). Immunoprecipitation with Bcl-10 antibodies is depicted in lanes 2, 4, and 6 of FIG. 24B. Immunoprecipitation with T7 control antibodies is depicted in lanes 1, 3 and 5 of FIG. 24B.

In the experiments described above, cells were lysed in 50 mM Tris, pH 8.0, 120 mM NaCl, 1 mM EDTA, 0.5% Nonidet P-40 buffer and incubated with indicated antibodies. The immune complexes were precipitated with protein G-Sepharose (Amersham Pharmacia Bio), washed extensively, and then subjected to SDS-polyacrylamide gel electrophoresis and immunoblotted with polyclonal anti-FLAG (Santa Cruz Biotechnology, Inc.) or anti-Bcl-10 antibodies.

Modulation of NF-κB Activity by CARD-10

Figure 25A:
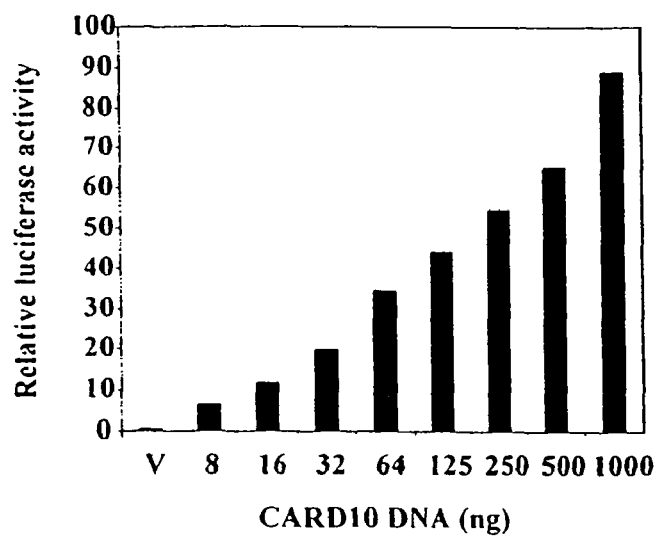
FIG. 25A depicts the results of experiments demonstrating that CARD-10 activates NF-PB in a concentration-dependent manner.

The ability of CARD-10 to induce NF-κB activity was evaluated by using a luciferase reporter gene assay. When CARD-10 was expressed in 293T cells, NF-κB activity was induced 90-fold as compared to empty vector, in a CARD-10 concentration-dependent manner (FIG. 25A). Induction of NF-κB activity was dependent on the IKK complex, since dominant-negative versions of IKK-γ and IKK-β blocked the ability of CARD-10 to induce the activation of NF-κB.

Figure 25B:
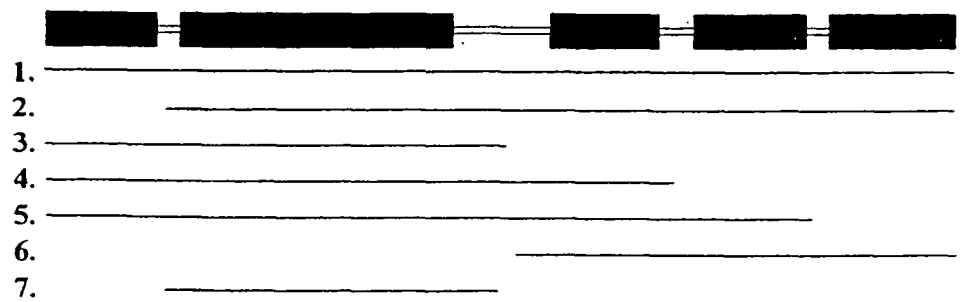
FIG. 25B is a schematic depiction of deletion mutants of CARD-10 used to map domains involved in the induction of NF-PB activity. The bars indicate the domains contained in the constructs: construct 1 (residues 1-1032 of SEQ ID NO:8); construct 2 (residues 131-1032 of SEQ ID NO:8); construct 3 (residues 1-492 of SEQ ID NO:8); construct 4 (residues 1-683 of SEQ ID NO:8); construct 5 (residues 1-825 of SEQ ID NO:8); construct 6 (residues 493-1032 of SEQ ID NO:8); and construct 7 (residues 131-432 of SEQ ID NO:8).
Figure 25C:
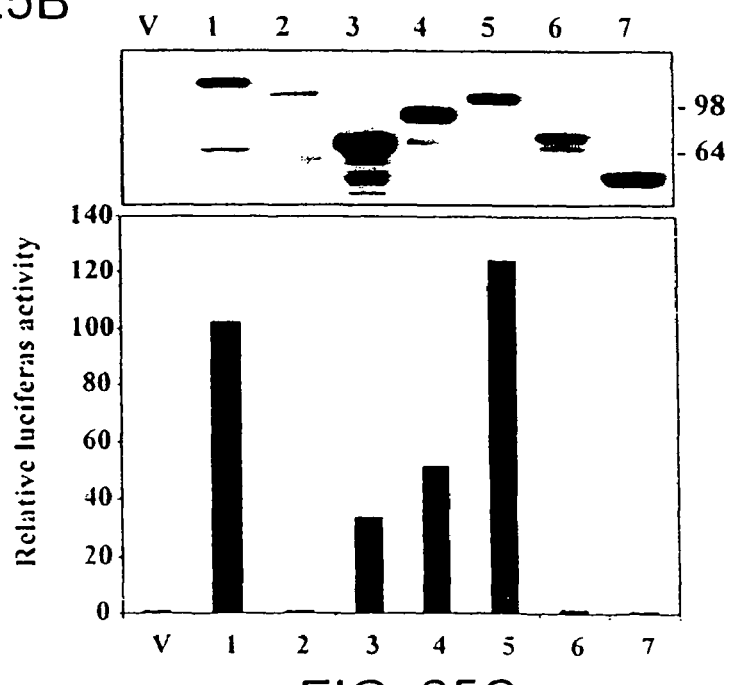
FIG. 25C depicts the results of experiments demonstrating the induction of NF-PB activity by CARD-10 deletion mutants.

To determine the role of individual CARD-10 domains in NF-κB signaling, N- and C-terminal truncation mutants of CARD-10 were constructed (FIG. 25B). The N-terminal CARD domain of CARD-10 was essential for NF-κB signaling, since deletion of this domain eliminated the induction of NF-kB activity (FIG. 25C, lanes 2, 6, and 7). Immunoblot analysis revealed that the truncation mutants were expressed at a level comparable to the wild type protein. Deletion of the C-terminal GUK domain did not interfere with the ability of CARD-10 to induce NF-κB activity (FIG. 25C, lane 5). However, further deletion of the SH3 and PDZ domains reduced the levels of NF-κB activity to levels 2 to 3-fold less than that obtained with wild type protein (FIG. 25C, lanes 3 and 4). Immunoblot analysis revealed that the C-terminal truncated proteins were expressed at levels similar to each other and the wild type protein (FIG. 25C, upper panel), indicating that reductions in activity were not due to reduced levels of expression. Thus, the PDZ and SH3 domains appear to be required for maximal activation of NF-kB activity by CARD-10.

For the NF-κB assays described above, 293T cells were transfected with the following plasmids: 900 ng of pNF-κB luciferase reporter (Stratagene); 100 ng of pRL-TK renilla reporter (Promega); and 1000 ng of indicated expression plasmids. Cells were harvested 24 hours after transfection, and firefly luciferase activity was determined using the Dual-Luciferase Reporter Assay System (Promega). In addition, renilla luciferase activity was determined and used to normalize transfection efficiencies.

The finding that CARD-10 both binds to Bcl-10 and signals NF-κB activation through its N-terminal CARD domain suggests that CARD-10 functions as an upstream activator of Bcl-10. CARD-10 is one of four CARD proteins identified thus far that assemble together with Bcl-10 and signal the activation of NF-κB (Bertin et al. 2000 J. Biol. Chem. 275: 41082). These molecules (CARD-10, CARD-9, CARD-11, and CARD-14) likely function to transduce distinct upstream stimuli to the activation of Bcl-10 and NF-κB. This subclass of CARD proteins are related in both sequence and structure. In addition to containing closely related N-terminal CARDs that interact specifically with Bcl-10, each molecule contains a coiled-coiled domain that could mediate self-association resulting in aggregation and activation of Bcl-10 in response to upstream signals. Bcl-10 might then engage and oligomerize IKKγ resulting in the activation of the IKK complex and NF-κB (Poyet et al. 2000 J. Biol. Chem. 275:37966; Inohara et al. 2000 J. Biol. Chem. 275:27823). Thus, CARD-10 and the other Bcl-10 activators (e.g., CARD-9, CARD-11 and CARD-14) likely function in a manner analogous to Apaf-1 and CARD-4, molecules that induce oligomerization and activation of their respective downstream CARD-binding partners. CARD-10, CARD-11, and CARD-14 each contain a C-terminal PDZ/SH3/GUK domain, the presence of which suggests a role for these proteins in signal transduction by receptors at the plasma membrane. A recent study implicating Bcl-10 as a mediator of antigen receptor signaling in B and T cells suggests that CARD-10 and the other CARD/MAGUK family members might function to recruit Bcl-10 to receptor complexes. For example, signaling complexes at the plasma membrane (e.g., T and B cell receptors) may recruit and activate the CARD/MAGUK proteins (CARD-10, CARD-11, and CARD-14) through their C-terminal PDZ/SH3/GUK domains. Bcl-10 might then engage and oligomerize IKKγ resulting in the activation of the IKK complex and NF-κB.

TABLE 1

Summary of Rat CARD-9, Human CARD-9, Human CARD-10, and Human CARD-11 Sequence Information

| Gene | cDNA | Protein | ORF | Figure |
|---|---|---|---|---|
| Rat CARD-9 | SEQ ID NO: 1 | SEQ ID NO: 2 | SEQ ID NO: 3 | FIGS. 1A-B |
| Human CARD-9 | SEQ ID NO: 4 | SEQ ID NO: 5 | SEQ ID NO: 6 | FIGS. 5A-B |
| Human CARD-10 | SEQ ID NO: 7 | SEQ ID NO: 8 | SEQ ID NO: 9 | FIGS. 10A-C |
| Human CARD-11 | SEQ ID NO: 10 | SEQ ID NO: 11 | SEQ ID NO: 12 | FIGS. 14A-C |

TABLE 2

Summary of Domains of Rat CARD-9

| Domain | Location |
|---|---|
| CARD | about amino acid residues 7-98 of SEQ ED NO: 2 |
| Coiled-coil | about amino acid residues 140-416 of SEQ ID NO: 2 |
| Indole-3-glycerol phosphate synthase | about amino acid residues 197-213 of SEQ ID NO: 2 |
| Cysteine rich repeat | about amino acid residues 285-338 of SEQ ID NO: 2 |

TABLE 3

Summary of Domains of Human CARD-9

| Domain | Location |
|---|---|
| CARD | about amino acid residues 7-98 of SEQ ID NO: 5 |
| Coiled-coil | about amino acid residues 140-416 of SEQ ID NO: 5 |
| Indole-3-glycerol phosphate synthase | about amino acid residues 197-213 of SEQ ID NO: 5 |
| Cysteine rich repeat | about amino acid residues 285-338 of SEQ ID NO: 5 |

TABLE 4

Summary of Domains of Human CARD-10

| Domain | Location |
|---|---|
| CARD | about amino acid residues 23-123 of SEQ ID NO: 8 |
| Coiled-coil | about amino acid residues 147-457 of SEQ ID NO: 8 |
| SH3 | about amino acid residues 704-772 of SEQ ID NO: 8 |

TABLE 4-continued

Summary of Domains of Human CARD-10

| Domain | Location |
|---|---|
| Guanylate kinase (GUK) | about amino acid residues 830-1032 of SEQ ID NO: 8 |
| tropomyosin | about amino acid residues 366-398 of SEQ ID NO: 8 |
| MAGUK | about amino acid residues 457-1032 of SEQ ID NO: 8 |

TABLE 5

Summary of Domains of Human CARD-11

| Domain | Location |
|---|---|
| CARD | about amino acid residues 6-112 of SEQ ID NO: 11 |
| Coiled-coil | about amino acid residues 130-431 of SEQ ID NO: 11 |
| PDZ | about amino acid residues 635-748 of SEQ ID NO: 11 |
| SH3 | about amino acid residues 766-834 of SEQ ID NO: 11 |
| Guanylate kinase (GUK) | about amino acid residues 882-1147 of SEQ ID NO: 11 |
| MAGUK | about amino acid residues 635-1147 of SEQ ID NO: 11 |

A region, the CARD domain, of rat CARD-9 (amino acid residues 7-98), human CARD-9 (amino acid residues 7-98), human CARD-10 (amino acid residues 23-123), and human CARD-11 (amino acid residues 6-112) proteins bears some similarity to the CARD domains of CARD-3, CARD-4, CARD-5, CARD-6, CARD-7, CARD-8, CARD-12, CARD-13, CARD-14, and CARD-15. Detailed information concerning CARD-3, CARD-4, CARD-5, CARD-6, CARD-7, CARD-8, and CARD-12 can be found in U.S. application Ser. No. 09/245,281, filed Feb. 5, 1999, U.S. application Ser. No. 09/207,359, filed Dec. 8, 1998, U.S. application Ser. No. 09/099,041, filed Jun. 17, 1998, U.S. application Ser. No. 09/019,942, filed Feb. 6, 1998, U.S. application Ser. No. 09/428,252, filed Oct. 27, 1999, and U.S. Application Ser. No. 60/161,822, filed Oct. 27, 1999. The entire content of each of these applications is incorporated herein by reference. Detailed information concerning CARD-13 and CARD-15 can be found in U.S. application Ser. No. 09/573,640, filed May 17, 2000. Detailed information concerning CARD-14 can be found in U.S. Application Ser. No. 60/181,159, filed Feb. 9, 2000, and U.S. patent application Ser. No. 09/767,215, filed Jan. 22, 2001. The entire content of these applications is incorporated herein by reference.

Membrane-Associated Protein Interactions

Protein-protein interactions are required for the proper assembly of membrane-associated protein complexes and for the localization of these complexes to the appropriate membrane domain. These membrane-associated complexes can include, e.g., transmembrane receptors, ion channels, cell adhesion molecules, and cytosolic signaling elements. A class of proteins known as membrane-associated guanylate kinases (MAGUKs) play an important role in coupling the activity of transmembrane receptors to downstream signaling molecules. Members of the MAGUK protein family contain a PDZ domain, an SH3 domain, and a guanylate kinase (GUK) domain. MAGUK proteins have been found to be associated with the plasma membrane, including the discrete focal structures that comprise the highly ordered synapses. Studies of MAGUKs suggest that they function as scaffolding proteins and that the PDZ domains are used to tether transmembrane proteins in specific structural domains within the plasma membrane (Fanning and Anderson (1999) *Current Opinion in Cell Biology* 11:432).

A C-terminal region of human CARD-11 (about amino acid residues 635-1147 of SEQ ID NO:11) and CARD-10 (about amino acid residues 457-1032 of SEQ ID NO:8) contains a series of domains found in members of the MAGUK protein family. All three of the domains of MAGUK family members are present in CARD-11: a PDZ domain (e.g., about amino acid residues 635-748 of SEQ ID NO:11); an SH3 domain (e.g., about amino acid residues 766-834 of SEQ ID NO:11); and a GUK domain (e.g., about amino acid residues 882-1147 of SEQ ID NO:11). CARD-10 possesses an SH3 domain (e.g., about amino acid residues 704-772 of SEQ ID NO:8) and a GUK domain (e.g., about amino acid residues 830-1032 of SEQ ID NO:8), as well as a region bearing homology to PDZ domains (e.g., about amino acid residues 457-703 of SEQ ID NO:8).

CARD-10 and CARD-11, like CARD-14, contain both a CARD domain and a MAGUK-homology region. The C-terminal MAGUK-homology regions of CARD-10 (about amino acid residues 457-1032 of SEQ ID NO:8) and CARD-11 (about amino acid residues 635-1147 of SEQ ID NO:11) likely function as sites of protein-protein interaction that lead to the activation of CARD-10 and CARD-11 by upstream signaling proteins. CARD-10 and CARD-11 are likely membrane-associated via PDZ interactions with a receptor. CARD-10 and/or CARD-11 may function to transmit signals from a receptor, e.g., an antigen receptor such as a T cell receptor or cell surface immunoglobulin, leading to the activation of Bcl-10 and the subsequent activation of NF-κB. The role of CARD-10 and CARD-11 in Bcl-10 and NF-κB pathways makes CARD-10 and CARD-11 therapeutic targets to block signaling mediated via these molecules. For example, CARD-10 and/or CARD-11 may function in antigen receptor signaling in B and T cells by recruiting Bcl-10 into plasma membrane associated complexes that form following receptor engagement. Thus, compounds that modulate CARD-10 and/or CARD-11 activity are expected to modulate Bcl-10 signaling, NF-κB signaling, and/or lymphocyte activation and proliferation.

Each of CARD-9, CARD-10, and CARD-11 are members of a family of molecules (the CARD-9, CARD-10, and CARD-11 family, respectively) having certain conserved structural and functional features. The term "family" when referring to the protein and nucleic acid molecules of the invention is intended to mean two or more proteins or nucleic acid molecules having a common structural domain and having sufficient amino acid or nucleotide sequence identity as defined herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 65% identity, preferably 75% identity, more preferably 85%, 95%, or 98% identity are defined herein as sufficiently identical.

As used interchangeably herein a "CARD-9, CARD-10, or CARD-11 activity", "biological activity of CARD-9, CARD- 10, or CARD-11" or "functional activity of CARD-9, CARD-10, or CARD-11", refers to an activity exerted by a CARD-9, CARD-10, or CARD-11 protein, polypeptide or nucleic acid molecule on a CARD-9, CARD-10, or CARD-11 responsive cell as determined in vivo, or in vitro, according to standard techniques. CARD-9, CARD-10, or CARD-11 may act as a pro-apoptotic protein or an anti-apoptotic protein (i.e., it might act to decrease or increase apoptosis). A CARD-9, CARD-10, or CARD-11 activity can be a direct activity, such as an association with or an enzymatic activity on a second protein or an indirect activity, such as a cellular signaling activity mediated by interaction of the CARD-9, CARD-10, or CARD-11 protein with a second protein.

In one embodiment, a CARD-9, CARD-10, or CARD-11 activity can include at least one or more of the following activities: (i) the ability to interact with proteins in an apoptotic, inflammation, and/or immune activation signaling pathway; (ii) the ability to interact with a CARD-9, CARD-10, or CARD-11; (iii) the ability to interact with Bcl-10; (iv) the ability to modulate phosphorylation of Bcl-10; (v) the ability to modulate the activity of NF-kB; (vi) the ability to modulate lymphocyte activation and or proliferation, e.g., antigen receptor-induced lymphocyte activation; (vii) the ability to regulate CNS development, e.g., neuronal survival and/or neural tube closure; (viii) the ability to interact with a membrane, e.g., a plasma membrane; (ix) the ability to interact, directly or indirectly, with one or more proteins having a CARD domain, e.g., a caspase, or an IAP (e.g., IAP-1 or IAP-2); (x) the ability to modulate the activity of a caspase, e.g., caspase-9; (xi) the ability to interact with an intracellular target protein; and (xii) the ability to interact with a heat shock protein, e.g., an interaction of the coiled-coil domain of CARD-9, CARD-10, or CARD-11 with a heat shock protein. CARD-9, CARD-10, or CARD-11 nucleic acid and polypeptides as well as modulators of activity of expression of CARD-9, CARD-10, or CARD-11 might be used to modulate an Apaf-1 signaling pathway. CARD-9, CARD-10, or CARD-11 may modulate the activity of a neurotrophin receptor and thus modulate apoptosis of neuronal cells. Accordingly, CARD-9, CARD-10, or CARD-11 nucleic acids and polypeptides as well as modulators of CARD-9, CARD-10, or CARD-11 activity or expression can be used to modulate apoptosis of neurons (e.g., for treatment of neurological disorders, particularly neurodegenerative disorders).

Accordingly, another embodiment of the invention features isolated CARD-9, CARD-10, or CARD-11 proteins and polypeptides having a CARD-9, CARD-10, or CARD-11 activity.

Various aspects of the invention are described in further detail in the following subsections.

I. Isolated Nucleic Acid Molecules

One aspect of the invention pertains to isolated nucleic acid molecules that encode CARD-9, CARD-10, or CARD-11 proteins or biologically active portions thereof, as well as nucleic acid molecules sufficient for use as hybridization probes to identify CARD-9, CARD-10, or CARD-11-encoding nucleic acids (e.g., CARD-9, CARD-10, or CARD-11 mRNA) and fragments for use as PCR primers for the amplification or mutation of CARD-9, CARD-10, or CARD-11 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) that which naturally flank the nucleic acid (i.e., sequences located at the 5' and 3' ends of the nucleic acid) in the genomic DNA of the organism from which the nucleic acid is derived. For example, in various embodiments, the isolated CARD-9, CARD-10, or CARD-11 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or a complement of any of these nucleotide sequences, can be isolated using standard molecular biology techniques and the sequence information provided herein. Using all or portion of the nucleic acid sequences of SEQ ID NO:1, SEQ ID NO:3, SEQ ID NO:4, SEQ ID NO:6, SEQ ID NO:7, SEQ ID NO:9, SEQ ID NO:10, or SEQ ID NO:12 as a hybridization probe, CARD-9, CARD-10, or CARD-11 nucleic acid molecules can be isolated using standard hybridization and cloning techniques (e.g., as described in Sambrook et al., eds., Molecular Cloning: A Laboratory Manual. 2nd, ed., Cold Spring Harbor Laboratory, Cold Spring Harbor Laboratory Press, Cold Spring Harbor, N.Y., 1989).

A nucleic acid of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to CARD-9, CARD-10, or CARD-11 nucleotide sequences can be prepared by standard synthetic techniques, e.g., using an automated DNA synthesizer.

In another embodiment, an isolated nucleic acid molecule of the invention comprises a nucleic acid molecule which is a complement of the nucleotide sequence shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, the nucleic acid molecule of the invention can comprise only a portion of a nucleic acid sequence encoding CARD-9, CARD-10, or CARD-11, for example, a fragment which can be used as a probe or primer or a fragment encoding a biologically active portion of CARD-9, CARD-10, or CARD-11. The nucleotide sequence determined from the cloning of the CARD-9, CARD-10, or CARD-11 gene allows for the generation of probes and primers designed for use in identifying and/or cloning CARD-9, CARD-10, or CARD-11 homologues in other cell types, e.g., from other tissues, as well as CARD-9, CARD-10, or CARD-11 homologues and orthologs from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or of a naturally occurring mutant of one of SEQ ID NO:1, SEQ ID NO:3, SEQ ID NO:4, SEQ ID NO:6, SEQ ID NO:7, SEQ ID NO:9, SEQ ID NO:10, or SEQ ID NO:12.

Probes based on the CARD-9, CARD-10, or CARD-11 nucleotide sequence can be used to detect transcripts or genomic sequences encoding the same or similar proteins. The probe comprises a label group attached thereto, e.g., a radioisotope, a fluorescent compound, an enzyme, or an enzyme co-factor. Such probes can be used as a part of a diagnostic test kit for identifying allelic variants and orthologs of the CARD-9, CARD-10, or CARD-11 proteins of the present invention, identifying cells or tissue which mis-express a CARD-9, CARD-10, or CARD-11 protein, such as by measuring a level of a CARD-9, CARD-10, or CARD-11-encoding nucleic acid in a sample of cells from a subject, e.g., detecting CARD-9, CARD-10, or CARD-1 mRNA levels or determining whether a genomic CARD-9, CARD-10, or CARD-11 gene has been mutated or deleted.

A nucleic acid fragment encoding a "biologically active portion" of CARD-9, CARD-10, or CARD-11 can be prepared by isolating a portion of SEQ ID NO:1, SEQ ID NO:3, SEQ ID NO:4, SEQ ID NO:6, SEQ ID NO:7, SEQ ID NO:9, SEQ ID NO:10, or SEQ ID NO:12, which encodes a polypeptide having a CARD-9, CARD-10, or CARD-11 biological activity, expressing the encoded portion of CARD-9, CARD-10, or CARD-11 protein (e.g., by recombinant expression in vitro) and assessing the activity of the encoded portion of CARD-9, CARD-10, or CARD-11. For example, a nucleic acid fragment encoding a biologically active portion of CARD-9, CARD-10, or CARD-11 includes a CARD domain, a coiled-coil domain, a PDZ domain, an SH3 domain, or a GUK domain.

The invention further encompasses nucleic acid molecules that differ from the nucleotide sequence of SEQ ID NO:1, SEQ ID NO:3, SEQ ID NO:4, SEQ ID NO:6, SEQ ID NO:7, SEQ ID NO:9, SEQ ID NO:10, or SEQ ID NO:12, due to degeneracy of the genetic code and thus encode the same CARD-9, CARD-10, or CARD-11 protein as that encoded by the nucleotide sequence shown in SEQ ID NO:1, SEQ ID NO:3, SEQ ID NO:4, SEQ ID NO:6, SEQ ID NO:7, SEQ ID NO:9, SEQ ID NO:10, or SEQ ID NO:12.

In addition to the CARD-9, CARD-10, or CARD-11 nucleotide sequence shown in SEQ ID NO:1, SEQ ID NO:3, SEQ ID NO:4, SEQ ID NO:6, SEQ ID NO:7, SEQ ID NO:9, SEQ ID NO:10, or SEQ ID NO:12, it will be appreciated by those skilled in the art that DNA sequence polymorphisms that lead to changes in the amino acid sequences of CARD-9, CARD-10, or CARD-11 may exist within a population (e.g., the human population). Such genetic polymorphism in the CARD-9, CARD-10, or CARD-11 gene may exist among individuals within a population due to natural allelic variation. As used herein, the terms "gene" and "recombinant gene" refer to nucleic acid molecules comprising an open reading frame encoding a CARD-9, CARD-10, or CARD-11 protein, preferably a mammalian CARD-9, CARD-10, or CARD-11 protein. Such natural allelic variations can typically result in 1-5% variance in the nucleotide sequence of the CARD-9, CARD-10, or CARD-11 gene. Any and all such nucleotide variations and resulting amino acid polymorphisms in CARD-9, CARD-10, or CARD-11 that are the result of natural allelic variation and that do not alter the functional activity of CARD-9, CARD-10, or CARD-11 are intended to be within the scope of the invention. Thus, e.g., 1%, 2%, 3%, 4%, or 5% of the amino acids in CARD-9, CARD-10, or CARD-11 (e.g., 1, 2, 3, 4, 5, 6, 8, 10, 15, or 20 amino acids) are replaced by another amino acid, preferably by conservative substitution.

Moreover, nucleic acid molecules encoding CARD-9, CARD-10, or CARD-11 proteins from other species (CARD-9, CARD-10, or CARD-11 orthologs/homologues), which have a nucleotide sequence which differs from that of a CARD-9, CARD-10, or CARD-11 disclosed herein, are intended to be within the scope of the invention.

Accordingly, in another embodiment, an isolated nucleic acid molecule of the invention is at least 150 (300, 325, 350, 375, 400, 425, 450, 500, 550, 600, 650, 700, 800, 900, 1000, 1200, 1400, 1600, 1800, 2000, 2200, 2400, 2600, 2800, 3000, 3200, 3400, 3600, 3800, 4000, 4200, or 4250) nucleotides in length and hybridizes under stringent conditions to the nucleic acid molecule comprising the nucleotide sequence, preferably the coding sequence, of SEQ ID NO:1, SEQ ID NO:3, SEQ ID NO:4, SEQ ID NO:6, SEQ ID NO:7, SEQ ID NO:9, SEQ ID NO:10, or SEQ ID NO:12.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1-6.3.6. An, non-limiting example of stringent hybridization conditions are hybridization in 6× sodium chloride/sodium citrate (SSC) at about 45° C., followed by one or more washes in 0.2×SSC, 0.1% SDS at 50-65 C (e.g., 50° C. or 60° C. or 65° C.). Preferably, the isolated nucleic acid molecule of the invention that hybridizes under stringent conditions corresponds to a naturally-occurring nucleic acid molecule. As used herein, a "naturally-occurring" nucleic acid molecule refers to an RNA or DNA molecule having a nucleotide sequence that occurs in a human cell in nature (e.g., encodes a natural protein).

In addition to naturally-occurring allelic variants of the CARD-9, CARD-10, or CARD-11 sequence that may exist in the population, the skilled artisan will further appreciate that changes can be introduced by mutation into the nucleotide sequence of SEQ ID NO:1, SEQ ID NO:3, SEQ ID NO:4, SEQ ID NO:6, SEQ ID NO:7, SEQ ID NO:9, SEQ ID NO:10, or SEQ ID NO:12, thereby leading to changes in the amino acid sequence of the encoded protein without altering the functional ability of the protein. For example, one can make nucleotide substitutions leading to amino acid substitutions at "non-essential" amino acid residues. A "non-essential" amino acid residue is a residue that can be altered from the wild-type sequence of CARD-9, CARD-10, or CARD-11 protein without altering the biological activity, whereas an "essential" amino acid residue is required for biological activity. For example, amino acid residues that are conserved among the CARD-9, CARD-10, or CARD-11, proteins of various species are predicted to be particularly unamenable to alteration.

For example, preferred CARD-9, CARD-10, or CARD-11 proteins of the present invention contain at least one CARD domain and at least one coiled-coil domain. Additionally a CARD-10 and CARD-11 protein also contains at least one SH3 domain and at least one GUK domain. A CARD-11 protein also contains at least one PDZ domain. Such conserved domains are less likely to be amenable to mutation. Other amino acid residues, however, (e.g., those that are not conserved or only semi-conserved among CARD-9, CARD- 10, or CARD-11 of various species) may not be essential for activity and thus are likely to be amenable to alteration.

Accordingly, another aspect of the invention pertains to nucleic acid molecules encoding CARD-9, CARD-10, or CARD-11 proteins that contain changes in amino acid residues that are not essential for activity. Such CARD-9, CARD-10, or CARD-11 proteins differ in amino acid sequence from SEQ ID NO:2, SEQ ID NO:5, SEQ ID NO:8, or SEQ ID NO:11 and yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of SEQ ID NO:2, SEQ ID NO:5, SEQ ID NO:8, or SEQ ID NO:11. An isolated nucleic acid molecule encoding a CARD-9, CARD-10, or CARD-11 protein having a sequence which differs from that of SEQ ID NO:1, SEQ ID NO:3, SEQ ID NO:4, SEQ ID NO:6, SEQ ID NO:7, SEQ ID NO:9, SEQ ID NO:10, or SEQ ID NO:12, can be created by introducing one or more nucleotide substitutions, additions or deletions into the nucleotide sequence of CARD-9, CARD-10, or CARD-11 (SEQ ID NO:1, SEQ ID NO:3, SEQ ID NO:4, SEQ ID NO:6, SEQ ID NO:7, SEQ ID NO:9, SEQ ID NO:10, or SEQ ID NO:12) such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. Thus, for example, 1%, 2%, 3%, 5%, or 10% of the amino acids can be replaced by conservative substitution. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in CARD-9, CARD-10, or CARD-11 is preferably replaced with another amino acid residue from the same side chain family. Alternatively, mutations can be introduced randomly along all or part of a CARD-9, CARD-10, or CARD-11 coding sequence, such as by saturation mutagenesis, and the resultant mutants can be screened for CARD-9, CARD-10, or CARD-11 biological activity to identify mutants that retain activity. Following mutagenesis, the encoded protein can be expressed recombinantly and the activity of the protein can be determined.

In an embodiment, a mutant CARD-9, CARD-10, or CARD-11 protein can be assayed for: (1) the ability to form protein:protein interactions with proteins in the apoptotic signaling pathway; (2) the ability to bind a CARD-9, CARD-10, or CARD-11 ligand; or (3) the ability to bind to an intracellular target protein.

The present invention encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid.

The antisense nucleic acid can be complementary to an entire CARD-9, CARD-10, or CARD-11 coding strand, or to only a portion thereof, e.g., all or part of the protein coding region (or open reading frame). An antisense nucleic acid molecule can be antisense to a noncoding region of the coding strand of a nucleotide sequence encoding CARD-9, CARD-10, or CARD-11. The noncoding regions ("5' and 3' untranslated regions") are the 5' and 3' sequences that flank the coding region and are not translated into amino acids. Given the coding strand sequences encoding CARD-9, CARD-10, or CARD-11 disclosed herein, antisense nucleic acids of the invention can be designed according to the rules of Watson and Crick base pairing. The antisense nucleic acid molecule can be complementary to the entire coding region of CARD-9, CARD-10, or CARD-11 mRNA, but more preferably is an oligonucleotide which is antisense to only a portion of the coding or noncoding region of CARD-9, CARD-10, or CARD-11 mRNA. For example, the antisense oligonucleotide can be complementary to the region surrounding the translation start site of CARD-9, CARD-10, or CARD-11 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a CARD-9, CARD-10, or CARD-11 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix.

An antisense nucleic acid molecule of the invention can be administered by direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585-591)) can be used to catalytically cleave CARD-9, CARD-10, or CARD-11 mRNA transcripts to thereby inhibit translation of CARD-9, CARD-10, or CARD-11 mRNA. A ribozyme having specificity for a CARD-9, CARD-10, or CARD-11-encoding nucleic acid can be designed based upon the nucleotide sequence of a CARD-9, CARD-10, or CARD-11 cDNA disclosed herein. For example, a derivative of a Tetrahymena L-19 IVS RNA can be constructed in which the nucleotide sequence of the active site is complementary to the nucleotide sequence to be cleaved in a CARD-9, CARD-10, or CARD-11-encoding mRNA. See, e.g., Cech et al. U.S. Pat. No. 4,987,071; and Cech et al. U.S. Pat. No. 5,116,742. Alternatively, CARD-9, CARD-10, or CARD-11 mRNA can be used to select a catalytic RNA having a specific ribonuclease activity from a pool of RNA molecules. See, e.g., Bartel and Szostak (1993) Science 261:1411-1418.

The invention also encompasses nucleic acid molecules which form triple helical structures. For example, CARD-9, CARD-10, or CARD-11 gene expression can be inhibited by targeting nucleotide sequences complementary to the regulatory region of the CARD-9, CARD-10, or CARD-11 (e.g., the CARD-9, CARD-10, or CARD-11 promoter and/or enhancers) to form triple helical structures that prevent transcription of the CARD-9, CARD-10, or CARD-11 gene in target cells. See generally, Helene (1991) Anticancer Drug Des. 6(6):569-84; Helene (1992) Ann. N.Y. Acad. Sci. 660:27-36; and Maher (1992) Bioassays 14(12):807-15.

In embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4(1):5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) Proc. Natl. Acad. Sci. USA 93:14670-675.

PNAs of CARD-9, CARD-10, or CARD-11 can be used for therapeutic and diagnostic applications. For example, PNAs can be used as antisense or antigene agents for sequence-specific modulation of gene expression by, e.g., inducing transcription or translation arrest or inhibiting replication. PNAs of CARD-9, CARD-10, or CARD-11 can also be used, e.g., in the analysis of single base pair mutations in a gene by, e.g., PNA directed PCR clamping; as artificial restriction enzymes when used in combination with other enzymes, e.g., S1 nucleases (Hyrup (1996) supra; or as probes or primers for DNA sequence and hybridization (Hyrup (1996) supra; Perry-O'Keefe et al. (1996) Proc. Natl. Acad. Sci. USA 93: 14670-675).

In another embodiment, PNAs of CARD-9, CARD-10, or CARD-11 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of CARD-9, CARD-10, or CARD-11 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) Nucleic Acids Research 24(17):3357-63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag et al. (1989) Nucleic Acid Res. 17:5973-88). PNA monomers are then coupled in a stepwise manner to produce a chimeric molecule with a 5' PNA segment and a 3' DNA segment (Finn et al. (1996) Nucleic Acids Research 24(17):3357-63). Alternatively, chimeric molecules can be synthesized with a 5' DNA segment and a 3' PNA segment (Peterser et al. (1975) Bioorganic Med. Chem. Lett. 5:1119-11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958-976) or intercalating agents (see, e.g., Zon (1988) Pharm. Res. 5:539-549). To this end, the oligonucleotide may be conjugated to another molecule, e.g., a peptide, hybridization triggered cross-linking agent, transport agent, hybridization-triggered cleavage agent, etc.

II. Isolated CARD-9, CARD-10, or CARD-11 Proteins and Anti-CARD-9, CARD-10, or CARD-11 Antibodies.

One aspect of the invention pertains to isolated CARD-9, CARD-10, or CARD-11 proteins, and biologically active portions thereof, as well as polypeptide fragments suitable for use as immunogens to raise anti-CARD-9, CARD-10, or CARD-11 antibodies. In one embodiment, native CARD-9, CARD-10, or CARD-11 proteins can be isolated from cells or tissue sources by an appropriate purification scheme using standard protein purification techniques. In another embodiment, CARD-9, CARD-10, or CARD-11 proteins are produced by recombinant DNA techniques. Alternative to recombinant expression, a CARD-9, CARD-10, or CARD-11 protein or polypeptide can be synthesized chemically using standard peptide synthesis techniques.

An "isolated" or "purified" protein or biologically active portion thereof is substantially free of cellular material or other contaminating proteins from the cell or tissue source from which the CARD-9, CARD-10, or CARD-11 protein is derived, or substantially free from chemical precursors or other chemicals when chemically synthesized. The language "substantially free of cellular material" includes preparations of CARD-9, CARD-10, or CARD-11 protein in which the protein is separated from cellular components of the cells from which it is isolated or recombinantly produced. Thus, CARD-9, CARD-10, or CARD-11 protein that is substantially free of cellular material includes preparations of CARD-9, CARD-10, or CARD-11 protein having less than about 30%, 20%, 10%, or 5% (by dry weight) of non-CARD-9, CARD-10, or CARD-11 protein (also referred to herein as a "contaminating protein"). When the CARD-9, CARD-10, or CARD-11 protein or biologically active portion thereof is recombinantly produced, it is also preferably substantially free of culture medium, i.e., culture medium represents less than about 20%, 10%, or 5% of the volume of the protein preparation. When CARD-9, CARD-10, or CARD-11 protein is produced by chemical synthesis, it is preferably substantially free of chemical precursors or other chemicals, i.e., it is separated from chemical precursors or other chemicals which are involved in the synthesis of the protein. Accordingly such preparations of CARD-9, CARD-10, or CARD-11 protein have less than about 30%, 20%, 10%, 5% (by dry weight) of chemical precursors or non-CARD-9, CARD-10, or CARD-11 chemicals.

Biologically active portions of a CARD-9, CARD-10, or CARD-11 protein include peptides comprising amino acid sequences sufficiently identical to or derived from the amino acid sequence of the CARD-9, CARD-10, or CARD-11 protein (e.g., the amino acid sequence shown in SEQ ID NO:2, SEQ ID NO:5, SEQ ID NO:8, or SEQ ID NO:11), which include less amino acids than the full length CARD-9, CARD-10, or CARD-11 protein, and exhibit at least one activity of a CARD-9, CARD-10, or CARD-11 protein. Typically, biologically active portions comprise a domain or motif with at least one activity of the CARD-9, CARD-10, or CARD-11 protein. A biologically active portion of a CARD-9, CARD-10, or CARD-11 protein can be a polypeptide which is, for example, 10, 25, 50, 100, 150, 200, 250, 300 or more amino acids in length. Preferred biologically active polypeptides include one or more identified CARD-9, CARD-10, or CARD-11 structural domains, e.g., the CARD domain, the coiled-coil domain, the PDZ domain, the SH3 domain, or the GUK domain.

Moreover, other biologically active portions, in which other regions of the protein are deleted, can be prepared by recombinant techniques and evaluated for one or more of the functional activities of a native CARD-9, CARD-10, or CARD-11 protein.

Rat CARD-9, human CARD-9, human CARD-10, and human CARD-11 protein have the amino acid sequences of SEQ ID NO:2, SEQ ID NO:5, SEQ ID NO:8, or SEQ ID NO:11. Other useful CARD-9, CARD-10, or CARD-11 proteins are substantially identical to SEQ ID NO:2, SEQ ID NO:5, SEQ ID NO:8, or SEQ ID NO:11 and retain the functional activity of the protein of SEQ ID NO:2, SEQ ID NO:5, SEQ ID NO:8, or SEQ ID NO:11, yet differ in amino acid sequence due to natural allelic variation or mutagenesis.

A useful CARD-9, CARD-10, or CARD-11 protein is a protein which includes an amino acid sequence at least about 45%, preferably 55%, 65%, 75%, 85%, 95%, or 99% identical to the amino acid sequence of SEQ ID NO:2, SEQ ID NO:5, SEQ ID NO:8, or SEQ ID NO:11, and retains the functional activity of the CARD-9, CARD-10, or CARD-11 protein of SEQ ID NO:2, SEQ ID NO:5, SEQ ID NO:8, or SEQ ID NO:11.

The determination of percent homology between two sequences can be accomplished using a mathematical algorithm. A preferred, non-limiting example of a mathematical algorithm utilized for the comparison of two sequences is the algorithm of Karlin and Altschul (1990) Proc. Nat'l Acad. Sci. USA 87:2264-2268, modified as in Karlin and Altschul (1993) Proc. Nat'l Acad. Sci. USA 90:5873-5877. Such an algorithm is incorporated into the NBLAST and XBLAST programs of Altschul, et al. (1990) J. Mol. Biol. 215:403-410. BLAST nucleotide searches can be performed with the NBLAST program, score=100, wordlength=12 to obtain nucleotide sequences similar or homologous to nucleic acid molecules of the invention. To obtain gapped alignments for comparison purposes, Gapped BLAST can be utilized as described in Altschul et al. (1997) Nucleic Acids Res. 25:3389-3402. When utilizing BLAST and Gapped BLAST programs, the default parameters of the respective programs (e.g., XBLAST and NBLAST) can be used. See the website for the National Center for Biotechnology Information, Bethesda, Md. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. When utilizing the ALIGN program for comparing nucleic acid sequences, a gap length penalty of 12, and a gap penalty of 4 can be used.

Another preferred example of a mathematical algorithm utilized for the comparison of sequences is the Needleman and Wunsch (J. Mol. Biol. (1970) 48:444-453) algorithm which has been incorporated into the GAP program in the GCG software package (available at the bioinformatics page of the website maintained by Accelrys, Inc., San Diego, Calif., USA), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6.

The percent identity between two sequences can be determined using techniques similar to those described above, with or without allowing gaps. In calculating percent identity, typically exact matches are counted.

The invention also provides CARD-9, CARD-10, or CARD-11 chimeric or fusion proteins. As used herein, a CARD-9, CARD-10, or CARD-11 "chimeric protein" or "fusion protein" comprises a CARD-9, CARD-10, or CARD-11 polypeptide operatively linked to a non-CARD-9, CARD-10, or CARD-11 polypeptide. A "CARD-9, CARD-10, or CARD-11 polypeptide" refers to a polypeptide having an amino acid sequence corresponding to all or a portion (preferably a biologically active portion) of a CARD-9, CARD-10, or CARD-1, whereas a "non-CARD-9, CARD-10, or CARD-11 polypeptide" refers to a polypeptide having an amino acid sequence corresponding to a protein which is not substantially identical to the CARD-9, CARD-10, or CARD-11 protein, e.g., a protein which is different from the CARD-9, CARD-10, or CARD-11 proteins and which is derived from the same or a different organism. Within the fusion protein, the term "operatively linked" is intended to indicate that the CARD-9, CARD-10, or CARD-11 polypeptide and the non-CARD-9, CARD-10, or CARD-11 polypeptide are fused in-frame to each other. The heterologous polypeptide can be fused to the N-terminus or C-terminus of the CARD-9, CARD-10, or CARD-11 polypeptide.

One useful fusion protein is a GST fusion protein in which the CARD-9, CARD-10, or CARD-11 sequences are fused to the C-terminus of the GST sequences. Such fusion proteins can facilitate the purification of recombinant CARD-9, CARD-10, or CARD-11. In another embodiment, the fusion protein contains a signal sequence from another protein. In certain host cells (e.g., mammalian host cells), expression and/or secretion of CARD-9, CARD-10, or CARD-11 can be increased through use of a heterologous signal sequence. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Molecular cloning, Sambrook et al, second edition, Cold spring harbor laboratory press, 1989) and the protein A secretory signal (Pharmacia Biotech; Piscataway, N.J.).

In yet another embodiment, the fusion protein is a CARD-9, CARD-10, or CARD-11-immunoglobulin fusion protein in which all or part of CARD-9, CARD-10, or CARD-11 is fused to sequences derived from a member of the immunoglobulin protein family. The CARD-9, CARD-10, or CARD-11-immunoglobulin fusion proteins of the invention can be incorporated into pharmaceutical compositions and administered to a subject to inhibit an interaction between a CARD-9, CARD-10, or CARD-11 ligand and a CARD-9, CARD-10, or CARD-11 protein on the surface of a cell, to thereby suppress CARD-9, CARD-10, or CARD-11-mediated signal transduction in vivo. The CARD-9, CARD-10, or CARD-11-immunoglobulin fusion proteins can be used to affect the bioavailability of a CARD-9, CARD-10, or CARD-11 cognate ligand. Inhibition of the CARD-9, CARD-10, or CARD-11 ligand/CARD-9, CARD-10, or CARD-11 interaction may be useful therapeutically for both the treatment of proliferative and differentiative disorders, as well as modulating (e.g., promoting or inhibiting) cell survival. Moreover, the CARD-9, CARD-10, or CARD-11-immunoglobulin fusion proteins of the invention can be used as immunogens to produce anti-CARD-9, CARD-10, or CARD-11 antibodies in a subject, to purify CARD-9, CARD-10, or CARD-11 ligands and in screening assays to identify molecules which inhibit the interaction of CARD-9, CARD-10, or CARD-11 with a CARD-9, CARD-10, or CARD-11 ligand.

Preferably, a CARD-9, CARD-10, or CARD-11 chimeric or fusion protein of the invention is produced by standard recombinant DNA techniques. For example, DNA fragments coding for the different polypeptide sequences are ligated together in-frame in accordance with conventional techniques, for example by employing blunt-ended or staggered-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al. eds., John Wiley & Sons: 1992). Moreover, many expression vectors are commercially available that already encode a fusion moiety (e.g., a GST polypeptide). A CARD-9, CARD-10, or CARD-11-encoding nucleic acid can be cloned into such an expression vector such that the fusion moiety is linked in-frame to the CARD-9, CARD-10, or CARD-11 protein.

The present invention also pertains to variants of the CARD-9, CARD-10, or CARD-11 proteins which function as either CARD-9, CARD-10, or CARD-11 agonists (mimetics) or as CARD-9, CARD-10, or CARD-11 antagonists. Variants of the CARD-9, CARD-10, or CARD-11 proteins can be generated by mutagenesis, e.g., discrete point mutation or truncation of the CARD-9, CARD-10, or CARD-11 proteins. An agonist of the CARD-9, CARD-10, or CARD-11 protein can retain substantially the same, or a subset, of the biological activities of the naturally occurring form of the CARD-9, CARD-10, or CARD-11 protein. An antagonist of the CARD-9, CARD-10, or CARD-11 protein can inhibit one or more of the activities of the naturally occurring form of the CARD-9, CARD-10, or CARD-11 protein by, for example, competitively binding to a downstream or upstream member of a cellular signaling cascade which includes the CARD-9, CARD-10, or CARD-11 protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the CARD-9, CARD-10, or CARD-11 proteins.

Variants of the CARD-9, CARD-10, or CARD-11 protein which function as either CARD-9, CARD-10, or CARD-11 agonists (mimetics) or as CARD-9, CARD-10, or CARD-11 antagonists can be identified by screening combinatorial libraries of mutants, e.g., truncation mutants of the CARD-9, CARD-10, or CARD-11 protein for CARD-9, CARD-10, or CARD-11 protein agonist or antagonist activity. In one embodiment, a variegated library of CARD-9, CARD-10, or CARD-11 variants is generated by combinatorial mutagenesis at the nucleic acid level and is encoded by a variegated gene library. A variegated library of CARD-9, CARD-10, or CARD-11 variants can be produced by, for example, enzymatically ligating a mixture of synthetic oligonucleotides into gene sequences such that a degenerate set of potential CARD-9, CARD-10, or CARD-11 sequences is expressible as individual polypeptides, or alternatively, as a set of larger fusion proteins (e.g., for phage display) containing the set of CARD-9, CARD-10, or CARD-11 sequences therein. There are a variety of methods which can be used to produce libraries of potential CARD-9, CARD-10, or CARD-11 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CARD-9, CARD-10, or CARD-11 sequences. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

Useful fragments of CARD-9, CARD-10, or CARD-11, include fragments comprising or consisting of a domain or subdomain described herein, e.g., a CARD domain, a coiled-coil domain, a PDZ domain, an SH3 domain, or a GUK domain.

In addition, libraries of fragments of the CARD-9, CARD-10, or CARD-11 protein coding sequence can be used to generate a variegated population of CARD-9, CARD-10, or CARD-11 fragments for screening and subsequent selection of variants of a CARD-9, CARD-10, or CARD-11 protein. In one embodiment, a library of coding sequence fragments can be generated by treating a double stranded PCR fragment of a CARD-9, CARD-10, or CARD-11 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the CARD-9, CARD-10, or CARD-11 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CARD-9, CARD-10, or CARD-11 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify CARD-9, CARD-10, or CARD-11 variants (Arkin and Yourvan (1992) Proc. Natl. Acad. Sci. USA 89:7811-7815; Delgrave et al. (1993) Protein Engineering 6(3):327-331).

An isolated CARD-9, CARD-10, or CARD-11 protein, or a portion or fragment thereof, can be used as an immunogen to generate antibodies that bind CARD-9, CARD-10, or CARD-11 using standard techniques for polyclonal and monoclonal antibody preparation. The full-length CARD-9, CARD-10, or CARD-11 protein can be used or, alternatively, the invention provides antigenic peptide fragments of CARD-9, CARD-10, or CARD-11 for use as immunogens. The antigenic peptide of CARD-9, CARD-10, or CARD-11 comprises at least 8 (preferably 10, 15, 20, or 30) amino acid residues of the amino acid sequence shown in SEQ ID NO:2, SEQ ID NO:5, SEQ ID NO:8, or SEQ ID NO:11 and encompasses an epitope of CARD-9, CARD-10, or CARD-11 such that an antibody raised against the peptide forms a specific immune complex with CARD-9, CARD-10, or CARD-11.

Useful antibodies include antibodies which bind to a domain or subdomain of CARD-9, CARD-10, or CARD-11 described herein (e.g., a CARD domain, a coiled-coil domain, a PDZ domain, an SH3 domain, or a GUK domain).

Preferred epitopes encompassed by the antigenic peptide are regions of CARD-9, CARD-10, or CARD-11 that are located on the surface of the protein, e.g., hydrophilic regions. Other important criteria include a preference for a terminal sequence, high antigenic index (e.g., as predicted by Jameson-Wolf algorithm), ease of peptide synthesis (e.g., avoidance of prolines); and high surface probability (e.g., as predicted by the Emini algorithm; FIGS. 3, 7, 12, and 16).

A CARD-9, CARD-10, or CARD-11 immunogen typically is used to prepare antibodies by immunizing a suitable subject, (e.g., rabbit, goat, mouse or other mammal) with the immunogen. An appropriate immunogenic preparation can contain, for example, recombinantly expressed CARD-9, CARD-10, or CARD-11 protein or a chemically synthesized CARD-9, CARD-10, or CARD-11 polypeptide. The preparation can further include an adjuvant, such as Freund's complete or incomplete adjuvant, or similar immunostimulatory agent. Immunization of a suitable subject with an immunogenic CARD-9, CARD-10, or CARD-11 preparation induces a polyclonal anti-CARD-9, CARD-10, or CARD-11 antibody response.

Accordingly, another aspect of the invention pertains to anti-CARD-9, CARD-10, or CARD-11 antibodies. The term "antibody" as used herein refers to immunoglobulin molecules and immunologically active portions of immunoglobulin molecules, i.e., molecules that contain an antigen binding site which specifically binds an antigen, such as CARD-9, CARD-10, or CARD-11. A molecule which specifically binds to CARD-9, CARD-10, or CARD-11 is a molecule which binds CARD-9, CARD-10, or CARD-11, but does not substantially bind other molecules in a sample, e.g., a biological sample, which naturally contains CARD-9, CARD-10, or CARD-11. Examples of immunologically active portions of immunoglobulin molecules include F(ab) and F(ab')2 fragments which can be generated by treating the antibody with an enzyme such as pepsin. The invention provides polyclonal and monoclonal antibodies that bind CARD-9, CARD-10, or CARD-11. The term "monoclonal antibody" or "monoclonal antibody composition", as used herein, refers to a population of antibody molecules that contain only one species of an antigen binding site capable of immunoreacting with a particular epitope of CARD-9, CARD-10, or CARD-11. A monoclonal antibody composition thus typically displays a single binding affinity for a particular CARD-9, CARD-10, or CARD-11 protein with which it immunoreacts.

Polyclonal anti-CARD-9, CARD-10, or CARD-11 antibodies can be prepared as described above by immunizing a suitable subject with a CARD-9, CARD-10, or CARD-11 immunogen. The anti-CARD-9, CARD-10, or CARD-11 antibody titer in the immunized subject can be monitored over time by standard techniques, such as with an enzyme linked immunosorbent assay (ELISA) using immobilized CARD-9, CARD-10, or CARD-11. If desired, the antibody molecules directed against CARD-9, CARD-10, or CARD-11 can be isolated from the mammal (e.g., from the blood) and further purified by well-known techniques, such as protein A chromatography to obtain the IgG fraction. At an appropriate time after immunization, e.g., when the anti-CARD-9, CARD-10, or CARD-11 antibody titers are highest, antibody-producing cells can be obtained from the subject and used to prepare monoclonal antibodies by standard techniques, such as the hybridoma technique originally described by Kohler and Milstein (1975) Nature 256:495-497, the human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77-96) or trioma techniques. The technology for producing various antibodies monoclonal antibody hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with a CARD-9, CARD-10, or CARD-11 immunogen as described above, and the culture supernatants of the resulting hybridoma cells are screened to identify a hybridoma producing a monoclonal antibody that binds CARD-9, CARD-10, or CARD-11.

Any of the many well known protocols used for fusing lymphocytes and immortalized cell lines can be applied for the purpose of generating an anti-CARD-9, CARD-10, or CARD-11 monoclonal antibody (see, e.g., Current Protocols in Immunology, supra; Galfre et al. (1977) Nature 266:55052; R. H. Kenneth, in Monoclonal Antibodies: A New Dimension In Biological Analyses, Plenum Publishing Corp., New York, N.Y. (1980); and Lerner (1981) Yale J. Biol. Med., 54:387-402). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind CARD-9, CARD-10, or CARD-11, e.g., using a standard ELISA assay.

Alternative to preparing monoclonal antibody-secreting hybridomas, a monoclonal anti-CARD-9, CARD-10, or CARD-11 antibody can be identified and isolated by screening a recombinant combinatorial immunoglobulin library (e.g., an antibody phage display library) with CARD-9, CARD-10, or CARD-11 to thereby isolate immunoglobulin library members that bind CARD-9, CARD-10, or CARD-11. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370-1372; Hay et al. (1992) Hum. Antibod. Hybridomas 3:81-85; Huse et al. (1989) Science 246:1275-1281; Griffiths et al. (1993) EMBO J. 12:725-734.

Additionally, recombinant anti-CARD-9, CARD-10, or CARD-11 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Canc. Res. 47:999-1005; Wood et al. (1985) Nature 314:446-449; and Shaw et al. (1988) J. Natl. Cancer Inst. 80:1553-1559); Morrison, (1985) Science 229:1202-1207; Oi et al. (1986) Bio/Techniques 4:214; U.S. Pat. No. 5,225,539; Jones et al. (1986) Nature 321:552-525; Verhoeyan et al. (1988) Science 239:1534; and Beidler et al. (1988) J. Immunol. 141:4053-4060.

An anti-CARD-9, CARD-10, or CARD-11 antibody (e.g., monoclonal antibody) can be used to isolate CARD-9, CARD-10, or CARD-11 by standard techniques, such as affinity chromatography or immunoprecipitation. An anti-CARD-9, CARD-10, or CARD-11 antibody can facilitate the purification of natural CARD-9, CARD-10, or CARD-11 from cells and of recombinantly produced CARD-9, CARD-10, or CARD-11 expressed in host cells. Moreover, an anti-CARD-9, CARD-10, or CARD-11 antibody can be used to detect CARD-9, CARD-10, or CARD-11 protein (e.g., in a cellular lysate or cell supernatant) in order to evaluate the abundance and pattern of expression of the CARD-9, CARD-10, or CARD-11 protein. Anti-CARD-9, CARD-10, or CARD-11 antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 (IL-1), interleukin-2 (IL-2), interleukin-6 (IL-6), granulocyte macrophase colony stimulating factor (GM-CSF), granulocyte colony stimulating factor (G-CSF), or other growth factors.

Techniques for conjugating such therapeutic moiety to antibodies are well known, see, e.g., Amon et al., "Monoclonal Antibodies for Immunotargeting of Drugs in Cancer Therapy", in Monoclonal Antibodies and Cancer Therapy, Reisfeld et al. (eds.), pp. 243-56 (Alan R. Liss, Inc. 1985); Hellstrom et al., "Antibodies for Drug Delivery", in Controlled Drug Delivery (2nd Ed.), Robinson et al. (eds.), pp. 623-53 (Marcel Dekker, Inc. 1987); Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985); "Analysis, Results, and Future Prospective of The Therapeutic Use of Radiolabeled Antibody In Cancer Therapy", in Monoclonal Antibodies for Cancer Detection and Therapy, Baldwin et al. (eds.), pp. 303-16 (Academic Press 1985), and Thorpe et al., "The Preparation and Cytotoxic Properties of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676,980.

In addition, antibodies of the invention, either conjugated or not conjugated to a therapeutic moiety, can be administered together or in combination with a therapeutic moiety such as a cytotoxin, a therapeutic agent or a radioactive metal ion. The order of administration of the antibody and therapeutic moiety can vary. For example, in some embodiments, the antibody is administered concurrently (through the same or different delivery devices, e.g., syringes) with the therapeutic moiety. Alternatively, the antibody can be administered separately and prior to the therapeutic moiety. Still alternatively, the therapeutic moiety is administered separately and prior to the antibody. In many embodiments, these administration regimens will be continued for days, months or years.

III. Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exist in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. This skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a work processing test file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or a target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs know in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of know algorithms are disclosed publicly and a variety of commercially available software for conducting search means are and can be used in the computer-based systems of the present invention. Examples of such software includes, but is not limited to, MacPattern (EMBL), BLASTIN and BLASTX (NCBIA).

For example, software which implements the BLAST (Altschul et al. (1990) J. of Mol. Biol. 215:403-410) and BLAZE (Brutlag et al. (1993) Comp. Chem. 17:203-207) search algorithms on a Sybase system can be used to identify open reading frames (ORFs) of the sequences of the invention which contain homology to ORFs or proteins from other libraries. Such ORFs are protein-encoding fragments and are useful in producing commercially important proteins such as enzymes used in various reactions and in the production of commercially useful metabolites.

IV. Recombinant Expression Vectors and Host Cells

Another aspect of the invention pertains to vectors, preferably expression vectors, containing a nucleic acid encoding CARD-9, CARD-10, or CARD-11 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., CARD-9, CARD-10, or CARD-11 proteins, mutant forms of CARD-9, CARD-10, or CARD-11, fusion proteins, etc.).

The recombinant expression vectors of the invention can be designed for expression of CARD-9, CARD-10, or CARD-11 in prokaryotic or eukaryotic cells, e.g., bacterial cells such as *E. coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al. (1988) Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident e prophage harboring a T7 gn1 gene under the transcriptional control of the lacUV5 promoter.

One strategy to maximize recombinant protein expression in E. coli is to express the protein in a bacterial having an impaired capacity to proteolytically cleave the recombinant protein (Gottesman, Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111-2118). Such alteration of nucleic acid sequences of the invention can be carried out by standard DNA synthesis techniques.

In another embodiment, the CARD-9, CARD-10, or CARD-11 expression vector is a yeast expression vector. Examples of vectors for expression in yeast S. cerivisae include pYepSec1 (Baldari et al. (1987) EMBO J. 6:229-234), pMFa (Kurjan and Herskowitz, (1982) Cell 30:933-943), pJRY88 (Schultz et al. (1987) Gene 54:113-123), pYES2 (Invitrogen Corporation, San Diego, Calif.), pGBT9 (Clontech, Palo Alto, Calif.), pGAD10 (Clontech, Palo Alto, Calif.), pYADE4 and pYGAE2 and pYPGE2 (Brunelli and Pall (1993) Yeast 9:1299-1308), pYPGE15 (Brunelli and Pall (1993) Yeast 9:1309-1318), pACTII (Dr. S. E. Elledge, Baylor College of Medicine), and picZ (InVitrogen Corp, San Diego, Calif.).

Alternatively, CARD-9, CARD-10, or CARD-11 can be expressed in insect cells using baculovirus expression vectors. Baculovirus vectors available for expression of proteins in cultured insect cells (e.g., Sf 9 cells) include the pAc series (Smith et al. (1983) Mol. Cell. Biol. 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed (1987) Nature 329:840), pCI (Promega), and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra). In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the α-fetoprotein promoter (Campes and Tilghman (1989) Genes Dev. 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to CARD-9, CARD-10, or CARD-11 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention pertains to host cells into which a recombinant expression vector of the invention or isolated nucleic acid molecule of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, CARD-9, CARD-10, or CARD-11 protein can be expressed in bacterial cells such as E. coli, insect cells, yeast or mammalian cells (such as Chinese hamster ovary cells (CHO) or COS cells). Other suitable host cells are known to those skilled in the art.

Vector DNA or an isolated nucleic acid molecule of the invention can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In some cases vector DNA is retained by the host cell. In other cases the host cell does not retain vector DNA and retains only an isolated nucleic acid molecule of the invention carried by the vector. In some cases, and isolated nucleic acid molecule of the invention is used to transform a cell without the use of a vector.

In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding CARD-9, CARD-10, or CARD-11 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a CARD-9, CARD-10, or CARD-11 protein. Accordingly, the invention further provides methods for producing CARD-9, CARD-10, or CARD-11 protein using the host cells of the invention. In one embodiment, the method comprises culturing the host cell of the invention (into which a recombinant expression vector or isolated nucleic acid molecule encoding CARD-9, CARD-10, or CARD-11 has been introduced) in a suitable medium such that CARD-9, CARD-10, or CARD-11 protein is produced. In another embodiment, the method further comprises isolating CARD-9, CARD-10, or CARD-11 from the medium or the host cell.

The host cells of the invention can also be used to produce nonhuman transgenic animals. For example, in one embodiment, a host cell of the invention is a fertilized oocyte or an embryonic stem cell into which CARD-9, CARD-10, or CARD-11-coding sequences have been introduced. Such host cells can then be used to create non-human transgenic animals in which exogenous CARD-9, CARD-10, or CARD-11 sequences have been introduced into their genome or homologous recombinant animals in which endogenous CARD-9, CARD-10, or CARD-11 sequences have been altered. Such animals are useful for studying the function and/or activity of CARD-9, CARD-10, or CARD-11 and for identifying and/or evaluating modulators of CARD-9, CARD-10, or CARD-11 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous CARD-9, CARD-10, or CARD-11 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing CARD-9, CARD-10, or CARD-11-encoding nucleic acid into the male pronuclei of a fertilized oocyte, e.g., by microinjection, retroviral infection, and allowing the oocyte to develop in a pseudopregnant female foster animal. The CARD-9, CARD-10, or CARD-11 cDNA sequence, e.g., that of SEQ ID NO:1, SEQ ID NO:3, SEQ ID NO:4, SEQ ID NO:6, SEQ ID NO:7, SEQ ID NO:9, SEQ ID NO:10, or SEQ ID NO:12 can be introduced as a transgene into the genome of a non-human animal. Alternatively, a nonhuman homolog or ortholog of the human CARD-9, CARD-10, or CARD-11 gene, such as a mouse CARD-9, CARD-10, or CARD-11 gene, can be isolated based on hybridization to the human CARD-9, CARD-10, or CARD-11 cDNA and used as a transgene. Intronic sequences and polyadenylation signals can also be included in the transgene to increase the efficiency of expression of the transgene. A tissue-specific regulatory sequence(s) can be operably linked to the CARD-9, CARD-10, or CARD-1 transgene to direct expression of CARD-9, CARD-10, or CARD-1 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the CARD-9, CARD-10, or CARD-11 transgene in its genome and/or expression of CARD-9, CARD-10, or CARD-11 mRNA in tissues or cells of the animals. A transgenic founder animal can then be used to breed additional animals carrying the transgene. Moreover, transgenic animals carrying a transgene encoding CARD-9, CARD-10, or CARD-11 can further be bred to other transgenic animals carrying other transgenes.

To create an homologous recombinant animal, a vector is prepared which contains at least a portion of a CARD-9, CARD-10, or CARD-11 gene (e.g., a human or a non-human homolog of the CARD-9, CARD-10, or CARD-11 gene, e.g., a murine CARD-9, CARD-10, or CARD-11 gene) into which a deletion, addition or substitution has been introduced to thereby alter, e.g., functionally disrupt, the CARD-9, CARD-10, or CARD-11 gene. In an embodiment, the vector is designed such that, upon homologous recombination, the endogenous CARD-9, CARD-10, or CARD-11 gene is functionally disrupted (i.e., no longer encodes a functional protein; also referred to as a "knock out" vector). Alternatively, the vector can be designed such that, upon homologous recombination, the endogenous CARD-9, CARD-10, or CARD-11 gene is mutated or otherwise altered but still encodes functional protein (e.g., the upstream regulatory region can be altered to thereby alter the expression of the endogenous CARD-9, CARD-10, or CARD-11 protein). In the homologous recombination vector, the altered portion of the CARD-9, CARD-10, or CARD-11 gene is flanked at its 5' and 3' ends by additional nucleic acid of the CARD-9, CARD-10, or CARD-11 gene to allow for homologous recombination to occur between the exogenous CARD-9, CARD-10, or CARD-11 gene carried by the vector and an endogenous CARD-9, CARD-10, or CARD-11 gene in an embryonic stem cell. The additional flanking CARD-9, CARD-10, or CARD-11 nucleic acid is of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced CARD-9, CARD-10, or CARD-11 gene has homologously recombined with the endogenous CARD-9, CARD-10, or CARD-11 gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823-829 and in PCT Publication Nos. WO 90/11354, WO 91/01140, WO 92/0968, and WO 93/04169.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232-6236. Another example of a recombinase system is the FLP recombinase system of *Saccharomyces cerevisiae* (O'Gorman et al. (1991) Science 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810-813 and PCT Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

In another embodiment, the expression characteristics of an endogenous CARD-9, CARD-10, or CARD-11 gene within a cell line or microorganism may be modified by inserting a heterologous DNA regulatory element into the genome of a stable cell line or cloned microorganism such that the inserted regulatory element is operatively linked with the endogenous CARD-9, CARD-10, or CARD-11 gene. For example, an endogenous CARD-9, CARD-10, or CARD-11 which is normally "transcriptionally silent," i.e. a CARD-9, CARD-10, or CARD-11 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous CARD-9, CARD-10, or CARD-11 gene may be activated by insertion of a promiscuous regulatory element that works across cell types.

A heterologous regulatory element may be inserted into a stable cell line or cloned microorganism, such that it is operatively linked with an endogenous CARD-9, CARD-10, or CARD-11 gene, using techniques, such as targeted homologous recombination, which are well known to those of skill in the art, and described e.g., in Chappel, U.S. Pat. No. 5,272,071; PCT publication No. WO 91/06667, published May 16, 1991.

V. Pharmaceutical Compositions

The CARD-9, CARD-10, or CARD-11 nucleic acid molecules, CARD-9, CARD-10, or CARD-11 proteins, and anti-CARD-9, CARD-10, or CARD-11 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more additional active compounds.

The agent which modulates expression or activity may, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a CARD-9, CARD-10, or CARD-11 protein or anti-CARD-9, CARD-10, or CARD-11 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The nucleic acid molecules of the invention can be inserted into vectors and used as gene therapy vectors. Gene therapy vectors can be delivered to a subject by, for example, intravenous injection, local administration (U.S. Pat. No. 5,328, 470) or by stereotactic injection (see, e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

VI. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology), c) predictive medicine (e.g., diagnostic assays, prognostic assays, monitoring clinical trials, and pharmacogenomics); and d) methods of treatment (e.g., therapeutic and prophylactic). A CARD-9, CARD-10, or CARD-11 protein interacts with other cellular proteins and can thus be used for (i) regulation of cellular proliferation; (ii) regulation of cellular differentiation; and (iii) regulation of cell survival. The isolated nucleic acid molecules of the invention can be used to express CARD-9, CARD-10, or CARD-11 protein (e.g., via a recombinant expression vector in a host cell in gene therapy applications), to detect CARD-9, CARD-10, or CARD-11 mRNA (e.g., in a biological sample) or a genetic lesion in a CARD-9, CARD-10, or CARD-11 gene, and to modulate CARD-9, CARD-10, or CARD-11 activity. In addition, the CARD-9, CARD-10, or CARD-11 proteins can be used to screen drugs or compounds which modulate the CARD-9, CARD-10, or CARD-11 activity or expression as well as to treat disorders characterized by insufficient or excessive production of CARD-9, CARD-10, or CARD-11 protein or production of CARD-9, CARD-10, or CARD-11 protein forms which have decreased or aberrant activity compared to CARD-9, CARD-10, or CARD-11 wild type protein. In addition, the anti-CARD-9, CARD-10, or CARD-11 antibodies of the invention can be used to detect and isolate CARD-9, CARD-10, or CARD-11 proteins and modulate CARD-9, CARD-10, or CARD-11 activity.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to CARD-9, CARD-10, or CARD-11 proteins or biologically active portions thereof or have a stimulatory or inhibitory effect on, for example, CARD-9, CARD-10, or CARD-11 expression or CARD-9, CARD-10, or CARD-11 activity. Examples of biologically active portions of CARD-9 include: amino acids 7-98 encoding a CARD domain; amino acids 140-416 encoding a coiled-coil domain; amino acids 197-213 encoding an indole-3-glycerol phosphate synthase homology region; and amino acids 285-338 encoding a cysteine rich repeat homology region. Examples of biologically active portions of human CARD-10 include: amino acids 23-123 encoding a CARD domain; amino acids 147-457 encoding a coiled-coil domain; amino acids 704-772 encoding an SH3 domain; amino acids 830-1032 encoding a GUK domain; and amino acids 366-398 encoding a tropomyosin domain. Examples of biologically active portions of human CARD-11 include: amino acids 6-112 encoding a CARD domain; amino acids 130-431 encoding a coiled-coil domain; amino acids 635-748 encoding a PDZ domain; amino acids 766-834 encoding an SH3 domain; and amino acids 882-1147 encoding a GUK domain.

Among the screening assays provided by the invention are screening to identify molecules that prevent the dimerization of CARD-9, CARD-10, or CARD-11 and screening to identify molecules which block the binding of a CARD containing polypeptide to CARD-9, CARD-10, or CARD-11. Screening assays, e.g., dimerization assays, can employ full-length CARD-9, CARD-10, or CARD-1 or a portion of CARD-9, CARD-10, or CARD-11, e.g., the CARD domain, the coiled-coil domain, the PDZ domain, the SH3 domain, or the GUK domain.

Screening assays can be used to identify molecules which modulate a CARD-9, CARD-10, or CARD-11 mediated increase in transcription of genes having an AP-1 or NF-κB binding site. For example, expression of a reporter gene under the control of NF-κB (or AP-1) is measured in the presence and absence of a candidate molecule and in the presence and absence of CARD-9, CARD-10, or CARD-11 to identify those molecules which alter expression of the reporter in a CARD-9, CARD-10, or CARD-11 dependent manner. In addition, screening assays can be used to identify molecules that modulate a CARD-9, CARD-10, or CARD-11 mediated increase in CHOP phosphorylation. For example, the expression of a reporter gene under the control of CHOP is measured in the presence and absence of a candidate small molecule and in the presence and absence of CARD-9, CARD-10, or CARD-11 to identify those molecules that alter expression of the reporter in a CARD-9, CARD-10, or CARD-11 dependent manner. A screening assay can be carried out to identify molecules which modulate the CARD-9, CARD-10, or CARD-11 mediated increase in CHOP phosphorylation. For example, CHOP phosphorylation is measured in the presence and absence of a candidate molecule and in the presence and absence of CARD-9, CARD-10, or CARD-11. Phosphorylation of CHOP can be measured using an antibody which binds to phosphorylated CHOP, but not to non-phosphorylated CHOP.

Screening assays can also be used to identify molecules that modulate activity mediated by a domain of CARD-9, CARD-10, or CARD-11. For example, enzymatic activity mediated by the GUK of CARD-10 or CARD-11 may be measured by a GTP binding assay. Test compounds or agents may be evaluated for their ability to either increase or decrease the GTP-binding ability of the GUK domain of CARD-10 or CARD-11.

In one embodiment, the invention provides assays for screening candidate or test compounds which bind to or modulate the activity of a CARD-9, CARD-10, or CARD-11 proteins or polypeptides or biologically active portions thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145). Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412-421), or on beads (Lam (1991) Nature 354:82-84), chips (Fodor (1993) Nature 364:555-556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; and Felici (1991) J. Mol. Biol. 222:301-310).

In one embodiment, an assay is one in which a polypeptide of the invention, or a biologically active portion thereof, is contacted with a test compound and the ability of the test compound to bind to the polypeptide determined. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

Determining the ability of the test compound to modulate the activity of CARD-9, CARD-10, or CARD-11 or a biologically active portion thereof can be accomplished, for example, by determining the ability of the CARD-9, CARD-10, or CARD-11 protein to bind to or interact with a CARD-9, CARD-10, or CARD-11 target molecule. As used herein, a "target molecule" is a molecule with which a CARD-9, CARD-10, or CARD-11 protein binds or interacts in nature, for example, a molecule associated with the internal surface of a cell membrane or a cytoplasmic molecule. A CARD-9, CARD-10, or CARD-11 target molecule can be a non-CARD-9, CARD-10, or CARD-11 molecule or a CARD-9, CARD-10, or CARD-11 protein or polypeptide of the present invention. In one embodiment, a CARD-9, CARD-10, or CARD-11 target molecule is a component of an apoptotic signal transduction pathway. The target, for example, can be a second intracellular protein which has catalytic activity or a protein which facilitates the association of downstream signaling molecules with CARD-9, CARD-10, or CARD-11.

Determining the ability of the test compound to modulate the activity of CARD-9, CARD-10, or CARD-11 or a biologically active portion thereof can be accomplished, for example, by determining the ability of the CARD-9, CARD-10, or CARD-11 protein to bind to or interact with any of the specific proteins listed in the previous paragraph as CARD-9, CARD-10, or CARD-11 target molecules. In another embodiment, CARD-9, CARD-10, or CARD-11 target molecules include all proteins that bind to a CARD-9, CARD-10, or CARD-11 protein or a fragment thereof in a two-hybrid system binding assay which can be used without undue experimentation to isolate such proteins from cDNA or genomic two-hybrid system libraries. The binding assays described in this section can be cell-based or cell free (described subsequently).

Determining the ability of the CARD-9, CARD-10, or CARD-11 protein to bind to or interact with a CARD-9, CARD-10, or CARD-11 target molecule can be accomplished by one of the methods described above for determining direct binding. In an embodiment, determining the ability of the CARD-9, CARD-10, or CARD-11 protein to bind to or interact with a CARD-9, CARD-10, or CARD-11 target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a CARD-9, CARD-10, or CARD-11-responsive regulatory element operatively linked to a nucleic acid encoding a detectable marker, e.g. luciferase), or detecting a cellular response, for example, cell survival, cellular differentiation, or cell proliferation. The activity of a target molecule can be monitored by assaying the caspase 9-mediated apoptosis cellular response or caspase 9 enzymatic activity. In addition, and in another embodiment, genes induced by CARD-9, CARD-10, or CARD-11 expression can be identified by expressing CARD-9, CARD-10, or CARD-11 in a cell line and conducting a transcriptional profiling experiment wherein the mRNA expression patterns of the cell line transformed with an empty expression vector and the cell line transformed with a CARD-9, CARD-10, or CARD-11 expression vector are compared. The promoters of genes induced by CARD-9, CARD-10, or CARD-11 expression can be operatively linked to reporter genes suitable for screening such as luciferase, secreted alkaline phosphatase, or beta-galactosidase and the resulting constructs could be introduced into appropriate expression vectors. A recombinant cell line containing CARD-9, CARD-10, or CARD-11 and transfected with an expression vector containing a CARD-9, CARD-10, or CARD-11 responsive promoter operatively linked to a reporter gene can be used to identify test compounds that modulate CARD-9, CARD-10, or CARD-11 activity by assaying the expression of the reporter gene in response to contacting the recombinant cell line with test compounds. CARD-9, CARD-10, or CARD-11 agonists can be identified as increasing the expression of the reporter gene and CARD-9, CARD-10, or CARD-11 antagonists can be identified as decreasing the expression of the reporter gene.

In another embodiment of the invention, the ability of a test compound to modulate the activity of CARD-9, CARD-10, or CARD-11, or biologically active portions thereof can be determined by assaying the ability of the test compound to modulate CARD-9, CARD-10, or CARD-11-dependent pathways or processes where the CARD-9, CARD-10, or CARD-11 target proteins that mediate the CARD-9, CARD-10, or CARD-11 effect are known or unknown. Potential CARD-9, CARD-10, or CARD-11-dependent pathways or processes include, but are not limited to, the modulation of cellular signal transduction pathways and their related second messenger molecules (e.g., intracellular $Ca^{2+}$, diacylglycerol, IP3, cAMP etc.), cellular enzymatic activities, cellular responses (e.g., cell survival, cellular differentiation, or cell proliferation), or the induction or repression of cellular or heterologous mRNAs or proteins. CARD-9, CARD-10, or CARD-11-dependent pathways or processes could be assayed by standard cell-based or cell free assays appropriate for the specific pathway or process under study. In another embodiment, cells cotransfected with CARD-9, CARD-10, or CARD-11 and a NF-κB luciferase reporter gene could be contacted with a test compound and test compounds that block CARD-9, CARD-10, or CARD-11 activity could be identified by their reduction of CARD-9, CARD-10, or CARD-11-dependent NF-kB pathway luciferase reporter gene expression. Test compounds that agonize CARD-9, CARD-10, or CARD-11 would be expected to increase reporter gene expression. In another embodiment, CARD-9, CARD-10, or CARD-11 could be expressed in a cell line and the recombinant CARD-9, CARD-10, or CARD-11-expressing cell line could be contacted with a test compound. Test compounds that inhibit CARD-9, CARD-10, or CARD-11 activity could be identified by their reduction of CARD-9, CARD-10, or CARD-11-depended NF-kB pathway stimulation as measured by the assay of a NF-kB pathway reporter gene, NF-kB nuclear localization, IκB phosphorylation or proteolysis, or other standard assays for NF-kB pathway activation known to those skilled in the art.

In yet another embodiment, an assay of the present invention is a cell-free assay comprising contacting a CARD-9, CARD-10, or CARD-11 protein or biologically active portion thereof with a test compound and determining the ability of the test compound to bind to the CARD-9, CARD-10, or CARD-11 protein or biologically active portion thereof. Binding of the test compound to the CARD-9, CARD-10, or CARD-11 protein can be determined either directly or indirectly as described above. In one embodiment, a competitive binding assay includes contacting the CARD-9, CARD-10, or CARD-11 protein or biologically active portion thereof with a compound known to bind CARD-9, CARD-10, or CARD-11 to form an assay mixture, contacting the assay mixture with a test compound, and determining the ability of the test compound to interact with a CARD-9, CARD-10, or CARD-11 protein, wherein determining the ability of the test compound to interact with a CARD-9, CARD-10, or CARD-11 protein comprises determining the ability of the test compound to preferentially bind to CARD-9, CARD-10, or CARD-11 or biologically active portion thereof as compared to the known binding compound.

In another embodiment, an assay is a cell-free assay comprising contacting CARD-9, CARD-10, or CARD-11 protein or biologically active portion thereof with a test compound and determining the ability of the test compound to modulate (e.g., stimulate or inhibit) the activity of the CARD-9, CARD-10, or CARD-11 protein or biologically active portion thereof. Determining the ability of the test compound to modulate the activity of CARD-9, CARD-10, or CARD-11 can be accomplished, for example, by determining the ability of the CARD-9, CARD-10, or CARD-11 protein to bind to or interact with a CARD-9, CARD-10, or CARD-11 target molecule, e.g., Bcl-10, by one of the methods described above for determining direct binding. In an alternative embodiment, determining the ability of the test compound to modulate the activity of CARD-9, CARD-10, or CARD-11 can be accomplished by determining the ability of the CARD-9, CARD-10, or CARD-11 protein to further modulate a CARD-9, CARD-10, or CARD-11 target molecule. For example, the catalytic/enzymatic activity of the target molecule on an appropriate substrate can be determined as previously described.

In yet another embodiment, the cell-free assay comprises contacting the CARD-9, CARD-10, or CARD-11 protein or biologically active portion thereof with a known compound which binds CARD-9, CARD-10, or CARD-11 to form an assay mixture, contacting the assay mixture with a test compound, and determining the ability of the test compound to interact with a CARD-9, CARD-10, or CARD-11 protein, wherein determining the ability of the test compound to interact with a CARD-9, CARD-10, or CARD-11 protein comprises determining the ability of the CARD-9, CARD-10, or CARD-11 protein to preferentially bind to or modulate the activity of a CARD-9, CARD-10, or CARD-11 target molecule. The cell-free assays of the present invention are amenable to use of either the soluble form or a membrane-associated form of CARD-9, CARD-10, or CARD-11. A membrane-associated form of CARD-9, CARD-10, or CARD-11 refers to CARD-9, CARD-10, or CARD-11 that interacts with a membrane-bound target molecule. In the case of cell-free assays comprising the membrane-associated form of CARD-9, CARD-10, or CARD-11, it may be desirable to utilize a solubilizing agent such that the membrane-associated form of CARD-9, CARD-10, or CARD-11 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

A variety of methods can be used to identify compounds which inhibit the interaction between CARD-9, CARD-10, or CARD-11 and Bcl-10. Among these methods is the reverse two-hybrid screen (Huang and Schreiber (1997) *Proc. Natl. Acad. Sci. USA* 94:13396-401; Vidal et al. and (1996) *Proc. Natl. Acad. Sci. USA* 93:10315-20; and Vidal et al. (1996) *Proc. Natl. Acad. Sci. USA* 93:10321-6). To create a high throughput assay, the reverse two hybrid screen can be combined with nanodroplet technology (Huang and Schreiber (1997) supra; and Borchardt et al. (1997) *Chem. and Biol.* 4:961-68). Nanodroplet technology employs 100-200 nl droplets which contain cells, defined media, and beads to which are attached test compounds. The screening can take place in the nanodroplets, and the test compounds can be attached to the beads so that their release can be controlled photochemically.

A scintillation proximity assay can be used to identify molecules which modulate the interaction between Bcl-10 and CARD-9, CARD-10, or CARD-11. In a scintillation proximity assay designed to measure the interaction between two proteins, one of the two proteins is radioactively labeled, e.g., tritiated, and the other protein is not. The two interacting proteins are incubated in the presence and absence of a test compound. The unlabeled protein is captured by a solid support material, e.g., a bead, impregnated with a fluorescer. The fraction of the radiolabeled protein that binds to the captured unlabeled protein is in close enough proximity to the solid support material to activate the fluorescer to produce light energy. The vast majority of the radiolabeled protein that does not bind to the unlabeled protein is too far from the solid support material to activate the fluorescer. Thus, the level of light energy produced by the fluorescer is indicative of the amount of radiolabeled protein bound to the unlabeled protein captured by the solid support material. Scintillation proximity assays are described in U.S. Pat. No. 4,568,649.

In more than one embodiment of the above assay methods of the present invention, it may be desirable to immobilize either CARD-9, CARD-10, or CARD-11 or its target molecule to facilitate separation of complexed from uncomplexed forms of one or both of the proteins, as well as to accommodate automation of the assay. Binding of a test compound to CARD-9, CARD-10, or CARD-11, or interaction of CARD-9, CARD-10, or CARD-11 with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/CARD-9, CARD-10, or CARD-11 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or CARD-9, CARD-10, or CARD-11 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CARD-9, CARD-10, or CARD-11 binding or activity determined using standard techniques. In an alternative embodiment, MYC or HA epitope tag CARD-9, CARD-10, or CARD-11 fusion proteins or MYC or HA epitope tag target fusion proteins can be adsorbed onto anti-MYC or anti-HA antibody coated microbeads or onto anti-MYC or anti-HA antibody coated microtitre plates, which are then combined with the test compound or the test compound and either the non-adsorbed target protein or CARD-9, CARD-10, or CARD-11 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CARD-9, CARD-10, or CARD-11 binding or activity determined using standard techniques.

Other techniques for immobilizing proteins on matrices can also be used in the screening assays of the invention. For example, CARD-9, CARD-10, or CARD-11 or its target molecule can be immobilized utilizing conjugation of biotin and streptavidin. Biotinylated CARD-9, CARD-10, or CARD-11 target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with CARD-9, CARD-10, or CARD-11 or target molecules but which do not interfere with binding of the protein to its target molecule can be derivatized to the wells of the plate, and unbound target or protein trapped in the wells by antibody conjugation. Methods for detecting such complexes, in addition to those described above for the GST-immobilized complexes and epitope tag immobilized complexes, include immunodetection of complexes using antibodies reactive with the CARD-9, CARD-10, or CARD-11 or target molecule, as well as enzyme-linked assays which rely on detecting an enzymatic activity associated with the CARD-9, CARD-10, or CARD-11 or a target molecule.

In another embodiment, modulators of CARD-9, CARD-10, or CARD-1 expression are identified in a method in which a cell is contacted with a candidate compound and the expression of the CARD-9, CARD-10, or CARD-11 promoter, mRNA or protein in the cell is determined. The level of expression of CARD-9, CARD-10, or CARD-11 mRNA or protein in the presence of the candidate compound is compared to the level of expression of CARD-9, CARD-10, or CARD-11 mRNA or protein in the absence of the candidate compound. The candidate compound can then be identified as a modulator of CARD-9, CARD-10, or CARD-11 expression based on this comparison. For example, when expression of CARD-9, CARD-10, or CARD-11 mRNA or protein is greater (statistically significantly greater) in the presence of the candidate compound than in its absence, the candidate compound is identified as a stimulator of CARD-9, CARD-10, or CARD-11 mRNA or protein expression. Alternatively, when expression of CARD-9, CARD-10, or CARD-11 mRNA or protein is less (statistically significantly less) in the presence of the candidate compound than in its absence, the candidate compound is identified as an inhibitor of CARD-9, CARD-10, or CARD-11 mRNA or protein expression. The level of CARD-9, CARD-10, or CARD-11 mRNA or protein expression in the cells can be determined by methods described herein for detecting CARD-9, CARD-10, or CARD-11 mRNA or protein. The activity of the CARD-9, CARD-10, or CARD-11 promoter can be assayed by linking the CARD-9, CARD-10, or CARD-11 promoter to a reporter gene such as luciferase, secreted alkaline phosphatase, or beta-galactosidase and introducing the resulting construct into an appropriate vector, transfecting a host cell line, and measuring the activity of the reporter gene in response to test compounds.

In yet another aspect of the invention, the CARD-9, CARD-10, or CARD-11 proteins can be used as "bait proteins" in a two-hybrid assay (for a discussion of a mammalian two-hybrid assay, see e.g., Hosfield and Chang (1999) *Strategies Newsletter* 2(2):62-65) or three hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and PCT Publication No. WO 94/10300), to identify other proteins, which bind to or interact with CARD-9, CARD-10, or CARD-11 ("CARD-9, CARD-10, or CARD-11-binding proteins" or "CARD-9, CARD-10, or CARD-11-bp") and modulate CARD-9, CARD-10, or CARD-11 activity. Such CARD-9, CARD-10, or CARD-11-binding proteins are also likely to be involved in the propagation of signals by the CARD-9, CARD-10, or CARD-11 proteins as, for example, upstream or downstream elements of the CARD-9, CARD-10, or CARD-11 pathway.

The two-hybrid system is based on the modular nature of most transcription factors, which consist of separable DNA-binding and activation domains. Briefly, the assay utilizes two different DNA constructs. In one construct, the gene that codes for CARD-9, CARD-10, or CARD-11 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a CARD-9, CARD-10, or CARD-11-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with CARD-9, CARD-10, or CARD-11.

In an embodiment of the invention, the ability of a test compound to modulate the activity of CARD-9, CARD-10, or CARD-11, or a biologically active portion thereof can be determined by assaying the ability of the test compound to block the binding of CARD-9, CARD-10, or CARD-11 to its target proteins in a yeast or mammalian two-hybrid system assay. This assay could be automated for high throughput drug screening purposes. In another embodiment of the invention, CARD-9, CARD-10, or CARD-11 and a target protein could be configured in the reverse two-hybrid system (Vidal et al. (1996) Proc. Natl. Acad. Sci. USA 93:10321-6 and Vidal et al. (1996) Proc. Natl. Acad. Sci. USA 93:10315-20) designed specifically for efficient drug screening. In the reverse two-hybrid system, inhibition of a CARD-9, CARD-10, or CARD-11 physical interaction with a target protein would result in induction of a reporter gene in contrast to the normal two-hybrid system where inhibition of CARD-9, CARD-10, or CARD-11 physical interaction with a target protein would lead to reporter gene repression. The reverse two-hybrid system is preferred for drug screening because reporter gene induction is more easily assayed than report gene repression.

Alternative embodiments of the invention are proteins found to physically interact with proteins that bind to CARD-9, CARD-10, or CARD-11. CARD-9, CARD-10, or CARD-11 interactors could be configured into two-hybrid system baits and used in two-hybrid screens to identify additional members of the CARD-9, CARD-10, or CARD-11 pathway. The interactors of CARD-9, CARD-10, or CARD-11 interactors identified in this way could be useful targets for therapeutic intervention in CARD-9, CARD-10, or CARD-11 related diseases and pathologies and an assay of their enzymatic or binding activity could be useful for the identification of test compounds that modulate CARD-9, CARD-10, or CARD-11 activity.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, CARD-9, CARD-10, or CARD-11 nucleic acid molecules described herein or fragments thereof, can be used to map the location of CARD-9, CARD-10, or CARD-11 genes on a chromosome. The mapping of the CARD-9, CARD-10, or CARD-11 sequences to chromosomes is an important first step in correlating these sequences with genes associated with disease.

Briefly, CARD-9, CARD-10, or CARD-11 genes can be mapped to chromosomes by preparing PCR primers (preferably 15-25 bp in length) from the CARD-9, CARD-10, or CARD-11 sequences. Computer analysis of CARD-9, CARD-10, or CARD-11 sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the CARD-9, CARD-10, or CARD-11 sequences will yield an amplified fragment. Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) Science 220:919-924). Somatic cell hybrids containing only fragments of human chromosomes can also be produced using human chromosomes with translocations and deletions.

PCR mapping of somatic cell hybrids is a rapid procedure for assigning a particular sequence to a particular chromosome. Three or more sequences can be assigned per day using a single thermal cycler. Using the CARD-9, CARD-10, or CARD-11 sequences to design oligonucleotide primers, sub-localization can be achieved with panels of fragments from specific chromosomes. Other mapping strategies which can similarly be used to map a CARD-9, CARD-10, or CARD-11 sequence to its chromosome include in situ hybridization (described in Fan et al. (1990) Proc. Natl. Acad. Sci. USA 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature, 325:783-787.

Moreover, differences in the DNA sequences between individuals affected and unaffected with a disease associated with the CARD-9, CARD-10, or CARD-11 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

A CARD-9, CARD-10, or CARD-11 polypeptide and fragments and sequences thereof and antibodies specific thereto can be used to map the location of the gene encoding the polypeptide on a chromosome. This mapping can be carried out by specifically detecting the presence of the polypeptide in members of a panel of somatic cell hybrids between cells of a first species of animal from which the protein originates and cells from a second species of animal and then determining which somatic cell hybrid(s) expresses the polypeptide and noting the chromosome(s) from the first species of animal that it contains. For examples of this technique, see Pajunen et al. (1988) Cytogenet. Cell Genet. 47:37-41 and Van Keuren et al. (1986) Hum. Genet. 74:34-40. Alternatively, the presence of the CARD-9, CARD-10, or CARD-11 polypeptide in the somatic cell hybrids can be determined by assaying an activity or property of the polypeptide, for example, enzymatic activity, as described in Bordelon-Riser et al. (1979) Somatic Cell Genetics 5:597-613 and Owerbach et al. (1978) Proc. Natl. Acad. Sci. USA 75:5640-5644.

2. Tissue Typing

The CARD-9, CARD-10, or CARD-11 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the CARD-9, CARD-10, or CARD-11 sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The CARD-9, CARD-10, or CARD-11 sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, SEQ ID NO:4, SEQ ID NO:7, or SEQ ID NO:10 can comfortably provide positive individual identification with a panel of perhaps 10 to 1,000 primers which each yield a noncoding amplified sequence of 100 bases. If predicted coding sequences, such as those in SEQ ID NO:3, SEQ ID NO:6, SEQ ID NO:9, or SEQ ID NO:12 are used, a more appropriate number of primers for positive individual identification would be 500-2,000.

If a panel of reagents from CARD-9, CARD-10, or CARD-11 sequences described herein is used to generate a unique identification database for an individual, those same reagents can later be used to identify tissue from that individual. Using the unique identification database, positive identification of the individual, living or dead, can be made from extremely small tissue samples.

3. Use of Partial Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, SEQ ID NO:4, SEQ ID NO:7, or SEQ ID NO:10 are particularly appropriate for this use as greater numbers of polymorphisms occur in the noncoding regions, making it easier to differentiate individuals using this technique. Examples of polynucleotide reagents include the CARD-9, CARD-10, or CARD-11 sequences or portions thereof, e.g., fragments derived from the noncoding regions of SEQ ID NO:1, SEQ ID NO:4, SEQ ID NO:7, or SEQ ID NO:10 which have a length of at least 20 or 30 bases.

The sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such CARD-9, CARD-10, or CARD-11 probes can be used to identify tissue by species and/or by organ type.

In a similar fashion, these reagents, e.g., CARD-9, CARD-10, or CARD-11 primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining CARD-9, CARD-10, or CARD-11 protein and/or nucleic acid expression as well as CARD-9, CARD-10, or CARD-11 activity, in the context of a biological sample (e.g., blood, serum, cells, tissue) to thereby determine whether an individual is afflicted with a disease or disorder, or is at risk of developing a disorder, associated with aberrant CARD-9, CARD-10, or CARD-11 expression or activity. The invention also provides for prognostic (or predictive) assays for determining whether an individual is at risk of developing a disorder associated with CARD-9, CARD-10, or CARD-11 protein, nucleic acid expression or activity. For example, mutations in a CARD-9, CARD-10, or CARD-11 gene can be assayed in a biological sample. Such assays can be used for prognostic or predictive purpose to thereby prophylactically treat an individual prior to the onset of a disorder characterized by or associated with CARD-9, CARD-10, or CARD-11 protein, nucleic acid expression or activity.

Another aspect of the invention provides methods for determining CARD-9, CARD-10, or CARD-11 protein, nucleic acid expression or CARD-9, CARD-10, or CARD-11 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs or other compounds) on the expression or activity of CARD-9, CARD-10, or CARD-11 in clinical trials.

These and other agents are described in further detail in the following sections.

1. Diagnostic Assays

An exemplary method for detecting the presence or absence of CARD-9, CARD-10, or CARD-11 in a biological sample involves obtaining a biological sample from a test subject and contacting the biological sample with a compound or an agent capable of detecting CARD-9, CARD-10, or CARD-11 protein or nucleic acid (e.g., mRNA, genomic DNA) that encodes CARD-9, CARD-10, or CARD-11 protein such that the presence of CARD-9, CARD-10, or CARD-11 is detected in the biological sample. An agent for detecting CARD-9, CARD-10, or CARD-11 mRNA or genomic DNA is a labeled nucleic acid probe capable of hybridizing to CARD-9, CARD-10, or CARD-11 mRNA or genomic DNA.

The nucleic acid probe can be, for example, a full-length CARD-9, CARD-10, or CARD-11 nucleic acid, such as the nucleic acid of SEQ ID NO:1, SEQ ID NO:3, SEQ ID NO:4, SEQ ID NO:6, SEQ ID NO:7, SEQ ID NO:9, SEQ ID NO:10, SEQ ID NO:12, or a portion thereof, such as an oligonucleotide of at least 15, 30, 50, 100, 250, 300, 350, 400, 450, 500, 550, 600, 650, 700, 800, 900, 1000, 1200, 1400, 1600, 1800, 2000, 2200, 2400, 2600, 2800, 3000, 3200, 3400, 3600, 3800, 4000, 4200, or 4250 nucleotides in length and sufficient to specifically hybridize under stringent conditions to mRNA or genomic DNA. Other suitable probes for use in the diagnostic assays of the invention are described herein.

An agent for detecting CARD-9, CARD-10, or CARD-11 protein can be an antibody capable of binding to CARD-9, CARD-10, or CARD-11 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect CARD-9, CARD-10, or CARD-11 mRNA, protein, or genomic DNA in a biological sample in vitro as well as in vivo. For example, in vitro techniques for detection of CARD-9, CARD-10, or CARD-11 mRNA include Northern hybridizations and in situ hybridizations. In vitro techniques for detection of CARD-9, CARD-10, or CARD-11 protein include enzyme linked immunosorbent assays (ELISAs), Western blots, immunoprecipitations and immunofluorescence. In vitro techniques for detection of CARD-9, CARD-10, or CARD-11 genomic DNA include Southern hybridizations. Furthermore, in vivo techniques for detection of CARD-9, CARD-10, or CARD-11 protein include introducing into a subject a labeled anti-CARD-9, CARD-10, or CARD-11 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A biological sample is a peripheral blood leukocyte sample isolated by conventional means from a subject.

In another embodiment, the methods further involve obtaining a control biological sample from a control subject, contacting the control sample with a compound or agent capable of detecting CARD-9, CARD-10, or CARD-11 protein, mRNA, or genomic DNA, such that the presence of CARD-9, CARD-10, or CARD-11 protein, mRNA or genomic DNA is detected in the biological sample, and comparing the presence of CARD-9, CARD-10, or CARD-11 protein, mRNA or genomic DNA in the control sample with the presence of CARD-9, CARD-10, or CARD-11 protein, mRNA or genomic DNA in the test sample.

The invention also encompasses kits for detecting the presence of CARD-9, CARD-10, or CARD-11 in a biological sample (a test sample). Such kits can be used to determine if a subject is suffering from or is at increased risk of developing a disorder associated with aberrant expression of CARD-9, CARD-10, or CARD-11 (e.g., an immunological disorder). For example, the kit can comprise a labeled compound or agent capable of detecting CARD-9, CARD-10, or CARD-11 protein or mRNA in a biological sample and means for determining the amount of CARD-9, CARD-10, or CARD-11 in the sample (e.g., an anti-CARD-9, CARD-10, or CARD-11 antibody or an oligonucleotide probe which binds to DNA encoding CARD-9, CARD-10, or CARD-11, e.g., SEQ ID NO:1, SEQ ID NO:3, SEQ ID NO:4, SEQ ID NO:6, SEQ ID NO:7, SEQ ID NO:9, SEQ ID NO:10, SEQ ID NO:12). Kits may also include instruction for observing that the tested subject is suffering from or is at risk of developing a disorder associated with aberrant expression of CARD-9, CARD-10, or CARD-11 if the amount of CARD-9, CARD-10, or CARD-11 protein or mRNA is above or below a normal level.

For antibody-based kits, the kit may comprise, for example: (1) a first antibody (e.g., attached to a solid support) which binds to CARD-9, CARD-10, or CARD-11 protein; and, optionally, (2) a second, different antibody which binds to CARD-9, CARD-10, or CARD-11 protein or the first antibody and is conjugated to a detectable agent. For oligonucleotide-based kits, the kit may comprise, for example: (1) a oligonucleotide, e.g., a detectably labeled oligonucleotide, which hybridizes to a CARD-9, CARD-10, or CARD-11 nucleic acid sequence or (2) a pair of primers useful for amplifying a CARD-9, CARD-10, or CARD-11 nucleic acid molecule.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of CARD-9, CARD-10, or CARD-11.

2. Prognostic Assays

The methods described herein can furthermore be utilized as diagnostic or prognostic assays to identify subjects having or at risk of developing a disease or disorder associated with aberrant CARD-9, CARD-10, or CARD-11 expression or activity. For example, the assays described herein, such as the preceding diagnostic assays or the following assays, can be utilized to identify a subject having or at risk of developing a disorder associated with CARD-9, CARD-10, or CARD-11 protein, nucleic acid expression or activity. Alternatively, the prognostic assays can be utilized to identify a subject having or at risk for developing such a disease or disorder. Thus, the present invention provides a method in which a test sample is obtained from a subject and CARD-9, CARD-10, or CARD-11 protein or nucleic acid (e.g., mRNA, genomic DNA) is detected, wherein the presence of CARD-9, CARD-10, or CARD-11 protein or nucleic acid is diagnostic for a subject having or at risk of developing a disease or disorder associated with aberrant CARD-9, CARD-10, or CARD-11 expression or activity. As used herein, a "test sample" refers to a biological sample obtained from a subject of interest. For example, a test sample can be a biological fluid (e.g., serum), cell sample, or tissue. Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant CARD-9, CARD-10, or CARD-11 expression or activity. For example, such methods can be used to determine whether a subject can be effectively treated with a specific agent or class of agents (e.g., agents of a type which decrease CARD-9, CARD-10, or CARD-11 activity). Thus, the present invention provides methods for determining whether a subject can be effectively treated with an agent for a disorder associated with aberrant CARD-9, CARD-10, or CARD-11 expression or activity in which a test sample is obtained and CARD-9, CARD-10, or CARD-11 protein or nucleic acid is detected (e.g., wherein the presence of CARD-9, CARD-10, or CARD-11 protein or nucleic acid is diagnostic for a subject that can be administered the agent to treat a disorder associated with aberrant CARD-9, CARD-10, or CARD-11 expression or activity).

The methods of the invention can also be used to detect genetic lesions or mutations in a CARD-9, CARD-10, or CARD-11 gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion characterized by at least one of an alteration affecting the integrity of a gene encoding a CARD-9, CARD-10, or CARD-11-protein, or the mis-expression of the CARD-9, CARD-10, or CARD-11 gene. For example, such genetic lesions can be detected by ascertaining the existence of at least one of 1) a deletion of one or more nucleotides from a CARD-9, CARD-10, or CARD-11 gene; 2) an addition of one or more nucleotides to a CARD-9, CARD-10, or CARD-11 gene; 3) a substitution of one or more nucleotides of a CARD-9, CARD-10, or CARD-11 gene; 4) a chromosomal rearrangement of a CARD-9, CARD-10, or CARD-11 gene; 5) an alteration in the level of a messenger RNA transcript of a CARD-9, CARD-10, or CARD-11 gene; 6) aberrant modification of a CARD-9, CARD-10, or CARD-11 gene, such as of the methylation pattern of the genomic DNA; 7) the presence of a non-wild type splicing pattern of a messenger RNA transcript of a CARD-9, CARD-10, or CARD-11 gene (e.g., caused by a mutation in a splice donor or splice acceptor site); 8) a non-wild type level of a CARD-9, CARD-10, or CARD-11-protein; 9) allelic loss of a CARD-9, CARD-10, or CARD-11 gene; and 10) inappropriate post-translational modification of a CARD-9, CARD-10, or CARD-11-protein. As described herein, there are a large number of assay techniques known in the art which can be used for detecting lesions in a CARD-9, CARD-10, or CARD-11 gene. A biological sample is a peripheral blood leukocyte sample isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegrari et al. (1988) Science 241:1077-1080; and Nakazawa et al. (1994) Proc. Natl. Acad. Sci. USA 91:360-364), the latter of which can be particularly useful for detecting point mutations in the CARD-9, CARD-10, or CARD-11 gene (see, e.g., Abravaya et al. (1995) Nucleic Acids Res. 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a CARD-9, CARD-10, or CARD-11 gene under conditions such that hybridization and amplification of the CARD-9, CARD-10, or CARD-11-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874-1878), transcriptional amplification system (Kwoh, et al. (1989) Proc. Natl. Acad. Sci. USA 86:1173-1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a CARD-9, CARD-10, or CARD-11 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in CARD-9, CARD-10, or CARD-11 can be identified by hybridizing a sample and control nucleic acids, e.g., DNA or RNA, to high density arrays containing hundreds or thousands of oligonucleotides probes (Cronin et al. (1996) Human Mutation 7:244-255; Kozal et al. (1996) Nature Medicine 2:753-759). For example, genetic mutations in CARD-9, CARD-10, or CARD-11 can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the CARD-9, CARD-10, or CARD-11 gene and detect mutations by comparing the sequence of the sample CARD-9, CARD-10, or CARD-11 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the CARD-9, CARD-10, or CARD-11 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type CARD-9, CARD-10, or CARD-11 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) Proc. Natl. Acad Sci USA 85:4397; Saleeba et al (1992) Methods Enzymol. 217:286-295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in CARD-9, CARD-10, or CARD-11 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a CARD-9, CARD-10, or CARD-11 sequence, e.g., a wild-type CARD-9, CARD-10, or CARD-11 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in CARD-9, CARD-10, or CARD-11 genes. For example, single strand conformation polymorphism (SSCP) may be used to detect differences in electrophoretic mobility between mutant and wild type nucleic acids (Orita et al. (1989) Proc Natl. Acad. Sci. USA: 86:2766, see also Cotton (1993) Mutat. Res. 285: 125-144; and Hayashi (1992) Genet Anal Tech Appl 9:73-79). Single-stranded DNA fragments of sample and control CARD-9, CARD-10, or CARD-11 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In an embodiment, the subject method utilizes heteroduplex analysis to separate double stranded heteroduplex molecules on the basis of changes in electrophoretic mobility (Keen et al. (1991) Trends Genet. 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition, it may be desirable to introduce a novel restriction site in the region of the mutation to create cleavage-based detection (Gasparini et al. (1992) Mol. Cell. Probes 6:1). It is anticipated that in certain embodiments amplification may also be performed using Taq ligase for amplification (Barany (1991) Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a CARD-9, CARD-10, or CARD-11 gene.

Furthermore, any cell type or tissue, preferably peripheral blood leukocytes, in which CARD-9, CARD-10, or CARD-11 is expressed may be utilized in the prognostic assays described herein.

3. Pharmacogenomics

Agents, or modulators which have a stimulatory or inhibitory effect on CARD-9, CARD-10, or CARD-11 activity (e.g., CARD-9, CARD-10, or CARD-11 gene expression) as identified by a screening assay described herein can be administered to individuals to treat (prophylactically or therapeutically) disorders (e.g., an immunological disorder) associated with aberrant CARD-9, CARD-10, or CARD-11 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of CARD-9, CARD-10, or CARD-11 protein, expression of CARD-9, CARD-10, or CARD-11 nucleic acid, or mutation content of CARD-9, CARD-10, or CARD-11 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM exhibit no therapeutic response, as demonstrated for the analgesic effect of codeine mediated by its CYP2D6-formed metabolite morphine. The other extreme are the so-called ultra-rapid metabolizers who do not respond to standard doses. Recently, the molecular basis of ultra-rapid metabolism has been identified to be due to CYP2D6 gene amplification.

Thus, the activity of CARD-9, CARD-10, or CARD-11 protein, expression of CARD-9, CARD-10, or CARD-11 nucleic acid, or mutation content of CARD-9, CARD-10, or CARD-11 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a CARD-9, CARD-10, or CARD-11 modulator, such as a modulator identified by one of the exemplary screening assays described herein.

4. Monitoring of Effects During Clinical Trials

Monitoring the influence of agents (e.g., drugs, compounds) on the expression or activity of CARD-9, CARD-10, or CARD-11 (e.g., the ability to modulate aberrant cell proliferation and/or differentiation) can be applied not only in basic drug screening, but also in clinical trials. For example, the effectiveness of an agent determined by a screening assay as described herein to increase CARD-9, CARD-10, or CARD-11 gene expression, protein levels, or upregulate CARD-9, CARD-10, or CARD-11 activity, can be monitored in clinical trails of subjects exhibiting decreased CARD-9, CARD-10, or CARD-11 gene expression, protein levels, or downregulated CARD-9, CARD-10, or CARD-11 activity. Alternatively, the effectiveness of an agent determined by a screening assay to decrease CARD-9, CARD-10, or CARD-11 gene expression, protein levels, or downregulated CARD-9, CARD-10, or CARD-11 activity, can be monitored in clinical trials of subjects exhibiting increased CARD-9, CARD-10, or CARD-11 gene expression, protein levels, or upregulated CARD-9, CARD-10, or CARD-11 activity. In such clinical trials, the expression or activity of CARD-9, CARD-10, or CARD-11 and, preferably, other genes that have been implicated in, for example, a cellular proliferation disorder can be used as a "read out" or markers of the immune responsiveness of a particular cell.

For example, and not by way of limitation, genes, including CARD-9, CARD-10, or CARD-11, that are modulated in cells by treatment with an agent (e.g., compound, drug or small molecule) which modulates CARD-9, CARD-10, or CARD-11 activity (e.g., identified in a screening assay as described herein) can be identified. Thus, to study the effect of agents on cellular proliferation disorders, for example, in a clinical trial, cells can be isolated and RNA prepared and analyzed for the levels of expression of CARD-9, CARD-10, or CARD-11 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of CARD-9, CARD-10, or CARD-11 or other genes. In this way, the gene expression pattern can serve as a marker, indicative of the physiological response of the cells to the agent. Accordingly, this response state may be determined before, and at various points during, treatment of the individual with the agent.

In an embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a CARD-9, CARD-10, or CARD-11 protein, mRNA, or genomic DNA in the preadministration sample; (iii) obtaining one or more post-administration samples from the subject; (iv) detecting the level of expression or activity of the CARD-9, CARD-10, or CARD-11 protein, mRNA, or genomic DNA in the post-administration samples; (v) comparing the level of expression or activity of the CARD-9, CARD-10, or CARD-11 protein, mRNA, or genomic DNA in the pre-administration sample with the CARD-9, CARD-10, or CARD-11 protein, mRNA, or genomic DNA in the post administration sample or samples; and (vi) altering the administration of the agent to the subject accordingly. For example, increased administration of the agent may be desirable to increase the expression or activity of CARD-9, CARD-10, or CARD-11 to higher levels than detected, i.e., to increase the effectiveness of the agent. Alternatively, decreased administration of the agent may be desirable to decrease expression or activity of CARD-9, CARD-10, or CARD-11 to lower levels than detected, i.e., to decrease the effectiveness of the agent.

5. Transcriptional Profiling

The CARD-9, CARD-10, or CARD-11 nucleic acid molecules described herein, including small oligonucleotides, can be used in transcriptionally profiling. For example, these nucleic acids can be used to examine the expression of CARD-9, CARD-10, or CARD-11 in normal tissue or cells and in tissue or cells subject to a disease state, e.g., tissue or cells derived from a patient having a disease of interest or cultured cells which model or reflect a disease state of interest, e.g., cells of a cultured tumor cell line. By measuring expression of CARD-9, CARD-10, or CARD-11, together or individually, a profile of expression in normal and disease states can be developed. This profile can be used diagnostically and to examine the effectiveness of a therapeutic regime.

C. Methods of Treatment

The present invention provides for both prophylactic and therapeutic methods of treating a subject at risk of (or susceptible to) a disorder or having a disorder associated with aberrant CARD-9, CARD-10, or CARD-11 expression or activity, examples of which are provided herein.

1. Prophylactic Methods

In one aspect, the invention provides a method for preventing in a subject, a disease or condition associated with an aberrant CARD-9, CARD-10, or CARD-11 expression or activity, by administering to the subject an agent which modulates CARD-9, CARD-10, or CARD-11 expression or at least one CARD-9, CARD-10, or CARD-11 activity. Subjects at risk for a disease which is caused or contributed to by aberrant CARD-9, CARD-10, or CARD-11 expression or activity can be identified by, for example, any or a combination of diagnostic or prognostic assays as described herein. Administration of a prophylactic agent can occur prior to the manifestation of symptoms characteristic of the CARD-9, CARD-10, or CARD-11 aberrancy, such that a disease or disorder is prevented or, alternatively, delayed in its progression. Depending on the type of CARD-9, CARD-10, or CARD-11 aberrancy, for example, a CARD-9, CARD-10, or CARD-11 agonist or CARD-9, CARD-10, or CARD-11 antagonist agent can be used for treating the subject. The appropriate agent can be determined based on screening assays described herein.

2. Therapeutic Methods

Another aspect of the invention pertains to methods of modulating CARD-9, CARD-10, or CARD-11 expression or activity for therapeutic purposes. The modulatory method of the invention involves contacting a cell with an agent that modulates one or more of the activities of CARD-9, CARD-10, or CARD-11 protein activity associated with the cell. An agent that modulates CARD-9, CARD-10, or CARD-11 protein activity can be an agent as described herein, such as a nucleic acid or a protein, a naturally-occurring cognate ligand of a CARD-9, CARD-10, or CARD-11 protein, a peptide, a CARD-9, CARD-10, or CARD-11 peptidomimetic, or other small molecule. In one embodiment, the agent stimulates one or more of the biological activities of CARD-9, CARD-10, or CARD-11 protein. Examples of such stimulatory agents include active CARD-9, CARD-10, or CARD-11 protein and a nucleic acid molecule encoding CARD-9, CARD-10, or CARD-11 that has been introduced into the cell. In another embodiment, the agent inhibits one or more of the biological activities of CARD-9, CARD-10, or CARD-11 protein.

Examples of such inhibitory agents include antisense CARD-9, CARD-10, or CARD-11 nucleic acid molecules and anti-CARD-9, CARD-10, or CARD-11 antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a CARD-9, CARD-10, or CARD-11 protein or nucleic acid molecule or a disorder related to CARD-9, CARD-10, or CARD-11 expression or activity. In one embodiment, the method involves administering an agent (e.g., an agent identified by a screening assay described herein), or combination of agents that modulates (e.g., upregulates or down-regulates) CARD-9, CARD-10, or CARD-11 expression or activity. In another embodiment, the method involves administering a CARD-9, CARD-10, or CARD-11 protein or nucleic acid molecule as therapy to compensate for reduced or aberrant CARD-9, CARD-10, or CARD-11 expression or activity. Stimulation of CARD-9, CARD-10, or CARD-11 activity is desirable in situations in which CARD-9, CARD-10, or CARD-11 is abnormally downregulated and/or in which increased CARD-9, CARD-10, or CARD-11 activity is likely to have a beneficial effect. Conversely, inhibition of CARD-9, CARD-10, or CARD-11 activity is desirable in situations in which CARD-9, CARD-10, or CARD-11 is abnormally upregulated, e.g., in myocardial infarction, and/or in which decreased CARD-9, CARD-10, or CARD-11 activity is likely to have a beneficial effect.

The contents of all references, patents and published patent applications cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

SEQUENCE LISTING

```
<160> NUMBER OF SEQ ID NOS: 19

<210> SEQ ID NO 1
<211> LENGTH: 1879
<212> TYPE: DNA
<213> ORGANISM: Rattus norvegicus
<220> FEATURE:
<221> NAME/KEY: CDS
<222> LOCATION: (113)...(1720)

<400> SEQUENCE: 1
ccacgcgtcc gagcatctcc acactcccag aggctcgctc ctggagtgcc catagcccag        60
gcagcatcca gctggcaggt ggctcccaca ggaccctgag cctacagagg ac atg tca       118
                                                           Met Ser
                                                             1 gac tat gaa aat gac gac gag tgc tgg agt gcc ctg gag agc ttc cgg        166
Asp Tyr Glu Asn Asp Asp Glu Cys Trp Ser Ala Leu Glu Ser Phe Arg
        5                  10                  15 gtg aag cta atc tct gtc att gac ccc tca cga atc aca ccc tat ctg        214
Val Lys Leu Ile Ser Val Ile Asp Pro Ser Arg Ile Thr Pro Tyr Leu
 20                  25                  30 cgc cag tgc aaa gtc ctg aac ccc gat gat gag gag cag gtg ctc agt        262
Arg Gln Cys Lys Val Leu Asn Pro Asp Asp Glu Glu Gln Val Leu Ser
 35                  40                  45                  50 gac ccc aac ctg gtc atc cgc aag cgg aaa gtg ggt gtg ctc ctg gac        310
Asp Pro Asn Leu Val Ile Arg Lys Arg Lys Val Gly Val Leu Leu Asp
                 55                  60                  65 atc ctg cag cgg aca ggc cac aag ggc tac gtg gcc ttt ctt gag agt        358
Ile Leu Gln Arg Thr Gly His Lys Gly Tyr Val Ala Phe Leu Glu Ser
                 70                  75                  80 ctg gaa ctc tac tac cct cag tta tac agg aaa gtc act ggc aag gag        406
Leu Glu Leu Tyr Tyr Pro Gln Leu Tyr Arg Lys Val Thr Gly Lys Glu
             85                  90                  95 cca gcg cgt gtc ttc tcc atg atc atc gac gca tca ggg gag tcg ggc        454
Pro Ala Arg Val Phe Ser Met Ile Ile Asp Ala Ser Gly Glu Ser Gly
        100                 105                 110 ctg acg cag ctg ctg atg aca gag gtc atg aag ctg cag aag aag gtt        502
Leu Thr Gln Leu Leu Met Thr Glu Val Met Lys Leu Gln Lys Lys Val
115                 120                 125                 130 cag gac ctg acg gcc ctt ctg agc tcc aag gat gac ttc atc aag gag        550
```

```
Gln Asp Leu Thr Ala Leu Leu Ser Ser Lys Asp Asp Phe Ile Lys Glu
            135                 140                 145 ctg agg gta aag gac agc ctc ctg cgc aag cac cag gag cgg gtg cag    598
Leu Arg Val Lys Asp Ser Leu Leu Arg Lys His Gln Glu Arg Val Gln
            150                 155                 160 cgg ctc aag gag gag tgt gag ctg agc agt gcc gag ctg aag cgc tgc    646
Arg Leu Lys Glu Glu Cys Glu Leu Ser Ser Ala Glu Leu Lys Arg Cys
            165                 170                 175 aag gat gag aac tac gac ctg gcc atg cgc ctg gct cac ctg agt gaa    694
Lys Asp Glu Asn Tyr Asp Leu Ala Met Arg Leu Ala His Leu Ser Glu
            180                 185                 190 gag aag gga gca gca ctc atg cgg aac cgt gac ctg cag ctt gag gtg    742
Glu Lys Gly Ala Ala Leu Met Arg Asn Arg Asp Leu Gln Leu Glu Val
195                 200                 205                 210 gac cag ctc agg cac agc ctc atg aag gca gag gat gac tgc aag gtg    790
Asp Gln Leu Arg His Ser Leu Met Lys Ala Glu Asp Asp Cys Lys Val
                215                 220                 225 gag cgc aaa cac aca ctg aag ctc cgg cac gcc atg gag cag cgg cct    838
Glu Arg Lys His Thr Leu Lys Leu Arg His Ala Met Glu Gln Arg Pro
                230                 235                 240 agc cag gag ctg ctg tgg gac ctg cag cag gag agg gac ttg ttg cag    886
Ser Gln Glu Leu Leu Trp Asp Leu Gln Gln Glu Arg Asp Leu Leu Gln
            245                 250                 255 gcc cgg gtg cag gag ctg gag gtc tcc gtg cag gag ggt aag cta cac    934
Ala Arg Val Gln Glu Leu Glu Val Ser Val Gln Glu Gly Lys Leu His
            260                 265                 270 agg aat agc cca tac atc cag gtg ctg gag gag gac tgg cgt cag gca    982
Arg Asn Ser Pro Tyr Ile Gln Val Leu Glu Glu Asp Trp Arg Gln Ala
275                 280                 285                 290 ctg cag gaa cac cag gag cag gcc agc acc atc ttc tcc cta cga aag   1030
Leu Gln Glu His Gln Glu Gln Ala Ser Thr Ile Phe Ser Leu Arg Lys
                295                 300                 305 gac ctc cgc cag gct gag gcc ctc cgg acc cgg tgc atg gag gaa aag   1078
Asp Leu Arg Gln Ala Glu Ala Leu Arg Thr Arg Cys Met Glu Glu Lys
            310                 315                 320 gag atg ttc gag ctg cag tgc ctg gcc ttg cgc aag gat gcc aag atg   1126
Glu Met Phe Glu Leu Gln Cys Leu Ala Leu Arg Lys Asp Ala Lys Met
            325                 330                 335 tac aag gac cgg atc gag gct atc ctg cag cag atg gag gaa gtc tcc   1174
Tyr Lys Asp Arg Ile Glu Ala Ile Leu Gln Gln Met Glu Glu Val Ser
            340                 345                 350 att gag cgg gac cag gct atg acc tca agg gaa gag ctg cat gca cag   1222
Ile Glu Arg Asp Gln Ala Met Thr Ser Arg Glu Glu Leu His Ala Gln
355                 360                 365                 370 tgt gcc caa agc ttt cag gac aaa gat aag ctg cga aag cag gtt cga   1270
Cys Ala Gln Ser Phe Gln Asp Lys Asp Lys Leu Arg Lys Gln Val Arg
                375                 380                 385 gaa ctg gat gag aag gcc gac gag ttg cag ctg cag ctg ttc cag acc   1318
Glu Leu Asp Glu Lys Ala Asp Glu Leu Gln Leu Gln Leu Phe Gln Thr
            390                 395                 400 gag agc cga tta ctg gcc gct gag ggc aga ctc aag cag cag caa ttg   1366
Glu Ser Arg Leu Leu Ala Ala Glu Gly Arg Leu Lys Gln Gln Gln Leu
            405                 410                 415 gac atg ctc atc ctg agc tct gac ttg gaa gac agt tcc ccc agg aac   1414
Asp Met Leu Ile Leu Ser Ser Asp Leu Glu Asp Ser Ser Pro Arg Asn
420                 425                 430 tcc cag gag ctt tca ctg cct cag gac ctg gag gat gcc cag ctc       1462
Ser Gln Glu Leu Ser Leu Pro Gln Asp Leu Glu Asp Ala Gln Leu
            435                 440                 445             450 tca gac aaa ggt gtc ctg gca gac agg gag agc cca gag cag ccc ttc   1510
```

```
Ser Asp Lys Gly Val Leu Ala Asp Arg Glu Ser Pro Glu Gln Pro Phe
            455                 460                 465 gtg gtt ctg aac aag aag cat ctt tcg cag acc cat gac acg gtg ccc    1558
Val Val Leu Asn Lys Lys His Leu Ser Gln Thr His Asp Thr Val Pro
            470                 475                 480 agc agc agc gag ccc ccg gag aag gag cgg cgg cgc ctc aag gag agc    1606
Ser Ser Ser Glu Pro Pro Glu Lys Glu Arg Arg Arg Leu Lys Glu Ser
            485                 490                 495 ttc gag aac tac cgc agg aag cgg gcg ctc cgc aag atg cag aac agc    1654
Phe Glu Asn Tyr Arg Arg Lys Arg Ala Leu Arg Lys Met Gln Asn Ser
500                 505                 510 tgg cga cag gga gaa ggg gat cac ggg aat acg aca ggc agc gac aac    1702
Trp Arg Gln Gly Glu Gly Asp His Gly Asn Thr Thr Gly Ser Asp Asn
515                 520                 525                 530 acc gac acc gag ggc tcc tagaggacca cgccgaggct gagcgtctgt           1750
Thr Asp Thr Glu Gly Ser
            535 gtaattgtga agggatgctg cgggttttt tactgtacgc tacacatacg ttgtacaagt   1810 attagaaaaa aatgcagcct aataaaatga cctctgagct gaaaaaaaaa aaaaaaaaa   1870 aaaaaaaaa                                                          1879

<210> SEQ ID NO 2
<211> LENGTH: 536
<212> TYPE: PRT
<213> ORGANISM: Rattus norvegicus

<400> SEQUENCE: 2

Met Ser Asp Tyr Glu Asn Asp Asp Glu Cys Trp Ser Ala Leu Glu Ser
1               5                   10                  15

Phe Arg Val Lys Leu Ile Ser Val Ile Asp Pro Ser Arg Ile Thr Pro
            20                  25                  30

Tyr Leu Arg Gln Cys Lys Val Leu Asn Pro Asp Asp Glu Glu Gln Val
        35                  40                  45

Leu Ser Asp Pro Asn Leu Val Ile Arg Lys Arg Lys Val Gly Val Leu
    50                  55                  60

Leu Asp Ile Leu Gln Arg Thr Gly His Lys Gly Tyr Val Ala Phe Leu
65                  70                  75                  80

Glu Ser Leu Glu Leu Tyr Tyr Pro Gln Leu Tyr Arg Lys Val Thr Gly
                85                  90                  95

Lys Glu Pro Ala Arg Val Phe Ser Met Ile Ile Asp Ala Ser Gly Glu
            100                 105                 110

Ser Gly Leu Thr Gln Leu Leu Met Thr Glu Val Met Lys Leu Gln Lys
        115                 120                 125

Lys Val Gln Asp Leu Thr Ala Leu Leu Ser Ser Lys Asp Asp Phe Ile
    130                 135                 140

Lys Glu Leu Arg Val Lys Asp Ser Leu Leu Arg Lys His Gln Glu Arg
145                 150                 155                 160

Val Gln Arg Leu Lys Glu Glu Cys Glu Leu Ser Ser Ala Glu Leu Lys
                165                 170                 175

Arg Cys Lys Asp Glu Asn Tyr Asp Leu Ala Met Arg Leu Ala His Leu
            180                 185                 190

Ser Glu Glu Lys Gly Ala Ala Leu Met Arg Asn Arg Asp Leu Gln Leu
        195                 200                 205

Glu Val Asp Gln Leu Arg His Ser Leu Met Lys Ala Glu Asp Asp Cys
    210                 215                 220

Lys Val Glu Arg Lys His Thr Leu Lys Leu Arg His Ala Met Glu Gln
```

```
            225                 230                 235                 240
Arg Pro Ser Gln Glu Leu Leu Trp Asp Leu Gln Gln Glu Arg Asp Leu
                245                 250                 255

Leu Gln Ala Arg Val Gln Glu Leu Glu Val Ser Val Gln Glu Gly Lys
            260                 265                 270

Leu His Arg Asn Ser Pro Tyr Ile Gln Val Leu Glu Glu Asp Trp Arg
        275                 280                 285

Gln Ala Leu Gln Glu His Gln Glu Gln Ala Ser Thr Ile Phe Ser Leu
    290                 295                 300

Arg Lys Asp Leu Arg Gln Ala Glu Ala Leu Arg Thr Arg Cys Met Glu
305                 310                 315                 320

Glu Lys Glu Met Phe Glu Leu Gln Cys Leu Ala Leu Arg Lys Asp Ala
                325                 330                 335

Lys Met Tyr Lys Asp Arg Ile Glu Ala Ile Leu Gln Gln Met Glu Glu
            340                 345                 350

Val Ser Ile Glu Arg Asp Gln Ala Met Thr Ser Arg Glu Glu Leu His
        355                 360                 365

Ala Gln Cys Ala Gln Ser Phe Gln Asp Lys Asp Lys Leu Arg Lys Gln
    370                 375                 380

Val Arg Glu Leu Asp Glu Lys Ala Asp Glu Leu Gln Leu Gln Leu Phe
385                 390                 395                 400

Gln Thr Glu Ser Arg Leu Leu Ala Ala Glu Gly Arg Leu Lys Gln Gln
                405                 410                 415

Gln Leu Asp Met Leu Ile Leu Ser Ser Asp Leu Glu Asp Ser Ser Pro
            420                 425                 430

Arg Asn Ser Gln Glu Leu Ser Leu Pro Gln Asp Leu Glu Glu Asp Ala
        435                 440                 445

Gln Leu Ser Asp Lys Gly Val Leu Ala Asp Arg Glu Ser Pro Glu Gln
    450                 455                 460

Pro Phe Val Val Leu Asn Lys Lys His Leu Ser Gln Thr His Asp Thr
465                 470                 475                 480

Val Pro Ser Ser Glu Pro Pro Glu Lys Glu Arg Arg Leu Lys
                485                 490                 495

Glu Ser Phe Glu Asn Tyr Arg Arg Lys Arg Ala Leu Arg Lys Met Gln
                500                 505                 510

Asn Ser Trp Arg Gln Gly Glu Gly Asp His Gly Asn Thr Thr Gly Ser
            515                 520                 525

Asp Asn Thr Asp Thr Glu Gly Ser
        530                 535

<210> SEQ ID NO 3
<211> LENGTH: 1608
<212> TYPE: DNA
<213> ORGANISM: Rattus norvegicus

<400> SEQUENCE: 3
atgtcagact atgaaaatga cgacgagtgc tggagtgccc tggagagctt ccgggtgaag      60
ctaatctctg tcattgaccc ctcacgaatc acacccatc tgcgccagtg caaagtcctg      120
aaccccgatg atgaggagca ggtgctcagt gaccccaacc tggtcatccg caagcggaaa      180
gtgggtgtgc tcctggacat cctgcagcgg acaggccaca agggctacgt ggcctttctt      240
gagagtctgg aactctacta ccctcagtta tacaggaaag tcactggcaa ggagccagcg      300
cgtgtcttct ccatgatcat cgacgcatca ggggagtcgg gcctgacgca gctgctgatg      360
acagaggtca tgaagctgca gaagaaggtt caggacctga cggcccttct gagctccaag      420
```

```
gatgacttca tcaaggagct gagggtaaag gacagcctcc tgcgcaagca ccaggagcgg      480
gtgcagcggc tcaaggagga gtgtgagctg agcagtgccg agctgaagcg ctgcaaggat      540
gagaactacg acctggccat cgcctggct cacctgagtg aagagaaggg agcagcactc       600
atgcggaacc gtgacctgca gcttgaggtg accagctca ggcacagcct catgaaggca       660
gaggatgact gcaaggtgga gcgcaaacac acactgaagc tccggcacgc catggagcag      720
cggcctagcc aggagctgct gtgggacctg cagcaggaga gggacttgtt gcaggcccgg      780
gtgcaggagc tggaggtctc cgtgcaggag ggtaagctac acaggaatag cccatacatc      840
caggtgctgg aggaggactg gcgtcaggca ctgcaggaac caggagca ggccagcacc        900 atcttctccc tacgaaagga cctccgccag gctgaggccc tccggacccg gtgcatggag      960
gaaaaggaga tgttcgagct gcagtgcctg gccttgcgca aggatgccaa gatgtacaag     1020
gaccggatcg aggctatcct gcagcagatg gaggaagtct ccattgagcg ggaccaggct     1080
atgacctcaa gggaagagct gcatgcacag tgtgcccaaa gctttcagga caaagataag     1140
ctgcgaaagc aggttcgaga actggatgag aaggccgacg agttgcagct gcagctgttc     1200
cagaccgaga gccgattact ggccgctgag ggcagactca gcagcagca attggacatg      1260 ctcatcctga gctctgactt ggaagacagt tcccccagga actcccagga gctttcactg     1320
cctcaggacc tggaggagga tgcccagctc tcagacaaag tgtcctggc agacagggag      1380 agcccagagc agcccttcgt ggttctgaac aagaagcatc tttcgcagac ccatgacacg     1440
gtgcccagca gcagcgagcc cccggagaag gagcggcggc gcctcaagga gagcttcgag     1500
aactaccgca ggaagcgggc gctccgcaag atgcagaaca gctggcgaca gggagaaggg     1560
gatcacggga atacgacagg cagcgacaac accgacaccg agggctcc                  1608

<210> SEQ ID NO 4
<211> LENGTH: 2098
<212> TYPE: DNA
<213> ORGANISM: Homo sapiens
<220> FEATURE:
<221> NAME/KEY: CDS
<222> LOCATION: (144)...(1751)

<400> SEQUENCE: 4
actataggga gtcgacccac gcgtccggct cctccctccc tgcagccccg ggcagcatct       60
cccagaggct ccgcggccca ggctcctggt gtgtctgcag tgcaggtggc tcctggaaga     120
ccctcagcct gcctgctgag gcc atg tcg gac tac gag aac gat gac gag tgc     173
                         Met Ser Asp Tyr Glu Asn Asp Asp Glu Cys
                          1               5                  10 tgg aac gtc ctg gag ggc ttc cgg gtg acg ctc acc tcg gtc atc gac       221
Trp Asn Val Leu Glu Gly Phe Arg Val Thr Leu Thr Ser Val Ile Asp
              15                  20                  25 ccc tca cgc atc aca cct tac ctg cgg cag tgc aag gtc ctg aac cct       269
Pro Ser Arg Ile Thr Pro Tyr Leu Arg Gln Cys Lys Val Leu Asn Pro
          30                  35                  40 gat gat gag gag cag gtg ctc agc gac ccc aac ctg gtc atc cgc aaa       317
Asp Asp Glu Glu Gln Val Leu Ser Asp Pro Asn Leu Val Ile Arg Lys
      45                  50                  55 cgg aaa gtg ggt gtg ctc ctg gac atc ctg cag cgg acc ggc cac aag       365
Arg Lys Val Gly Val Leu Leu Asp Ile Leu Gln Arg Thr Gly His Lys
  60                  65                  70 ggc tac gtg gcc ttc ctc gag agc ctg gag ctc tac tac ccg cag ctg       413
Gly Tyr Val Ala Phe Leu Glu Ser Leu Glu Leu Tyr Tyr Pro Gln Leu
75                  80                  85                  90
```

```
                                                    -continued
tac aag aag gtc aca ggc aag gag cca gcc cgc gtc ttc tcc atg atc         461
Tyr Lys Lys Val Thr Gly Lys Glu Pro Ala Arg Val Phe Ser Met Ile
                 95                 100                 105 atc gac gcg tcc ggg gag tca ggc ctg act cag ctg ctg atg act gag         509
Ile Asp Ala Ser Gly Glu Ser Gly Leu Thr Gln Leu Leu Met Thr Glu
             110                 115                 120 gtc atg aag ctg cag aag aag gtg cag gac ctg acc gcg ctg ctg agc         557
Val Met Lys Leu Gln Lys Lys Val Gln Asp Leu Thr Ala Leu Leu Ser
         125                 130                 135 tcc aaa gat gac ttc atc aag gag ctg cgg gtg aag gac agc ctg ctg         605
Ser Lys Asp Asp Phe Ile Lys Glu Leu Arg Val Lys Asp Ser Leu Leu
     140                 145                 150 cgc aag cac cag gag cgt gtg cag agg ctc aag gag gag tgc gag gcc         653
Arg Lys His Gln Glu Arg Val Gln Arg Leu Lys Glu Glu Cys Glu Ala
155                 160                 165                 170 ggc agc cgc gag ctc aag cgc tgc aag gag gag aac tac gac ctg gcc         701
Gly Ser Arg Glu Leu Lys Arg Cys Lys Glu Glu Asn Tyr Asp Leu Ala
                 175                 180                 185 atg cgc ctg gcg cac cag agt gag gag aag ggc gcc gcg ctc atg cgg         749
Met Arg Leu Ala His Gln Ser Glu Glu Lys Gly Ala Ala Leu Met Arg
             190                 195                 200 aac cgt gac ctg cag ctg gag att gac cag ctc aag cac agc ctc atg         797
Asn Arg Asp Leu Gln Leu Glu Ile Asp Gln Leu Lys His Ser Leu Met
         205                 210                 215 aag gcc gag gac gac tgc aag gtg gag cgc aag cac acg ctg aag ctc         845
Lys Ala Glu Asp Asp Cys Lys Val Glu Arg Lys His Thr Leu Lys Leu
     220                 225                 230 agg cac gcc atg gag cag cgg ccc agc cag gag ctg ctg tgg gag ctg         893
Arg His Ala Met Glu Gln Arg Pro Ser Gln Glu Leu Leu Trp Glu Leu
235                 240                 245                 250 cag cag gag aag gcc ctg ctc cag gcc cgg gtg cag gag ctg gag gcc         941
Gln Gln Glu Lys Ala Leu Leu Gln Ala Arg Val Gln Glu Leu Glu Ala
                 255                 260                 265 tcc gtc cag gag ggg aag ctg gac agg agc agc ccc tac atc cag gta         989
Ser Val Gln Glu Gly Lys Leu Asp Arg Ser Ser Pro Tyr Ile Gln Val
             270                 275                 280 ctg gag gag gac tgg cgg cag gcg ctg cgg gac cac cag gag cag gcc        1037
Leu Glu Glu Asp Trp Arg Gln Ala Leu Arg Asp His Gln Glu Gln Ala
         285                 290                 295 aac acc atc ttc tcc ctg cgc aag gac ctc cgc cag ggc gag gcc cga        1085
Asn Thr Ile Phe Ser Leu Arg Lys Asp Leu Arg Gln Gly Glu Ala Arg
     300                 305                 310 cgc ctc cgg tgc atg gag gag aag gag atg ttc gag ctg cag tgc ctg        1133
Arg Leu Arg Cys Met Glu Glu Lys Glu Met Phe Glu Leu Gln Cys Leu
315                 320                 325                 330 gca cta cgt aag gac tcc aag atg tac aag gac cgc atc gag gcc atc        1181
Ala Leu Arg Lys Asp Ser Lys Met Tyr Lys Asp Arg Ile Glu Ala Ile
                 335                 340                 345 ctg ctg cag atg gag gag gtc gcc att gag cgg gac cag gcc ata gcc        1229
Leu Leu Gln Met Glu Glu Val Ala Ile Glu Arg Asp Gln Ala Ile Ala
             350                 355                 360 acg cgg gag gag ctg cac gca cag cac gcc cgg ggc ctg cag gag aag        1277
Thr Arg Glu Glu Leu His Ala Gln His Ala Arg Gly Leu Gln Glu Lys
         365                 370                 375 gac gcg ctg cgc aag cag gtg cgg gag ctg ggc gag aag gcg gat gag        1325
Asp Ala Leu Arg Lys Gln Val Arg Glu Leu Gly Glu Lys Ala Asp Glu
     380                 385                 390 ctg cag ctg cag gtg ttc cag tgt gag gcg cag cta ctg gcc gtg gag        1373
Leu Gln Leu Gln Val Phe Gln Cys Glu Ala Gln Leu Leu Ala Val Glu
395                 400                 405                 410
```

```
ggc agg ctc agg cgg cag cag ctg gag acg ctc gtc ctg agc tcc gac     1421
Gly Arg Leu Arg Arg Gln Gln Leu Glu Thr Leu Val Leu Ser Ser Asp
            415                 420                 425 ctg gaa gat ggc tca ccc agg agg tcc cag gag ctc tca ctc ccc cag     1469
Leu Glu Asp Gly Ser Pro Arg Arg Ser Gln Glu Leu Ser Leu Pro Gln
        430                 435                 440 gac ctg gag gac acc cag ctc tca gac aaa ggc tgc ctt gcc ggc ggg     1517
Asp Leu Glu Asp Thr Gln Leu Ser Asp Lys Gly Cys Leu Ala Gly Gly
                445                 450                 455 ggg agc ccg aaa cag ccc ttt gca gct ctg cac cag gag cag gtt ttg     1565
Gly Ser Pro Lys Gln Pro Phe Ala Ala Leu His Gln Glu Gln Val Leu
    460                 465                 470 cgg aac ccc cat gac gca ggc ctg agc agc ggg gag ccg ccc gag aag     1613
Arg Asn Pro His Asp Ala Gly Leu Ser Ser Gly Glu Pro Pro Glu Lys
475                 480                 485                 490 gag cgg cgg cgc ctc aaa gag agt ttt gag aac tac cgc agg aag cgc     1661
Glu Arg Arg Arg Leu Lys Glu Ser Phe Glu Asn Tyr Arg Arg Lys Arg
                495                 500                 505 gcc ctc agg aag atg cag aaa gga tgg cgg cag ggg gag gag gac cgg     1709
Ala Leu Arg Lys Met Gln Lys Gly Trp Arg Gln Gly Glu Glu Asp Arg
        510                 515                 520 gag aac acc acg ggc agc gac aac acc gac act gag ggc tcc             1751
Glu Asn Thr Thr Gly Ser Asp Asn Thr Asp Thr Glu Gly Ser
                525                 530                 535 tagccgcagc agcgcaggcc ccgaccaggg cacacccacc ggcccggcct gccacccggg    1811
ggtgccgacg ccctggggcg cagacttccc cgagccgtcg ctgacttggc ctggaacgag    1871
gaatctggtg ccctgaaagg cccagccgga ctgccgggca ttggggccgt ttgttaagcg    1931
gcactcattt tgcggaggcc atgcgggtgc tcaccacccc catgcacacg ccatctgtgt    1991
aacttcagga tctgttctgt ttcaccatgt aacacacaat acatgcatgc actgtattag    2051
tgttaagaaa acacagctgc gtaaataaac agcacgggtg acccgca                   2098
```

<210> SEQ ID NO 5
<211> LENGTH: 536
<212> TYPE: PRT
<213> ORGANISM: Homo sapiens

<400> SEQUENCE: 5

```
Met Ser Asp Tyr Glu Asn Asp Asp Glu Cys Trp Asn Val Leu Glu Gly
1               5                   10                  15

Phe Arg Val Thr Leu Thr Ser Val Ile Asp Pro Ser Arg Ile Thr Pro
            20                  25                  30

Tyr Leu Arg Gln Cys Lys Val Leu Asn Pro Asp Asp Glu Glu Gln Val
        35                  40                  45

Leu Ser Asp Pro Asn Leu Val Ile Arg Lys Arg Lys Val Gly Val Leu
    50                  55                  60

Leu Asp Ile Leu Gln Arg Thr Gly His Lys Gly Tyr Val Ala Phe Leu
65                  70                  75                  80

Glu Ser Leu Glu Leu Tyr Tyr Pro Gln Leu Tyr Lys Lys Val Thr Gly
                85                  90                  95

Lys Glu Pro Ala Arg Val Phe Ser Met Ile Ile Asp Ala Ser Gly Glu
            100                 105                 110

Ser Gly Leu Thr Gln Leu Leu Met Thr Glu Val Met Lys Leu Gln Lys
        115                 120                 125

Lys Val Gln Asp Leu Thr Ala Leu Leu Ser Ser Lys Asp Asp Phe Ile
    130                 135                 140

Lys Glu Leu Arg Val Lys Asp Ser Leu Leu Arg Lys His Gln Glu Arg
```

```
                145                 150                 155                 160
Val Gln Arg Leu Lys Glu Glu Cys Glu Ala Gly Ser Arg Glu Leu Lys
                    165                 170                 175

Arg Cys Lys Glu Glu Asn Tyr Asp Leu Ala Met Arg Leu Ala His Gln
                180                 185                 190

Ser Glu Glu Lys Gly Ala Ala Leu Met Arg Asn Arg Asp Leu Gln Leu
            195                 200                 205

Glu Ile Asp Gln Leu Lys His Ser Leu Met Lys Ala Glu Asp Cys
        210                 215                 220

Lys Val Glu Arg Lys His Thr Leu Lys Leu Arg His Ala Met Glu Gln
225                 230                 235                 240

Arg Pro Ser Gln Glu Leu Leu Trp Glu Leu Gln Gln Glu Lys Ala Leu
                245                 250                 255

Leu Gln Ala Arg Val Gln Glu Leu Glu Ala Ser Val Gln Glu Gly Lys
                260                 265                 270

Leu Asp Arg Ser Ser Pro Tyr Ile Gln Val Leu Glu Glu Asp Trp Arg
                275                 280                 285

Gln Ala Leu Arg Asp His Gln Glu Gln Ala Asn Thr Ile Phe Ser Leu
        290                 295                 300

Arg Lys Asp Leu Arg Gln Gly Glu Ala Arg Arg Leu Arg Cys Met Glu
305                 310                 315                 320

Glu Lys Glu Met Phe Glu Leu Gln Cys Leu Ala Leu Arg Lys Asp Ser
                325                 330                 335

Lys Met Tyr Lys Asp Arg Ile Glu Ala Ile Leu Leu Gln Met Glu Glu
                340                 345                 350

Val Ala Ile Glu Arg Asp Gln Ala Ile Ala Thr Arg Glu Glu Leu His
        355                 360                 365

Ala Gln His Ala Arg Gly Leu Gln Glu Lys Asp Ala Leu Arg Lys Gln
        370                 375                 380

Val Arg Glu Leu Gly Glu Lys Ala Asp Glu Leu Gln Leu Gln Val Phe
385                 390                 395                 400

Gln Cys Glu Ala Gln Leu Leu Ala Val Glu Gly Arg Leu Arg Arg Gln
                405                 410                 415

Gln Leu Glu Thr Leu Val Leu Ser Ser Asp Leu Glu Asp Gly Ser Pro
                420                 425                 430

Arg Arg Ser Gln Glu Leu Ser Leu Pro Gln Asp Leu Glu Asp Thr Gln
                435                 440                 445

Leu Ser Asp Lys Gly Cys Leu Ala Gly Gly Ser Pro Lys Gln Pro
        450                 455                 460

Phe Ala Ala Leu His Gln Glu Gln Val Leu Arg Asn Pro His Asp Ala
465                 470                 475                 480

Gly Leu Ser Ser Gly Glu Pro Pro Glu Lys Glu Arg Arg Leu Lys
                485                 490                 495

Glu Ser Phe Glu Asn Tyr Arg Arg Lys Arg Ala Leu Arg Lys Met Gln
                500                 505                 510

Lys Gly Trp Arg Gln Gly Glu Glu Asp Arg Glu Asn Thr Thr Gly Ser
            515                 520                 525

Asp Asn Thr Asp Thr Glu Gly Ser
        530                 535

<210> SEQ ID NO 6
<211> LENGTH: 1608
<212> TYPE: DNA
<213> ORGANISM: Homo sapiens
```

-continued

```
<400> SEQUENCE: 6
atgtcggact acgagaacga tgacgagtgc tggaacgtcc tggagggctt ccgggtgacg     60
ctcacctcgg tcatcgaccc ctcacgcatc acaccttacc tgcggcagtg caaggtcctg    120
aaccctgatg atgaggagca ggtgctcagc gaccccaacc tggtcatccg caaacggaaa    180
gtgggtgtgc tcctggacat cctgcagcgg accggccaca agggctacgt ggccttcctc    240
gagagcctgg agtctactac cccgcagctg tacaagaagg tcacaggcaa ggagccagcc    300
cgcgtcttct ccatgatcat cgacgcgtcc ggggagtcag gcctgactca gctgctgatg    360
actgaggtca tgaagctgca gaagaaggtg caggacctga ccgcgctgct gagctccaaa    420
gatgacttca tcaaggagct gcgggtgaag gacagcctgc tgcgcaagca ccaggagcgt    480
gtgcagaggc tcaaggagga gtgcgaggcc ggcagccgcg agctcaagcg ctgcaaggag    540
gagaactacg acctggccat cgcctggcg caccagagtg aggagaaggg cgccgcgctc    600
atgcggaacc gtgacctgca gctggagatt gaccagctca gcacagcct catgaaggcc    660 gaggacgact gcaaggtgga gcgcaagcac acgctgaagc tcaggcacgc catggagcag    720
cggcccagcc aggagctgct gtgggagctg cagcaggaga aggccctgct ccaggcccgg    780
gtgcaggagc tggaggcctc cgtccaggag gggaagctgg acaggagcag cccctacatc    840
caggtactgg aggaggactg gcggcaggcg ctgcgggacc accaggagca ggccaacacc    900
atcttctccc tgcgcaagga cctccgccag ggcgaggccc gacgcctccg gtgcatggag    960
gagaaggaga tgttcgagct gcagtgcctg gcactacgta aggactccaa gatgtacaag   1020
gaccgcatcg aggccatcct gctgcagatg gaggaggtcg ccattgagcg ggaccaggcc   1080
atagccacgc gggaggagct gcacgcacag cacgcccggg gcctgcagga aggacgcg    1140 ctgcgcaagc aggtgcggga gctgggcgag aaggcggatg agctgcagct gcaggtgttc   1200
cagtgtgagg cgcagctact ggccgtggag ggcaggctca gcggcagca gctggagacg   1260 ctcgtcctga gctccgacct ggaagatggc tcacccagga ggtcccagga gctctcactc   1320
ccccaggacc tggaggacac ccagctctca gacaaaggct gccttgccgg cggggggagc   1380
ccgaaacagc cctttgcagc tctgcaccag gagcaggttt gcggaaccc ccatgacgca   1440 ggcctgagca gcggggagcc gcccgagaag gagcggcggc gcctcaaaga gagttttgag   1500
aactaccgca ggaagcgcgc cctcaggaag atgcagaaag gatggcggca ggggaggag   1560 gaccgggaga acaccacggg cagcgacaac accgacactg agggctcc                1608
```

```
<210> SEQ ID NO 7
<211> LENGTH: 3949
<212> TYPE: DNA
<213> ORGANISM: Homo sapiens
<220> FEATURE:
<221> NAME/KEY: CDS
<222> LOCATION: (41)...(3136)

<400> SEQUENCE: 7
ccccgtgcgc ctcttgcccg cagaccctga ggacacggcc atg ccg ggc cgg gcg      55
                                             Met Pro Gly Arg Ala
                                              1               5 gag gcg ggg gag gcc gag gag gag gcc ggg gcc ggc tcg ggg tct gag    103
Glu Ala Gly Glu Ala Glu Glu Glu Ala Gly Ala Gly Ser Gly Ser Glu
             10                  15                  20 gcg gag gag gac gcg ctg tgg gag cga atc gag ggc gtc cgg cat cgg    151
Ala Glu Glu Asp Ala Leu Trp Glu Arg Ile Glu Gly Val Arg His Arg
         25                  30                  35 ctg gct cgc gcc ctg aac ccg gcc aag ctc acg ccg tat ctg cgc cag    199
```

```
Leu Ala Arg Ala Leu Asn Pro Ala Lys Leu Thr Pro Tyr Leu Arg Gln
         40                  45                  50 tgc cgg gtc atc gac gag cag gac gag gag gag gtg ctg agc acc tac     247
Cys Arg Val Ile Asp Glu Gln Asp Glu Glu Glu Val Leu Ser Thr Tyr
 55                  60                  65 cgc ttc ccg tgc cgc gtc aac cgc acc ggg cgc ctg atg gac atc ttg     295
Arg Phe Pro Cys Arg Val Asn Arg Thr Gly Arg Leu Met Asp Ile Leu
 70                  75                  80                  85 cgc tgc cgt ggc aag agg ggc tat gag gcc ttc ctg gaa gcc ctg gag     343
Arg Cys Arg Gly Lys Arg Gly Tyr Glu Ala Phe Leu Glu Ala Leu Glu
             90                  95                 100 ttc tac tac ccc gaa cac ttc acg ctg ctc acg ggc cag gaa ccc gcc     391
Phe Tyr Tyr Pro Glu His Phe Thr Leu Leu Thr Gly Gln Glu Pro Ala
            105                 110                 115 cag cgc tgc tcc atg atc ctc gat gag gag ggg cct gag ggc ctg acc     439
Gln Arg Cys Ser Met Ile Leu Asp Glu Glu Gly Pro Glu Gly Leu Thr
        120                 125                 130 caa ttc ttg atg aca gag gtg cga cgg ctg cgg gaa gct cgc aag agc     487
Gln Phe Leu Met Thr Glu Val Arg Arg Leu Arg Glu Ala Arg Lys Ser
135                 140                 145 cag ctg cag cgg gag cag caa ctg cag gcc cgg ggc cgg gtg ctc gag     535
Gln Leu Gln Arg Glu Gln Gln Leu Gln Ala Arg Gly Arg Val Leu Glu
150                 155                 160                 165 gag gag cgg gca ggg ctg gag cag cgg ctg cgg gac cag cag cag gct     583
Glu Glu Arg Ala Gly Leu Glu Gln Arg Leu Arg Asp Gln Gln Gln Ala
                170                 175                 180 cag gag cgc tgt caa cgg ctg cgg gag gac tgg gag gcg ggc agc ctg     631
Gln Glu Arg Cys Gln Arg Leu Arg Glu Asp Trp Glu Ala Gly Ser Leu
            185                 190                 195 gag ctg ctg cgg ctc aag gat gag aac tac atg atc gcc atg cgc ctg     679
Glu Leu Leu Arg Leu Lys Asp Glu Asn Tyr Met Ile Ala Met Arg Leu
            200                 205                 210 gca cag ctc agt gag gag aag aac tcg gct gta ctt cgc agc cgt gac     727
Ala Gln Leu Ser Glu Glu Lys Asn Ser Ala Val Leu Arg Ser Arg Asp
        215                 220                 225 ctg cag ctg gcg gtg gat cag ctc aag ctc aaa gtg agt cgg ctg gag     775
Leu Gln Leu Ala Val Asp Gln Leu Lys Leu Lys Val Ser Arg Leu Glu
230                 235                 240                 245 gaa gag tgt gca ctg ctt cga agg gcc agg ggc ccg ccc cct ggg gca     823
Glu Glu Cys Ala Leu Leu Arg Arg Ala Arg Gly Pro Pro Pro Gly Ala
                250                 255                 260 gag gag aag gag aag gag aag gag aag gag aag gag cca gac aat gtg     871
Glu Glu Lys Glu Lys Glu Lys Glu Lys Glu Lys Glu Pro Asp Asn Val
            265                 270                 275 gac ctt gtc tct gag ctg cgt gct gag aac cag cag ctg acg gcg tca     919
Asp Leu Val Ser Glu Leu Arg Ala Glu Asn Gln Gln Leu Thr Ala Ser
            280                 285                 290 ctg cgg gag ttg cag gag ggc ctg cag cag gag gcg agc cgg ccg ggg     967
Leu Arg Glu Leu Gln Glu Gly Leu Gln Gln Glu Ala Ser Arg Pro Gly
        295                 300                 305 gcc ccg ggc tcc gag cgc atc ctg ctg gac atc cta gag cat gac tgg    1015
Ala Pro Gly Ser Glu Arg Ile Leu Leu Asp Ile Leu Glu His Asp Trp
310                 315                 320                 325 cgg gag gcg cag gac agc agg cag gag ctg tgc cag aag ctg cat gcc    1063
Arg Glu Ala Gln Asp Ser Arg Gln Glu Leu Cys Gln Lys Leu His Ala
                330                 335                 340 gtg cag ggg gag ctg cag tgg gcc gag gag ctg cgc gac cag tac ctg    1111
Val Gln Gly Glu Leu Gln Trp Ala Glu Glu Leu Arg Asp Gln Tyr Leu
            345                 350                 355 cag gag atg gaa gac ctg cgg ctc aag cac cgc acg ctg cag aag gac    1159
```

```
                Gln Glu Met Glu Asp Leu Arg Leu Lys His Arg Thr Leu Gln Lys Asp
                    360                 365                 370 tgt gac ctg tac aag cac cgc atg gcc act gtc ctg gcc caa ctg gag          1207
Cys Asp Leu Tyr Lys His Arg Met Ala Thr Val Leu Ala Gln Leu Glu
            375                 380                 385 gag att gag aag gag cga gac cag gcc atc cag agc cgt gac cgg atc          1255
Glu Ile Glu Lys Glu Arg Asp Gln Ala Ile Gln Ser Arg Asp Arg Ile
390                 395                 400                 405 cag ttg cag tac tca cag agc ctc atc gag aag gac cag tac cgc aag          1303
Gln Leu Gln Tyr Ser Gln Ser Leu Ile Glu Lys Asp Gln Tyr Arg Lys
                410                 415                 420 cag gtg cgg ggc ctg gag gcg gag cgg gat gag ctg ctg aca acg ctc          1351
Gln Val Arg Gly Leu Glu Ala Glu Arg Asp Glu Leu Leu Thr Thr Leu
            425                 430                 435 acc agc ctg gag ggc acc aag gct ctg ctg gag gtt cag ctg cag cgg          1399
Thr Ser Leu Glu Gly Thr Lys Ala Leu Leu Glu Val Gln Leu Gln Arg
440                 445                 450 gcc cag ggt ggc acc tgc ctc aag gcc tgt gcc tcc tcc cat tcc ctg          1447
Ala Gln Gly Gly Thr Cys Leu Lys Ala Cys Ala Ser Ser His Ser Leu
        455                 460                 465 tgc tcc aac ctc agc agc act tgg agc ctg agc gag ttc ccc tcc cct          1495
Cys Ser Asn Leu Ser Ser Thr Trp Ser Leu Ser Glu Phe Pro Ser Pro
470                 475                 480                 485 ctg gga ggc cca gaa gca act ggg gag gca gct gtc atg ggg gga cct          1543
Leu Gly Gly Pro Glu Ala Thr Gly Glu Ala Ala Val Met Gly Gly Pro
                490                 495                 500 gag cct cac aac tcg gag gaa gcc aca gac agt gaa aag gag atc aat          1591
Glu Pro His Asn Ser Glu Glu Ala Thr Asp Ser Glu Lys Glu Ile Asn
            505                 510                 515 cgg ctc tcc atc ctg ccc ttc ccc ccc agt gcc ggc tcc atc ctc cgc          1639
Arg Leu Ser Ile Leu Pro Phe Pro Pro Ser Ala Gly Ser Ile Leu Arg
        520                 525                 530 cgg cag cgt gag gaa gac ccc gca ccc cct aag aga tcc ttc agc agc          1687
Arg Gln Arg Glu Glu Asp Pro Ala Pro Pro Lys Arg Ser Phe Ser Ser
535                 540                 545 atg tca gac atc aca ggg agt gtg aca ctt aag ccc tgg tcc cct ggc          1735
Met Ser Asp Ile Thr Gly Ser Val Thr Leu Lys Pro Trp Ser Pro Gly
550                 555                 560                 565 ctc tct tcg tcc tca tcc tct gac agc gtg tgg cct ttg gga aag ccg          1783
Leu Ser Ser Ser Ser Ser Ser Asp Ser Val Trp Pro Leu Gly Lys Pro
                570                 575                 580 gaa ggc ctc ctg gct cgg ggc tgt ggc ctg gac ttc ctc aac agg tct          1831
Glu Gly Leu Leu Ala Arg Gly Cys Gly Leu Asp Phe Leu Asn Arg Ser
            585                 590                 595 ctg gct att cgg gtg tct ggc cgg agc ccc cca ggg ggc cca gag ccg          1879
Leu Ala Ile Arg Val Ser Gly Arg Ser Pro Pro Gly Gly Pro Glu Pro
        600                 605                 610 cag gac aag gga cca gat gga ctg tcg ttt tat ggg gac aga tgg tct          1927
Gln Asp Lys Gly Pro Asp Gly Leu Ser Phe Tyr Gly Asp Arg Trp Ser
615                 620                 625 ggg gct gtg gtg cgc agg gtg ctg tct ggg cct ggg tcc gcc agg atg          1975
Gly Ala Val Val Arg Arg Val Leu Ser Gly Pro Gly Ser Ala Arg Met
630                 635                 640                 645 gaa cca aga gag caa agg gtg gaa gct gct ggt ctg gag ggg gcg tgc          2023
Glu Pro Arg Glu Gln Arg Val Glu Ala Ala Gly Leu Glu Gly Ala Cys
                650                 655                 660 ctg gaa gcc gag gcc cag cag aga acc ttg ctc tgg aat cag ggg tcc          2071
Leu Glu Ala Glu Ala Gln Gln Arg Thr Leu Leu Trp Asn Gln Gly Ser
            665                 670                 675 aca ctc ccc tcc ctg atg gac tcg aag gcc tgc cag tcc ttc cac gag          2119
```

```
    Thr Leu Pro Ser Leu Met Asp Ser Lys Ala Cys Gln Ser Phe His Glu
            680                 685                 690 gcc cta gaa gcc tgg gca aag gga cca ggt gcc gag ccc ttc tac att         2167
Ala Leu Glu Ala Trp Ala Lys Gly Pro Gly Ala Glu Pro Phe Tyr Ile
        695                 700                 705 cgt gcc aac ctc acc ttg cct gag agg gca gat ccc cat gcc ctt tgc         2215
Arg Ala Asn Leu Thr Leu Pro Glu Arg Ala Asp Pro His Ala Leu Cys
710                 715                 720                 725 gtg aaa gcc caa gag atc ctt cga ctg gtg gac tcg gca tac aag cgg         2263
Val Lys Ala Gln Glu Ile Leu Arg Leu Val Asp Ser Ala Tyr Lys Arg
                730                 735                 740 agg cag gaa tgg ttc tgc acc cgg gtt gac ccc ctc act ctg cgg gac         2311
Arg Gln Glu Trp Phe Cys Thr Arg Val Asp Pro Leu Thr Leu Arg Asp
            745                 750                 755 ctg gac cgg ggc acc gtg ccc aat tat cag aga gcc cag cag ctc cta         2359
Leu Asp Arg Gly Thr Val Pro Asn Tyr Gln Arg Ala Gln Gln Leu Leu
        760                 765                 770 gaa gtt cag gag aaa tgc ctg ccc tcc agc cgg cac cga ggc ccc cgc         2407
Glu Val Gln Glu Lys Cys Leu Pro Ser Ser Arg His Arg Gly Pro Arg
775                 780                 785 agt aat ctg aag aag aga gcc ctg gac cag ctg cgg ctg gtg agg ccc         2455
Ser Asn Leu Lys Lys Arg Ala Leu Asp Gln Leu Arg Leu Val Arg Pro
790                 795                 800                 805 aag ccc gtg ggg gcg cct gca ggg gac tcc ccg gat cag ctg ctg ctg         2503
Lys Pro Val Gly Ala Pro Ala Gly Asp Ser Pro Asp Gln Leu Leu Leu
                810                 815                 820 gag ccc tgt gca gag ccg gag cgg agc ctc aga ccc tac agt ttg gtg         2551
Glu Pro Cys Ala Glu Pro Glu Arg Ser Leu Arg Pro Tyr Ser Leu Val
            825                 830                 835 cgg ccg cta ctg gtg tct gcc ctg cgg ccc gtg gtg ctg ttg cct gag         2599
Arg Pro Leu Leu Val Ser Ala Leu Arg Pro Val Val Leu Leu Pro Glu
        840                 845                 850 tgc ctg gcg ccc cgg ctc atc cgt aac ctg cta gac ctg ccc agc tcc         2647
Cys Leu Ala Pro Arg Leu Ile Arg Asn Leu Leu Asp Leu Pro Ser Ser
855                 860                 865 cgg ctg gac ttc caa gtg tgc cca gcg gaa agc ctc tct ggg gag gaa         2695
Arg Leu Asp Phe Gln Val Cys Pro Ala Glu Ser Leu Ser Gly Glu Glu
870                 875                 880                 885 ctg tgc cca tcc tca gcg cct gga gcc ccc aag gct cag cct gcc acc         2743
Leu Cys Pro Ser Ser Ala Pro Gly Ala Pro Lys Ala Gln Pro Ala Thr
                890                 895                 900 cct ggg cta ggc agc agg atc cgg gcc atc cag gag tct gtt ggg aag         2791
Pro Gly Leu Gly Ser Arg Ile Arg Ala Ile Gln Glu Ser Val Gly Lys
            905                 910                 915 aag cac tgc ctg ctg gag ctg ggt gct cgg ggt gtg cgg gag cgg gtg         2839
Lys His Cys Leu Leu Glu Leu Gly Ala Arg Gly Val Arg Glu Arg Val
        920                 925                 930 cag aac gag atc tac ccc atc gtc atc cac gtg gag gtg act gag aag         2887
Gln Asn Glu Ile Tyr Pro Ile Val Ile His Val Glu Val Thr Glu Lys
935                 940                 945 aat gtc cgg gaa gtc agg ggt ctg ctg ggc cgg ccg ggc tgg cgg gac         2935
Asn Val Arg Glu Val Arg Gly Leu Leu Gly Arg Pro Gly Trp Arg Asp
950                 955                 960                 965 tca gag ctg ctg cgg cag tgc cgt ggc tca gag cag gtg ctc tgg ggg         2983
Ser Glu Leu Leu Arg Gln Cys Arg Gly Ser Glu Gln Val Leu Trp Gly
                970                 975                 980 ctg ccc tgc tcc tgg gtg cag gtg ccc gcc cat gag tgg gga cac gca         3031
Leu Pro Cys Ser Trp Val Gln Val Pro Ala His Glu Trp Gly His Ala
            985                 990                 995 gag gag ctg gcc aag gtg gtg cgc ggc cgc atc ctg cag gag cag gcc         3079
```

```
                Glu Glu Leu Ala Lys Val Val Arg Gly Arg Ile Leu Gln Glu Gln Ala
                    1000                1005                1010 cgc ctc gtg tgg gtg gag tgc ggc agc agc aga ggc tgc ccc agc agc          3127
Arg Leu Val Trp Val Glu Cys Gly Ser Ser Arg Gly Cys Pro Ser Ser
    1015                1020                1025 agt gag gcc tgaggctcat ctgatacctg caccttctcc ccaagccagc                  3176
Ser Glu Ala
1030 gtggaccctg gtgtctatgg tgaagctggg ccctcccacc ctgagccttc ctagacccctt       3236 ggactctcag atgcagggcc cttggctctg gcctctcacc cccaaggctg tctctggccc        3296 tgccgagcct atgggagtcc cgggacagag tgcccactcc cctctacttg ctgctctggg        3356 cctccccacc tttcctgggg tctccacatt cccactagtg ggtcttatgt gtgtctgtgt        3416 cttctcctta aacactcgcc ctggagtctg ttctcacacc tgtgcgcagg tttgcacact        3476 caagttctca tgggcaggct caggtctgtc ccgctgccct gggcacgagg tctcctgagg        3536 acctgggcct gttctgctcc taggagacct gagcccgtta ccgcgtgact cccaccatcc        3596 agctcgcgct cctcgtggat tcagccatgc atggactggg gtgttccctg gcccatggtc       3656 acctgtgccc ctcgtgtctc ctcacatggg tgtctgtggt tctctcctgt gtaaatgtca       3716 cgccccaccc ctgtttcatg tgggcactaa cacgtgtgcg ttcctggcgg gcacacacag       3776 gaccgtgcct cacagggccc actccctgcc tatgcctccc tcttgggggg ccgaggaggg       3836 cggctgctct gtcatgagaa tgtacggccc gtggatgatt aacgggcctt tttcacttag       3896 aagctgcaca ttatggagca ttaaacactt ttgtcataaa aaaaaaaaaa aaa              3949

<210> SEQ ID NO 8
<211> LENGTH: 1032
<212> TYPE: PRT
<213> ORGANISM: Homo sapiens

<400> SEQUENCE: 8

Met Pro Gly Arg Ala Glu Ala Gly Glu Ala Glu Glu Ala Gly Ala
1               5                   10                  15

Gly Ser Gly Ser Glu Ala Glu Glu Asp Ala Leu Trp Glu Arg Ile Glu
            20                  25                  30

Gly Val Arg His Arg Leu Ala Arg Ala Leu Asn Pro Ala Lys Leu Thr
        35                  40                  45

Pro Tyr Leu Arg Gln Cys Arg Val Ile Asp Glu Gln Asp Glu Glu Glu
    50                  55                  60

Val Leu Ser Thr Tyr Arg Phe Pro Cys Arg Val Asn Arg Thr Gly Arg
65                  70                  75                  80

Leu Met Asp Ile Leu Arg Cys Arg Gly Lys Arg Gly Tyr Glu Ala Phe
                85                  90                  95

Leu Glu Ala Leu Glu Phe Tyr Tyr Pro Glu His Phe Thr Leu Leu Thr
            100                 105                 110

Gly Gln Glu Pro Ala Gln Arg Cys Ser Met Ile Leu Asp Glu Glu Gly
        115                 120                 125

Pro Glu Gly Leu Thr Gln Phe Leu Met Thr Glu Val Arg Arg Leu Arg
    130                 135                 140

Glu Ala Arg Lys Ser Gln Leu Gln Arg Glu Gln Leu Gln Ala Arg
145                 150                 155                 160

Gly Arg Val Leu Glu Glu Glu Arg Ala Gly Leu Glu Gln Arg Leu Arg
                165                 170                 175

Asp Gln Gln Gln Ala Gly Glu Arg Cys Gln Arg Leu Arg Glu Asp Trp
            180                 185                 190
```

```
Glu Ala Gly Ser Leu Glu Leu Leu Arg Leu Lys Asp Glu Asn Tyr Met
            195                 200                 205

Ile Ala Met Arg Leu Ala Gln Leu Ser Glu Glu Lys Asn Ser Ala Val
            210                 215                 220

Leu Arg Ser Arg Asp Leu Gln Leu Ala Val Asp Gln Leu Lys Leu Lys
225                 230                 235                 240

Val Ser Arg Leu Glu Glu Cys Ala Leu Leu Arg Arg Ala Arg Gly
            245                 250                 255

Pro Pro Pro Gly Ala Glu Glu Lys Glu Lys Glu Lys Glu Lys
            260                 265                 270

Glu Pro Asp Asn Val Asp Leu Val Ser Glu Leu Arg Ala Glu Asn Gln
            275                 280                 285

Gln Leu Thr Ala Ser Leu Arg Glu Leu Gln Glu Gly Leu Gln Gln Glu
            290                 295                 300

Ala Ser Arg Pro Gly Ala Pro Gly Ser Glu Arg Ile Leu Leu Asp Ile
305                 310                 315                 320

Leu Glu His Asp Trp Arg Glu Ala Gln Asp Ser Arg Gln Glu Leu Cys
            325                 330                 335

Gln Lys Leu His Ala Val Gln Gly Glu Leu Gln Trp Ala Glu Glu Leu
            340                 345                 350

Arg Asp Gln Tyr Leu Gln Glu Met Glu Asp Leu Arg Leu Lys His Arg
            355                 360                 365

Thr Leu Gln Lys Asp Cys Asp Leu Tyr Lys His Arg Met Ala Thr Val
            370                 375                 380

Leu Ala Gln Leu Glu Glu Ile Glu Lys Glu Arg Asp Gln Ala Ile Gln
385                 390                 395                 400

Ser Arg Asp Arg Ile Gln Leu Gln Tyr Ser Gln Ser Leu Ile Glu Lys
            405                 410                 415

Asp Gln Tyr Arg Lys Gln Val Arg Gly Leu Glu Ala Glu Arg Asp Glu
            420                 425                 430

Leu Leu Thr Thr Leu Thr Ser Leu Glu Gly Thr Lys Ala Leu Leu Glu
            435                 440                 445

Val Gln Leu Gln Arg Ala Gln Gly Gly Thr Cys Leu Lys Ala Cys Ala
            450                 455                 460

Ser Ser His Ser Leu Cys Ser Asn Leu Ser Ser Thr Trp Ser Leu Ser
465                 470                 475                 480

Glu Phe Pro Ser Pro Leu Gly Gly Pro Glu Ala Thr Gly Glu Ala Ala
            485                 490                 495

Val Met Gly Gly Pro Glu Pro His Asn Ser Glu Glu Ala Thr Asp Ser
            500                 505                 510

Glu Lys Glu Ile Asn Arg Leu Ser Ile Leu Pro Phe Pro Pro Ser Ala
            515                 520                 525

Gly Ser Ile Leu Arg Arg Gln Arg Glu Glu Asp Pro Ala Pro Lys
            530                 535                 540

Arg Ser Phe Ser Ser Met Ser Asp Ile Thr Gly Ser Val Thr Leu Lys
545                 550                 555                 560

Pro Trp Ser Pro Gly Leu Ser Ser Ser Ser Ser Asp Ser Val Trp
            565                 570                 575

Pro Leu Gly Lys Pro Glu Gly Leu Leu Ala Arg Gly Cys Gly Leu Asp
            580                 585                 590

Phe Leu Asn Arg Ser Leu Ala Ile Arg Val Ser Gly Arg Ser Pro Pro
            595                 600                 605

Gly Gly Pro Glu Pro Gln Asp Lys Gly Pro Asp Gly Leu Ser Phe Tyr
```

```
                610             615             620
Gly Asp Arg Trp Ser Gly Ala Val Val Arg Val Leu Ser Gly Pro
625             630             635             640

Gly Ser Ala Arg Met Glu Pro Arg Glu Gln Arg Val Glu Ala Gly
            645             650             655

Leu Glu Gly Ala Cys Leu Glu Ala Glu Ala Gln Gln Arg Thr Leu Leu
            660             665             670

Trp Asn Gln Gly Ser Thr Leu Pro Ser Leu Met Asp Ser Lys Ala Cys
            675             680             685

Gln Ser Phe His Glu Ala Leu Glu Ala Trp Ala Lys Gly Pro Gly Ala
690             695             700

Glu Pro Phe Tyr Ile Arg Ala Asn Leu Thr Leu Pro Glu Arg Ala Asp
705             710             715             720

Pro His Ala Leu Cys Val Lys Ala Gln Glu Ile Leu Arg Leu Val Asp
            725             730             735

Ser Ala Tyr Lys Arg Arg Gln Glu Trp Phe Cys Thr Arg Val Asp Pro
            740             745             750

Leu Thr Leu Arg Asp Leu Asp Arg Gly Thr Val Pro Asn Tyr Gln Arg
            755             760             765

Ala Gln Gln Leu Leu Glu Val Gln Glu Lys Cys Leu Pro Ser Ser Arg
            770             775             780

His Arg Gly Pro Arg Ser Asn Leu Lys Lys Arg Ala Leu Asp Gln Leu
785             790             795             800

Arg Leu Val Arg Pro Lys Pro Val Gly Ala Pro Ala Gly Asp Ser Pro
            805             810             815

Asp Gln Leu Leu Leu Glu Pro Cys Ala Glu Pro Glu Arg Ser Leu Arg
            820             825             830

Pro Tyr Ser Leu Val Arg Pro Leu Leu Val Ser Ala Leu Arg Pro Val
            835             840             845

Val Leu Leu Pro Glu Cys Leu Ala Pro Arg Leu Ile Arg Asn Leu Leu
850             855             860

Asp Leu Pro Ser Ser Arg Leu Asp Phe Gln Val Cys Pro Ala Glu Ser
865             870             875             880

Leu Ser Gly Glu Glu Leu Cys Pro Ser Ser Ala Pro Gly Ala Pro Lys
            885             890             895

Ala Gln Pro Ala Thr Pro Gly Leu Gly Ser Arg Ile Arg Ala Ile Gln
            900             905             910

Glu Ser Val Gly Lys Lys His Cys Leu Leu Glu Leu Gly Ala Arg Gly
            915             920             925

Val Arg Glu Arg Val Gln Asn Glu Ile Tyr Pro Ile Val Ile His Val
930             935             940

Glu Val Thr Glu Lys Asn Val Arg Glu Val Arg Gly Leu Leu Gly Arg
945             950             955             960

Pro Gly Trp Arg Asp Ser Glu Leu Leu Arg Gln Cys Arg Gly Ser Glu
            965             970             975

Gln Val Leu Trp Gly Leu Pro Cys Ser Trp Val Gln Val Pro Ala His
            980             985             990

Glu Trp Gly His Ala Glu Glu Leu Ala Lys Val Val Arg Gly Arg Ile
            995             1000            1005

Leu Gln Glu Gln Ala Arg Leu Val Trp Val Glu Cys Gly Ser Ser Arg
            1010            1015            1020

Gly Cys Pro Ser Ser Ser Glu Ala
1025            1030
```

<210> SEQ ID NO 9
<211> LENGTH: 3096
<212> TYPE: DNA
<213> ORGANISM: Homo sapiens

<400> SEQUENCE: 9

| | | | | | |
|---|---|---|---|---|---|
| atgccgggcc | gggcggaggc | gggggaggcc | gaggaggagg | ccgggccgg | ctcggggtct | 60 |
| gaggcggagg | aggacgcgct | gtgggagcga | atcgagggcg | tccggcatcg | gctggctcgc | 120 |
| gccctgaacc | cggccaagct | cacgccgtat | ctgcgccagt | gccgggtcat | cgacgagcag | 180 |
| gacgaggagg | aggtgctgag | cacctaccgc | ttcccgtgcc | gcgtcaaccg | cacccgggcgc | 240 |
| ctgatggaca | tcttgcgctg | ccgtggcaag | agggctatg | aggccttcct | ggaagccctg | 300 |
| gagttctact | accccgaaca | cttcacgctg | ctcacgggcc | aggaacccgc | ccagcgctgc | 360 |
| tccatgatcc | tcgatgagga | ggggcctgag | ggcctgaccc | aattcttgat | gacagaggtg | 420 |
| cgacggctgc | gggaagctcg | caagagccag | ctgcagcggg | agcagcaact | gcaggcccgg | 480 |
| ggccgggtgc | tcgaggagga | gcgggcaggg | ctggagcagc | ggctgcggga | ccagcagcag | 540 |
| gctcaggagc | gctgtcaacg | gctgcggag | gactgggagg | cgggcagcct | ggagctgctg | 600 |
| cggctcaagg | atgagaacta | catgatcgcc | atgcgcctgg | cacagctcag | tgaggagaag | 660 |
| aactcggctg | tacttcgcag | ccgtgacctg | cagctggcgg | tggatcagct | caagctcaaa | 720 |
| gtgagtcggc | tggaggaaga | gtgtgcactg | cttcgaaggg | ccaggggccc | gccccctggg | 780 |
| gcagaggaga | aggagaagga | gaaggagaag | gagaaggagc | cagacaatgt | ggaccttgtc | 840 |
| tctgagctgc | gtgctgagaa | ccagcagctg | acggcgtcac | tgcgggagtt | gcaggagggc | 900 |
| ctgcagcagg | aggcgagccg | gccggggggcc | ccgggctccg | agcgcatcct | gctggacatc | 960 |
| ctagagcatg | actggcggga | ggcgcaggac | agcaggcagg | agctgtgcca | gaagctgcat | 1020 |
| gccgtgcagg | gggagctgca | gtgggccgag | gagctgcgcg | accagtacct | gcaggagatg | 1080 |
| gaagacctgc | ggctcaagca | ccgcacgctg | cagaaggact | gtgacctgta | caagcaccgc | 1140 |
| atggccactg | tcctggccca | actggaggag | attgagaagg | agcgagacca | ggccatccag | 1200 |
| agccgtgacc | ggatccagtt | gcagtactca | cagagcctca | tcgagaagga | ccagtaccgc | 1260 |
| aagcaggtgc | ggggcctgga | ggcggagcgg | gatgagctgc | tgacaacgct | caccagcctg | 1320 |
| gagggcacca | aggctctgct | ggaggttcag | ctgcagcggg | cccagggtgg | cacctgcctc | 1380 |
| aaggcctgtg | cctcctccca | ttccctgtgc | tccaacctca | gcagcacttg | gagcctgagc | 1440 |
| gagttccccct | cccctctggg | aggcccagaa | gcaactgggg | aggcagctgt | catggggga | 1500 |
| cctgagcctc | acaactcgga | ggaagccaca | gacagtgaaa | aggagatcaa | tcggctctcc | 1560 |
| atcctgccct | ccccccccag | tgccggctcc | atcctccgcc | ggcagcgtga | ggaagacccc | 1620 |
| gcaccccta | agagatcctt | cagcagcatg | tcagacatca | cagggagtgt | gacacttaag | 1680 |
| ccctggtccc | ctggcctctc | ttcgtcctca | tcctctgaca | gcgtgtggcc | tttgggaaag | 1740 |
| ccggaaggcc | tcctggctcg | ggctgtggcc | ctggacttcc | tcaacaggtc | tctggctatt | 1800 |
| cgggtgtctg | gccggagccc | cccaggggcc | ccagagccgc | aggacaaggg | accagatgga | 1860 |
| ctgtcgtttt | atggggacag | atggtctggg | gctgtggtgc | gcagggtgct | gtctgggcct | 1920 |
| gggtccgcca | ggatggaacc | aagagagcaa | agggtgaag | ctgctggtct | ggagggggcg | 1980 |
| tgcctggaag | ccgaggccca | gcagagaacc | ttgctctgga | atcagggtc | cacactcccc | 2040 |
| tccctgatgg | actcgaaggc | ctgccagtcc | ttccacgagg | ccctagaagc | ctgggcaaag | 2100 |
| ggaccaggtg | ccgagcccctt | ctacattcgt | gccaacctca | ccttgcctga | gagggcagat | 2160 |

-continued

```
cccatgccc tttgcgtgaa agcccaagag atccttcgac tggtggactc ggcatacaag   2220
cggaggcagg aatggttctg cacccgggtt gaccccctca ctctgcggga cctggaccgg   2280
ggcaccgtgc ccaattatca gagagcccag cagctcctag aagttcagga gaaatgcctg   2340
ccctccagcc ggcaccgagg cccccgcagt aatctgaaga agagagccct ggaccagctg   2400
cggctggtga ggcccaagcc cgtggggggcg cctgcagggg actccccgga tcagctgctg   2460
ctggagccct gtgcagagcc ggagcggagc ctcagaccct acagtttggt gcggccgcta   2520
ctggtgtctg ccctgcggcc cgtggtgctg ttgcctgagt gcctggcgcc ccggctcatc   2580
cgtaacctgc tagacctgcc cagctcccgg ctggacttcc aagtgtgccc agcggaaagc   2640
ctctctgggg aggaactgtg cccatcctca gcgcctggag cccccaaggc tcagcctgcc   2700
acccctgggc taggcagcag gatccgggcc atccaggagt ctgttgggaa gaagcactgc   2760
ctgctggagc tgggtgctcg gggtgtgcgg gagcgggtgc agaacgagat ctaccccatc   2820
gtcatccacg tggaggtgac tgagaagaat gtccgggaag tcaggggtct gctgggccgg   2880
ccgggctggc gggactcaga gctgctgcgg cagtgccgtg gctcagagca ggtgctctgg   2940
gggctgccct gctcctgggt gcaggtgccc gcccatgagt ggggacacgc agaggagctg   3000
gccaaggtgg tgcgcggccg catcctgcag gagcaggccc gcctcgtgtg ggtggagtgc   3060
ggcagcagca gaggctgccc cagcagcagt gaggcc                            3096
```

<210> SEQ ID NO 10
<211> LENGTH: 4276
<212> TYPE: DNA
<213> ORGANISM: Homo sapiens
<220> FEATURE:
<221> NAME/KEY: CDS
<222> LOCATION: (328)...(3768)

<400> SEQUENCE: 10

```
ccacgcgtcc gccgcgccgc ccgcagcccc ctcccggccc tgcagcccct gggcgggcgg     60
cgcccctcgg aggacggctc cgggcccggg gggacggagg gcctggtcgc ctggaggaag    120
ccggaggcct gcgtggagga ggcgcccgc gcagctggct ggcggagcat gagcgcccca    180
gatcccaagc actgcaagtc cagatgcaac gggagcctgg ctcaagggac gacaagatcc    240
agccggaaag tgtagaagtc acaccccaat ggcgggatag cagcccctgt gtgtgagcac    300
ccctccatgc caggaggagg gccagag atg gat gac tac atg gag acg ctg aag    354
                            Met Asp Asp Tyr Met Glu Thr Leu Lys
                              1               5 gat gaa gag gac gcc ttg tgg gag aat gtg gag tgt aac cgg cac atg      402
Asp Glu Glu Asp Ala Leu Trp Glu Asn Val Glu Cys Asn Arg His Met
 10              15                  20                  25 ctc agc cgc tat atc aac cct gcc aag ctc acg ccc tac ctg cgt cag     450
Leu Ser Arg Tyr Ile Asn Pro Ala Lys Leu Thr Pro Tyr Leu Arg Gln
                 30                  35                  40 tgt aag gtc att gat gag cag gat gaa gat gaa gtg ctt aat gcc cct     498
Cys Lys Val Ile Asp Glu Gln Asp Glu Asp Glu Val Leu Asn Ala Pro
             45                  50                  55 atg ctg cca tcc aag atc aac cga gca ggc cgg ctg ttg gac att cta     546
Met Leu Pro Ser Lys Ile Asn Arg Ala Gly Arg Leu Leu Asp Ile Leu
         60                  65                  70 cat acc aag ggg caa agg ggc tat gtg gtc ttc ttg gag agc cta gaa     594
His Thr Lys Gly Gln Arg Gly Tyr Val Val Phe Leu Glu Ser Leu Glu
     75                  80                  85 ttt tat tac cca gaa ctg tac aaa ctg gtg act ggg aaa gag ccc act     642
Phe Tyr Tyr Pro Glu Leu Tyr Lys Leu Val Thr Gly Lys Glu Pro Thr
 90                  95                 100                 105
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| cgg | aga | ttc | tcc | acc | att | gtg | gtg | gag | gaa | ggc | cac | gag | ggc | ctc | acg | 690  |
| Arg | Arg | Phe | Ser | Thr | Ile | Val | Val | Glu | Glu | Gly | His | Glu | Gly | Leu | Thr |      |
|     |     |     |     | 110 |     |     |     |     | 115 |     |     |     |     | 120 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| cac | ttc | ctg | atg | aac | gag | gtc | atc | aag | ctg | cag | cag | cag | atg | aag | gcc | 738  |
| His | Phe | Leu | Met | Asn | Glu | Val | Ile | Lys | Leu | Gln | Gln | Gln | Met | Lys | Ala |      |
|     |     |     |     | 125 |     |     |     |     | 130 |     |     |     |     | 135 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| aag | gac | ctg | caa | cgc | tgc | gag | ctg | ctg | gcc | agg | ttg | cgg | cag | ctg | gag | 786  |
| Lys | Asp | Leu | Gln | Arg | Cys | Glu | Leu | Leu | Ala | Arg | Leu | Arg | Gln | Leu | Glu |      |
|     |     |     | 140 |     |     |     |     | 145 |     |     |     |     | 150 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gat | gag | aag | aag | cag | atg | acg | ctg | acg | cgc | gtg | gag | ctg | cta | acc | ttc | 834  |
| Asp | Glu | Lys | Lys | Gln | Met | Thr | Leu | Thr | Arg | Val | Glu | Leu | Leu | Thr | Phe |      |
|     | 155 |     |     |     |     | 160 |     |     |     |     | 165 |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| cag | gag | cgg | tac | tac | aag | atg | aag | gaa | gag | cgg | gac | agc | tac | aat | gac | 882  |
| Gln | Glu | Arg | Tyr | Tyr | Lys | Met | Lys | Glu | Glu | Arg | Asp | Ser | Tyr | Asn | Asp |      |
| 170 |     |     |     |     | 175 |     |     |     |     | 180 |     |     |     |     | 185 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gag | ctg | gtc | aag | gtg | aag | gac | gac | aac | tac | aac | tta | gcc | atg | cgc | tac | 930  |
| Glu | Leu | Val | Lys | Val | Lys | Asp | Asp | Asn | Tyr | Asn | Leu | Ala | Met | Arg | Tyr |      |
|     |     |     |     | 190 |     |     |     |     | 195 |     |     |     |     | 200 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gca | cag | ctc | agt | gag | gag | aag | aac | atg | gcg | gtc | atg | agg | agc | cga | gac | 978  |
| Ala | Gln | Leu | Ser | Glu | Glu | Lys | Asn | Met | Ala | Val | Met | Arg | Ser | Arg | Asp |      |
|     |     |     |     | 205 |     |     |     |     | 210 |     |     |     |     | 215 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ctc | caa | ctc | gag | atc | gat | cag | cta | aag | cac | cgg | ttg | aat | aag | atg | gag | 1026 |
| Leu | Gln | Leu | Glu | Ile | Asp | Gln | Leu | Lys | His | Arg | Leu | Asn | Lys | Met | Glu |      |
|     |     |     | 220 |     |     |     |     | 225 |     |     |     |     | 230 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gag | gaa | tgt | aag | ctg | gag | aga | aat | cag | tct | cta | aaa | ctg | aag | aat | gac | 1074 |
| Glu | Glu | Cys | Lys | Leu | Glu | Arg | Asn | Gln | Ser | Leu | Lys | Leu | Lys | Asn | Asp |      |
|     | 235 |     |     |     |     | 240 |     |     |     |     | 245 |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| att | gaa | aat | cgg | ccc | aag | aag | gag | cag | gtt | ctg | gaa | ctg | gag | cgg | gag | 1122 |
| Ile | Glu | Asn | Arg | Pro | Lys | Lys | Glu | Gln | Val | Leu | Glu | Leu | Glu | Arg | Glu |      |
| 250 |     |     |     |     | 255 |     |     |     |     | 260 |     |     |     |     | 265 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| aat | gaa | atg | ctg | aag | acc | aaa | aac | cag | gag | ctg | cag | tcc | atc | atc | cag | 1170 |
| Asn | Glu | Met | Leu | Lys | Thr | Lys | Asn | Gln | Glu | Leu | Gln | Ser | Ile | Ile | Gln |      |
|     |     |     |     | 270 |     |     |     |     | 275 |     |     |     |     | 280 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gcc | ggg | aag | cgc | agc | ctg | cca | gac | tca | gac | aag | gcc | atc | ctg | gac | atc | 1218 |
| Ala | Gly | Lys | Arg | Ser | Leu | Pro | Asp | Ser | Asp | Lys | Ala | Ile | Leu | Asp | Ile |      |
|     |     |     | 285 |     |     |     |     | 290 |     |     |     |     | 295 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ttg | gaa | cac | gac | cgc | aag | gag | gcc | ctg | gag | gac | agg | cag | gag | ctg | gtc | 1266 |
| Leu | Glu | His | Asp | Arg | Lys | Glu | Ala | Leu | Glu | Asp | Arg | Gln | Glu | Leu | Val |      |
|     |     | 300 |     |     |     |     | 305 |     |     |     |     | 310 |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| aac | agg | atc | tac | aac | ctg | cag | gag | gag | gcc | cgc | cag | gca | gag | gag | ctg | 1314 |
| Asn | Arg | Ile | Tyr | Asn | Leu | Gln | Glu | Glu | Ala | Arg | Gln | Ala | Glu | Glu | Leu |      |
|     | 315 |     |     |     |     | 320 |     |     |     |     | 325 |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| cga | gac | aag | tac | ctg | gag | gag | aag | gag | gac | ctg | gag | ctc | aag | tgc | tcg | 1362 |
| Arg | Asp | Lys | Tyr | Leu | Glu | Glu | Lys | Glu | Asp | Leu | Glu | Leu | Lys | Cys | Ser |      |
| 330 |     |     |     |     | 335 |     |     |     |     | 340 |     |     |     |     | 345 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| acc | ctg | gga | aag | gac | tgt | gaa | atg | tac | aag | cac | cgc | atg | aac | acg | gtc | 1410 |
| Thr | Leu | Gly | Lys | Asp | Cys | Glu | Met | Tyr | Lys | His | Arg | Met | Asn | Thr | Val |      |
|     |     |     |     | 350 |     |     |     |     | 355 |     |     |     |     | 360 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| atg | ctg | cag | ctg | gag | gag | gtg | gag | cgg | gag | cgg | gac | cag | gcc | ttc | cac | 1458 |
| Met | Leu | Gln | Leu | Glu | Glu | Val | Glu | Arg | Glu | Arg | Asp | Gln | Ala | Phe | His |      |
|     |     |     | 365 |     |     |     |     | 370 |     |     |     |     | 375 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| tcc | cga | gat | gaa | gct | cag | aca | cag | tac | tcg | cag | tgc | tta | atc | gaa | aag | 1506 |
| Ser | Arg | Asp | Glu | Ala | Gln | Thr | Gln | Tyr | Ser | Gln | Cys | Leu | Ile | Glu | Lys |      |
|     |     |     | 380 |     |     |     |     | 385 |     |     |     |     | 390 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gac | aag | tac | agg | aag | cag | atc | cgc | gag | ctg | gag | gag | aag | aac | gac | gag | 1554 |
| Asp | Lys | Tyr | Arg | Lys | Gln | Ile | Arg | Glu | Leu | Glu | Glu | Lys | Asn | Asp | Glu |      |
|     |     | 395 |     |     |     |     | 400 |     |     |     |     | 405 |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| atg | agg | atc | gag | atg | gtg | cgg | cgg | gag | gcc | tgc | atc | gtc | aac | ctg | gag | 1602 |
| Met | Arg | Ile | Glu | Met | Val | Arg | Arg | Glu | Ala | Cys | Ile | Val | Asn | Leu | Glu |      |
| 410 |     |     |     |     | 415 |     |     |     |     | 420 |     |     |     |     | 425 |      |

```
                                             -continued agc aag ctg cgg cgc ctc tcc aag gac agc aac aac ctg gac cag agt    1650
Ser Lys Leu Arg Arg Leu Ser Lys Asp Ser Asn Asn Leu Asp Gln Ser
            430                 435                 440 ctg ccc agg aac ctg cca gta acc atc atc tct cag gac ttt ggg gat    1698
Leu Pro Arg Asn Leu Pro Val Thr Ile Ile Ser Gln Asp Phe Gly Asp
        445                 450                 455 gcc agc ccc agg acc aat ggt caa gaa gct gac gat tct tcc acc tcg    1746
Ala Ser Pro Arg Thr Asn Gly Gln Glu Ala Asp Asp Ser Ser Thr Ser
    460                 465                 470 gag gag tca cct gaa gac agc aag tac ttc ctg ccc tac cat ccg ccc    1794
Glu Glu Ser Pro Glu Asp Ser Lys Tyr Phe Leu Pro Tyr His Pro Pro
475                 480                 485 cag cgc agg atg aac ctg aag ggc atc cag ctg cag aga gcc aaa tcc    1842
Gln Arg Arg Met Asn Leu Lys Gly Ile Gln Leu Gln Arg Ala Lys Ser
490                 495                 500                 505 ccc atc agc ctg aag cga aca tca gat ttt caa gcc aag ggg cac gag    1890
Pro Ile Ser Leu Lys Arg Thr Ser Asp Phe Gln Ala Lys Gly His Glu
        510                 515                 520 gaa gaa ggc acg gac gcc agc cct agc tcc tgc gga tct ctg ccc atc    1938
Glu Glu Gly Thr Asp Ala Ser Pro Ser Ser Cys Gly Ser Leu Pro Ile
    525                 530                 535 acc aac tcc ttc acc aag atg cag ccc ccg cgg agc cgc agc agc atc    1986
Thr Asn Ser Phe Thr Lys Met Gln Pro Pro Arg Ser Arg Ser Ser Ile
540                 545                 550 atg tca atc acc gcc gag ccc ccg gga aac gac tcc atc gtc aga cgc    2034
Met Ser Ile Thr Ala Glu Pro Pro Gly Asn Asp Ser Ile Val Arg Arg
555                 560                 565 tac aag gag gac gcg ccc cat cgc agc aca gtc gaa gaa gac aat gac    2082
Tyr Lys Glu Asp Ala Pro His Arg Ser Thr Val Glu Glu Asp Asn Asp
570                 575                 580                 585 agc ggc ggg ttt gac gcc tta gat ctg gat gat gac agt cac gaa cgc    2130
Ser Gly Gly Phe Asp Ala Leu Asp Leu Asp Asp Asp Ser His Glu Arg
            590                 595                 600 tac tcc ttc gga ccc tcc tcc atc cac tcc tcc tcc tcc cac caa        2178
Tyr Ser Phe Gly Pro Ser Ser Ile His Ser Ser Ser Ser Ser His Gln
        605                 610                 615 tcc gag ggc ctg gat gcc tac gac ctg gag cag gtc aac ctc atg ttc    2226
Ser Glu Gly Leu Asp Ala Tyr Asp Leu Glu Gln Val Asn Leu Met Phe
    620                 625                 630 agg aag ttc tct ctg gaa aga ccc ttc cgg cct tcg gtc acc tct gtg    2274
Arg Lys Phe Ser Leu Glu Arg Pro Phe Arg Pro Ser Val Thr Ser Val
635                 640                 645 ggg cac gtg cgg ggc cca ggg ccc tcg gtg cag cac acg acg ctg aat    2322
Gly His Val Arg Gly Pro Gly Pro Ser Val Gln His Thr Thr Leu Asn
650                 655                 660                 665 ggc gac agc ctc acc tcc cag ctc acc ctg ctg ggg ggc aac gcg cga    2370
Gly Asp Ser Leu Thr Ser Gln Leu Thr Leu Leu Gly Gly Asn Ala Arg
            670                 675                 680 ggg agc ttc gtg cac tcg gtc aag cct ggc tct ctg gcc gag aaa gcc    2418
Gly Ser Phe Val His Ser Val Lys Pro Gly Ser Leu Ala Glu Lys Ala
        685                 690                 695 ggc ctc cgt gag ggc cac cag ctg ctg ctg cta gaa ggc tgc atc cga    2466
Gly Leu Arg Glu Gly His Gln Leu Leu Leu Leu Glu Gly Cys Ile Arg
    700                 705                 710 ggc gag agg cag agt gtc ccg ttg gac aca tgc acc aaa gag gaa gcc    2514
Gly Glu Arg Gln Ser Val Pro Leu Asp Thr Cys Thr Lys Glu Glu Ala
715                 720                 725 cac tgg acc atc cag agg tgc agc ggc ccc gtc acg ctg cac tac aag    2562
His Trp Thr Ile Gln Arg Cys Ser Gly Pro Val Thr Leu His Tyr Lys
730                 735                 740                 745
```

```
gtc aac cac gaa ggg tac cgg aag ctg gtg aag gac atg gag gac ggc        2610
Val Asn His Glu Gly Tyr Arg Lys Leu Val Lys Asp Met Glu Asp Gly
            750                 755                 760 ctg atc aca tcg ggg gac tcg ttc tac atc cgg ctg aac ctg aac atc        2658
Leu Ile Thr Ser Gly Asp Ser Phe Tyr Ile Arg Leu Asn Leu Asn Ile
        765                 770                 775 tcc agc cag ctg gac gcc tgc acc atg tcc ctg aag tgt gac gat gtt        2706
Ser Ser Gln Leu Asp Ala Cys Thr Met Ser Leu Lys Cys Asp Asp Val
    780                 785                 790 gtg cac gtc cgt gac acc atg tac cag gac agg cac gag tgg ccg tgc        2754
Val His Val Arg Asp Thr Met Tyr Gln Asp Arg His Glu Trp Pro Cys
795                 800                 805 gcg cgg gtc gac cct ttc aca gac cat gac ctg gat atg ggc acc ata        2802
Ala Arg Val Asp Pro Phe Thr Asp His Asp Leu Asp Met Gly Thr Ile
810                 815                 820                 825 ccc agc tac agc cga gcc cag cag ctc ctg gtg aaa ctg cag cgc            2850
Pro Ser Tyr Ser Arg Ala Gln Gln Leu Leu Leu Val Lys Leu Gln Arg
                830                 835                 840 ctg atg cac cga ggc agc cgg gag gag gta gac ggc acc cac cac acc        2898
Leu Met His Arg Gly Ser Arg Glu Glu Val Asp Gly Thr His His Thr
            845                 850                 855 ctg cgg gca ctc cgg aac acc ctg cag ccg gaa gaa gcg ctt tca aca        2946
Leu Arg Ala Leu Arg Asn Thr Leu Gln Pro Glu Glu Ala Leu Ser Thr
        860                 865                 870 agc gac ccc cgg gtc agc ccc cgt ctc tcg cga gca agc ttc ctt ttt        2994
Ser Asp Pro Arg Val Ser Pro Arg Leu Ser Arg Ala Ser Phe Leu Phe
    875                 880                 885 ggc cag ctc ctt cag ttc gtc agc agg tcc gag aac aag tat aag cgg        3042
Gly Gln Leu Leu Gln Phe Val Ser Arg Ser Glu Asn Lys Tyr Lys Arg
890                 895                 900                 905 atg aac agc aat gag cgg gtc cgc atc atc tcg ggg agt ccg cta ggg        3090
Met Asn Ser Asn Glu Arg Val Arg Ile Ile Ser Gly Ser Pro Leu Gly
                910                 915                 920 agc ctg gcc cgg tcc tcg ctg gac gcc acc aag ctc ttg act gag aag        3138
Ser Leu Ala Arg Ser Ser Leu Asp Ala Thr Lys Leu Leu Thr Glu Lys
            925                 930                 935 cag gaa gag ctg gac cct gag agc gag ctg ggc aag aac ctc agc ctc        3186
Gln Glu Glu Leu Asp Pro Glu Ser Glu Leu Gly Lys Asn Leu Ser Leu
        940                 945                 950 atc ccc tac agc ctg gta cgc gcc ttc tac tgc gag cgc cgc cgg ccc        3234
Ile Pro Tyr Ser Leu Val Arg Ala Phe Tyr Cys Glu Arg Arg Arg Pro
    955                 960                 965 gtg ctc ttc aca ccc acc gtg ctg gcc aag acg ctg gtg cag agg ctg        3282
Val Leu Phe Thr Pro Thr Val Leu Ala Lys Thr Leu Val Gln Arg Leu
970                 975                 980                 985 ctc aac tcg gga ggt gcc atg gag ttc acc atc tgc aag tca gat atc        3330
Leu Asn Ser Gly Gly Ala Met Glu Phe Thr Ile Cys Lys Ser Asp Ile
                990                 995                 1000 gtc aca aga gat gag ttc ctc aga agg cag aag acg gag acc atc atc        3378
Val Thr Arg Asp Glu Phe Leu Arg Arg Gln Lys Thr Glu Thr Ile Ile
            1005                1010                1015 tac tcc cga gag aag aac ccc aac gcg ttc gaa tgc atc gcc cct gcc        3426
Tyr Ser Arg Glu Lys Asn Pro Asn Ala Phe Glu Cys Ile Ala Pro Ala
        1020                1025                1030 aac att gaa gct gtg gcc gcc aag aac aag cac tgc ctg ctg gag gct        3474
Asn Ile Glu Ala Val Ala Ala Lys Asn Lys His Cys Leu Leu Glu Ala
    1035                1040                1045 ggg atc ggc tgc aca aga gac ttg atc aag tcc aac atc tac ccc atc        3522
Gly Ile Gly Cys Thr Arg Asp Leu Ile Lys Ser Asn Ile Tyr Pro Ile
1050                1055                1060                1065
```

```
gtg ctc ttc atc cgg gtg tgt gag aag aac atc aag agg ttc aga aag    3570
Val Leu Phe Ile Arg Val Cys Glu Lys Asn Ile Lys Arg Phe Arg Lys
            1070                1075                1080 ctg ctg ccc cgg cct gag acg gag gag gag ttc ctg cgc gtg tgc cgg    3618
Leu Leu Pro Arg Pro Glu Thr Glu Glu Glu Phe Leu Arg Val Cys Arg
        1085                1090                1095 ctg aag gag aag gag ctg gag gcc ctg ccg tgc ctg tac gcc acg gtg    3666
Leu Lys Glu Lys Glu Leu Glu Ala Leu Pro Cys Leu Tyr Ala Thr Val
    1100                1105                1110 gaa cct gac atg tgg ggc agc gta gag gag ctg ctc cgc gtt gtc aag    3714
Glu Pro Asp Met Trp Gly Ser Val Glu Glu Leu Leu Arg Val Val Lys
1115                1120                1125 gac aag atc ggc gag gag cag cgc aag acc atc tgg gtg gac gag gac    3762
Asp Lys Ile Gly Glu Glu Gln Arg Lys Thr Ile Trp Val Asp Glu Asp
1130                1135                1140                1145 cag ctg tgaggcgggc gccctgggca gagagactct gtggcgcggg gcatcctatg     3818
Gln Leu aggcaggcac cctgggcaga gagatgcagt gggtgcgggg ggatcctgtg cccacagag    3878 ctgccccagc agacgctccg ccccacccgg tgatggagcc ccgggggggac agtcgtgcct   3938 ggggaggagc agggtacagc ccattccccc agccctggct gacctggcct agcagtttgg   3998
ccctgctggc cttagcaggg agacagggga gcaaagaacg ccaagccgga ggcccgaggc   4058
cagccggcct ctcgagagcc agagcagcag ttgaatgtaa tgctgggggac aggcatgctg  4118 ccgccagtag ggcggggacc cggacagcca ggtgactacc agtcctgggg acacactcac  4178
cataaacaca tccccaggca ggacagatcg gggaaggggt gtgtaccagg ctatgatttc  4238
tcttgcatta aatgtatta ttaaaaaaaa aaaaaaaa                           4276

<210> SEQ ID NO 11
<211> LENGTH: 1147
<212> TYPE: PRT
<213> ORGANISM: Homo sapiens

<400> SEQUENCE: 11

Met Asp Asp Tyr Met Glu Thr Leu Lys Asp Glu Glu Asp Ala Leu Trp
1               5                   10                  15

Glu Asn Val Glu Cys Asn Arg His Met Leu Ser Arg Tyr Ile Asn Pro
            20                  25                  30

Ala Lys Leu Thr Pro Tyr Leu Arg Gln Cys Lys Val Ile Asp Glu Gln
        35                  40                  45

Asp Glu Asp Glu Val Leu Asn Ala Pro Met Leu Pro Ser Lys Ile Asn
    50                  55                  60

Arg Ala Gly Arg Leu Leu Asp Ile Leu His Thr Lys Gly Gln Arg Gly
65                  70                  75                  80

Tyr Val Val Phe Leu Glu Ser Leu Glu Phe Tyr Tyr Pro Glu Leu Tyr
                85                  90                  95

Lys Leu Val Thr Gly Lys Glu Pro Thr Arg Arg Phe Ser Thr Ile Val
            100                 105                 110

Val Glu Glu Gly His Glu Gly Leu Thr His Phe Leu Met Asn Glu Val
        115                 120                 125

Ile Lys Leu Gln Gln Gln Met Lys Ala Lys Asp Leu Gln Arg Cys Glu
    130                 135                 140

Leu Leu Ala Arg Leu Arg Gln Leu Glu Asp Glu Lys Lys Gln Met Thr
145                 150                 155                 160

Leu Thr Arg Val Glu Leu Leu Thr Phe Gln Glu Arg Tyr Tyr Lys Met
                165                 170                 175
```

-continued

```
Lys Glu Glu Arg Asp Ser Tyr Asn Asp Glu Leu Val Lys Val Lys Asp
                180                 185                 190
Asp Asn Tyr Asn Leu Ala Met Arg Tyr Ala Gln Leu Ser Glu Glu Lys
            195                 200                 205
Asn Met Ala Val Met Arg Ser Arg Asp Leu Gln Leu Glu Ile Asp Gln
210                 215                 220
Leu Lys His Arg Leu Asn Lys Met Glu Glu Cys Lys Leu Glu Arg
225                 230                 235                 240
Asn Gln Ser Leu Lys Leu Lys Asn Asp Ile Glu Asn Arg Pro Lys Lys
                245                 250                 255
Glu Gln Val Leu Glu Leu Glu Arg Glu Asn Glu Met Leu Lys Thr Lys
            260                 265                 270
Asn Gln Glu Leu Gln Ser Ile Ile Gln Ala Gly Lys Arg Ser Leu Pro
            275                 280                 285
Asp Ser Asp Lys Ala Ile Leu Asp Ile Leu Glu His Asp Arg Lys Glu
            290                 295                 300
Ala Leu Glu Asp Arg Gln Glu Leu Val Asn Arg Ile Tyr Asn Leu Gln
305                 310                 315                 320
Glu Glu Ala Arg Gln Ala Glu Glu Leu Arg Asp Lys Tyr Leu Glu Glu
                325                 330                 335
Lys Glu Asp Leu Glu Leu Lys Cys Ser Thr Leu Gly Lys Asp Cys Glu
            340                 345                 350
Met Tyr Lys His Arg Met Asn Thr Val Met Leu Gln Leu Glu Glu Val
            355                 360                 365
Glu Arg Glu Arg Asp Gln Ala Phe His Ser Arg Asp Glu Ala Gln Thr
370                 375                 380
Gln Tyr Ser Gln Cys Leu Ile Glu Lys Asp Lys Tyr Arg Lys Gln Ile
385                 390                 395                 400
Arg Glu Leu Glu Glu Lys Asn Asp Glu Met Arg Ile Glu Met Val Arg
                405                 410                 415
Arg Glu Ala Cys Ile Val Asn Leu Glu Ser Lys Leu Arg Arg Leu Ser
            420                 425                 430
Lys Asp Ser Asn Asn Leu Asp Gln Ser Leu Pro Arg Asn Leu Pro Val
            435                 440                 445
Thr Ile Ile Ser Gln Asp Phe Gly Asp Ala Ser Pro Arg Thr Asn Gly
            450                 455                 460
Gln Glu Ala Asp Asp Ser Ser Thr Ser Glu Glu Ser Pro Glu Asp Ser
465                 470                 475                 480
Lys Tyr Phe Leu Pro Tyr His Pro Pro Gln Arg Arg Met Asn Leu Lys
                485                 490                 495
Gly Ile Gln Leu Gln Arg Ala Lys Ser Pro Ile Ser Leu Lys Arg Thr
            500                 505                 510
Ser Asp Phe Gln Ala Lys Gly His Glu Glu Gly Thr Asp Ala Ser
            515                 520                 525
Pro Ser Ser Cys Gly Ser Leu Pro Ile Thr Asn Ser Phe Thr Lys Met
            530                 535                 540
Gln Pro Pro Arg Ser Arg Ser Ser Ile Met Ser Ile Thr Ala Glu Pro
545                 550                 555                 560
Pro Gly Asn Asp Ser Ile Val Arg Tyr Lys Glu Asp Ala Pro His
                565                 570                 575
Arg Ser Thr Val Glu Glu Asp Asn Asp Ser Gly Gly Phe Asp Ala Leu
            580                 585                 590
Asp Leu Asp Asp Asp Ser His Glu Arg Tyr Ser Phe Gly Pro Ser Ser
```

```
                595                 600                 605
Ile His Ser Ser Ser Ser His Gln Ser Glu Gly Leu Asp Ala Tyr
610                 615                 620

Asp Leu Glu Gln Val Asn Leu Met Phe Arg Lys Phe Ser Leu Glu Arg
625                 630                 635                 640

Pro Phe Arg Pro Ser Val Thr Ser Val Gly His Val Arg Gly Pro Gly
                645                 650                 655

Pro Ser Val Gln His Thr Thr Leu Asn Gly Asp Ser Leu Thr Ser Gln
                660                 665                 670

Leu Thr Leu Leu Gly Gly Asn Ala Arg Gly Ser Phe Val His Ser Val
                675                 680                 685

Lys Pro Gly Ser Leu Ala Glu Lys Ala Gly Leu Arg Glu Gly His Gln
690                 695                 700

Leu Leu Leu Leu Glu Gly Cys Ile Arg Gly Glu Arg Gln Ser Val Pro
705                 710                 715                 720

Leu Asp Thr Cys Thr Lys Glu Glu Ala His Trp Thr Ile Gln Arg Cys
                725                 730                 735

Ser Gly Pro Val Thr Leu His Tyr Lys Val Asn His Glu Gly Tyr Arg
                740                 745                 750

Lys Leu Val Lys Asp Met Glu Asp Gly Leu Ile Thr Ser Gly Asp Ser
                755                 760                 765

Phe Tyr Ile Arg Leu Asn Leu Asn Ile Ser Ser Gln Leu Asp Ala Cys
770                 775                 780

Thr Met Ser Leu Lys Cys Asp Asp Val Val His Val Arg Asp Thr Met
785                 790                 795                 800

Tyr Gln Asp Arg His Glu Trp Pro Cys Ala Arg Val Asp Pro Phe Thr
                805                 810                 815

Asp His Asp Leu Asp Met Gly Thr Ile Pro Ser Tyr Ser Arg Ala Gln
                820                 825                 830

Gln Leu Leu Leu Val Lys Leu Gln Arg Leu Met His Arg Gly Ser Arg
                835                 840                 845

Glu Glu Val Asp Gly Thr His His Thr Leu Arg Ala Leu Arg Asn Thr
850                 855                 860

Leu Gln Pro Glu Glu Ala Leu Ser Thr Ser Asp Pro Arg Val Ser Pro
865                 870                 875                 880

Arg Leu Ser Arg Ala Ser Phe Leu Phe Gly Gln Leu Leu Gln Phe Val
                885                 890                 895

Ser Arg Ser Glu Asn Lys Tyr Lys Arg Met Asn Ser Asn Glu Arg Val
                900                 905                 910

Arg Ile Ile Ser Gly Ser Pro Leu Gly Ser Leu Ala Arg Ser Ser Leu
                915                 920                 925

Asp Ala Thr Lys Leu Leu Thr Glu Lys Gln Glu Glu Leu Asp Pro Glu
                930                 935                 940

Ser Glu Leu Gly Lys Asn Leu Ser Leu Ile Pro Tyr Ser Leu Val Arg
945                 950                 955                 960

Ala Phe Tyr Cys Glu Arg Arg Pro Val Leu Phe Thr Pro Thr Val
                965                 970                 975

Leu Ala Lys Thr Leu Val Gln Arg Leu Leu Asn Ser Gly Gly Ala Met
                980                 985                 990

Glu Phe Thr Ile Cys Lys Ser Asp Ile Val Thr Arg Asp Glu Phe Leu
                995                 1000                1005

Arg Arg Gln Lys Thr Glu Thr Ile Ile Tyr Ser Arg Glu Lys Asn Pro
1010                1015                1020
```

```
Asn Ala Phe Glu Cys Ile Ala Pro Ala Asn Ile Glu Ala Val Ala Ala
1025                1030                1035                1040

Lys Asn Lys His Cys Leu Leu Glu Ala Gly Ile Gly Cys Thr Arg Asp
            1045                1050                1055

Leu Ile Lys Ser Asn Ile Tyr Pro Ile Val Leu Phe Ile Arg Val Cys
        1060                1065                1070

Glu Lys Asn Ile Lys Arg Phe Arg Lys Leu Leu Pro Arg Pro Glu Thr
    1075                1080                1085

Glu Glu Glu Phe Leu Arg Val Cys Arg Leu Lys Glu Lys Glu Leu Glu
1090                1095                1100

Ala Leu Pro Cys Leu Tyr Ala Thr Val Glu Pro Asp Met Trp Gly Ser
1105                1110                1115                1120

Val Glu Glu Leu Leu Arg Val Val Lys Asp Lys Ile Gly Glu Glu Gln
            1125                1130                1135

Arg Lys Thr Ile Trp Val Asp Glu Asp Gln Leu
        1140                1145
```

```
<210> SEQ ID NO 12
<211> LENGTH: 3441
<212> TYPE: DNA
<213> ORGANISM: Homo sapiens

<400> SEQUENCE: 12
atggatgact acatggagac gctgaaggat gaagaggacg ccttgtggga gaatgtggag      60
tgtaaccggc acatgctcag ccgctatatc aaccctgcca agctcacgcc ctacctgcgt     120
cagtgtaagg tcattgatga gcaggatgaa gatgaagtgc ttaatgcccc tatgctgcca     180
tccaagatca accgagcagg ccggctgttg acattctac ataccaaggg gcaaaggggc      240
tatgtggtct tcttggagag cctagaattt tattacccag aactgtacaa actggtgact     300
gggaaagagc ccactcggag attctccacc attgtggtgg aggaaggcca cgagggcctc     360
acgcacttcc tgatgaacga ggtcatcaag ctgcagcagc agatgaaggc caaggacctg     420
caacgctgcg agctgctggc caggttgcgg cagctggagg atgagaagaa gcagatgacg     480
ctgacgcgcg tggagctgct aaccttccag gagcggtact acaagatgaa ggaagagcgg     540
gacagctaca tgacgagctg gtcaaggtg aaggacgaca actacaactt agccatgcgc     600
tacgcacagc tcagtgagga agaacatg gcggtcatga ggagccgaga cctccaactc       660
gagatcgatc agctaaagca ccggttgaat aagatggagg aggaatgtaa gctggagaga     720
aatcagtctc taaaactgaa gaatgacatt gaaaatcggc caagaagga gcaggttctg      780 gaactggagc gggagaatga aatgctgaag accaaaaacc aggagctgca gtccatcatc     840
caggccggga gcgcagcct gccagactca gacaaggcca tcctggacat cttggaacac     900
gaccgcaagg aggccctgga ggacaggcag gagctggtca caggatcta caacctgcag      960 gaggaggccc gccaggcaga ggagctgcga gacaagtacc tggaggagaa ggaggacctg    1020
gagctcaagt gctcgaccct gggaaaggac tgtgaaatgt acaagcaccg catgaacacg    1080
gtcatgctgc agctggagga ggtggagcgg agcgggacc aggccttcca ctcccgagat     1140
gaagctcaga cacagtactc gcagtgctta atcgaaaagg acaagtacag gaagcagatc    1200
cgcgagctgg aggagaagaa cgacgagatg aggatcgaga tggtgcggcg ggaggcctgc    1260
atcgtcaacc tggagagcaa gctgcggcgc ctctccaagg acagcaacaa cctggaccag    1320
agtctgccca ggaacctgcc agtaaccatc atctctcagg actttgggga tgccagcccc    1380
aggaccaatg gtcaagaagc tgacgattct tccacctcgg aggagtcacc tgaagacagc    1440
```

```
aagtacttcc tgccctacca tccgcccag cgcaggatga acctgaaggg catccagctg    1500
cagagagcca atcccccat cagcctgaag cgaacatcag attttcaagc caagggcac    1560 gaggaagaag gcacggacgc cagccctagc tcctgcggat ctctgcccat caccaactcc   1620
ttcaccaaga tgcagccccc ccggagccgc agcagcatca tgtcaatcac cgccgagccc   1680
ccgggaaacg actccatcgt cagacgctac aaggaggacg cgccccatcg cagcacagtc   1740
gaagaagaca atgacagcgg cgggtttgac gccttagatc tggatgatga cagtcacgaa   1800
cgctactcct tcggaccctc ctccatccac tcctcctcct cctcccacca atccgagggc   1860
ctggatgcct acgacctgga gcaggtcaac ctcatgttca ggaagttctc tctggaaaga   1920
cccttccggc cttcggtcac ctctgtgggg cacgtgcggg gcccagggcc ctcggtgcag   1980
cacacgacgc tgaatggcga cagcctcacc tcccagctca ccctgctggg ggcaacgcg    2040 cgagggagct tcgtgcactc ggtcaagcct ggctctctgg ccgagaaagc cggcctccgt   2100
gagggccacc agctgctgct gctagaaggc tgcatccgag gcgagaggca gagtgtcccg   2160
ttggacacat gcaccaaaga ggaagcccac tggaccatcc agaggtgcag cggccccgtc   2220
acgctgcact acaaggtcaa ccacgaaggg taccggaagc tggtgaagga catggaggac   2280
ggcctgatca catcggggga ctcgttctac atccggctga acctgaacat ctccagccag   2340
ctggacgcct gcaccatgtc cctgaagtgt gacgatgttg tgcacgtccg tgacaccatg   2400
taccaggaca ggcacgagtg gccgtgcgcg cgggtcgacc ctttcacaga ccatgacctg   2460
gatatgggca ccatacccag ctacagccga gcccagcagc tcctcctggt gaaactgcag   2520
cgcctgatgc accgaggcag ccgggaggag gtagacggca cccaccacac cctgcgggca   2580
ctccggaaca ccctgcagcc ggaagaagcg ctttcaacaa gcgacccccg ggtcagcccc   2640
cgtctctcgc gagcaagctt ccttttttggc cagctccttc agttcgtcag caggtccgag   2700
aacaagtata gcggatgaa cagcaatgag cgggtccgca tcatctcggg gagtccgcta   2760
gggagcctgg cccggtcctc gctggacgcc accaagctct tgactgagaa gcaggaagag   2820
ctggaccctg agagcgagct gggcaagaac ctcagcctca tccccctacag cctggtacgc   2880 gccttctact gcgagcgccg ccggcccgtg ctcttcacac ccaccgtgct ggccaagacg   2940
ctggtgcaga ggctgctcaa ctcgggaggt gccatggagt tcaccatctg caagtcagat   3000
atcgtcacaa gagatgagtt cctcagaagg cagaagacgg agaccatcat ctactcccga   3060
gagaagaacc ccaacgcgtt cgaatgcatc gcccctgcca acattgaagc tgtggccgcc   3120
aagaacaagc actgcctgct ggaggctggg atcggctgca caagagactt gatcaagtcc   3180
aacatctacc ccatcgtgct cttcatccgg gtgtgtgaga agaacatcaa gaggttcaga   3240
aagctgctgc cccggcctga gacgaggag gagttcctgc gcgtgtgccg gctgaaggag   3300
aaggagctgg aggccctgcc gtgcctgtac gccacggtgg aacctgacat gtggggcagc   3360
gtagaggagc tgctccgcgt tgtcaaggac aagatcggcg aggagcagcg caagaccatc   3420
tgggtggacg aggaccagct g                                           3441
```

<210> SEQ ID NO 13
<211> LENGTH: 89
<212> TYPE: PRT
<213> ORGANISM: Artificial Sequence
<220> FEATURE:
<223> OTHER INFORMATION: consensus sequence

<400> SEQUENCE: 13

Ala Glu Asp Asp Arg Arg Leu Leu Arg Lys Asn Arg Leu Glu Leu Leu
 1               5                  10                  15

-continued

```
Gly Glu Leu Thr Leu Ser Gly Leu Leu Asp His Leu Glu Lys Asn Val
             20                  25                  30

Leu Thr Glu Glu Glu Glu Lys Ile Lys Ala Lys Asn Thr Thr Arg
         35                  40                  45

Arg Asp Lys Ala Arg Glu Leu Ile Asp Ser Val Gln Lys Gly Asn
 50                  55                  60

Gln Ala Phe Gln Ile Phe Leu Gln Ala Leu Arg Glu Thr Asp Gln Glu
 65                  70                  75                  80

Leu Leu Ala Asp Leu Leu Leu Asp Glu
                 85

<210> SEQ ID NO 14
<211> LENGTH: 17
<212> TYPE: PRT
<213> ORGANISM: Artificial Sequence
<220> FEATURE:
<223> OTHER INFORMATION: consensus sequence

<400> SEQUENCE: 14

Gly Glu Ser Leu Met Arg Ala Glu Asp Val Arg Ala Ala Ile Arg Glu
 1               5                  10                  15

Leu

<210> SEQ ID NO 15
<211> LENGTH: 69
<212> TYPE: PRT
<213> ORGANISM: Artificial Sequence
<220> FEATURE:
<223> OTHER INFORMATION: consensus sequence

<400> SEQUENCE: 15

Pro Glu Cys Lys Gln Glu Val Leu Arg Arg Gln Gln Glu Ser Ala Glu
 1               5                  10                  15

Arg Asp Tyr Arg Leu Asp Pro Val Leu Tyr Lys Ala Cys Lys Ser Asp
             20                  25                  30

Ile Glu Lys Tyr Cys Ala Glu Ile Pro Asn Lys Glu Ser Ser Glu Asp
         35                  40                  45

Ala Ala Glu Val Gly Glu Gly Gln Val Leu Glu Cys Leu Met Glu Asn
 50                  55                  60

Lys Asp Asp Glu Glu
 65

<210> SEQ ID NO 16
<211> LENGTH: 34
<212> TYPE: PRT
<213> ORGANISM: Artificial Sequence
<220> FEATURE:
<223> OTHER INFORMATION: consensus sequence

<400> SEQUENCE: 16

Lys Lys Ile Gln Gln Thr Glu Glu Leu Asp Lys Ala Glu Glu Arg
 1               5                  10                  15

Leu Glu Lys Ala Gln Arg Glu Leu Glu Glu Glu Lys Lys Arg Glu
             20                  25                  30

Glu Ala

<210> SEQ ID NO 17
<211> LENGTH: 83
<212> TYPE: PRT
<213> ORGANISM: Artificial Sequence
<220> FEATURE:
```

```
<223> OTHER INFORMATION: consensus sequence

<400> SEQUENCE: 17

Glu Ile Thr Leu Glu Lys Gly Val Lys Arg Gly Gly Leu Gly Phe Ser
1               5                   10                  15

Ile Lys Gly Gly Ser Asp Lys Gly Ile Val Val Ser Glu Val Leu Pro
                20                  25                  30

Gly Ser Gly Ala Ala Glu Ala Gly Gly Arg Leu Lys Glu Gly Asp Val
            35                  40                  45

Ile Leu Ser Val Asn Gly Gln Asp Val Glu Asn Met Ser His Glu Arg
        50                  55                  60

Ala Val Leu Ala Ile Lys Gly Ser Gly Gly Glu Val Thr Leu Thr Val
65                  70                  75                  80

Leu Arg Asp

<210> SEQ ID NO 18
<211> LENGTH: 108
<212> TYPE: PRT
<213> ORGANISM: Artificial Sequence
<220> FEATURE:
<223> OTHER INFORMATION: consensus sequence

<400> SEQUENCE: 18

Thr Arg Pro Val Pro Arg Pro Gly Glu Val Asp Gly Lys Asp Tyr His
1               5                   10                  15

Phe Val Ser Ser Arg Glu Glu Met Glu Lys Asp Ile Ala Ala Asn Glu
                20                  25                  30

Phe Leu Glu Tyr Gly Glu Phe Gln Gly Asn Tyr Tyr Gly Thr Ser Leu
            35                  40                  45

Glu Thr Val Arg Gln Val Ala Lys Gln Gly Lys Ile Cys Ile Leu Asp
        50                  55                  60

Val Glu Pro Gln Gly Val Lys Arg Leu Arg Thr Ala Glu Leu Ser Asn
65                  70                  75                  80

Pro Ile Val Val Phe Ile Ala Pro Pro Ser Leu Gln Glu Leu Glu Lys
                85                  90                  95

Arg Leu Glu Gly Arg Asn Lys Glu Ser Glu Glu Ser
            100                 105

<210> SEQ ID NO 19
<211> LENGTH: 15
<212> TYPE: PRT
<213> ORGANISM: Homo sapiens

<400> SEQUENCE: 19

Gln Lys Gly Trp Arg Gln Gly Glu Glu Asp Arg Glu Asn Thr Thr
1               5                   10                  15
```

What is claimed is:

1. An isolated nucleic acid molecule selected from the group consisting of:

a) a nucleic acid molecule comprising a nucleotide sequence which is at least 85% identical to the nucleotide sequence of SEQ ID NO: 10, 12 or an entire complement thereof, wherein the nucleic acid molecule encodes a polypeptide which binds Bcl-10 and comprises a CARD domain;

b) a nucleic acid molecule comprising a fragment of at least 75 consecutive nucleotides of the nucleotide sequence of SEQ ID NO: 10, 12 or an entire complement thereof;

c) a nucleic acid molecule which encodes a polypeptide comprising an amino acid sequence at least 95% identical to SEQ ID NO: 11, wherein the polypeptide binds Bcl-10 and comprises a CARD domain;

d) a nucleic acid molecule which encodes a fragment of a polypeptide comprising the amino acid sequence of SEQ ID NO: 11, wherein the fragment comprises the CARD domain of residues 6-112 of SEQ ID NO:11, wherein the fragment binds Bcl-10; and e) a nucleic acid molecule which encodes a variant of the amino acid sequence of SEQ ID NO: 11, wherein the nucleic acid molecule hybridizes to the entire SEQ ID NO: 10, 12 or entire complement thereof under conditions of incubation at 45° C. in 6.0×SSC followed by washing in 0.2×SSC/0.1% SDS at 65° C., wherein the variant binds Bcl-10 and comprises a CARD domain.

2. An isolated nucleic acid molecule selected from the group consisting of:
   a) a nucleic acid comprising a nucleotide sequence which is at least 95% identical to the nucleotide sequence of SEQ ID NO: 10, 12 or an entire complement thereof; and
   b) a nucleic acid molecule which encodes a polypeptide comprising an amino acid sequence at least 95% identical to SEQ ID NO: 11,
   wherein the nucleic acid molecule encodes a polypeptide which binds Bcl-10 and comprises a CARD domain.

3. The nucleic acid molecule of claim 1 further comprising vector nucleic acid sequences.

4. The nucleic acid molecule of claim 1 further comprising nucleic acid sequences encoding a heterologous polypeptide.

5. A host cell which contains the nucleic acid molecule of claim 1.

6. The host cell of claim 5 which is a mammalian host cell.

7. A method for producing a polypeptide selected from the group consisting of:
   a) a polypeptide comprising an amino acid sequence at least 95% identical to SEQ ID NO: 11, wherein the polypeptide binds Bcl-10 and comprises a CARD domain;
   b) a polypeptide comprising a fragment of the amino acid sequence of SEQ ID NO:11, wherein the fragment comprises the CARD domain of residues 6-112 of SEQ ID NO:11, wherein the fragment binds Bcl-10; and
   c) a variant of the amino acid sequence of SEQ ID NO:11, wherein the variant is encoded by a nucleic acid molecule which hybridizes to the entire SEQ ID NO: 10, 12, or an entire complement thereof under conditions of incubation at 45° C. in 6.0×SSC followed by washing in 0.2×SSC/0.1% SDS at 65° C., wherein the variant binds Bcl-10 and comprises a CARD domain;
   comprising culturing the host cell of claim 5 under conditions in which the nucleic acid molecule is expressed.

8. A method for detecting the presence of a nucleic acid molecule of claim 1 in a sample, comprising the steps of:
   a) contacting the sample with a nucleic acid probe or primer which hybridizes under conditions of hybridization in 6× sodium chloride/sodium citrate (SSC) at about 45° C., followed by one or more washes in 0.2×SSC, 0.1% SDS at 50-65° C. to the nucleic acid molecule; and
   b) determining whether the nucleic acid probe or primer binds to a nucleic acid molecule in the sample.

9. The method of claim 8, wherein the sample comprises mRNA molecules and is contacted with a nucleic acid probe.

10. A kit comprising an oligonucleotide which hybridizes under conditions of hybridization in 6× sodium chloride/sodium citrate (SSC) at about 45° C., followed by one or more washes in 0.2×SSC, 0.1% SDS at 50-65° C. to a nucleic acid molecule of claim 1 and instructions for use.

11. The nucleic acid molecule of claim 1, wherein the fragment of the polypeptide further comprises amino acids 635-1147 of SEQ ID NO:11.

12. The nucleic acid molecule of claim 1, wherein the fragment of the polypeptide further comprises the coiled coil domain of amino acid residues 130-431 of SEQ ID NO:11.

13. An isolated nucleic acid molecule comprising SEQ ID NO:12 or an entire complement thereof.

14. The method of claim 8, wherein the probe comprises a label.

15. The method of claim 8, wherein the sample is a peripheral blood leukocyte sample.

* * * * *